US012569563B2

(12) United States Patent
Fischer et al.

(10) Patent No.: US 12,569,563 B2
(45) Date of Patent: Mar. 10, 2026

(54) SELECTIVE HDAC6 DEGRADERS AND METHODS OF USE THEREOF

(71) Applicant: DANA-FARBER CANCER INSTITUTE, INC., Boston, MA (US)

(72) Inventors: Eric S. Fischer, Chestnut Hill, MA (US); Yuan Xiong, Waltham, MA (US); Katherine Donovan, Brookline, MA (US); Nicholas Eleuteri, Braintree, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 960 days.

(21) Appl. No.: 17/773,785

(22) PCT Filed: Nov. 5, 2020

(86) PCT No.: PCT/US2020/059080

§ 371 (c)(1),
(2) Date: May 2, 2022

(87) PCT Pub. No.: WO2021/092151

PCT Pub. Date: May 14, 2021

(65) Prior Publication Data

US 2023/0011665 A1 Jan. 12, 2023

Related U.S. Application Data

(60) Provisional application No. 62/931,532, filed on Nov. 6, 2019.

(51) Int. Cl.
*A61K 47/54* (2017.01)
*A61K 47/55* (2017.01)

(52) U.S. Cl.
CPC ............ *A61K 47/545* (2017.08); *A61K 47/55* (2017.08)

(58) Field of Classification Search
CPC .................................................... A61K 47/575
See application file for complete search history.

(56) References Cited

U.S. PATENT DOCUMENTS

| | | | | |
|---|---|---|---|---|
| 10,669,253 | B2 * | 6/2020 | Bradner | C07D 487/04 |
| 2017/0121321 | A1 | 5/2017 | Crews et al. | |

FOREIGN PATENT DOCUMENTS

| | | | | | |
|---|---|---|---|---|---|
| WO | WO-2011088192 | A1 * | 7/2011 | | C07D 271/06 |
| WO | 2013066836 | A1 | 5/2013 | | |
| WO | WO-2016105518 | A1 * | 6/2016 | | A61P 1/04 |

OTHER PUBLICATIONS

Tan, Shuai, et al. "Design, synthesis and tumor cell growth inhibitory activity of 3-nitro-2H-cheromene derivatives as histone deacetylaes inhibitors." Bioorganic & Medicinal Chemistry 25.15 (2017): 4123-4132.), (Year: 2017).*
Rodríguez-Gimeno, Alejandra, and Carles Galdeano. "Drug Discovery Approaches to Target E3 Ligases." ChemBioChem 26.1 (2025): e202400656. (Year: 2025).*
Burslem, George M., et al. "Efficient synthesis of immunomodulatory drug analogues enables exploration of structure-degradation relationships." ChemMedChem 13.15 (2018): 1508-1512. (Year: 2018).*
Hatcher, et al., "Development of Highly Potent and Selective Steroidal Inhibitors and Degraders of CDK8," ACS Med. Chem. Lett., 2018, vol. 9, pp. 540-545.
Kim, et al., "Histone Deacetylase Inhibitors: Molecular Mechanisms of Action and Clinical Trials as Anti-Cancer Drugs," Am. J. Transl. Res., 2011, vol. 3, No. 2, pp. 166-179.
Scheepstra, et al., "Bivalent Ligands for Protein Degradation in Drug Discovery," Comput. Struct. Biotechnol. J., 2019, vol. 17, pp. 160-176.
Zhou, et al., "Discovery of a Small-Molecule Degrader of Bromodomain and Extra-Terminal (BET) Proteins with Picomolar Cellular Potencies and Capable of Achieving Tumor Regression," J. Med. Chem. 2018, vol. 61, pp. 462-481.
An et al., "Developing Potent PROTACs Tools for Selective Degradation of HDAC6 Protein", Protein Cell, 2019, vol. 10, No. 8, pp. 606-609.
Bantscheff et al., "Chemoproteomics Profiling of HDAC Inhibitors Reveals Selective Targeting of HDAC Complexes", Nat. Biotechnol., 2011, vol. 29, No. 3, pp. 255-265.
Wu et al., "Development of Multifunctional Histone Deacetylase 6 Degraders with Potent Antimyeloma Activity", J. Med. Chem., 2019, vol. 62, pp. 7042-7057.
Yang et al., "Development of The First Small Molecule Histone Deacetylase 6 (HDAC6) Degraders", Bioorg. Med. Chem. Lett., 2018, vol. 28, pp. 2493-2497.
Bekes, M. et al., "PROTAC targested protein degraders: the past is prologue", Nature Reviews, 2022, vol. 21, pp. 181-200.
Bondeson, D. P. et al., "Lessons in PROTAC design from selective degradation with a promiscuous warhead", Cell Chem. Biol., 2018, vol. 25, No. 1, pp. 78-87.
Li, X. et al., "Proteolysis-targeting chimera (PROTAC) for targeted protein degradation and cancer therapy", J. Hematol. Oncol., 2020, vol. 13, No. 50, 14 pages.
Nandave, M. et al., "PROTAC-mediated protein degradation: A paradigm shift in cancer therapeutics", Springer, 2024, 400 pages.
Tan, L. et al., "When Kinases Meet PROTACS", Chin. J. Chem., 2018, vol. 36, pp. 971-977.

* cited by examiner

*Primary Examiner* — Andrew D Kosar
*Assistant Examiner* — Connor K English
(74) *Attorney, Agent, or Firm* — ArentFox Schiff LLP; Daniel W. Clarke; Shawn P. Foley

(57) ABSTRACT

The present invention relates to bispecific compounds, compositions, and methods for treating diseases or conditions mediated by aberrant histone deacety lase 6 (HDAC6) activity.

20 Claims, 15 Drawing Sheets

| | Compound 2 | Compound 3 | Compound 7 | Compound 1 | Compound 8 |
|---|---|---|---|---|---|
| HDAC1 | -0.11 | -0.15 | -0.07 | -0.07 | -0.05 |
| HDAC2 | -0.02 | -0.12 | 0.03 | -0.05 | 0.15 |
| HDAC3 | -0.11 | -0.20 | -0.04 | -0.05 | -0.07 |
| HDAC4 | -0.01 | 0.04 | -0.01 | -0.01 | 0.00 |
| HDAC5 | -0.08 | 0.00 | 0.10 | -0.03 | -0.07 |
| HDAC6 | -1.88 | -1.86 | -1.66 | -1.62 | -1.48 |
| HDAC7 | -0.07 | 0.07 | -0.05 | 0.05 | 0.00 |
| HDAC8 | -0.31 | -0.47 | -0.11 | -0.12 | -0.04 |
| HDAC9 | 0.01 | 0.02 | 0.03 | 0.02 | 0.03 |
| HDAC10 | -0.60 | -0.51 | -0.19 | -0.21 | -0.23 |

SELECTIVE HDAC6 DEGRADERS AND METHODS OF USE THEREOF

RELATED APPLICATIONS

This application is a national stage application, filed under 35 U.S.C. § 371, of International Application No. PCT/US2020/059080, filed Nov. 5, 2020, which claims the benefit of priority under 35 U.S.C. § 119 (e) to U.S. Provisional Application No. 62/931,532, filed Nov. 6, 2019, each of which is incorporated herein by reference in its entirety.

BACKGROUND OF THE INVENTION

The modification of histones by acetylation/deacetylation plays a key role in the regulation of gene expression by changing the structure of chromatin and by modulating the accessibility of transcription factors to their target DNA sequences (Eckschlager et al., Int. J. Mol. Sci. 18:1414 (2017)). The acetylation state of histones and other proteins are maintained by histone acetyltransferases (HAT) and histone deacetylases (HDAC). HATs add acetyl groups to lysine residues, while HDACs remove the acetyl groups. Generally, the acetylation of histone promotes a more relaxed chromatin structure which allows for transcriptional activation (Xu et al., Oncogene 26:5541-5552 (2007)). In addition to regulating histone modification, HDACs also regulate the post-translational acetylation of many non-histone proteins, including transcription factors, chaperones, and signaling molecules, resulting in changes in protein stability, protein-protein interactions, and protein-DNA interactions (Glozak et al., Gene 363:15-23 (2005)). The balance between histone acetylation and deacetylation is usually well regulated, but the balance is often upset in diseases such as cancer and neurodegenerative diseases.

HDACs are composed of 18 members (isoforms) which are divided into four classes based on their homology. There are 11 conventional HDACs that require $Zn^{2+}$ as a cofactor for their deacetylase activity; they fall within classes I, II, and IV. Class I includes HDACs 1, 2, 3, and 8 are located only within the nucleus and are related to the yeast RPD3 gene. Class II includes HDACs 4, 5, 6, 7, 9, and 10 which are located in both the nucleus and the cytoplasm, and are related to yeast Hda1 gene. Class IV includes HDAC 11 and has features of both Class I and Class II HDACs. Unlike conventional HDACs, Class III HDACs are composed of seven mammalian sirtuins (SIRT1-7), which include nicotinamide adenine dinucleotide ($NAD^+$)-dependent protein deacetylases localized in the nucleus (SIRT1, SIRT6, and SIRT7), mitochondria (SIRT3, SIRT4, and SIRT5), and cytoplasm (SIRT2) (Kim et al., Am. J. Transl. Res. 3:166-179 (2011)).

In view of the many HDAC isoforms, HDAC inhibition has a narrow therapeutic window and the risk of causing several adverse side effects. Accordingly, there is a need for compounds that inhibit specific HDAC isoforms (e.g., HDAC6) while minimizing off-target toxicity caused by binding to other unintended HDAC isoforms, for use in treating diseases such as cancer and neurodegenerative diseases.

SUMMARY OF THE INVENTION

A first aspect of the present invention is directed to a bispecific compound having a structure represented by formula (I):

(I)

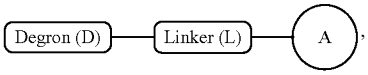, wherein

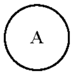

is a moiety represented by formula TL1 or TL2:

(TL1)

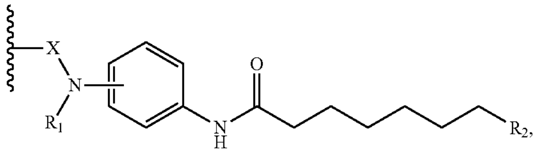, or (TL2)

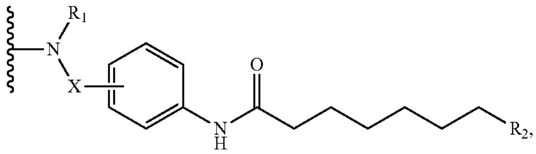, wherein

X is $CH_2$ or C═O;

$R_1$ is H or Me; and $R^2$ is

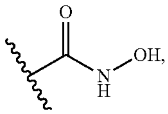,

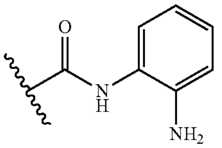,

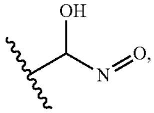,

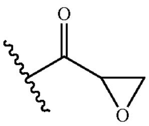,

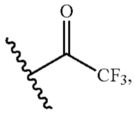,

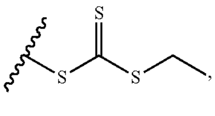,

-continued
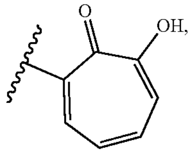
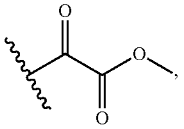
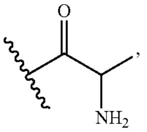
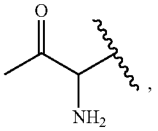
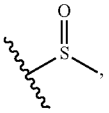
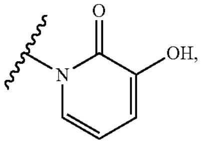
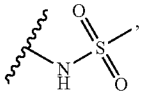
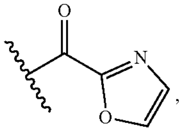
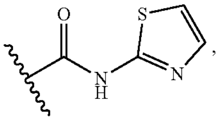
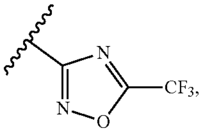
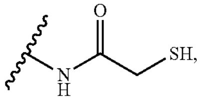
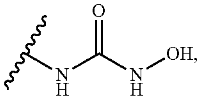
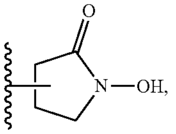
-continued
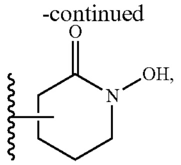
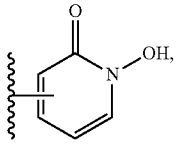
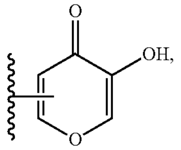
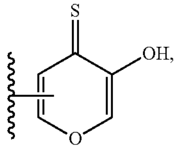
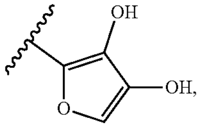
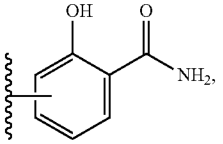
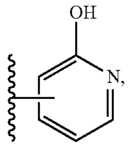
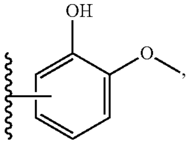
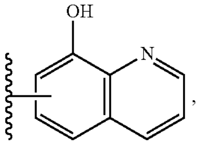
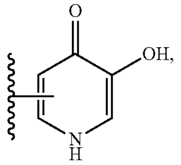
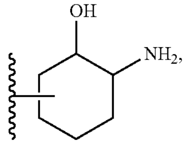
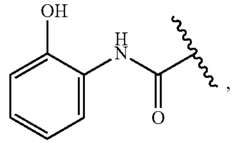

-continued

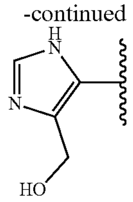
,

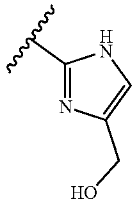
,

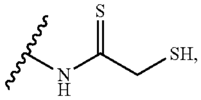
,

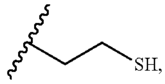
,

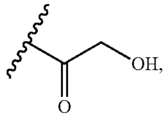
,

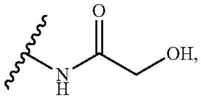
,

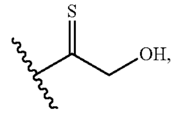
, or

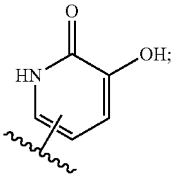
;

the degron represents a moiety that binds an E3 ubiquitin ligase, and the linker represents a moiety that covalently connects the degron, or a pharmaceutically acceptable salt or stereoisomer thereof.

Another aspect of the present invention is directed to a pharmaceutical composition containing a therapeutically effective amount of a bispecific compound of formula (I) or a pharmaceutically acceptable salt or stereoisomer thereof, and a pharmaceutically acceptable carrier.

In another aspect of the present invention, methods of making the bispecific compounds are provided.

A further aspect of the present invention is directed to a method of treating a disease or disorder characterized or mediated by aberrant HDAC6 activity, that includes administering a therapeutically effective amount of a bispecific compound of formula (I) or a pharmaceutically acceptable salt or stereoisomer thereof, to a subject in need thereof.

As shown in the working examples herein, bispecific compounds of formula I (also referred to herein as degraders) promote the degradation of HDAC6 while substantially sparing other HDAC isoforms. By conjugating low nanomole potency of HDAC targeting ligands with an E3 ligase binder, the inventive bispecific compounds are able to fast recruit E3 ligase, and therefore promote the degradation of HDAC6. The degraders may achieve high target selectivity with respect to degradation, beyond that expected from the constitutive binding ligands, therefore greatly reducing off-target effects.

Accordingly, the bispecific compounds of the present invention may serve as a set of new chemical tools for HDAC6 knockdown, exemplify a broadly applicable approach to arrive at degraders that are selective over non-selective binding ligands, and may provide effective treatments for HDAC6-mediated diseases and disorders such as cancer, neurodegenerative diseases, and autoimmune diseases.

DETAILED DESCRIPTION

Figure 1A:
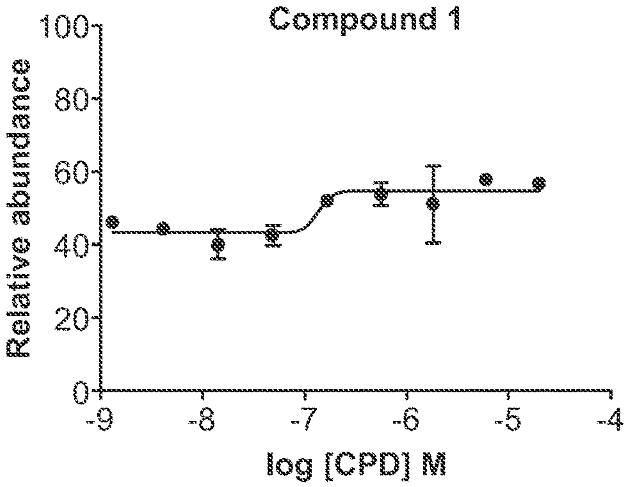
FIG. 1A-FIG. 1G are plots of the cellular CRBN engagement assay for inventive compounds 1-5, 7, and 8 where $IC_{50}$ values show the combinatorial effect of cell permeability and degrader's ability to engage CRBN in cell.
Figure 1B:
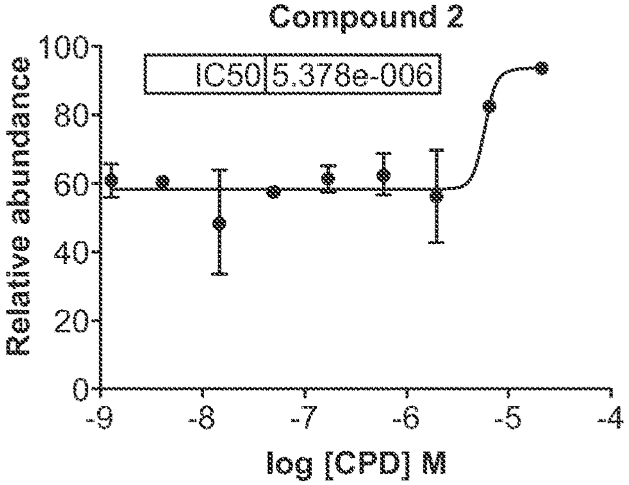
Figure 1C:
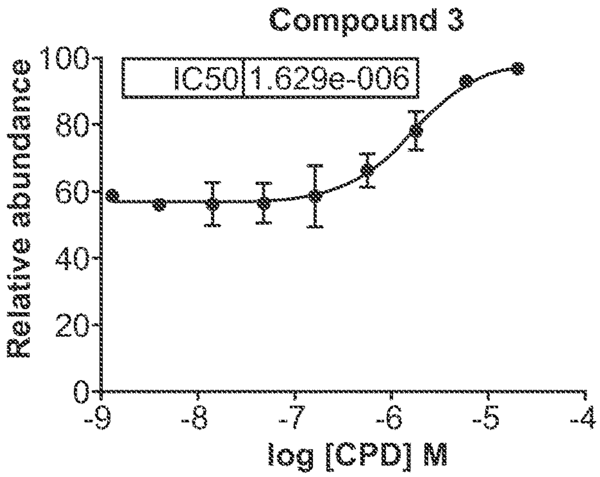
Figure 1D:
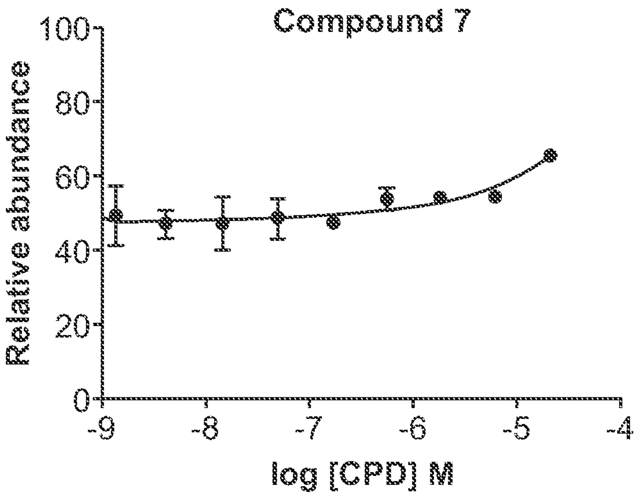
Figure 1E:
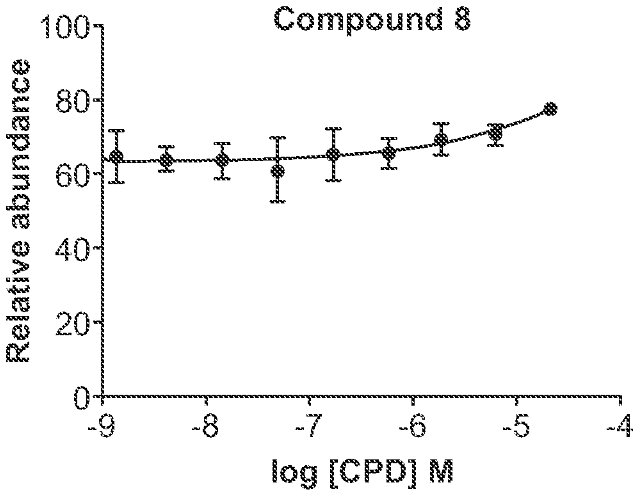
Figure 1F:
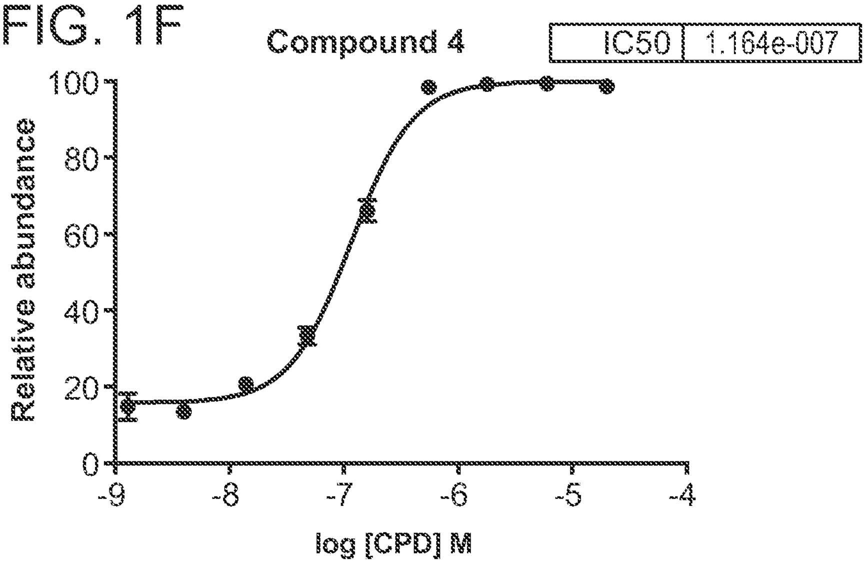
Figure 1G:
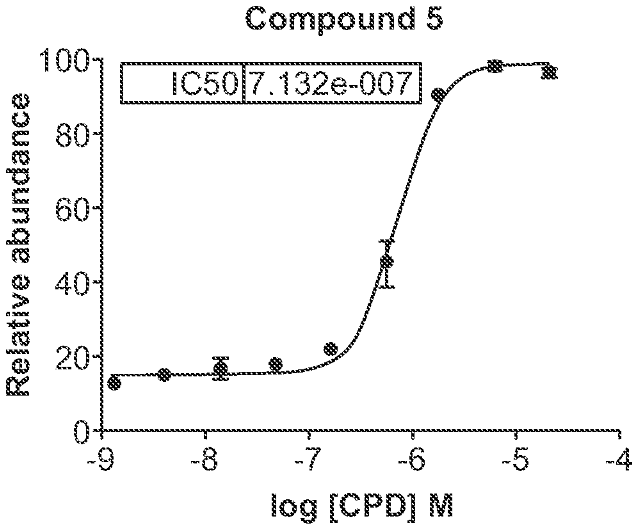
Figure 2A:
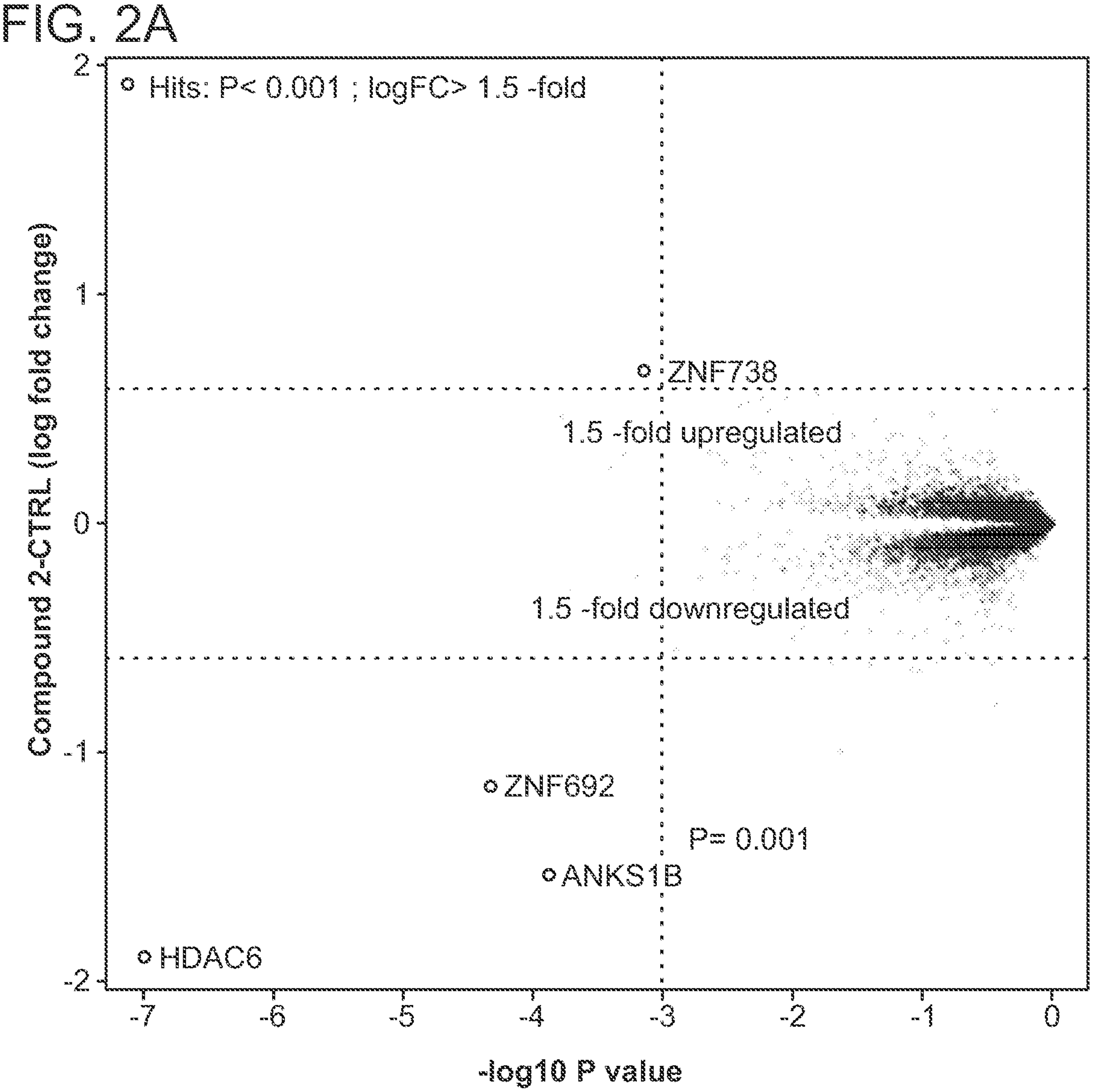
FIG. 2A-FIG. 2G are scatter plots that show the relative change in relative protein abundance with treatment of Kelly cells with compounds 1-5, 7, and 8 compared to dimethyl sulfoxide (DMSO) control. Significant changes were assessed by moderated t-test and displayed with $\log_2$ fold change on the y-axis and negative $\log_{10}$ P values on the x-axis for one independent biological replicate of inventive compound and three independent biological replicates of DMSO.
Figure 2B:
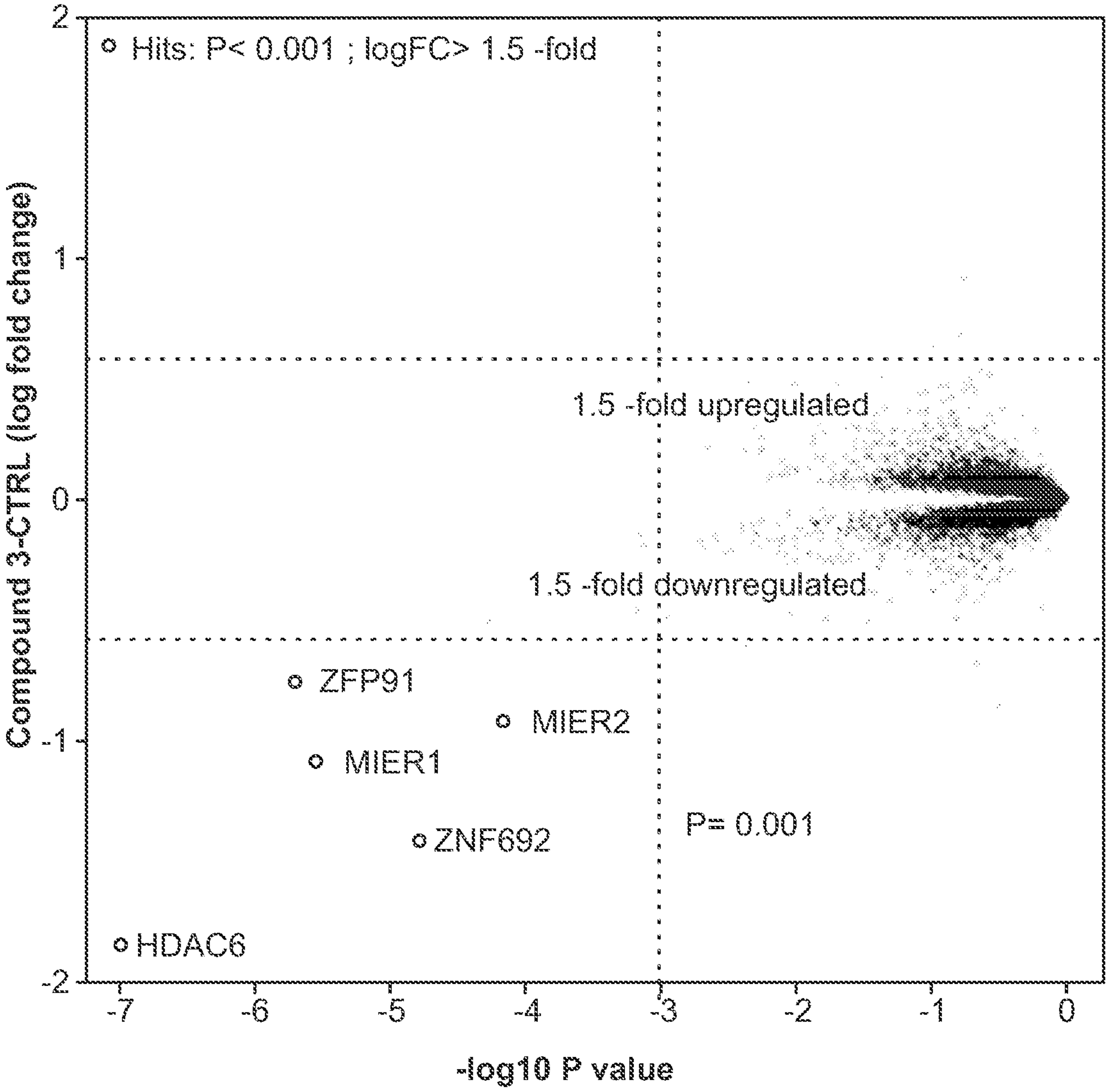
Figure 2C:
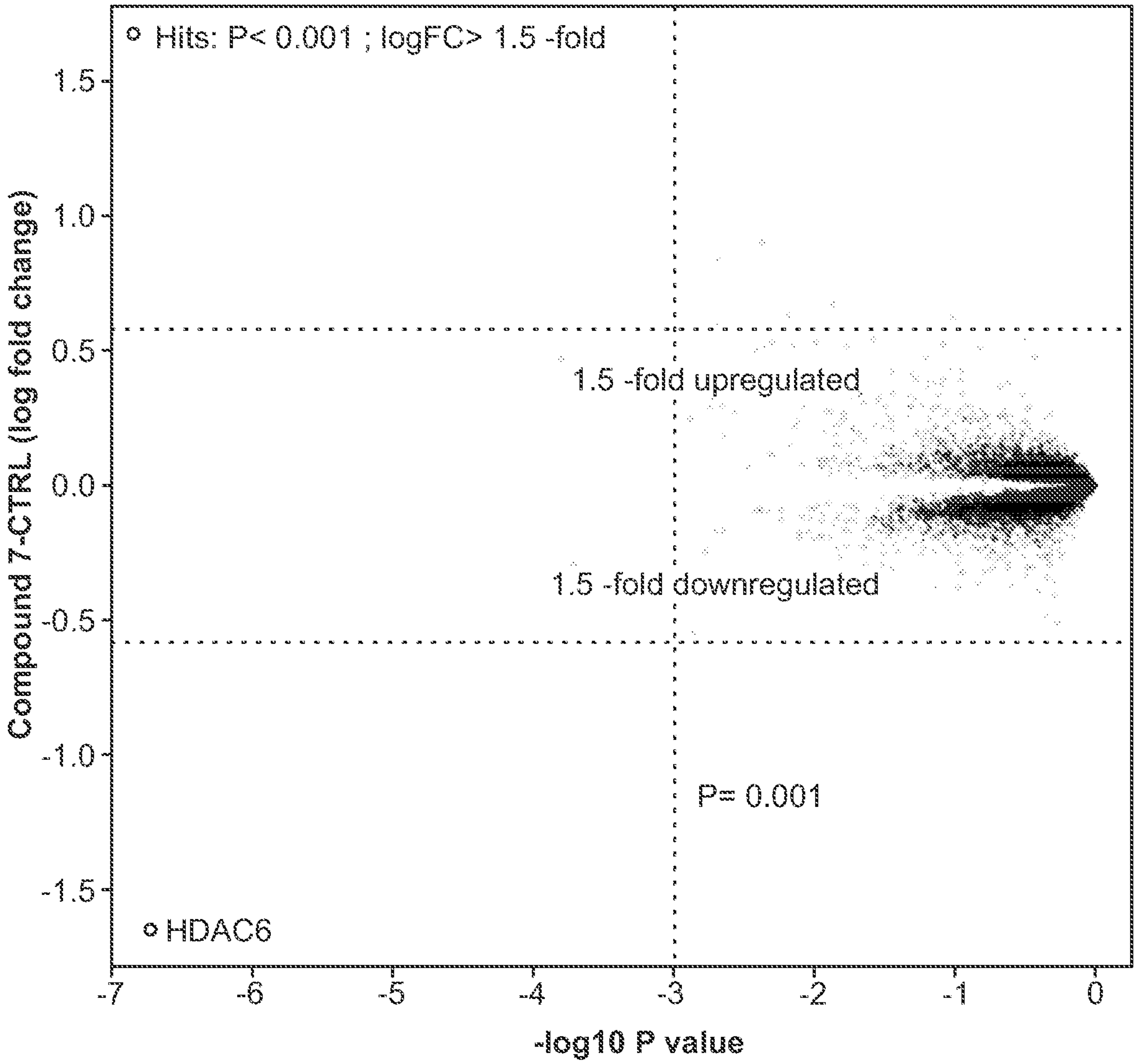
Figure 2D:
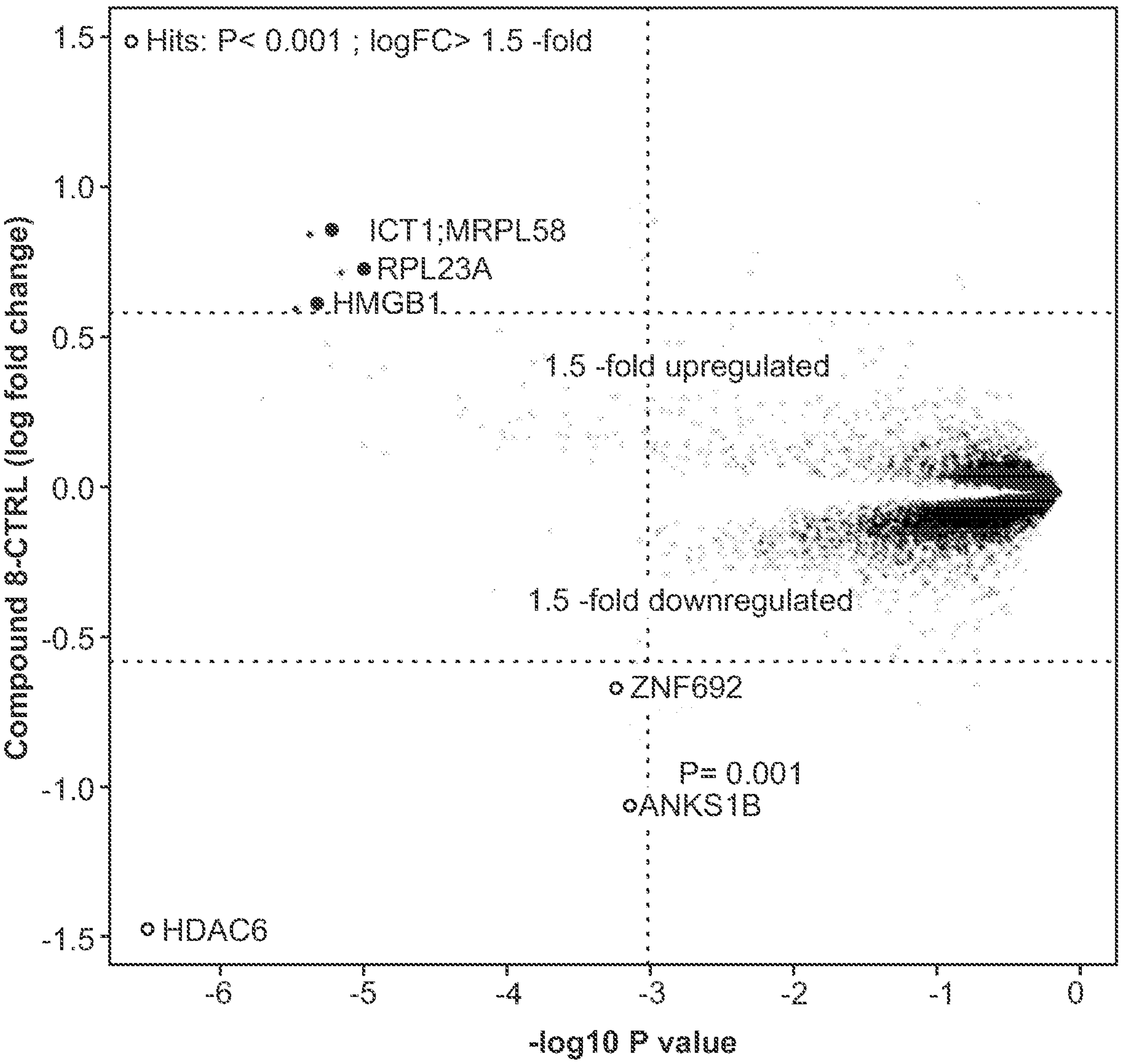
Figure 2E:
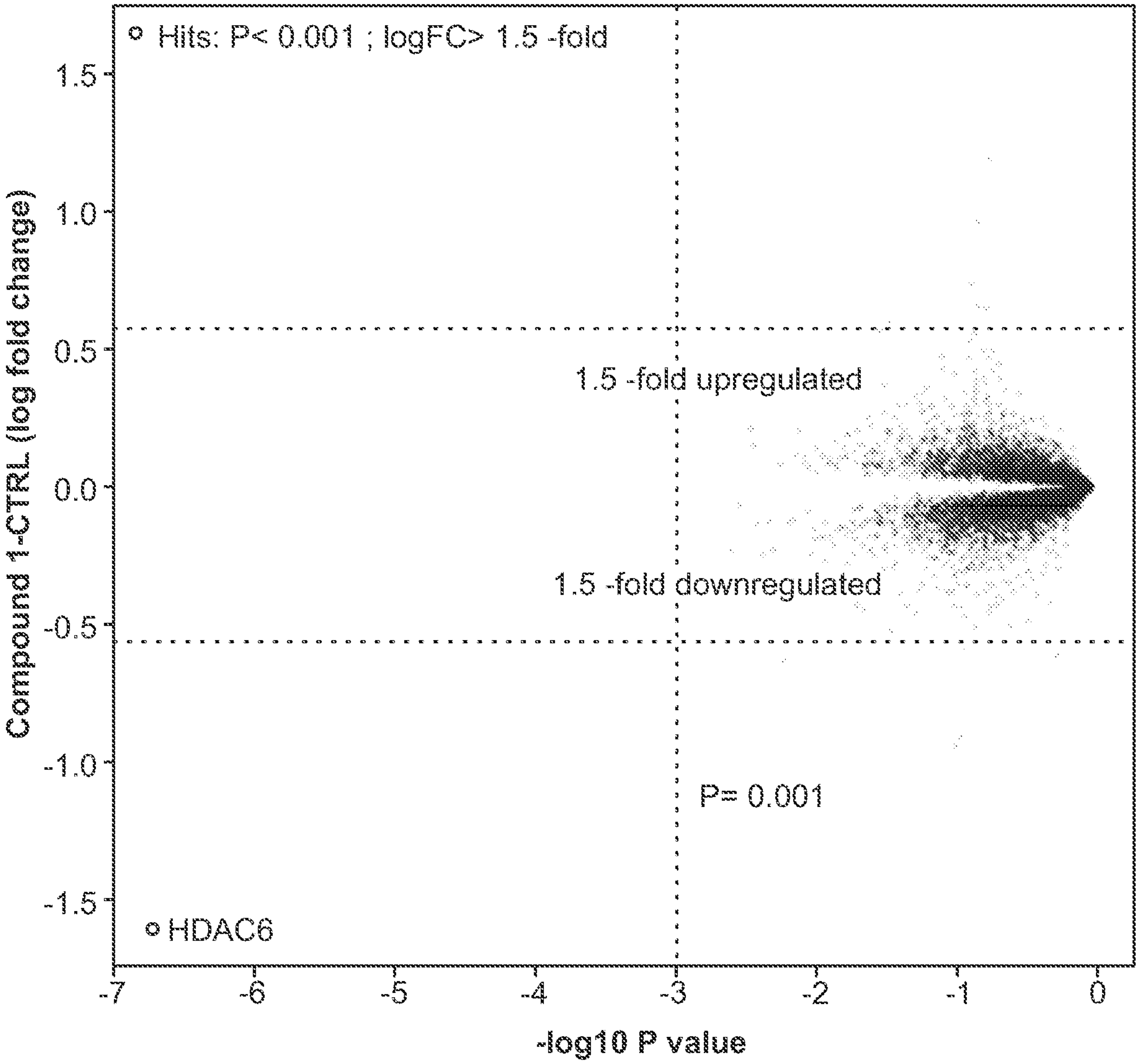
Figure 2F:
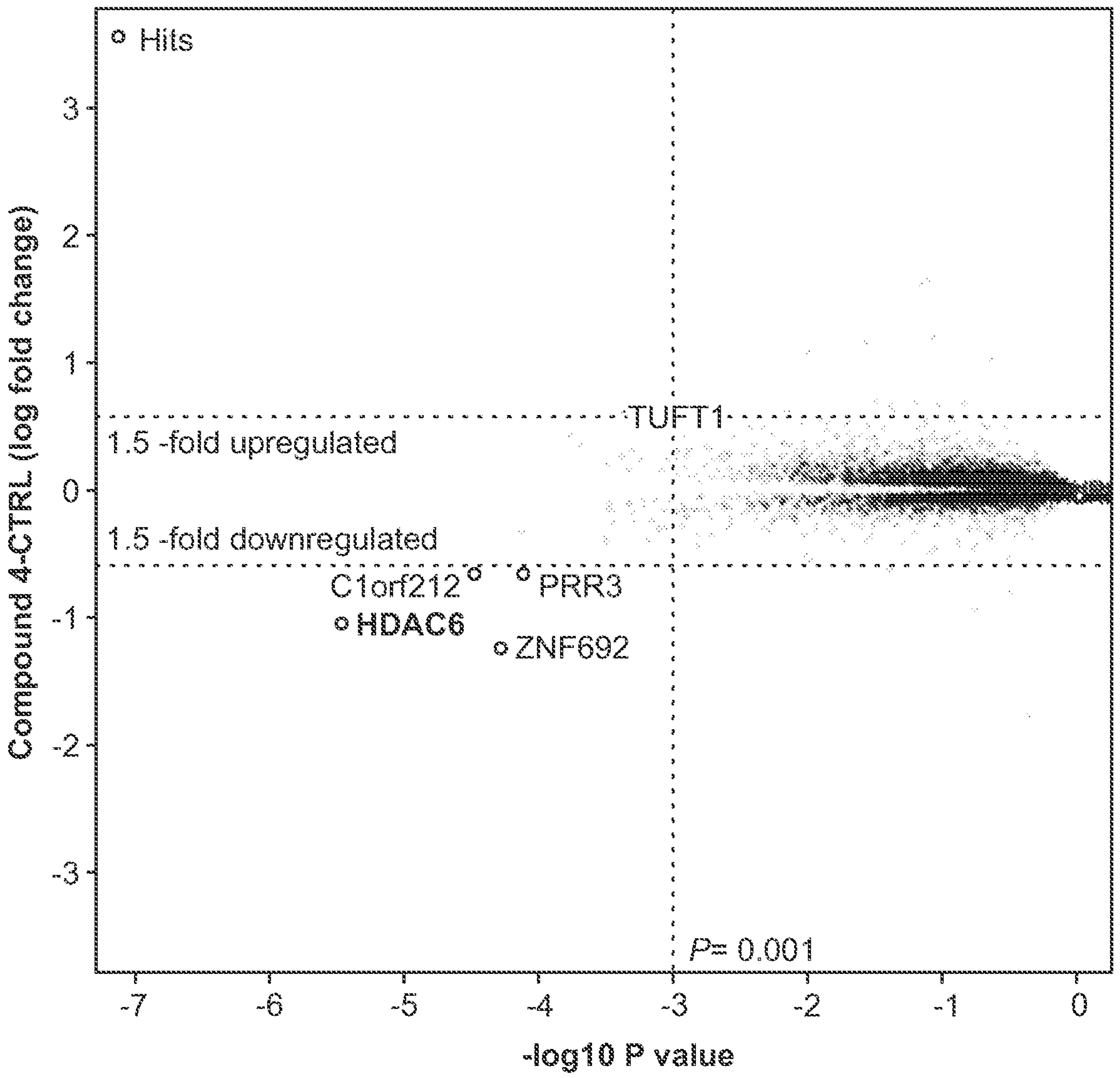
Figure 2G:
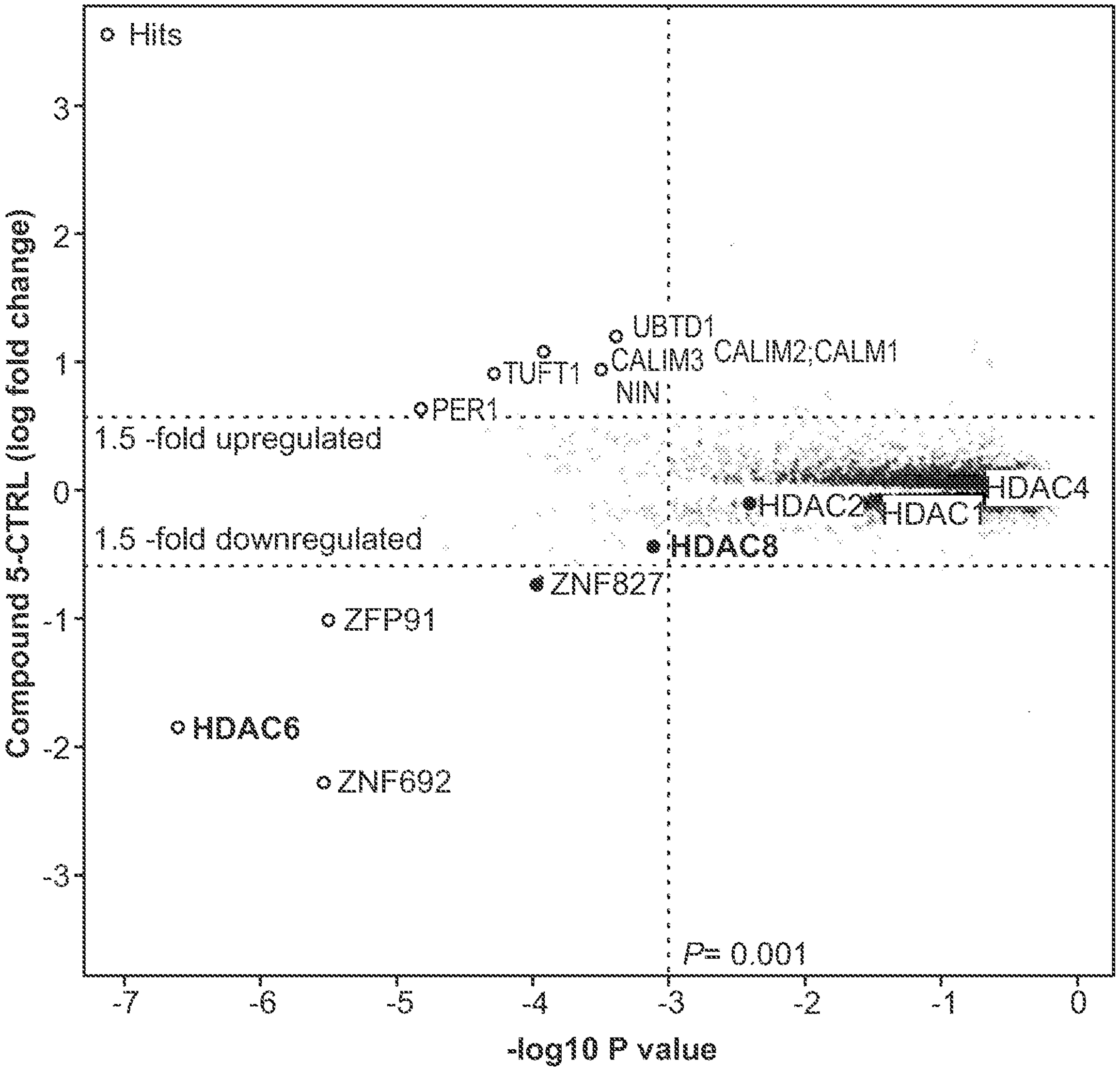

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Therefore, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

As used herein, the term "binder" refers a protein ligand. The functional consequences of binding the protein are not encompassed in this definition. Examples of binders include small-molecule inhibitors, activators, degraders, etc.

As used herein, the term "degrader" refers to a ligand for the protein of interest that results in degradation of that protein. Another commonly-used term is 'targeted protein degradation' to clarify that the degrader is a ligand for the protein of interest, as opposed to some indirect effect. Examples of degraders include PROTAC®s (proteolysis targeting chimera) or heterobispecific degraders, which consist of a ligand for an E3 ligase, such as cereblon, linked to a ligand for the protein to be degraded.

With respect to compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_3$-$C_5$ branched-chain alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbyl groups covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "alkoxylene" refers to a saturated monovalent aliphatic radicals of the general formula ($-O-C_nH_{2n}-$) where n represents an integer (e.g., 1, 2, 3, 4, 5, 6, or 7) and is inclusive of both straight-chain and branched-chain radicals. The alkoxylene chain may be attached to the rest of the molecule through a single bond and to the radical group through a single bond. In some embodiments, the alkoxylene group contains one to 3 carbon atoms (—O—$C_1$-$C_3$ alkoxylene). In other embodiments, an alkoxylene group contains one to 5 carbon atoms (—O—$C_1$-$C_5$ alkoxylene).

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Therefore, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl.

Therefore, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Therefore, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 5-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

The term heteroaryl also embraces N-heteroaryl groups which as used herein refers to a heteroaryl group, as defined above, and which contains at least one nitrogen atom and where the point of attachment of the N-heteroaryl group to the rest of the molecule is through a nitrogen atom in the heteroaryl group. The term heteroaryl further embraces C-heteroaryl groups which as used herein refer to a heteroaryl group as defined above and where the point of attachment of the heteroaryl group to the rest of the molecule is through a carbon atom in the heteroaryl group. The term heteroaryl further embraces heteroarylalkyl groups which as disclosed above refer to a group of the formula —$R^c$-heteroaryl, wherein $R^c$ is an alkylene chain as defined above. The term heteroaryl further embraces heteroaralkoxy (or heteroarylalkoxy) groups which as used herein refer to a group bonded through an oxygen atom of the formula —O—$R^c$-heteroaryl, where $R^c$ is an alkylene group as defined above.

Unless stated otherwise, and to the extent not further defined for any particular group(s), any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

To the extent not disclosed otherwise for any particular group(s), representative examples of substituents may therefore include alkyl, substituted alkyl (e.g., $C_1$-$C_6$, $C_1$-$C_5$, $C_1$-$C_4$, $C_1$-$C_3$, $C_1$-$C_2$, $C_1$), alkoxy (e.g., $C_1$-$C_6$, $C_1$-$C_5$, $C_1$-$C_4$, $C_1$-$C_3$, $C_1$-$C_2$, $C_1$), substituted alkoxy (e.g., $C_1$-$C_6$, $C_1$-$C_5$, $C_1$-$C_4$, $C_1$-$C_3$, $C_1$-$C_2$, $C_1$), haloalkyl (e.g., $CF_3$), alkenyl (e.g., $C_2$-$C_6$, $C_2$-$C_5$, $C_2$-$C_4$, $C_2$-$C_3$, $C_2$), substituted alkenyl (e.g., $C_2$-$C_6$, $C_2$-$C_5$, $C_2$-$C_4$, $C_2$-$C_3$, $C_2$), alkynyl (e.g., $C_2$-$C_6$, $C_2$-$C_5$, $C_2$-$C_4$, $C_2$-$C_3$, $C_2$), substituted alkynyl (e.g., $C_2$-$C_6$, $C_2$-$C_5$, $C_2$-$C_4$, $C_2$-$C_3$, $C_2$), cyclic (e.g., $C_3$-$C_{12}$, $C_5$-$C_6$), substituted cyclic (e.g., $C_3$-$C_{12}$, $C_5$-$C_6$), carbocyclic (e.g., $C_3$-$C_{12}$, $C_5$-$C_6$), substituted carbocyclic (e.g., $C_3$-$C_{12}$, $C_5$-$C_6$), heterocyclic (e.g., $C_3$-$C_{12}$, $C_5$-$C_6$), substituted heterocyclic (e.g., $C_3$-$C_{12}$, $C_5$-$C_6$), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., $C_6$-$C_{12}$, $C_6$), substituted aryloxy (e.g., $C_6$-$C_{12}$, $C_6$), alkylthio (e.g., $C_1$-$C_6$), substituted alkylthio (e.g., $C_1$-$C_6$), arylthio (e.g., $C_6$-$C_{12}$, $C_6$), substituted arylthio (e.g., $C_6$-$C_{12}$, $C_6$), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

The term "binding" as it relates to interaction between the targeting ligand and the targeted proteins, which in this invention is histone deacetylase 6 (HDAC6), typically refers to an inter-molecular interaction that is preferential (also referred to herein as "selective") in that binding of the targeting ligand with other proteins present in the cell, including other HDAC isoforms, is substantially less and functionally insignificant, at least from the standpoint of degradation. The terms "selective" and "selectivity" refer to the ability of the bifunctional compound to discriminate between molecular targets for degradation in a cell. A selective HDAC6 degrader described herein may have a $DC_{50}$ (half maximal degradation concentration for HDAC6 activity that is at least about 1, 2, 3, 4, 5, 6, 7, 8, 9, or 10-fold lower than the $DC_{50}$ for one or more of HDAC1, HDAC2, HDAC3, HDAC4, HDAC5, HDAC7, HDAC8, HDAC9, and/or HDAC10. Therefore, even though various bifunctional compounds of the present invention bind to other HDAC proteins, albeit with similar or much less affinity, they show selective degradation of HDAC6.

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, the bispecific compounds have a structure represented by formula (I):

(I)

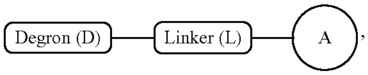

wherein

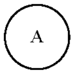

is a moiety represented by formula TL1 or TL2:

(TL1)

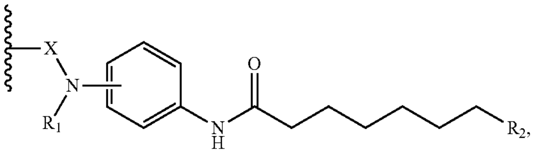

or (TL2)

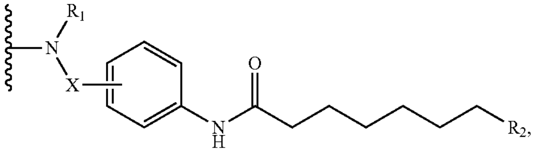

wherein

X is $CH_2$ or C═O;

$R_1$ is H or Me; and $R_2$ is

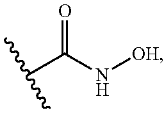

-continued

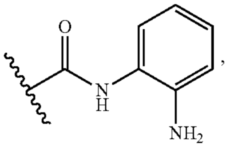

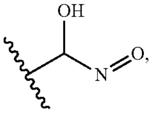

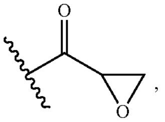

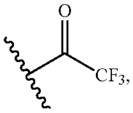

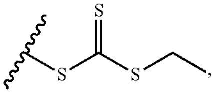

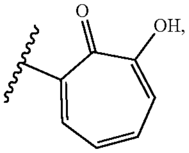

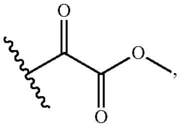

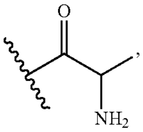

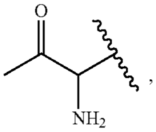

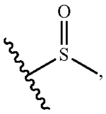

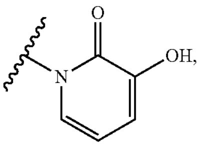

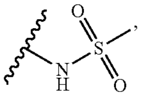

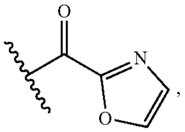

-continued
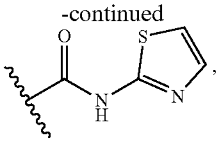
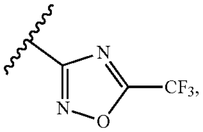
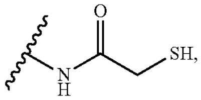
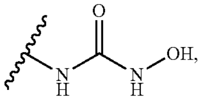
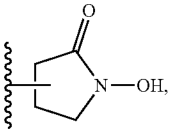
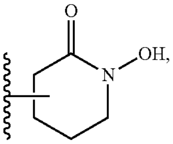
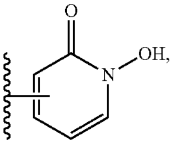
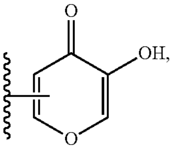
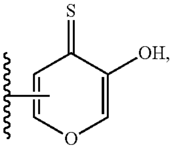
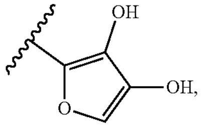
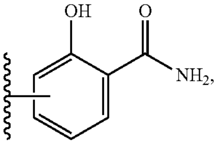
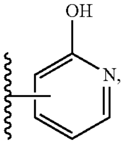
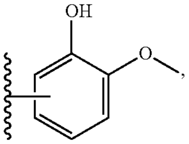
-continued
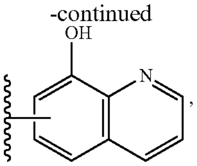
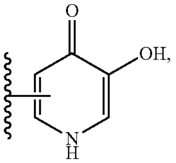
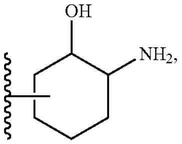
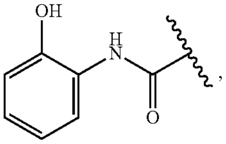
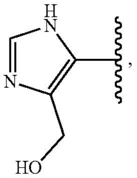
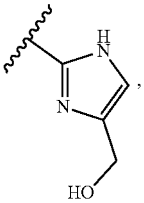
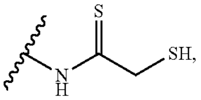
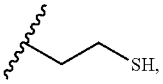
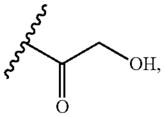
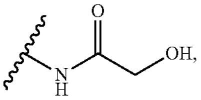
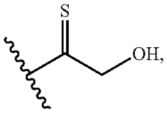
or
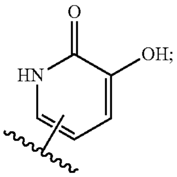
or a pharmaceutically acceptable salt or stereoisomer thereof.

Therefore, in some embodiments, the bispecific compounds of the present invention have a structure represented by formula (I-1):

(I-1)

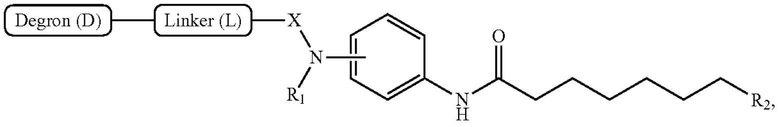

or a pharmaceutically acceptable salt or stereoisomer thereof.

Therefore, in some embodiments, the bispecific compounds of the present invention have a structure represented by formula (I-2):

(I-2)

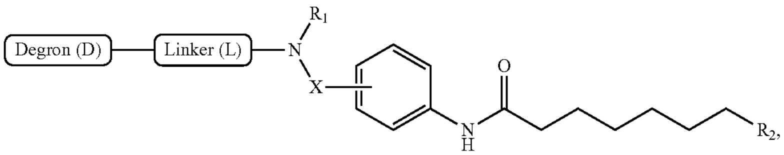

or a pharmaceutically acceptable salt or stereoisomer thereof.

In some embodiments, $R_2$ is

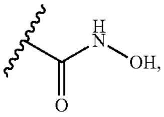

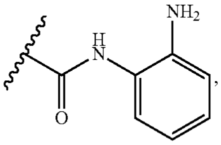

, or

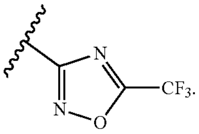

In some embodiments,

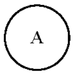

is represented by any one of the following structures:

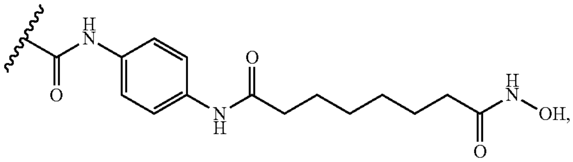

-continued

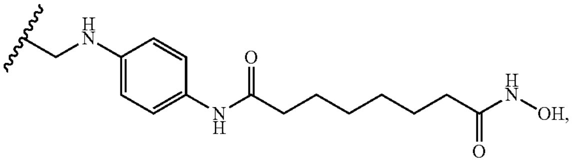

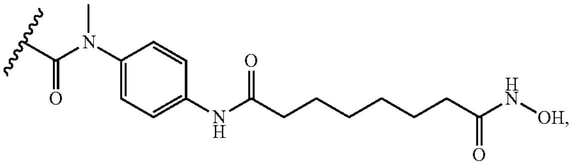

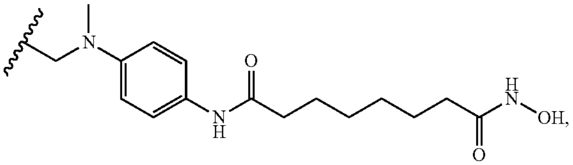

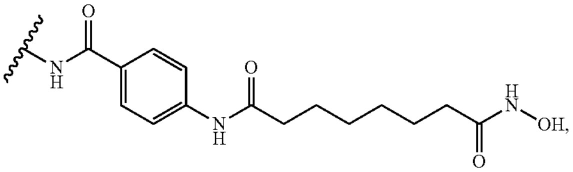

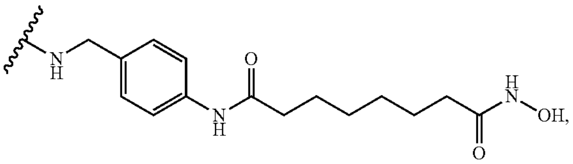

-continued

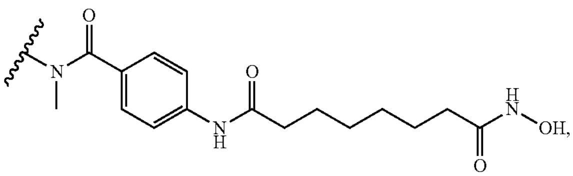,

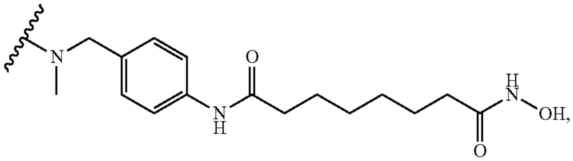,

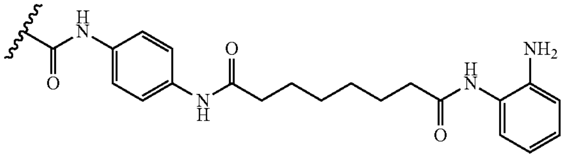,

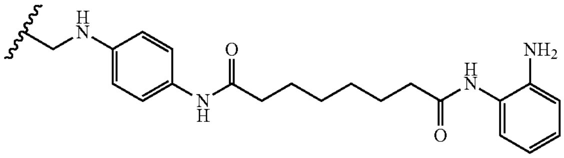,

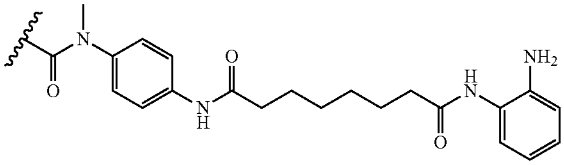,

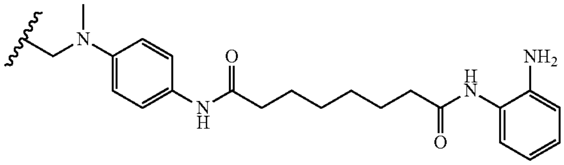,

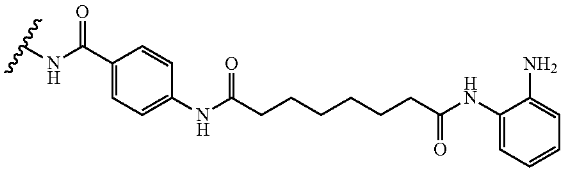,

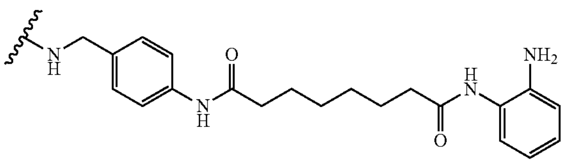,

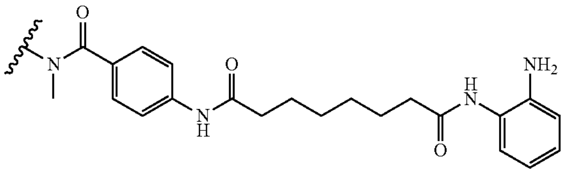,

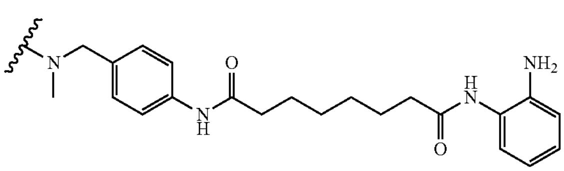,

-continued

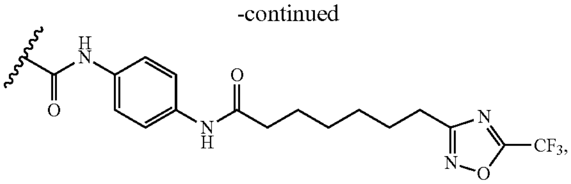,

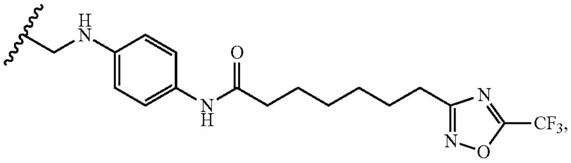,

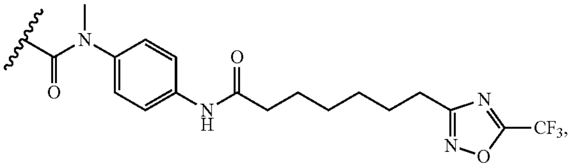,

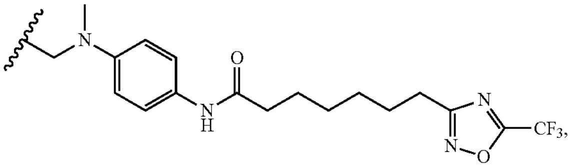,

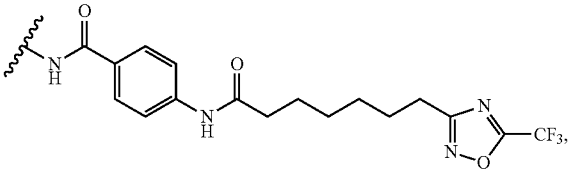,

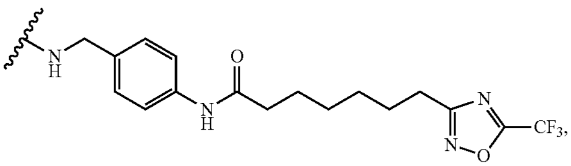,

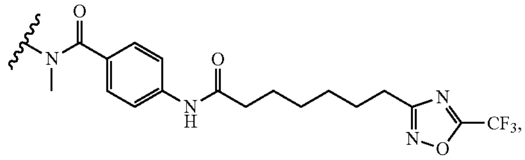 and

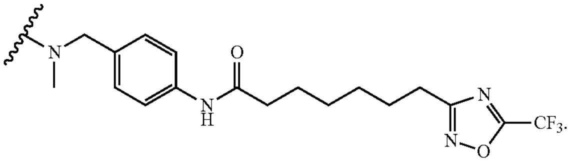.

Linkers

The linker ("L") provides a covalent attachment the targeting ligand and the degron. In some embodiments, the linker includes an alkylene chain (e.g., having 2-20 or 2-18 alkylene units). In other embodiments, the linker may include an alkylene chain or a bivalent alkylene chain, either of which may be interrupted by, and/or terminate (at either or both termini) at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, $—S(O)_2—$, —OS(O)—, —S(O)O—, —S(O)—, $—OS(O)_2—$, $—S(O)_2O—$, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of alkylene linkers that may be suitable for use in the present invention include the following:

(L1)

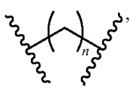

wherein n is an integer of 1-12 ("of" meaning inclusive), e.g., 1-12, 1-11, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10, examples of which include:

(L1-a)

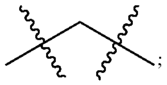

(L1-b)

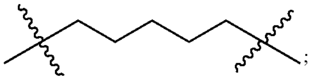

(L1-c)

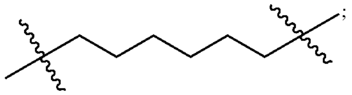

(L1-d)

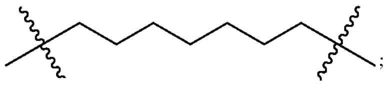

and (L1-e)

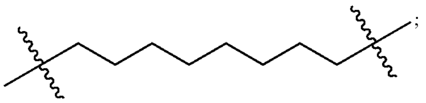

alkylene chains terminating in various functional groups (as described above), examples of which are as follows:

(L2-a)

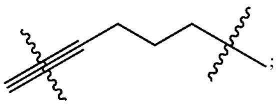

-continued (L2-b)

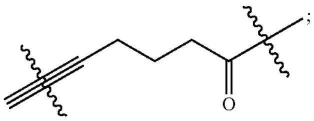

(L2-c)

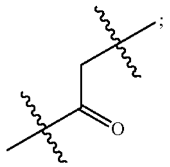

(L2-d)

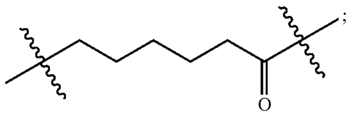

(L2-e)

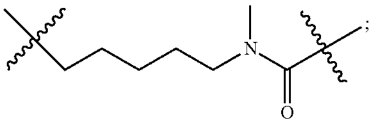

(L2-f)

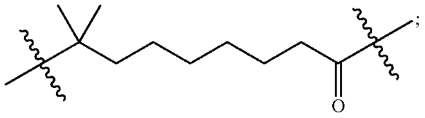

and (L2-g)

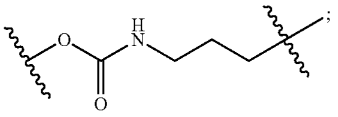

alkylene chains interrupted with various functional groups (as described above), examples of which are as follows:

(L3-a)

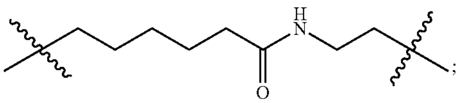

(L3-b)

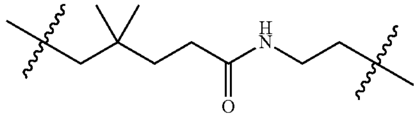

(L3-c)

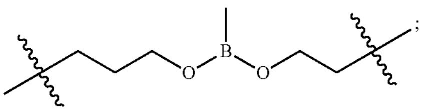

and (L3-d)

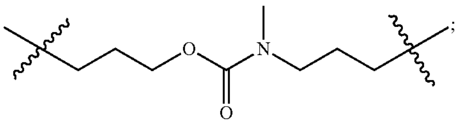

alkylene chains interrupted or terminating with heterocyclene groups, e.g., (L4)

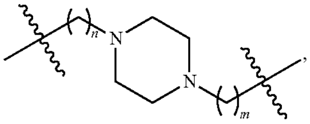

, wherein m and n are independently integers of 0-10, examples of which include:

(L4-a)

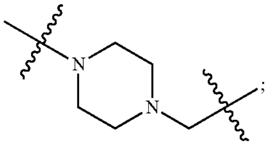

;

(L4-b)

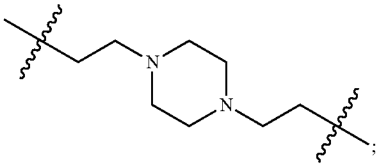

;

(L4-c)

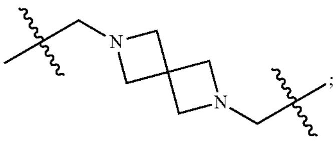

;

(L4-d)

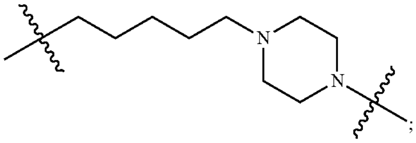

; and (L4-e)

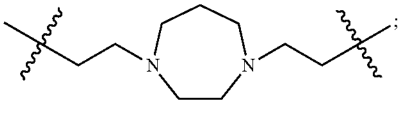

;

alkylene chains interrupted by amide, heterocyclene and/or aryl groups, examples of which include:

(L5-a)

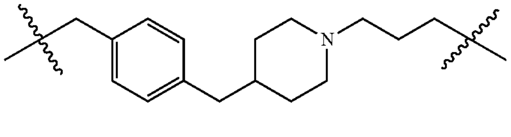

; and (L5-b)

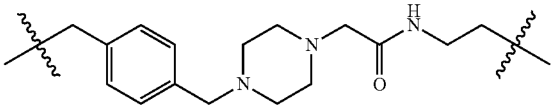

;

alkylene chains interrupted by heterocyclene and aryl groups, and a heteroatom, examples of which include:

(L6-a)

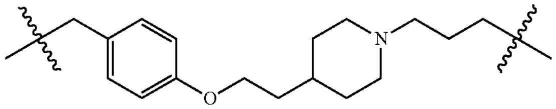

;

(L6-b)

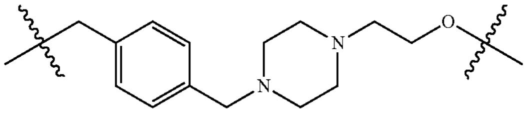

; and (L6-c)

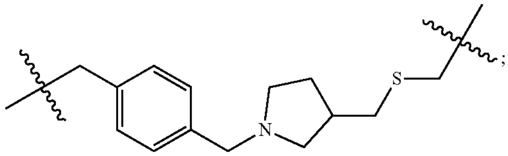

;

and alkylene chains interrupted by a heteroatom such as N, O or B, e.g., (L7)

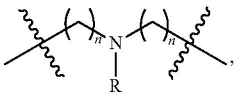

, wherein each n is independently an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H or C1 to C4 alkyl, an example of which is (L7-a)

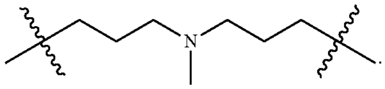

.

In some embodiments, the linker may include a polyethylene glycol chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_{20}$—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

In some embodiments, the linker includes a polyethylene glycol chain having 2-8 PEG units and terminating in

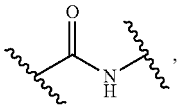,
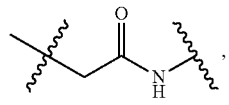, or
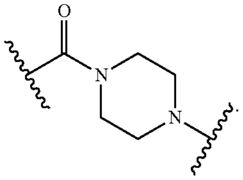.

In some embodiments, the linker includes a polyethylene glycol chain having 2-6 PEG units.

Examples of linkers that include a polyethylene glycol chain include:

(L8)

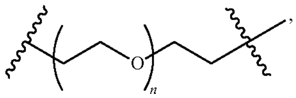, wherein n is an integer of 2-10, examples of which include:

(L8-a)

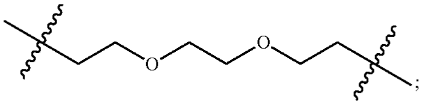;

(L8-b)

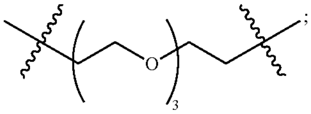;

(L8-c)

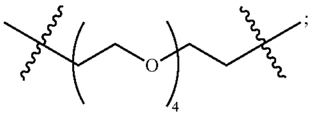; and (L8-d)

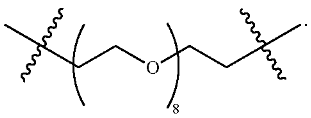.

In some embodiments, the polyethylene glycol-based linker may terminate in a functional group, examples of which are as follows:

(L9-a)

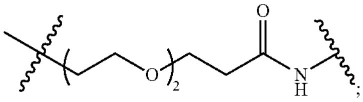;

-continued (L9-b)

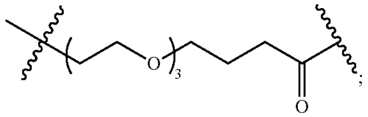;

(L9-c)

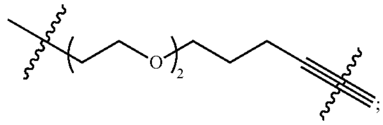;

(L9-d)

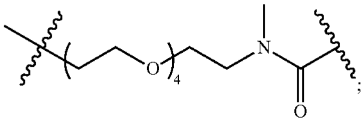; and (L9-e)

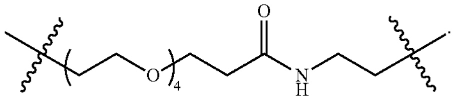.

In some embodiments, the linker is represented by any one of the following structures:

(L10-a)

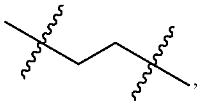, (L10-b)

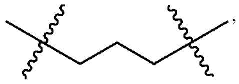, (L10-c)

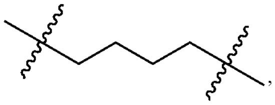, (L10-d)

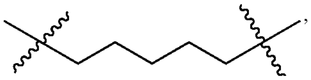, (L10-e)

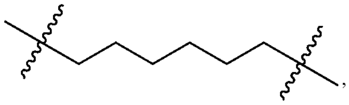, (L10-f)

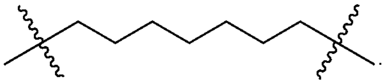.

(L10-g)

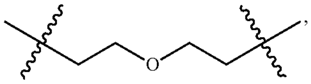, and (L10-h)

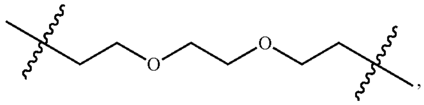,

Therefore, in some embodiments, bispecific compounds of the present invention may be represented by any one of the following structures:

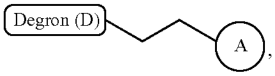,

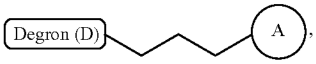,

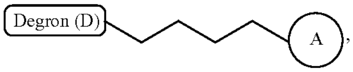,

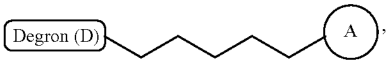,

-continued

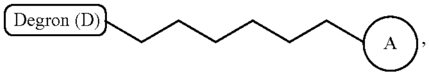,

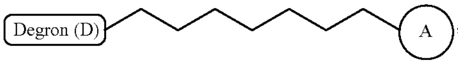,

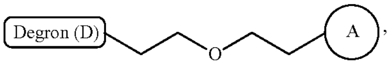, and

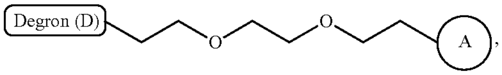, or a pharmaceutically acceptable salt or stereoisomer thereof.

In some embodiments, bispecific compounds of the present invention are represented by any of the following structures (with the degron shown generically):

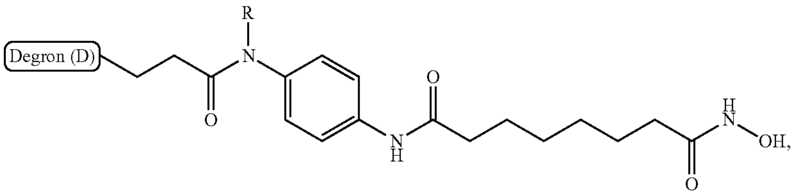,

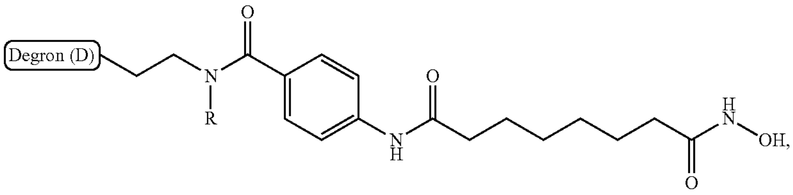,

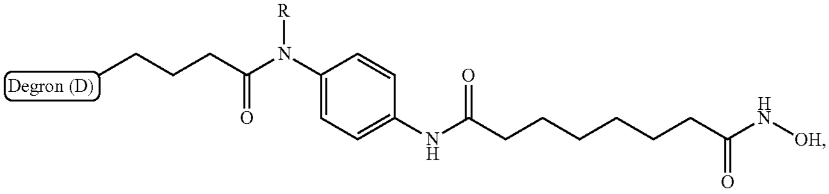,

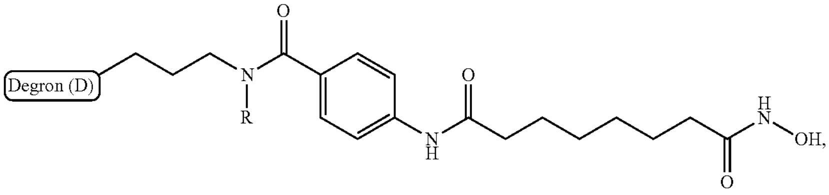,

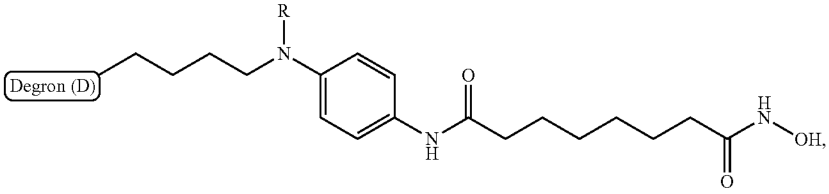,

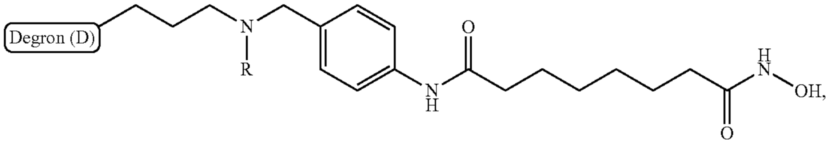,

-continued
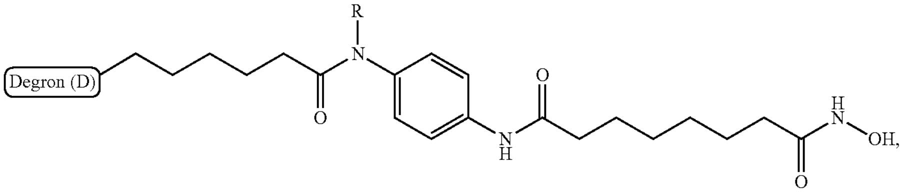
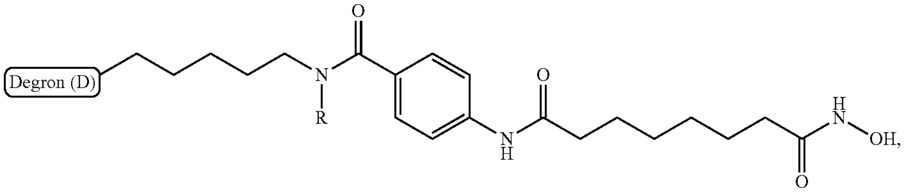
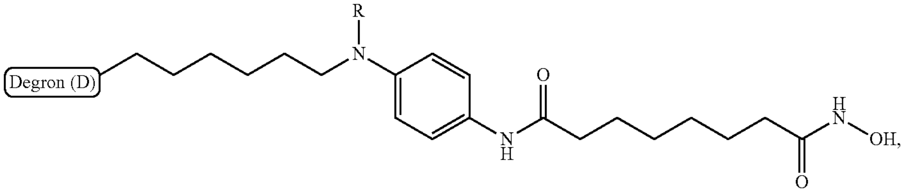
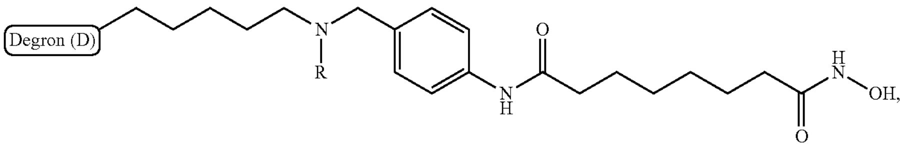
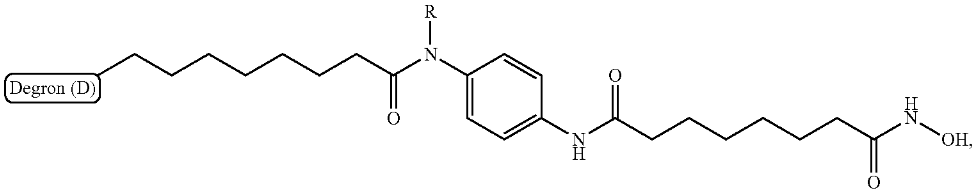
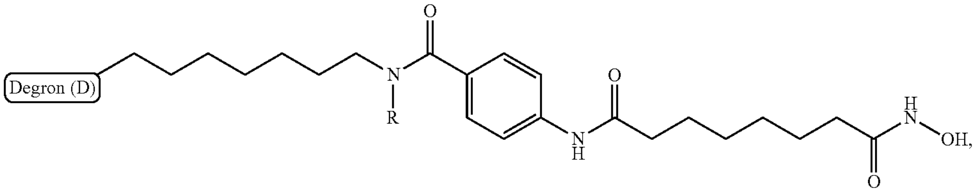
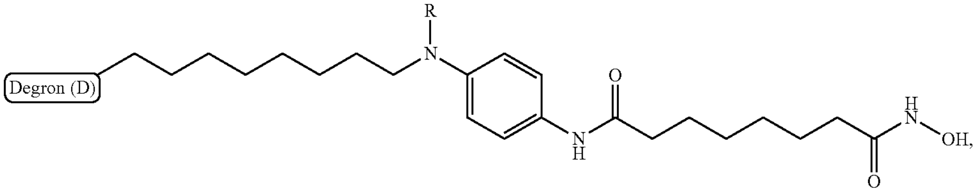
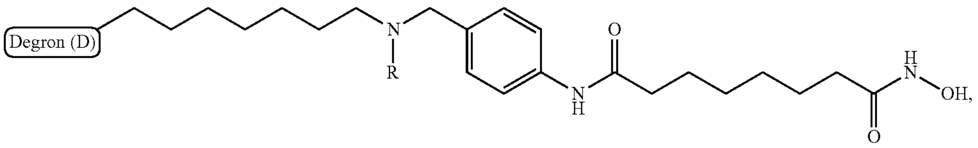
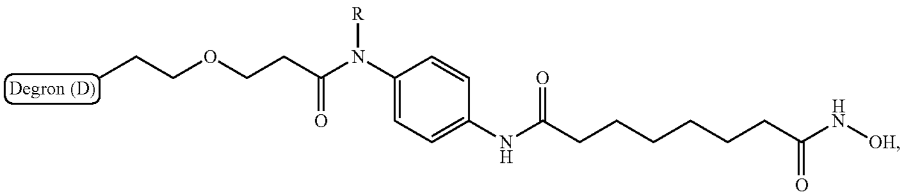

-continued
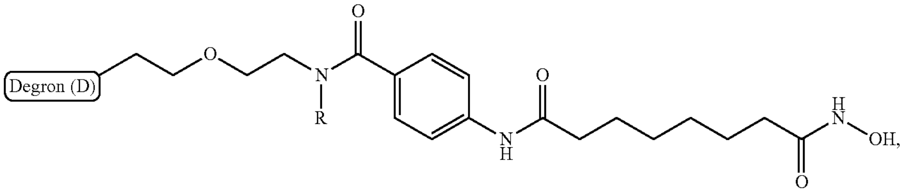
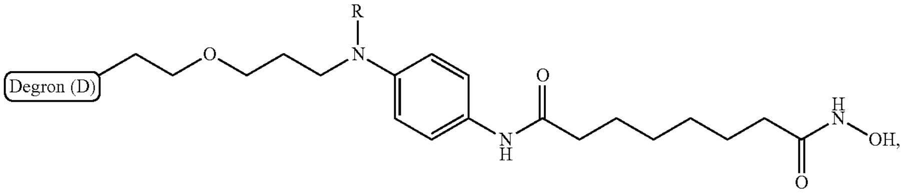
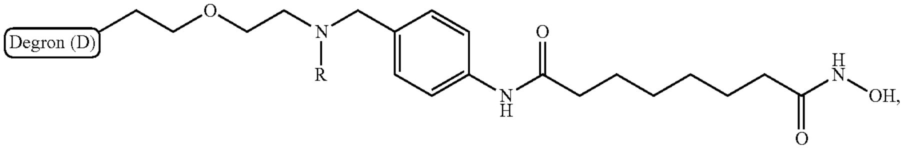
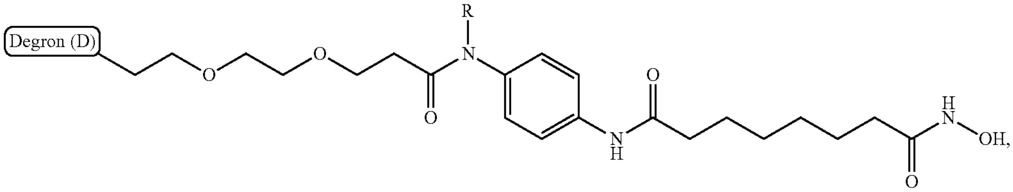
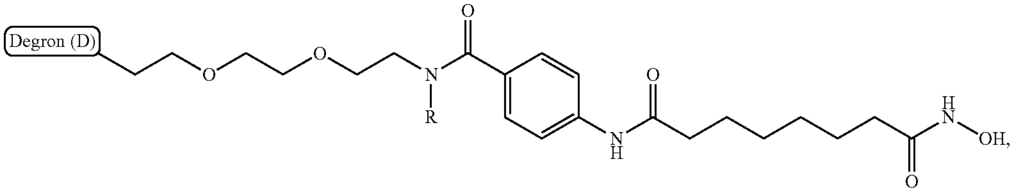
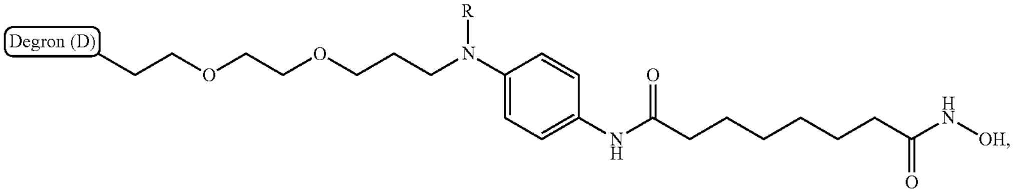
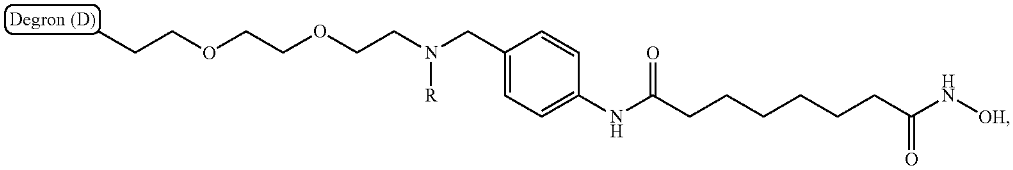
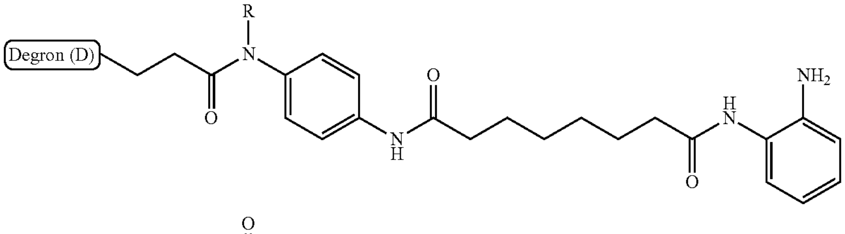
,
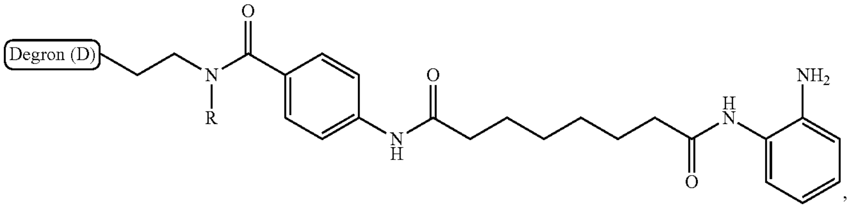
, -continued
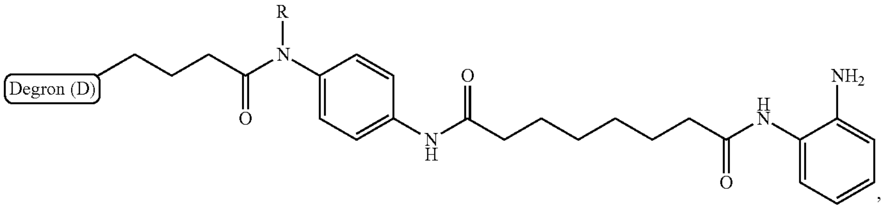
,
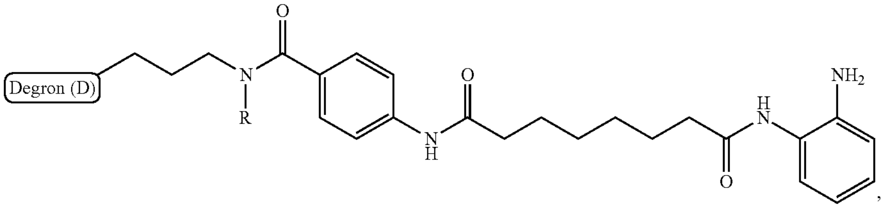
,
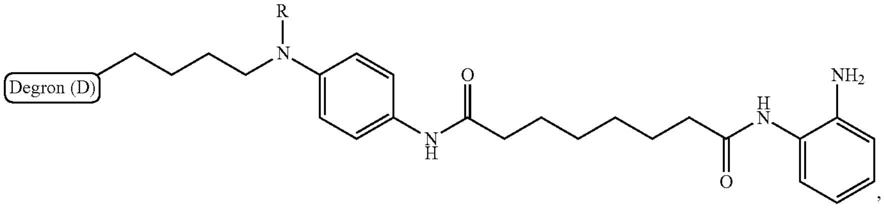
,
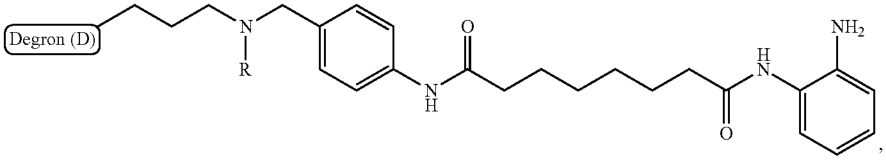
,
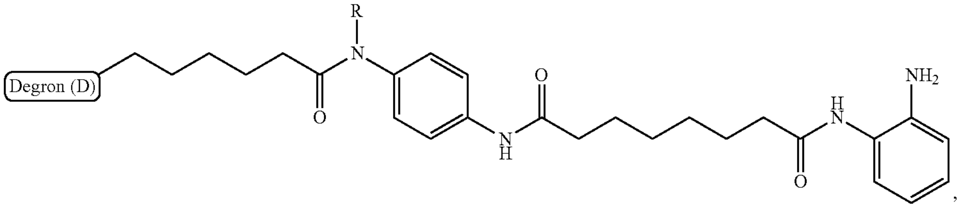
,
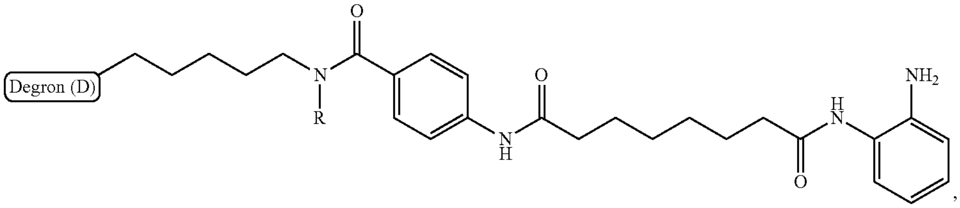
,
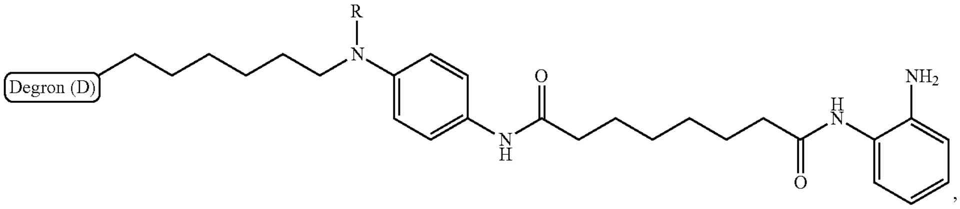
,
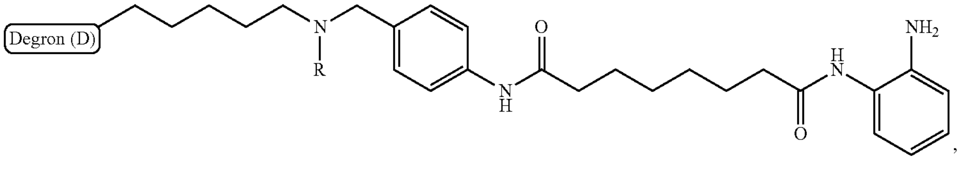
, -continued
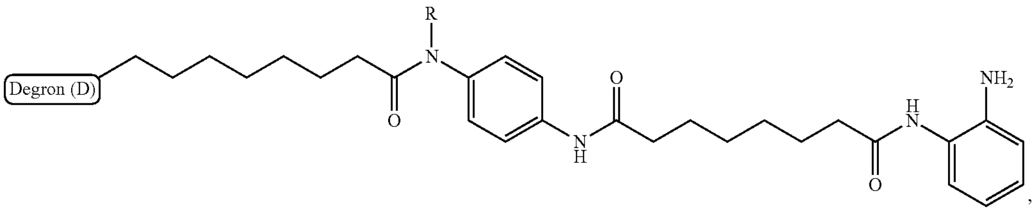
,
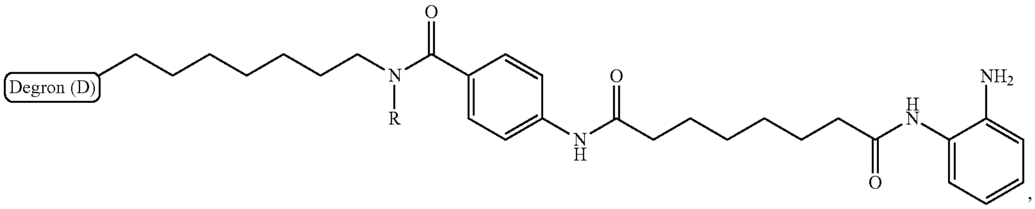
,
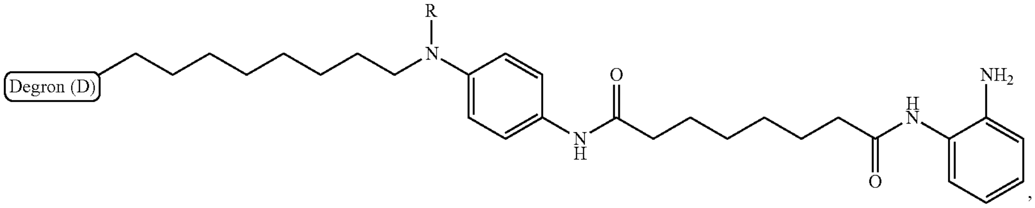
,
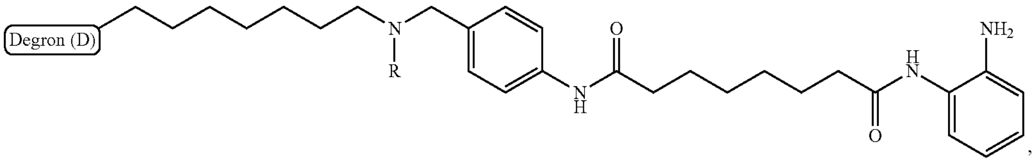
,
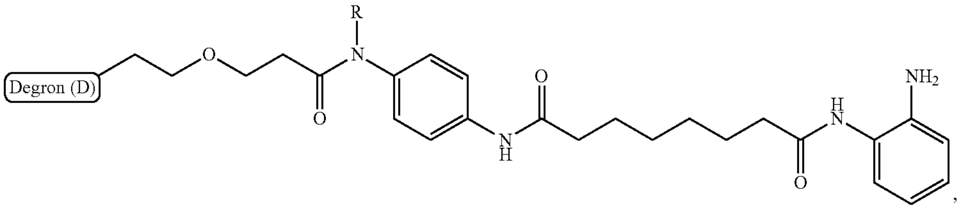
,
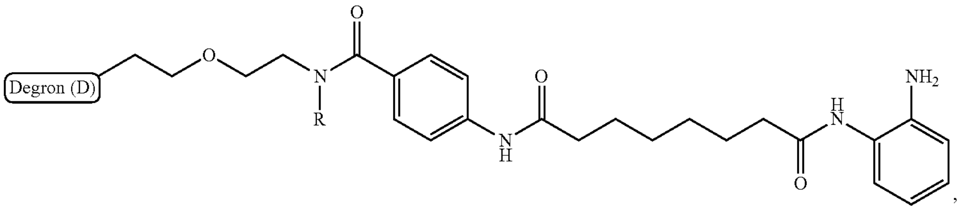
,
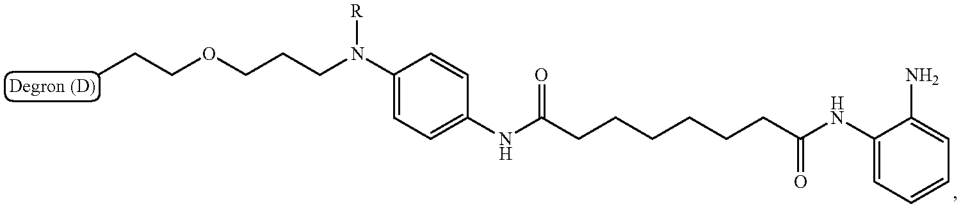
,
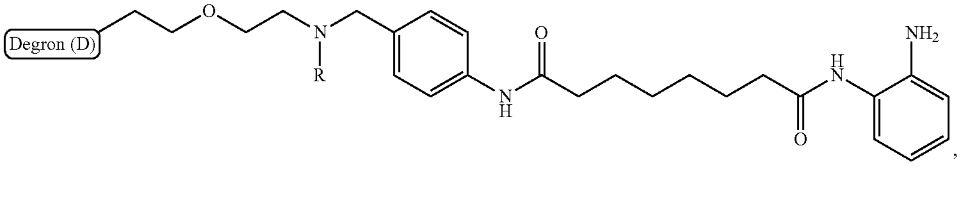
, -continued
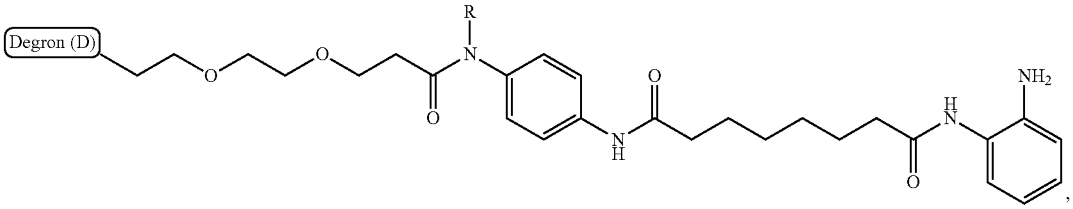
,
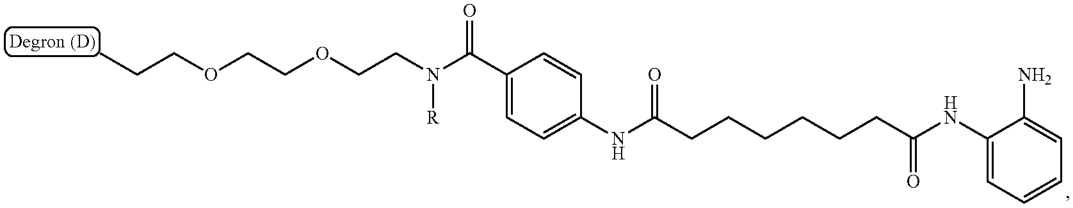
,
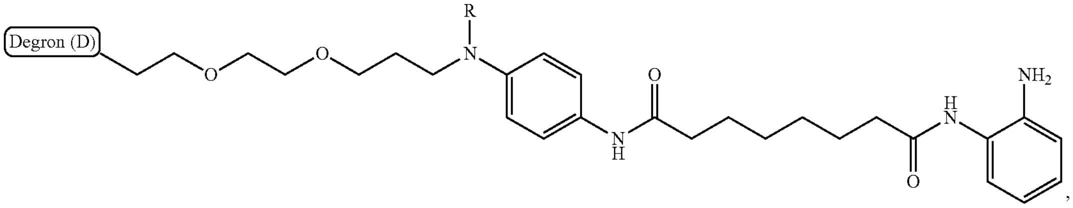
,
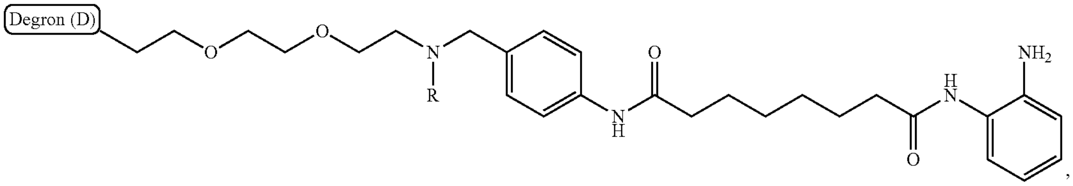
,
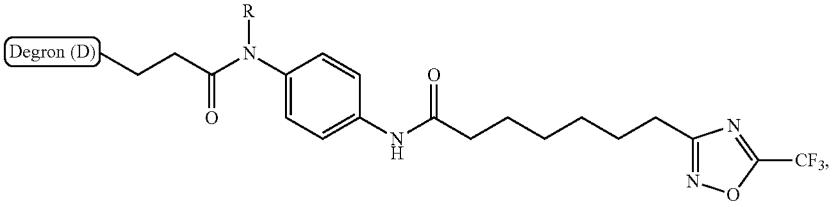
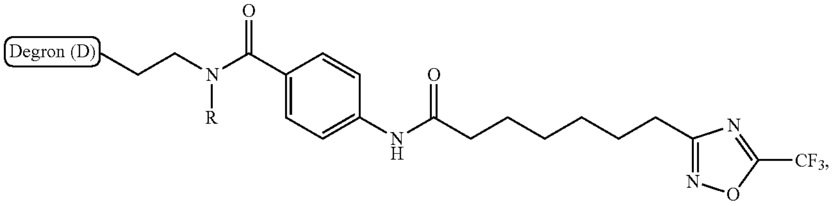
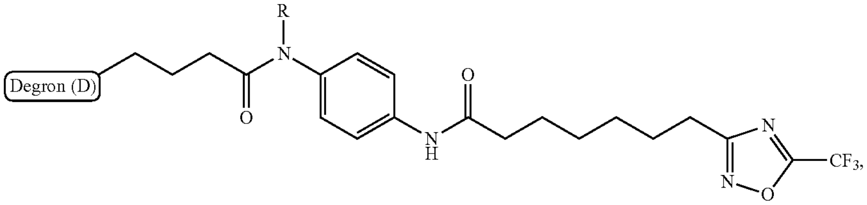
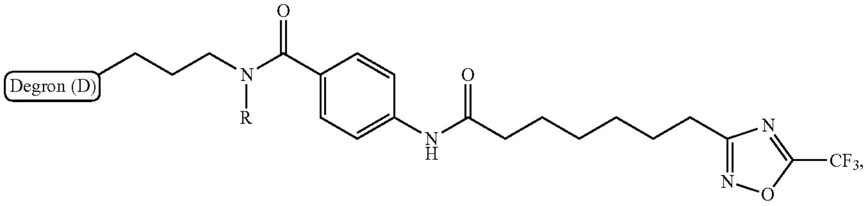

-continued
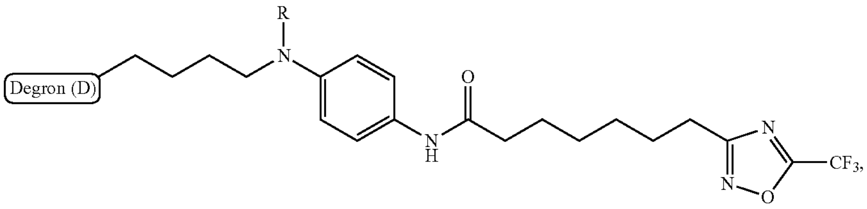
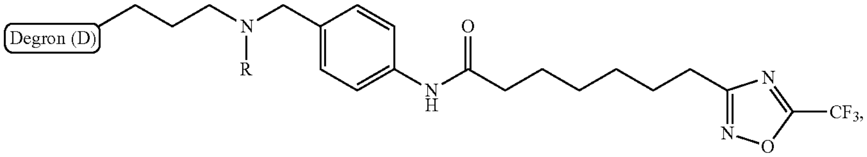
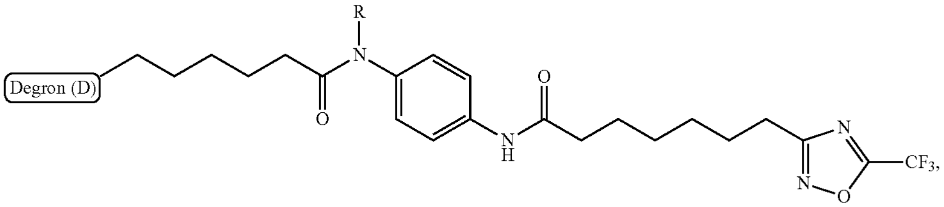
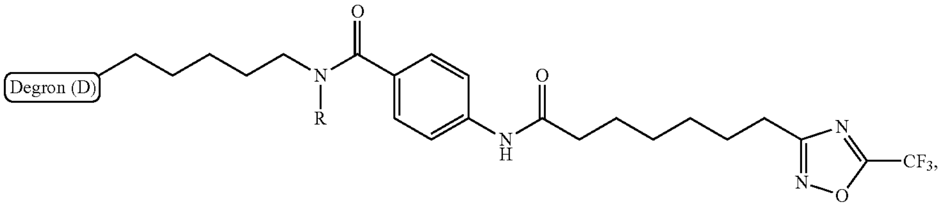
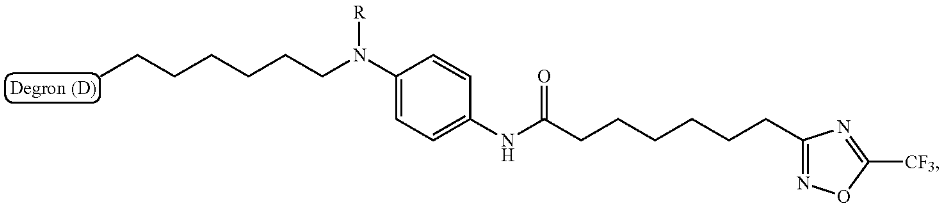
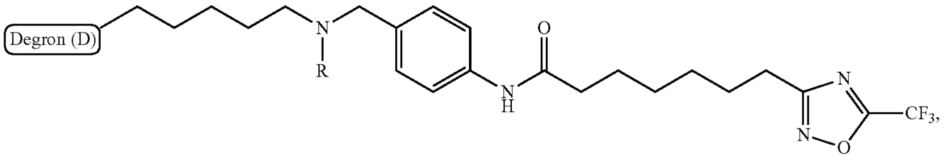
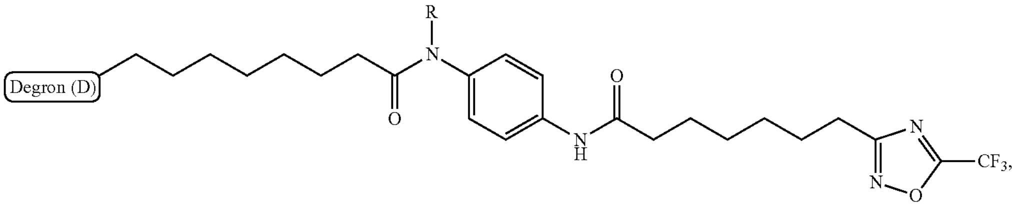
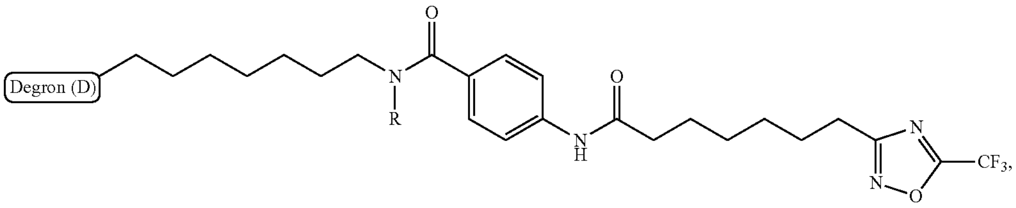

-continued
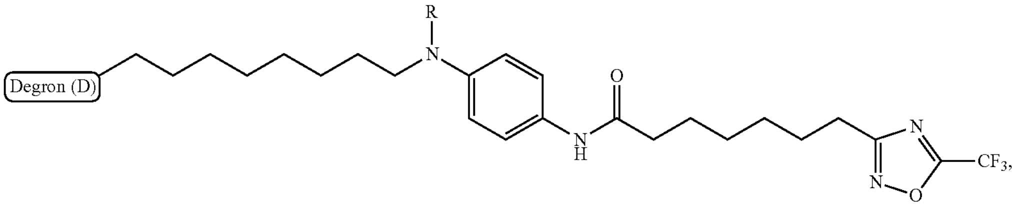
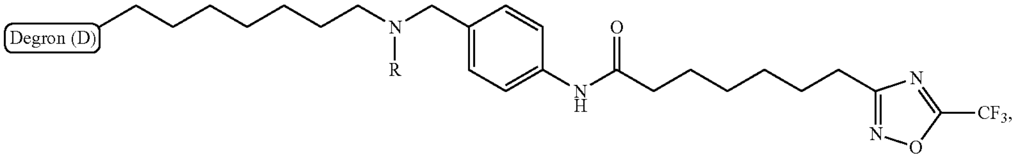
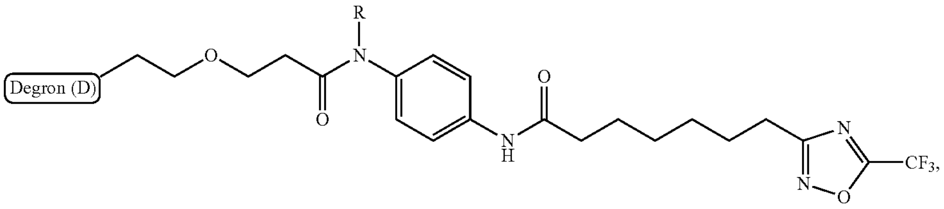
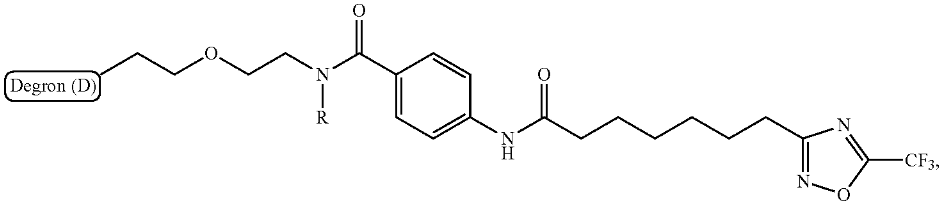
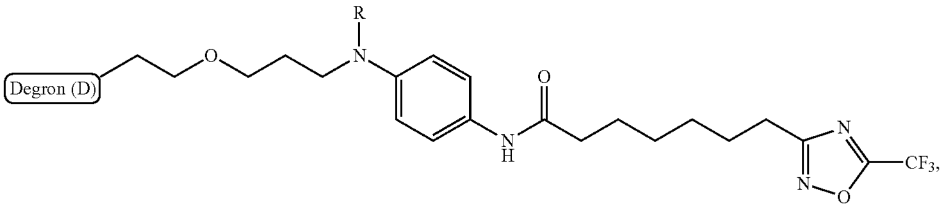
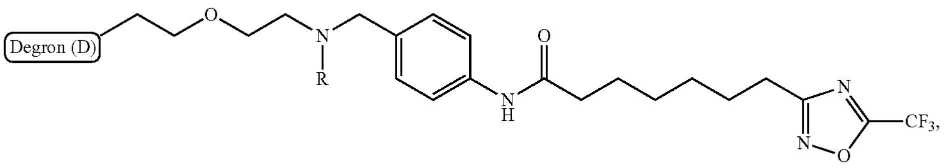
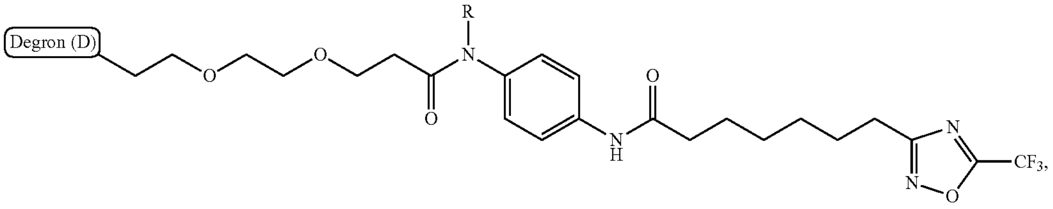
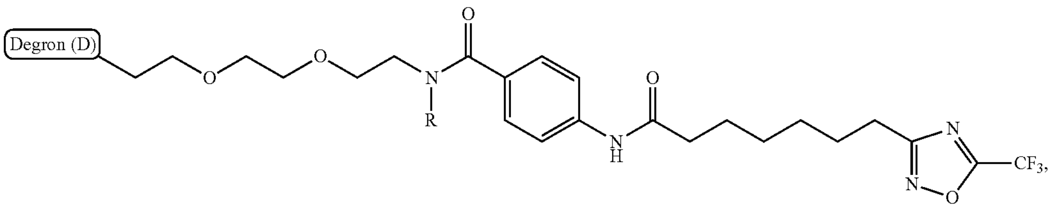

-continued

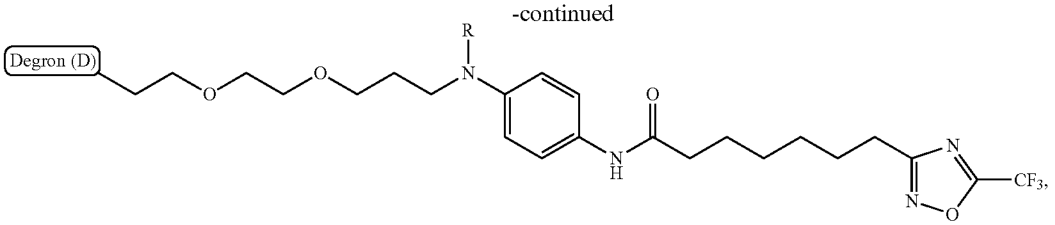

and

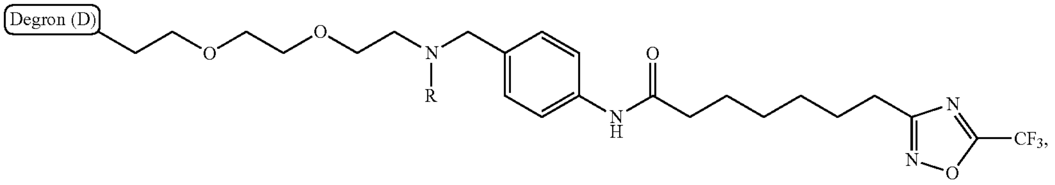

wherein R is H or Me, or a pharmaceutically acceptable salt or stereoisomer thereof.

Degrons

The Ubiquitin-Proteasome Pathway (UPP) is a critical cellular pathway that regulates key regulator proteins and degrades misfolded or abnormal proteins. UPP is central to multiple cellular processes. The covalent attachment of ubiquitin to specific protein substrates is achieved through the action of E3 ubiquitin ligases. These ligases include over 500 different proteins and are categorized into multiple classes defined by the structural element of their E3 functional activity.

In some embodiments, the degron binds the E3 ubiquitin ligase which is cereblon.

In some embodiments, the degron binds the E3 ubiquitin ligase which is cereblon. Representative examples of such degrons have structures represented by any one of the formulas (D1-D12):

(D1)

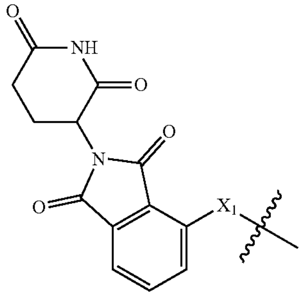

, (D2)

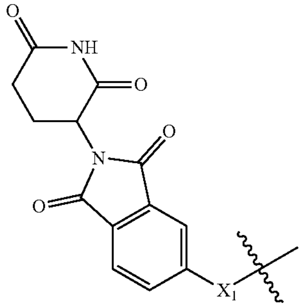

,

-continued (D3)

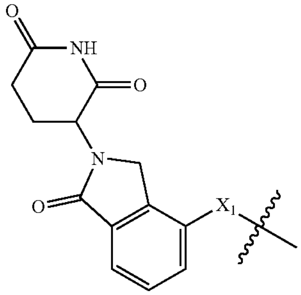

, (D4)

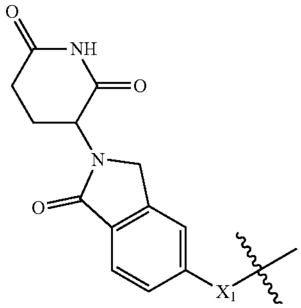

, (D5)

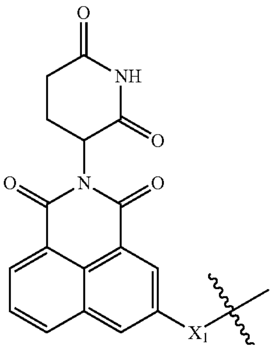

,

-continued
(D6)
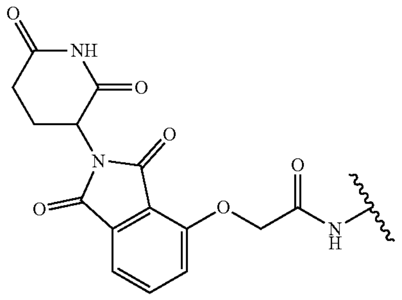
,
(D7)
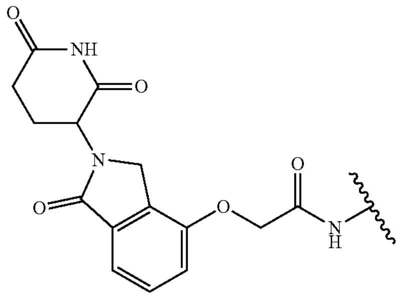
,
(D8)
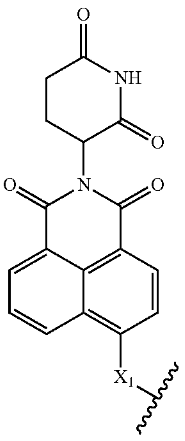
,
(D9)
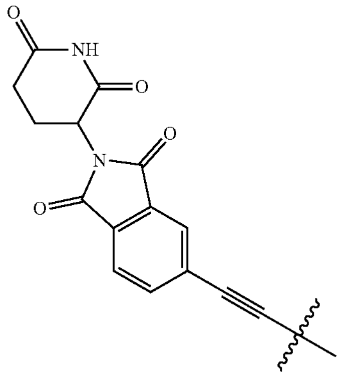
,
-continued
(D10)
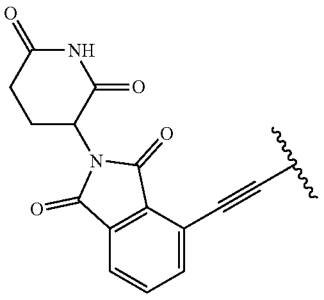
,
(D11)
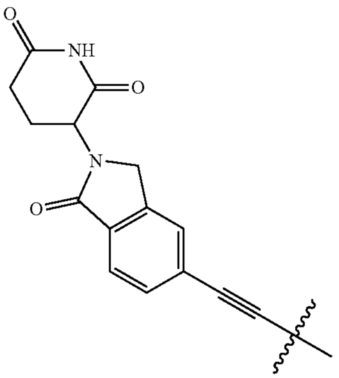
, and
(D12)
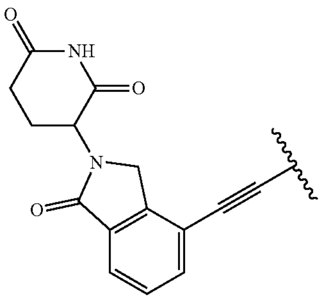
,
wherein $X_1$ is $CH_2$, NH, or O.
Yet other degrons that bind cereblon and which may be suitable for use in the present invention are disclosed in U.S. Pat. No. 9,770,512, and U.S. Patent Application Publication Nos. 2018/0015087, 2018/0009779, 2016/0243247, 2016/0235731, 2016/0235730, and 2016/0176916, and International Patent Publications WO 2017/197055, WO 2017/197051, WO 2017/197036, WO 2017/197056 and WO 2017/197046.

Therefore, in some embodiments, bispecific compounds of the present invention are represented by any of the following structures:
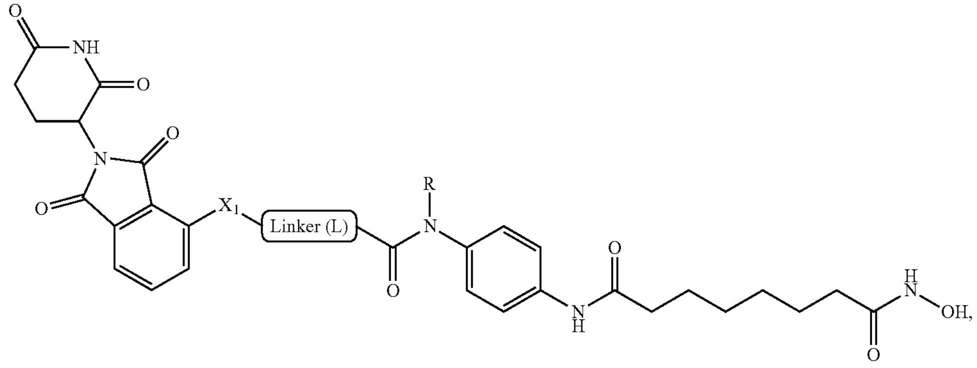
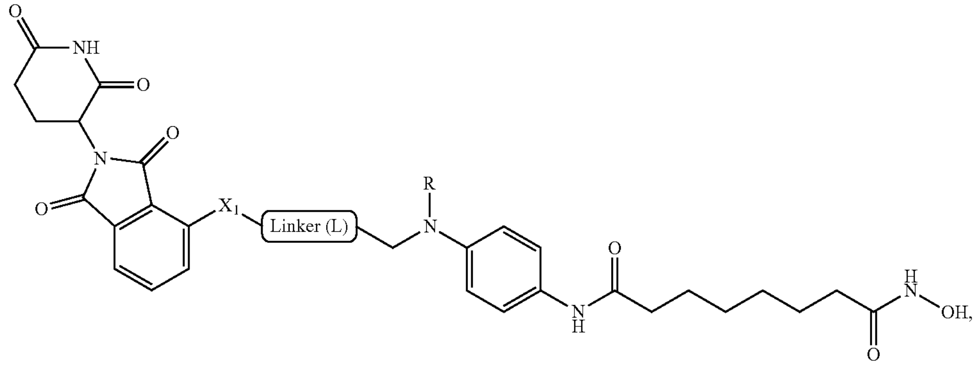
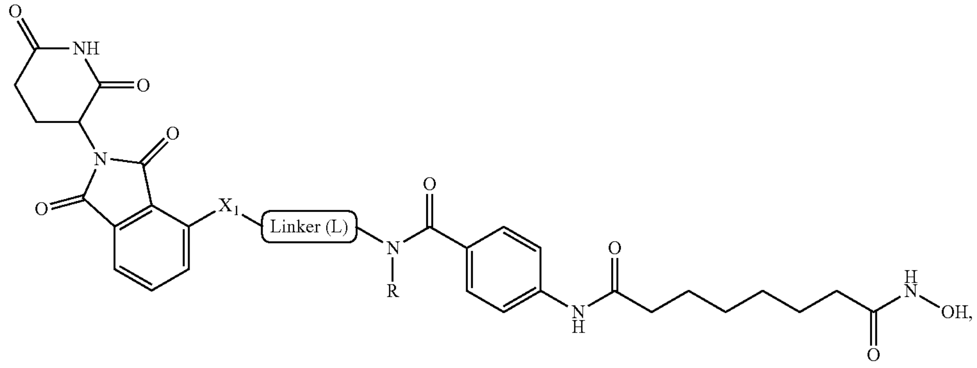
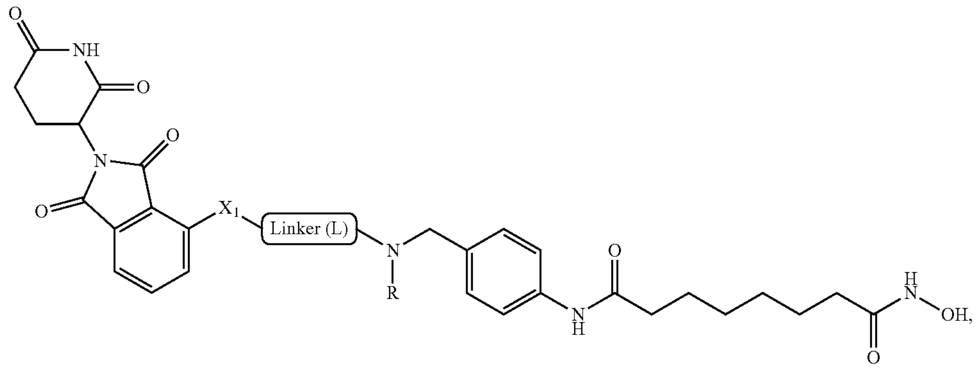

-continued
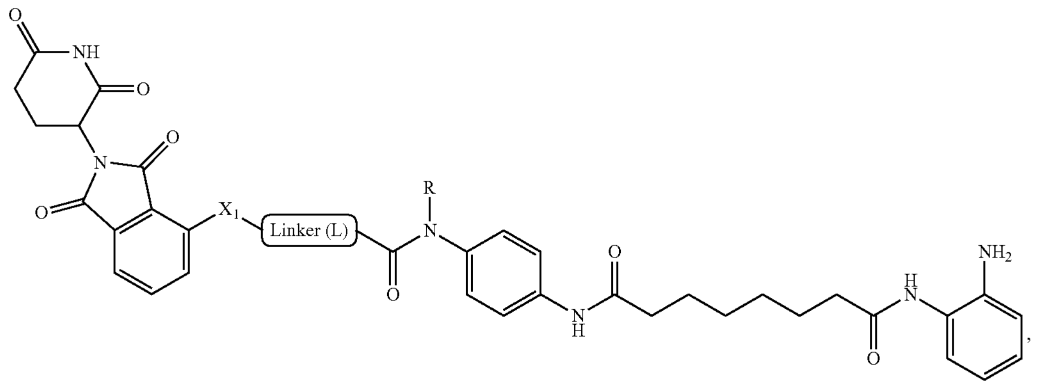
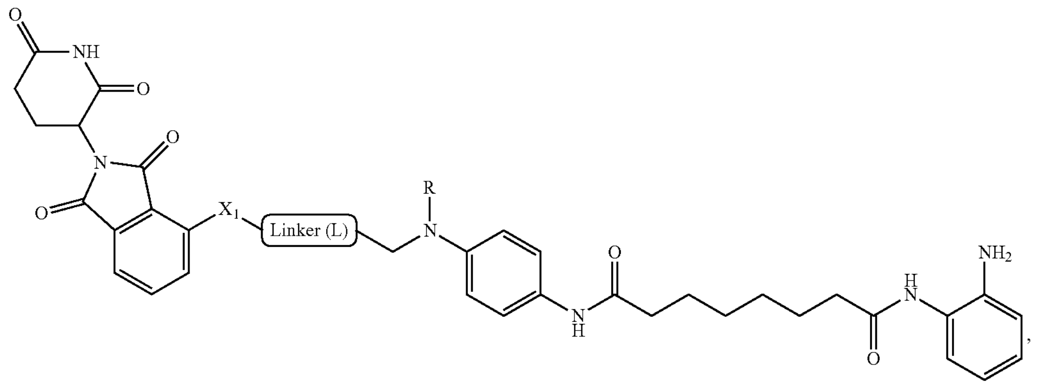
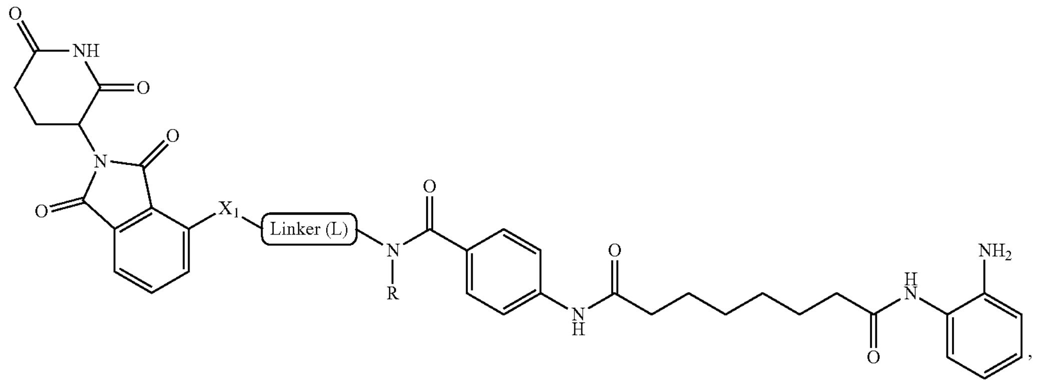
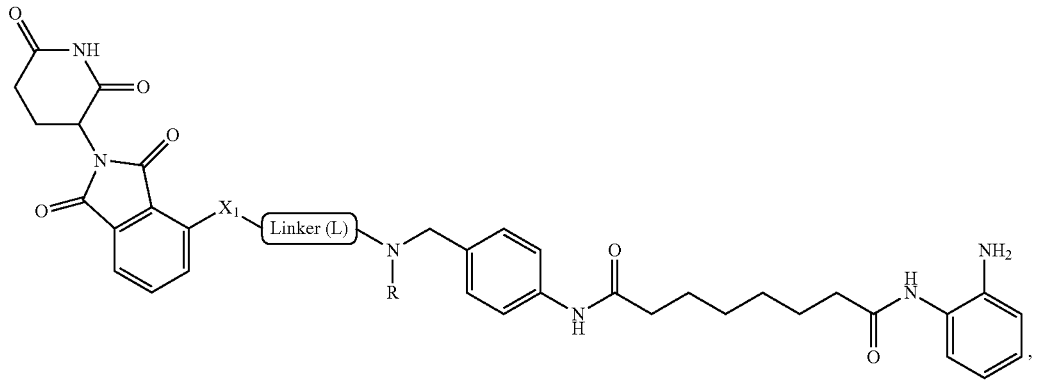

-continued
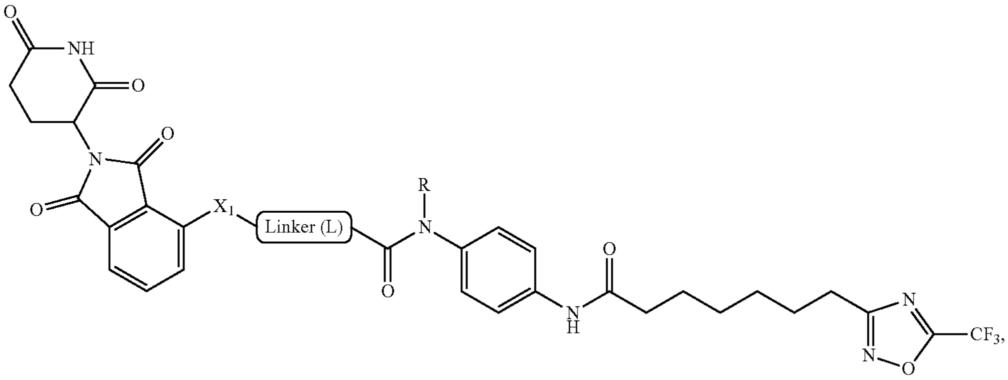
,
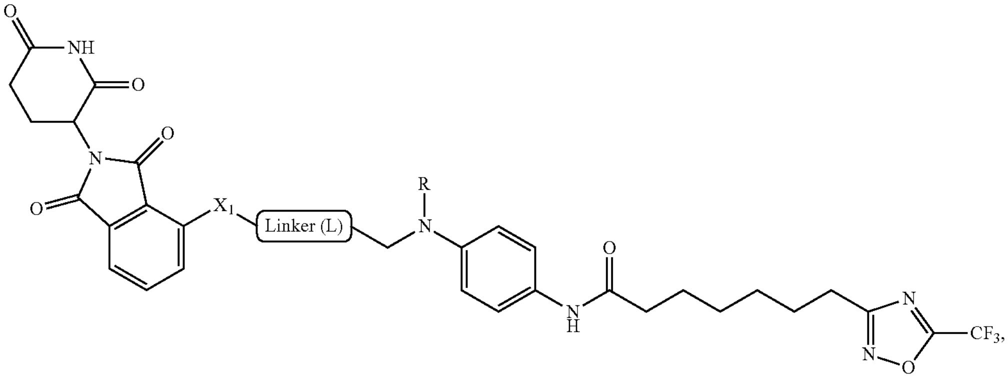
,
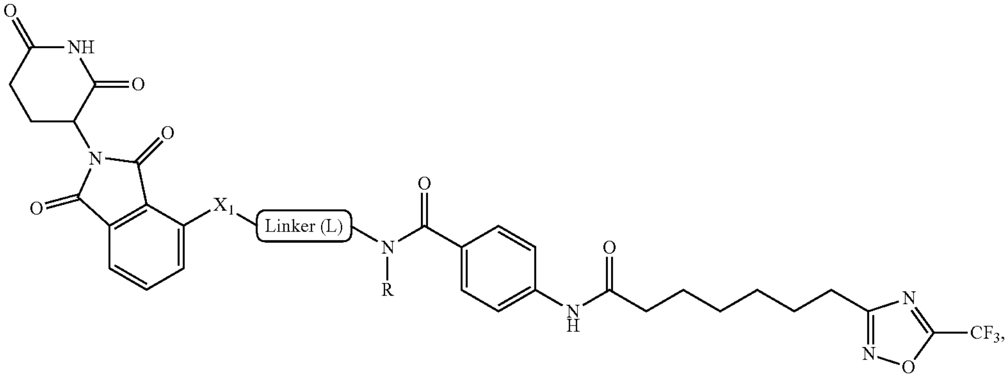
,
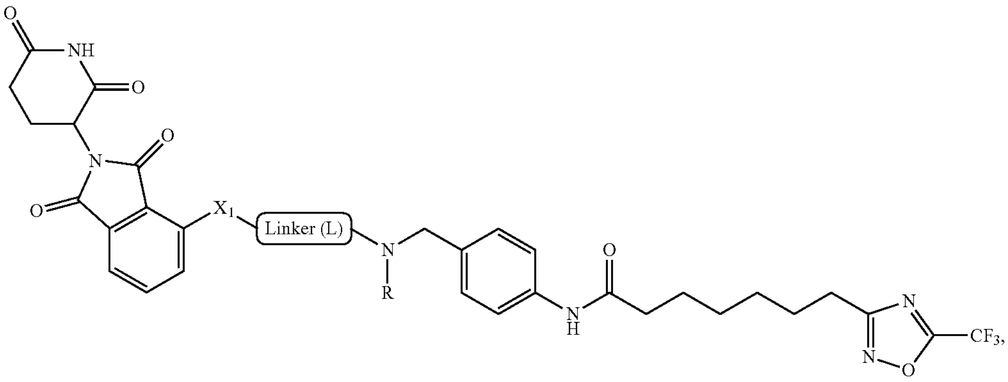
,

-continued
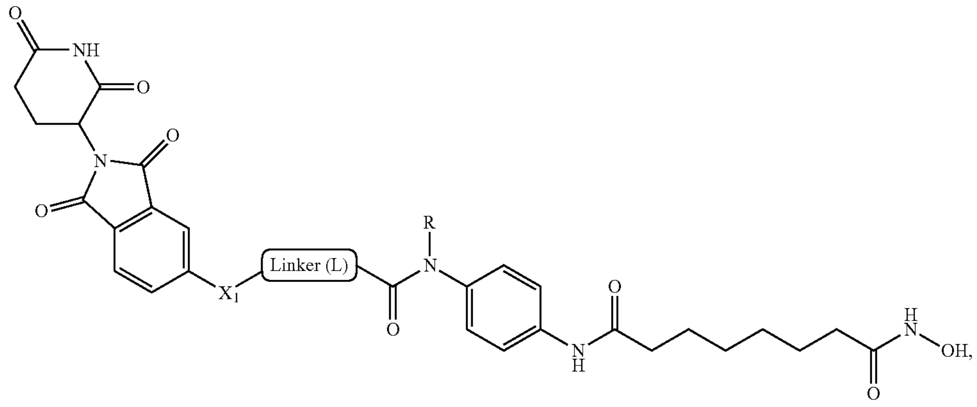
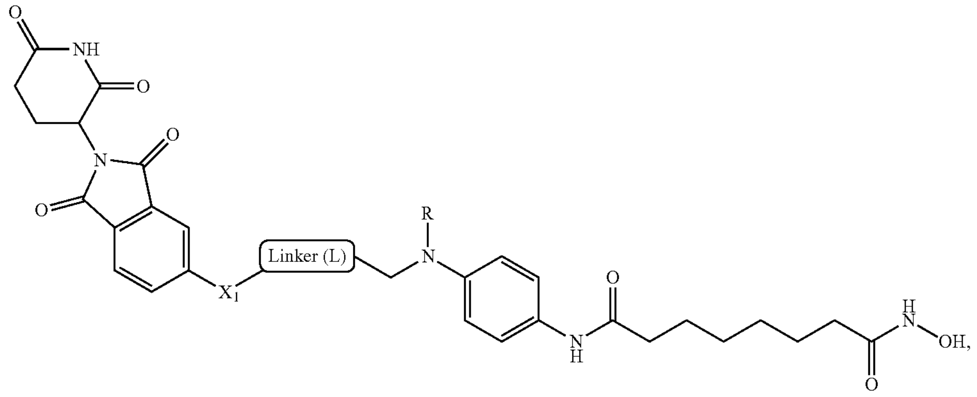
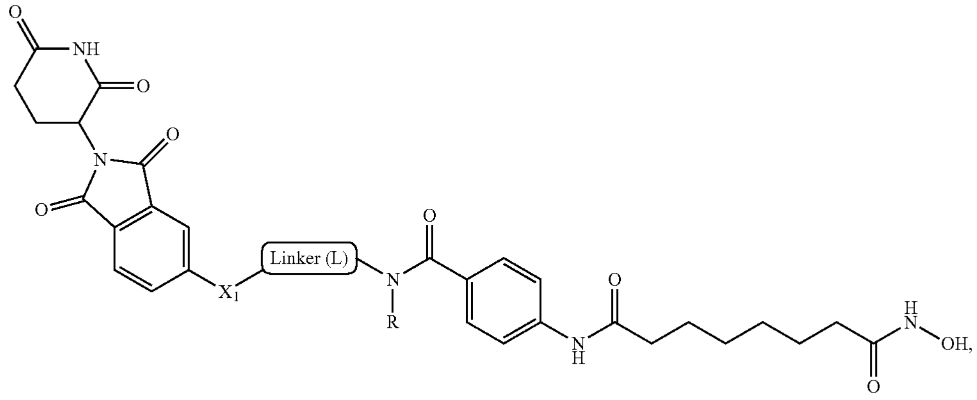
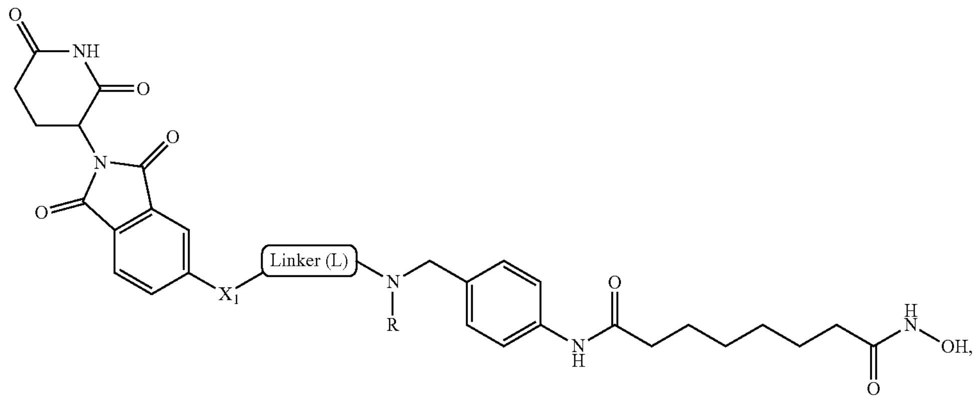

-continued
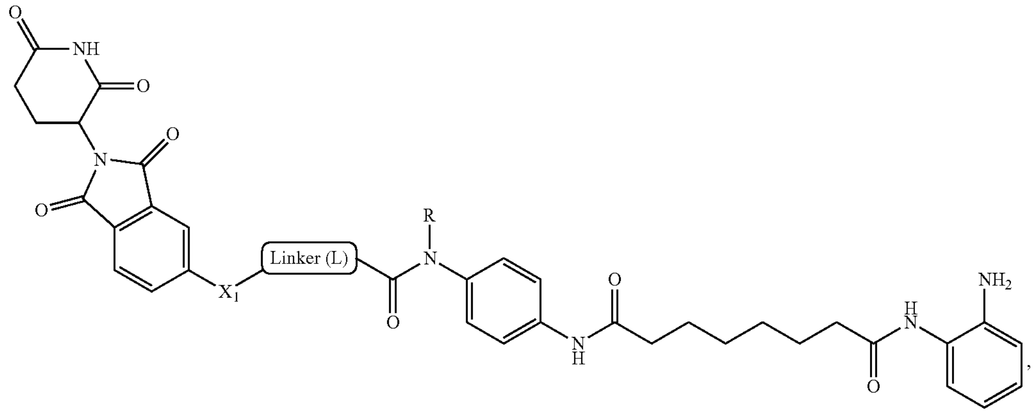
,
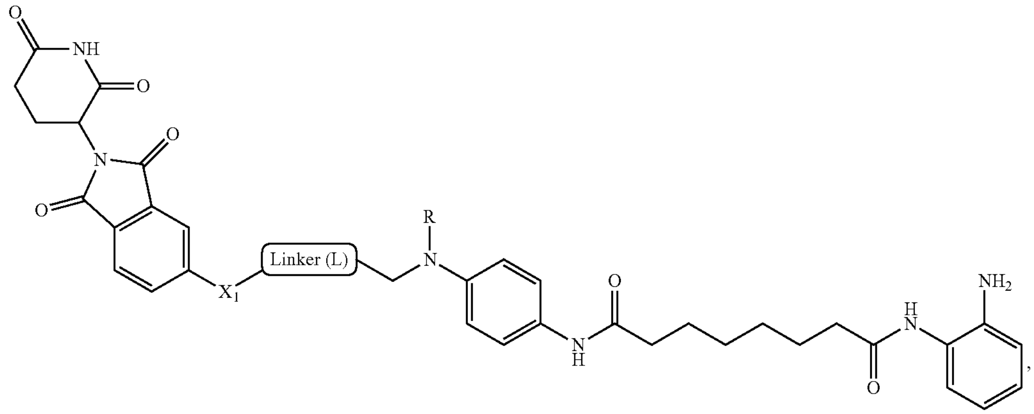
,
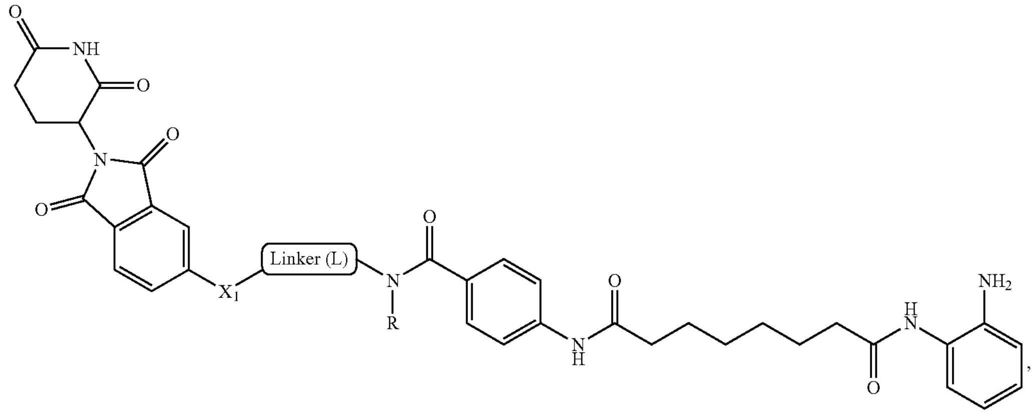
,
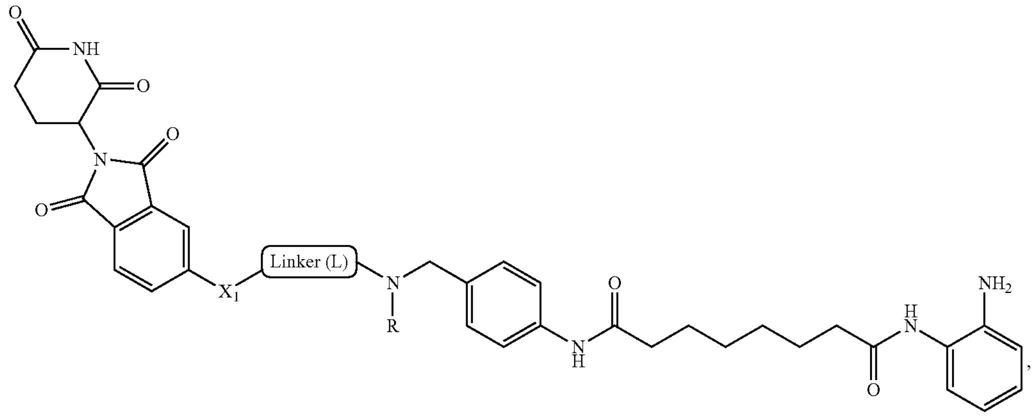
,

-continued
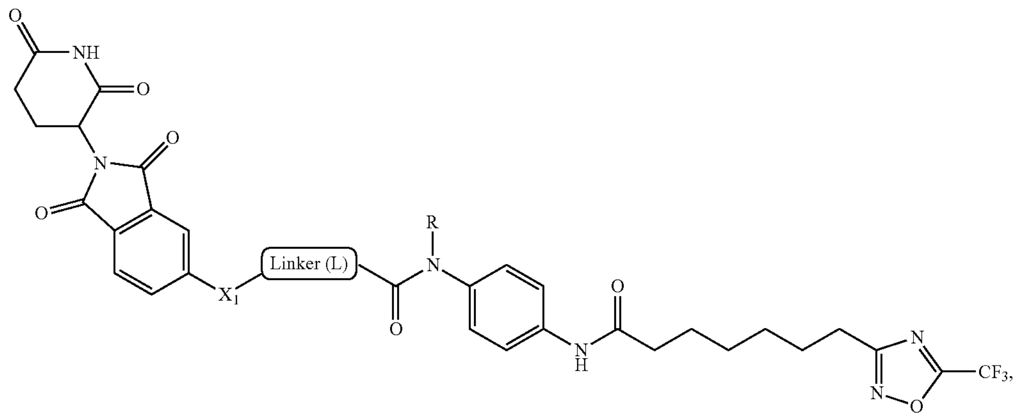
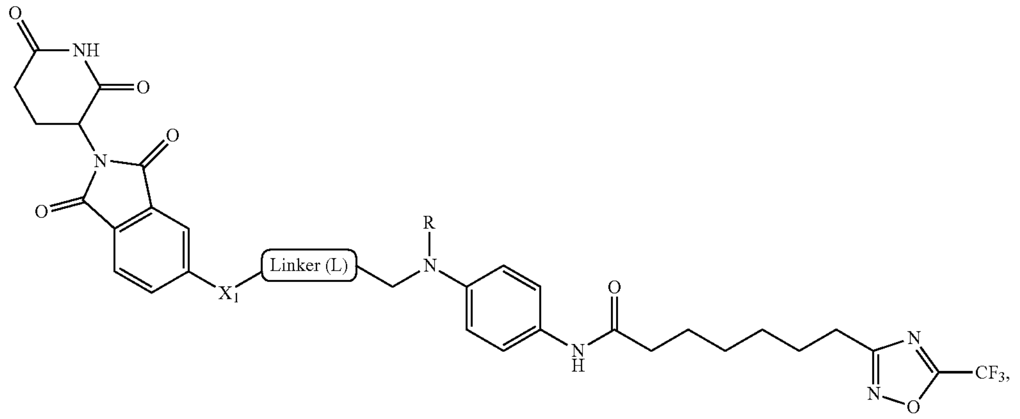
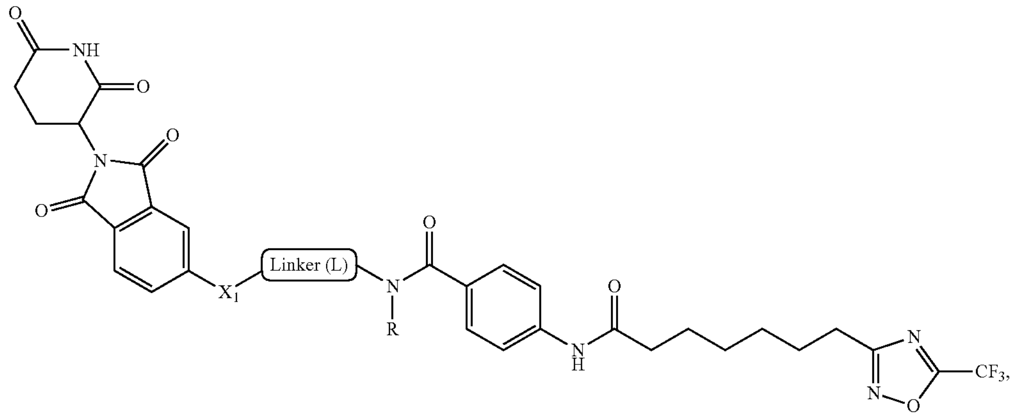
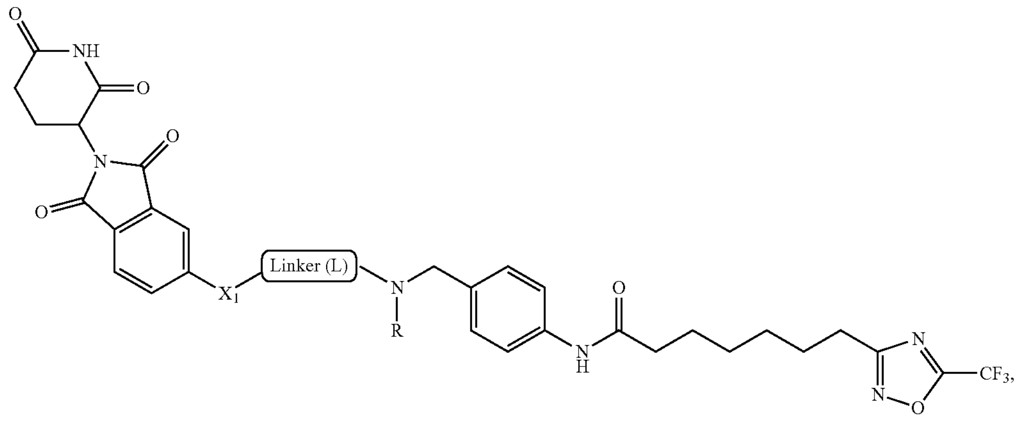

-continued
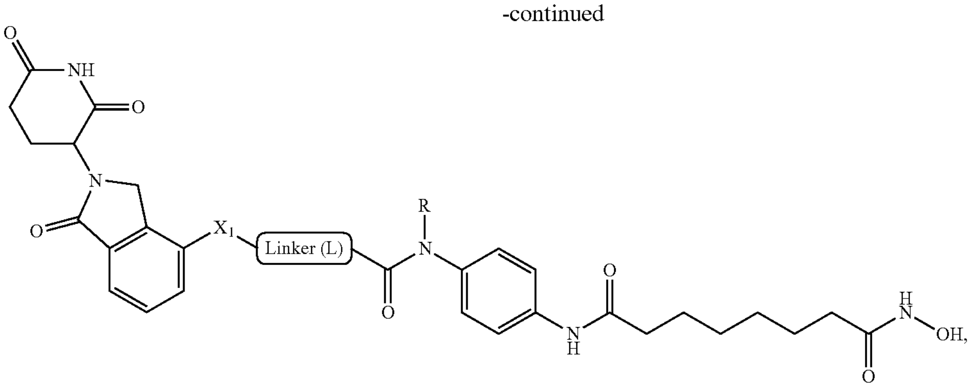
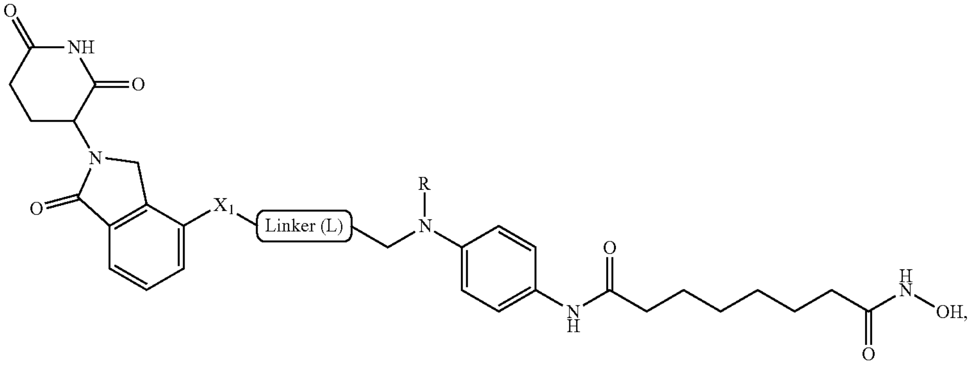
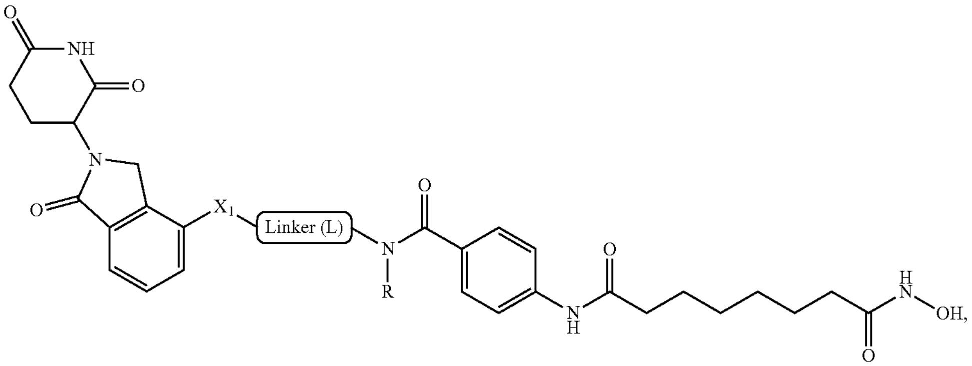
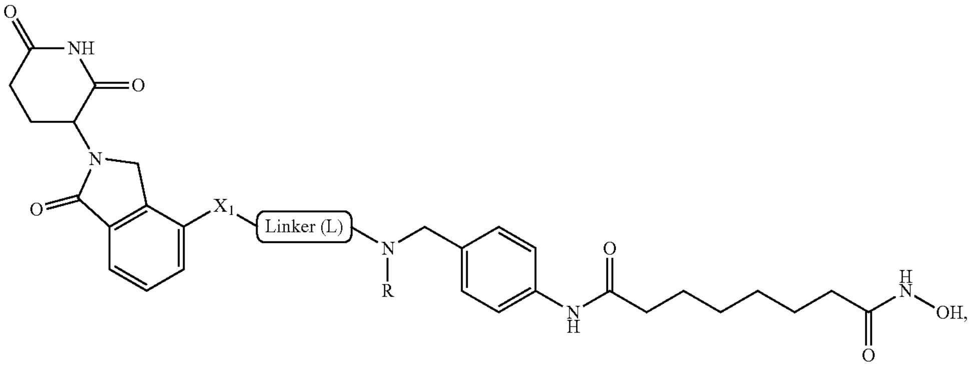

-continued
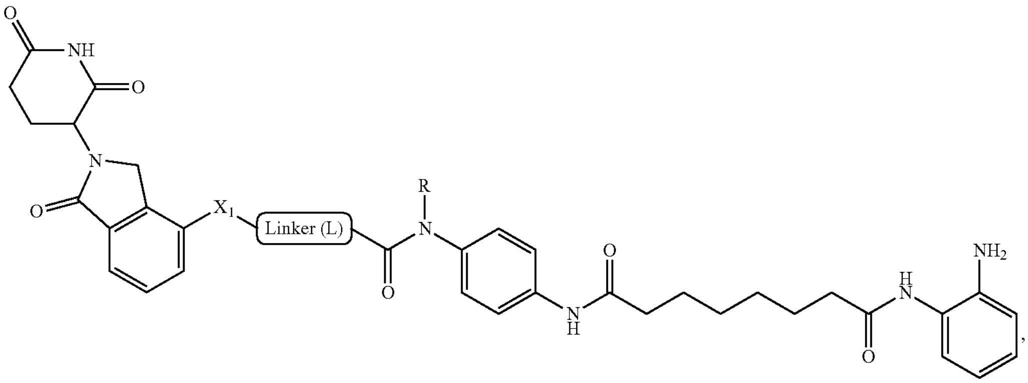
,
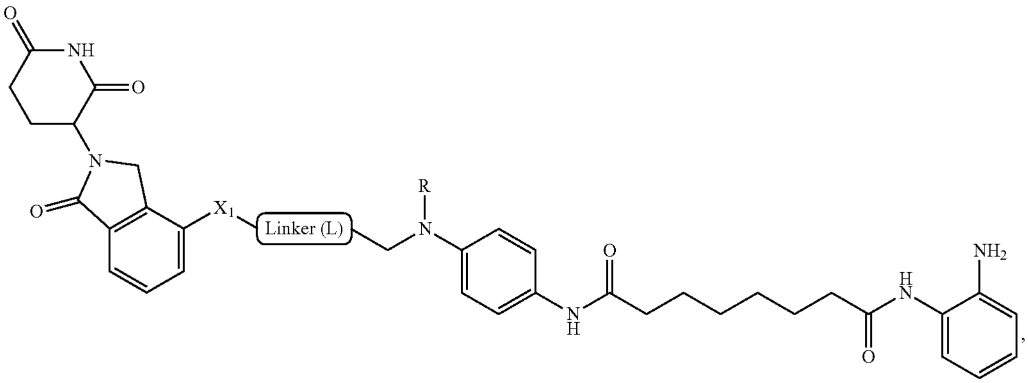
,
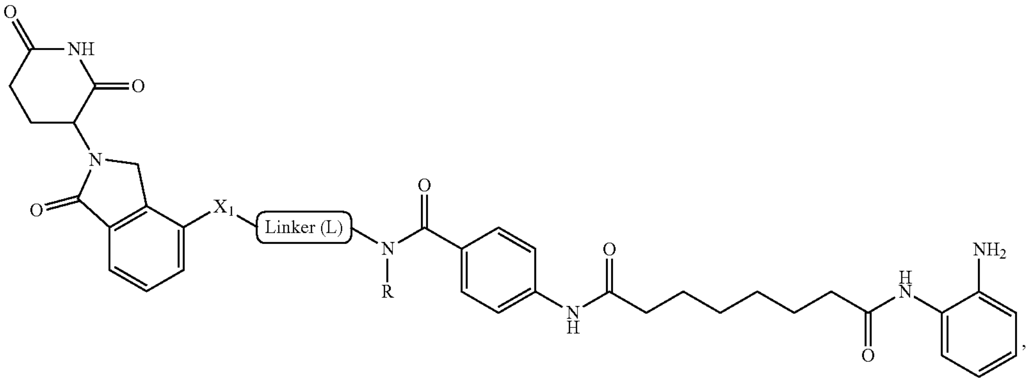
,
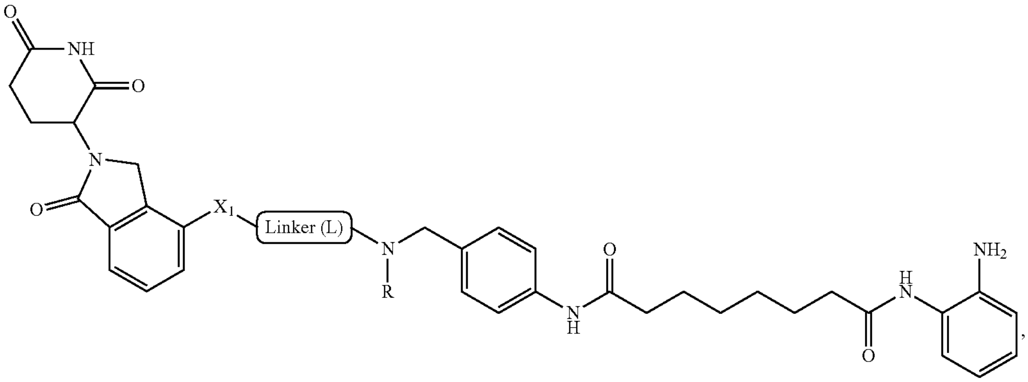
,

-continued
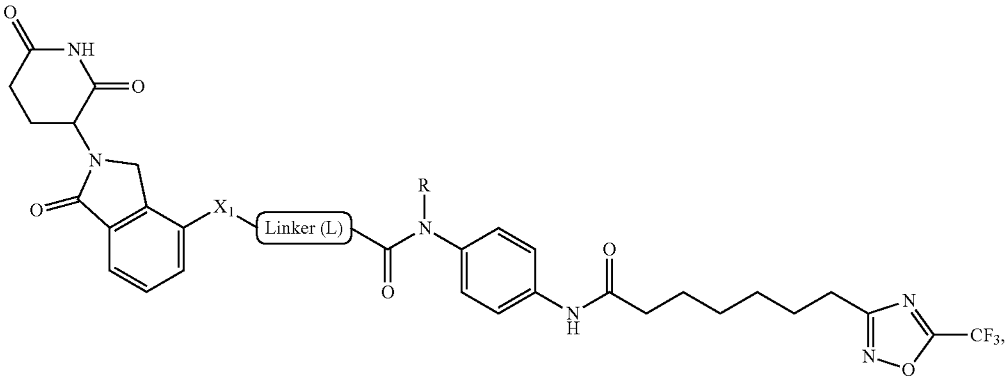
,
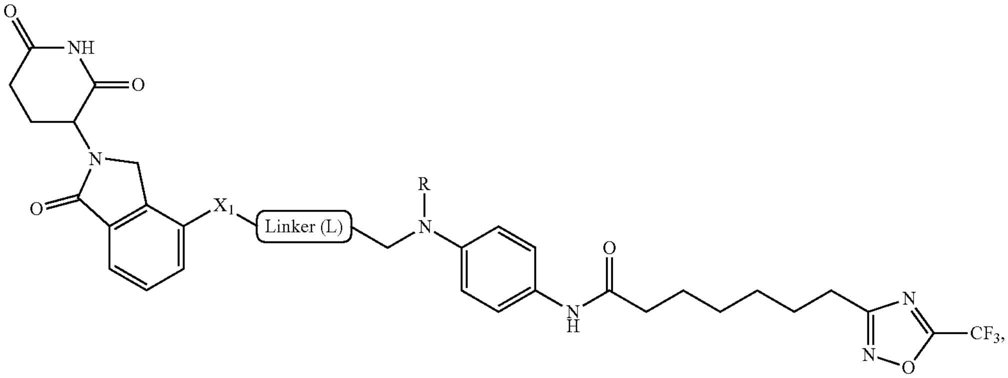
,
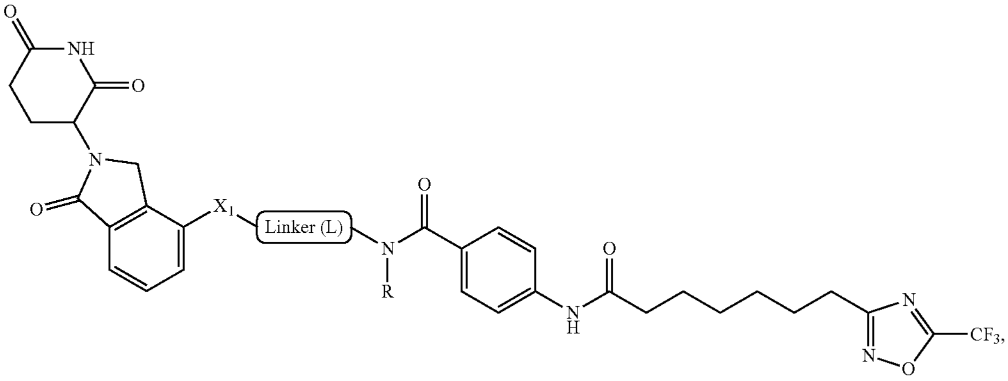
,
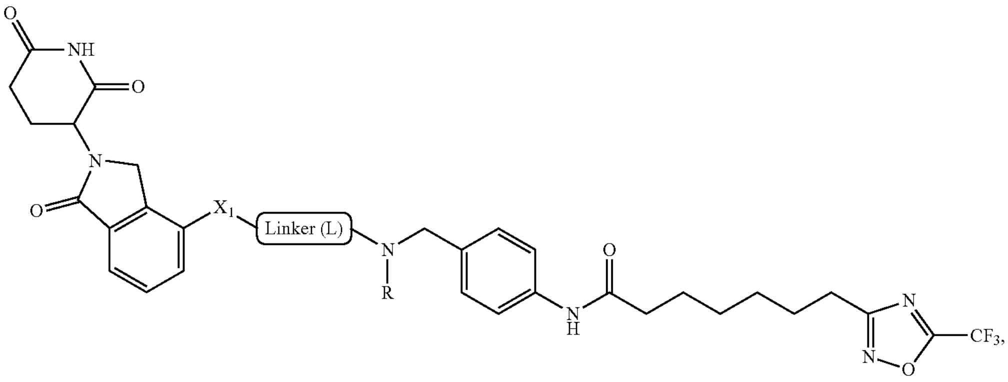
,

-continued
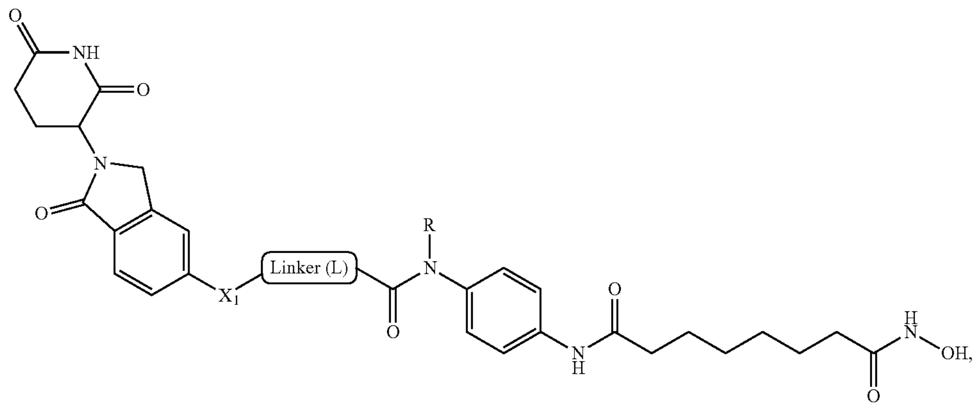
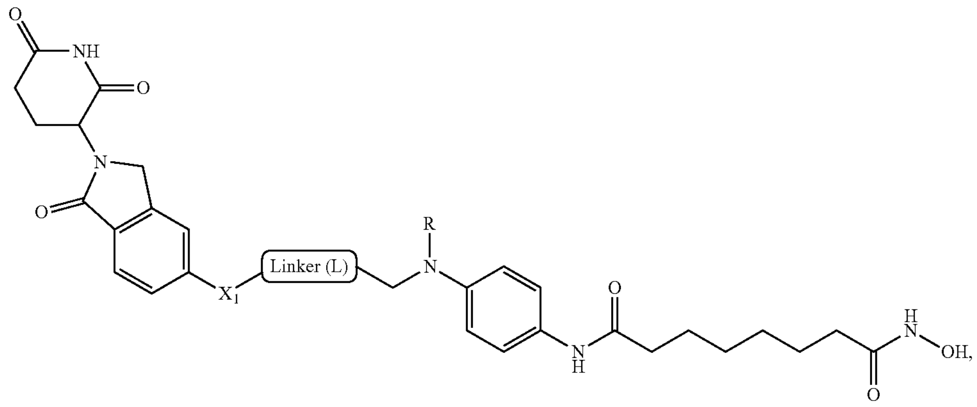
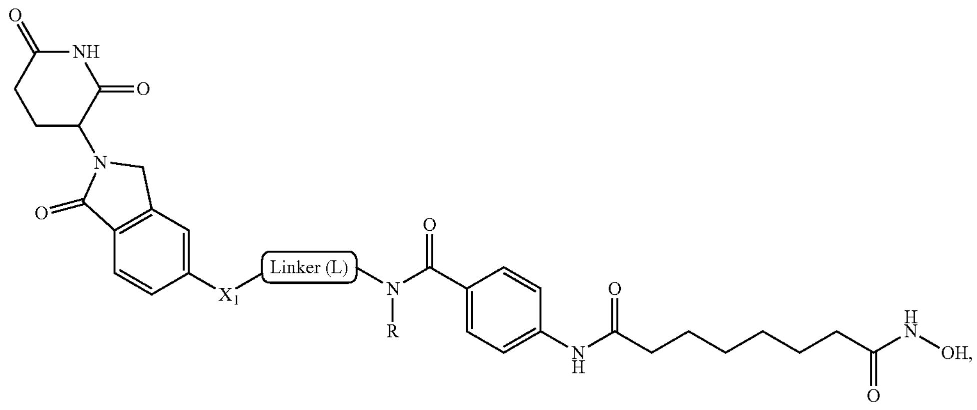
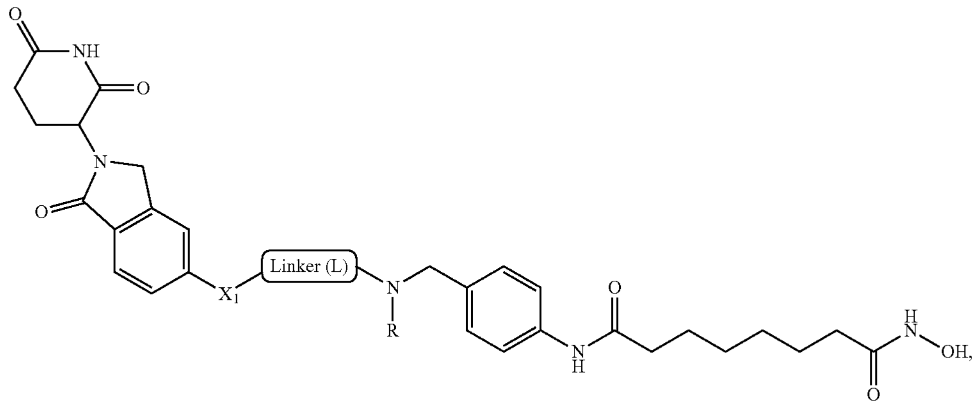

-continued
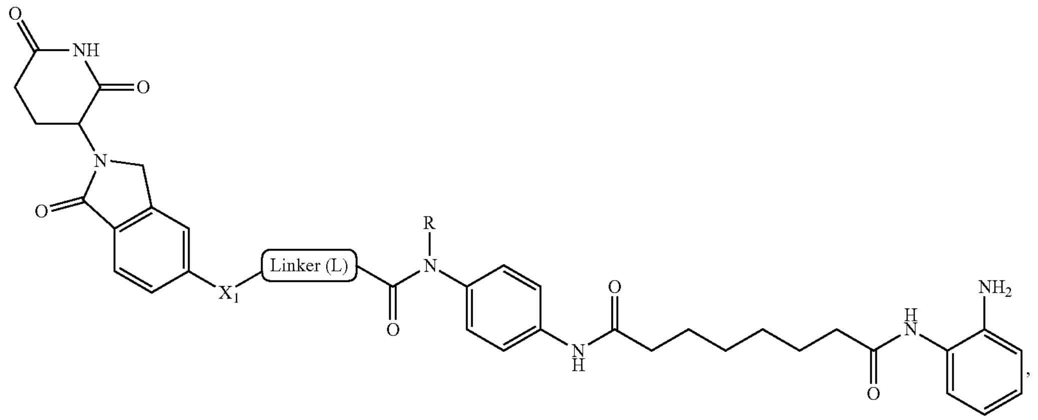
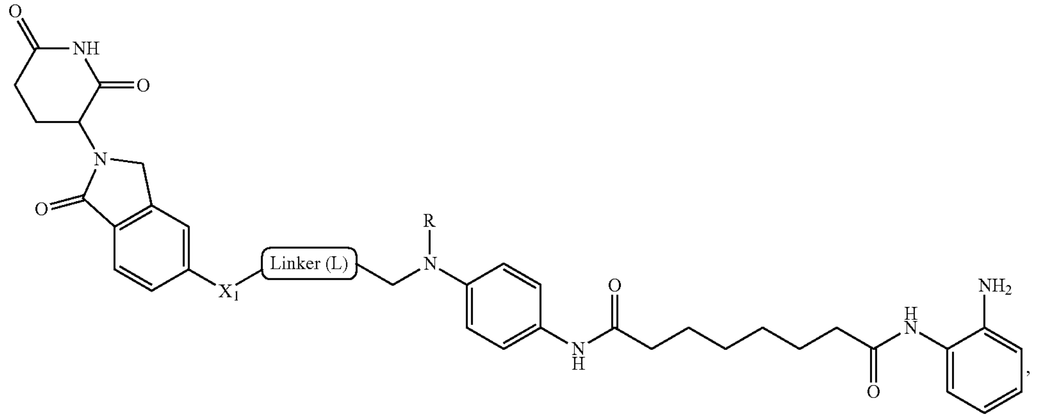
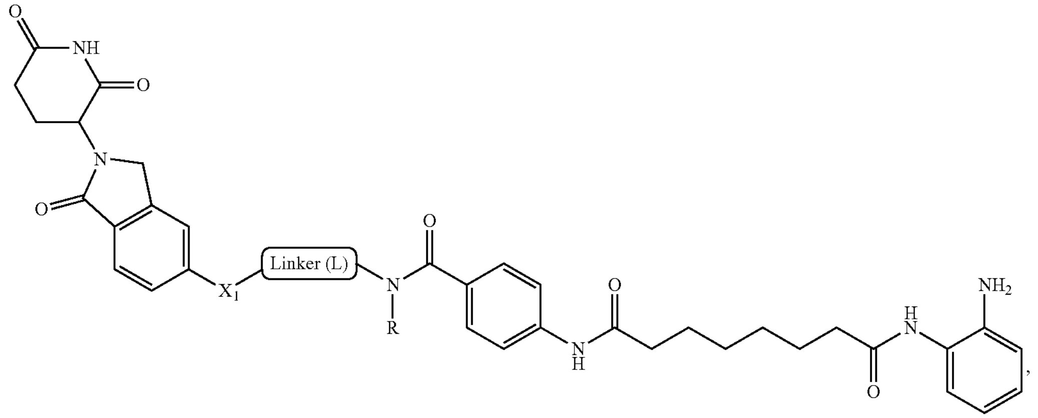
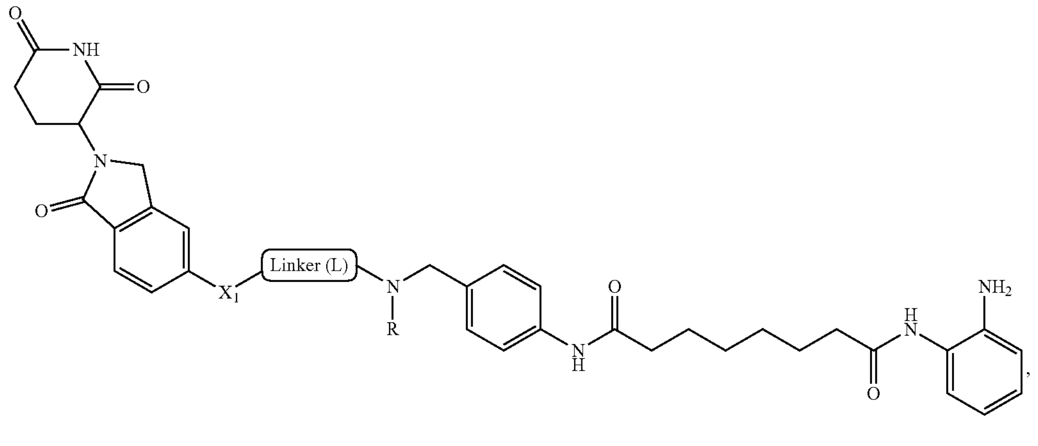

-continued
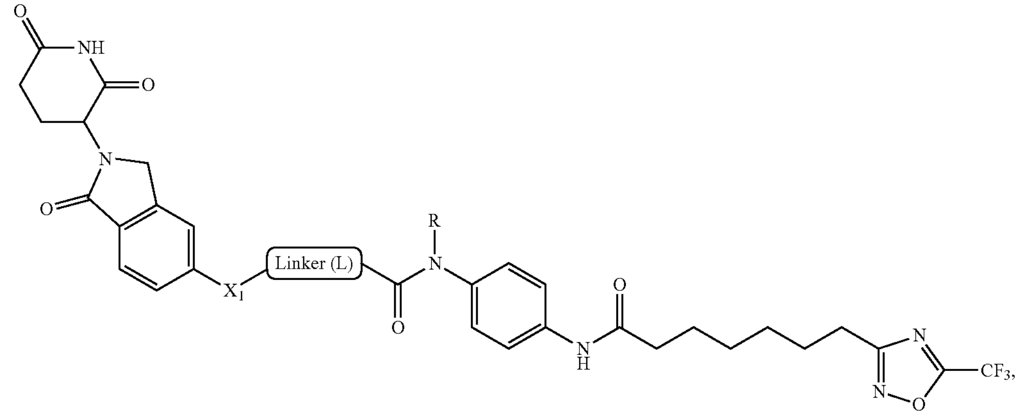
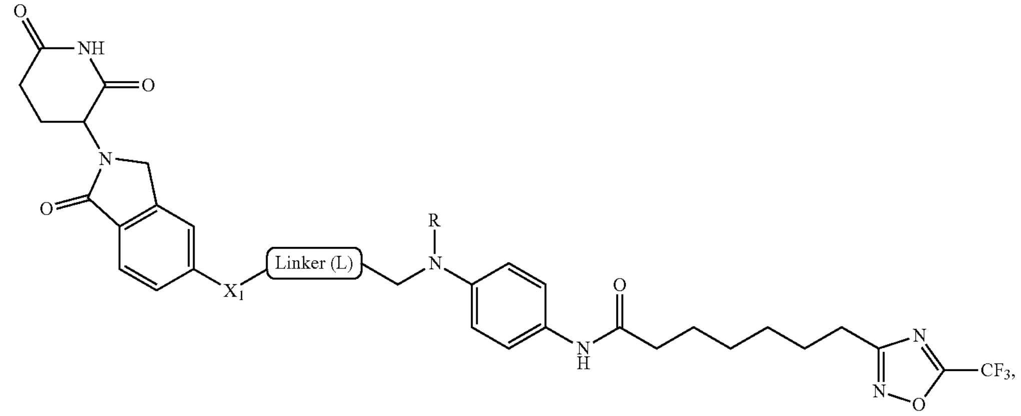
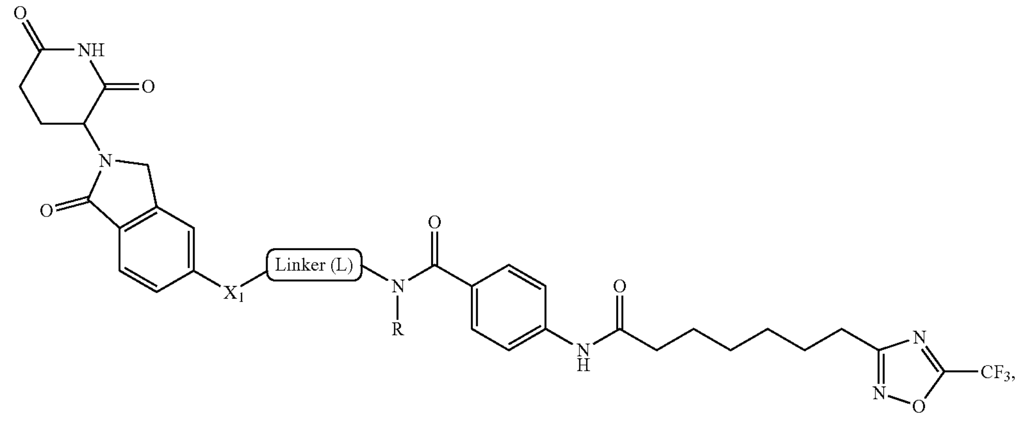
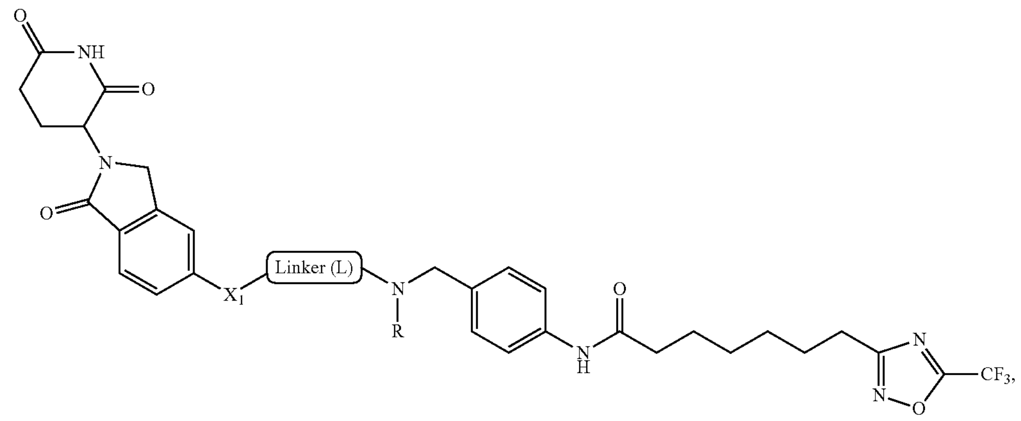

-continued
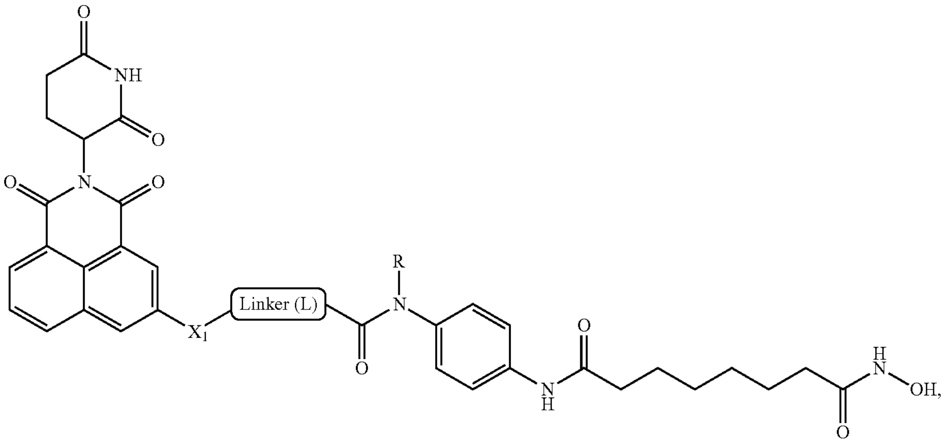
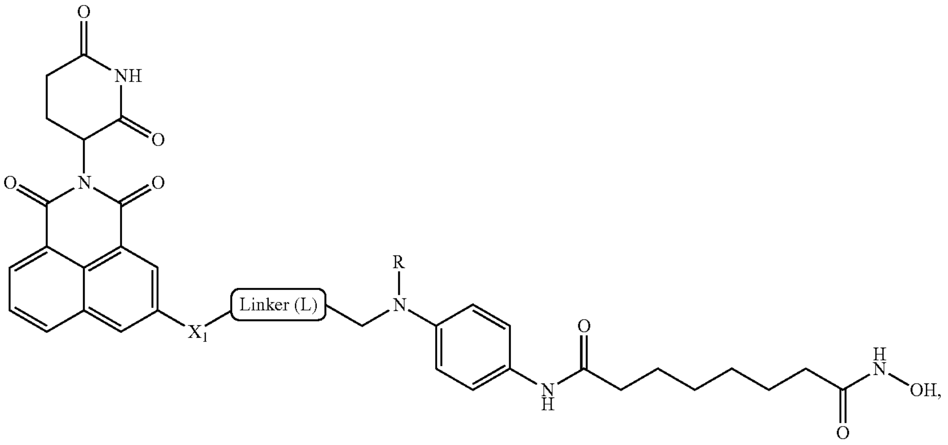
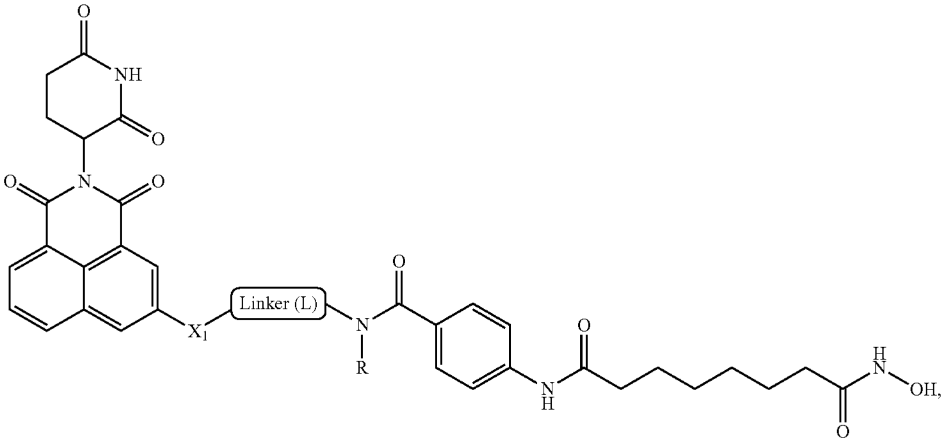

-continued
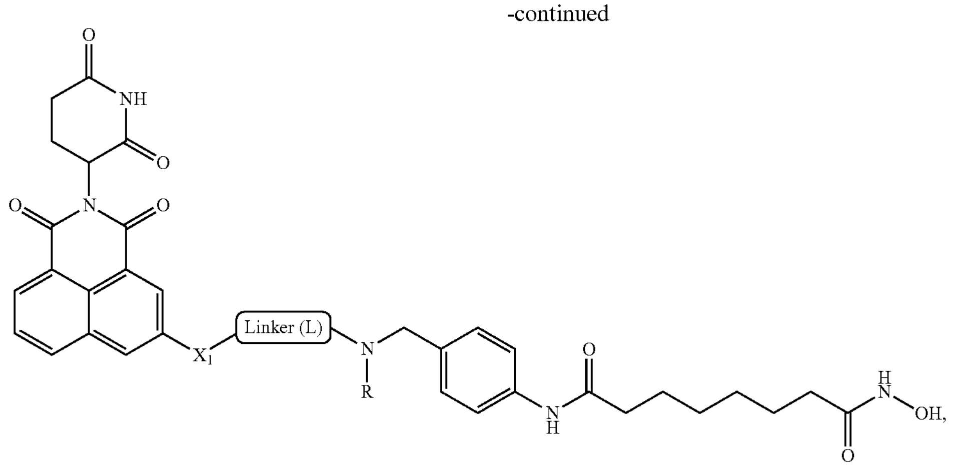
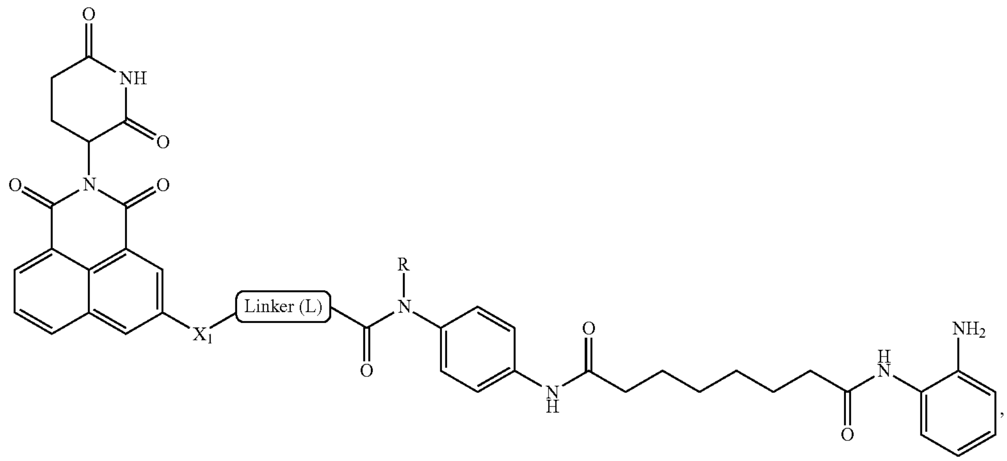
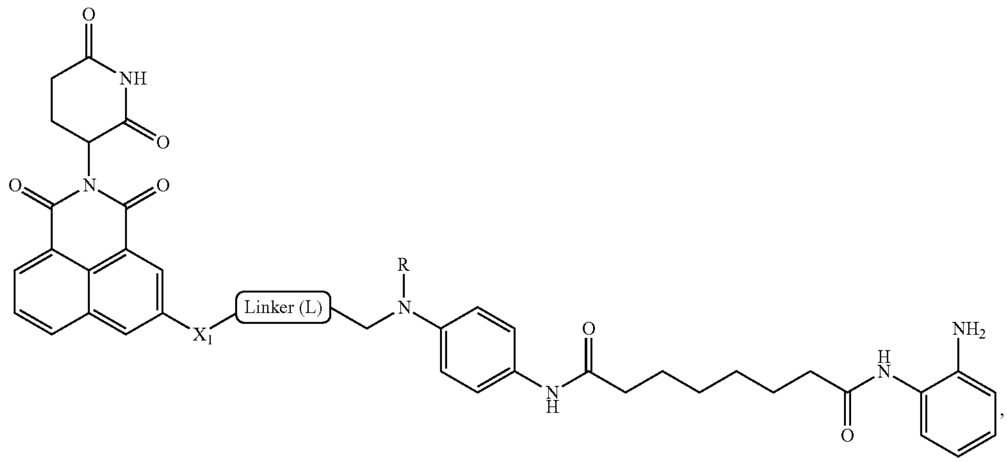
,

-continued
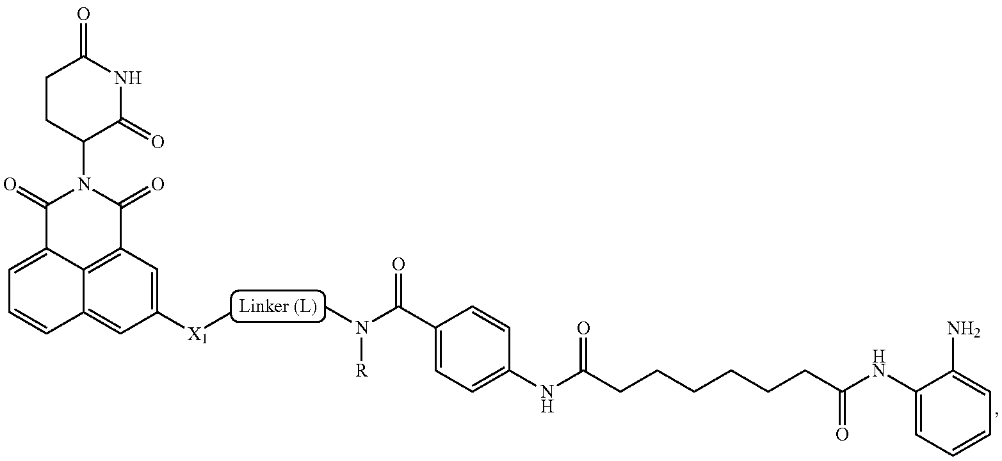
,
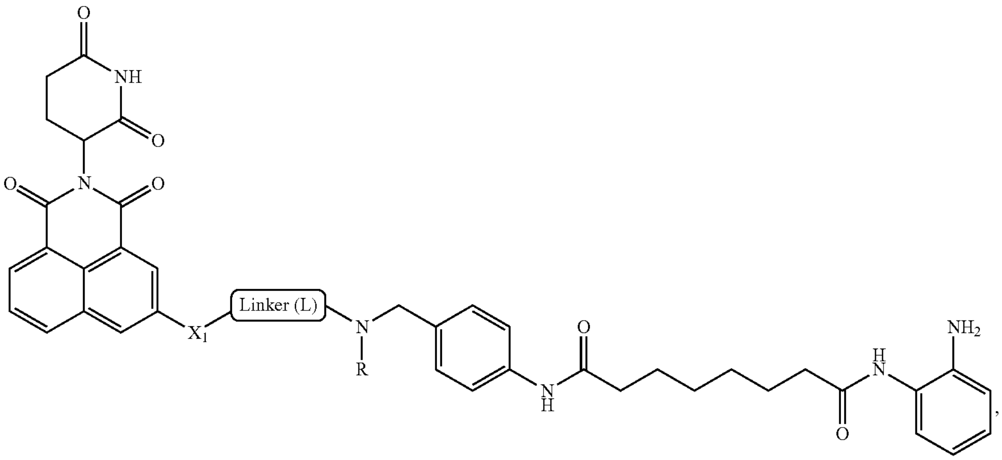
,
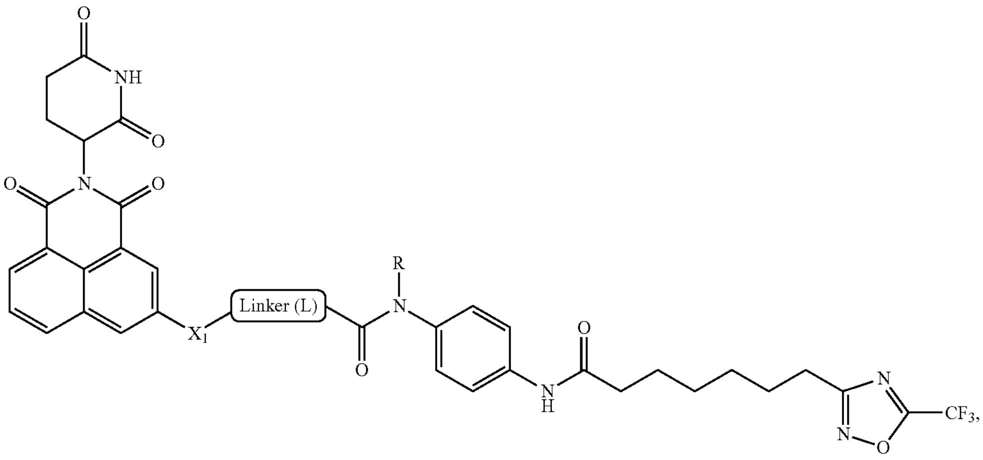
,

-continued
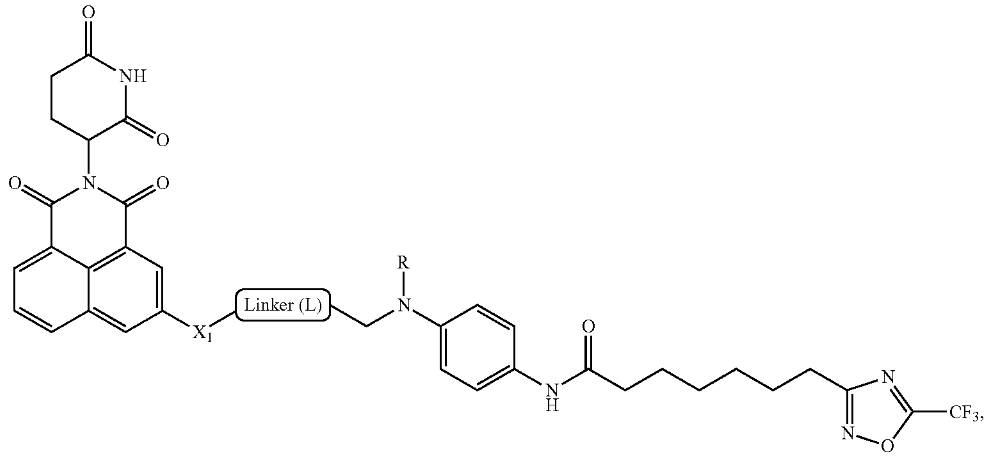
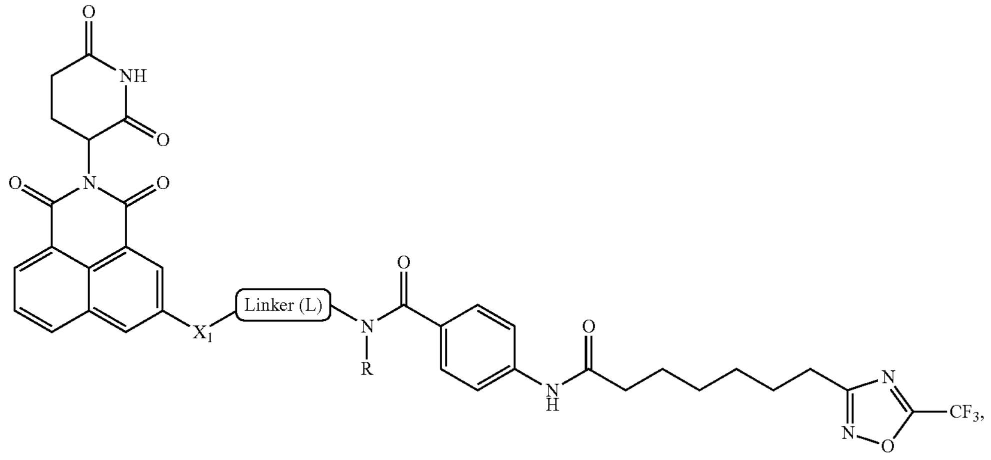
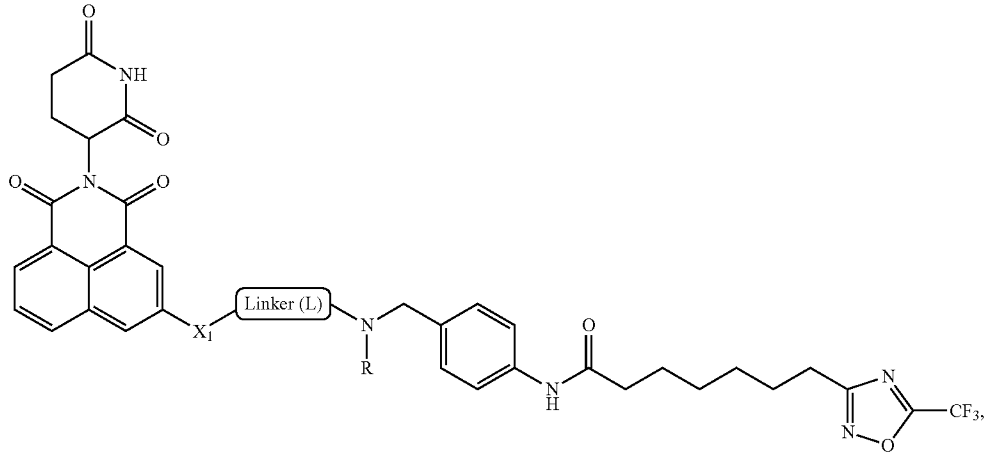
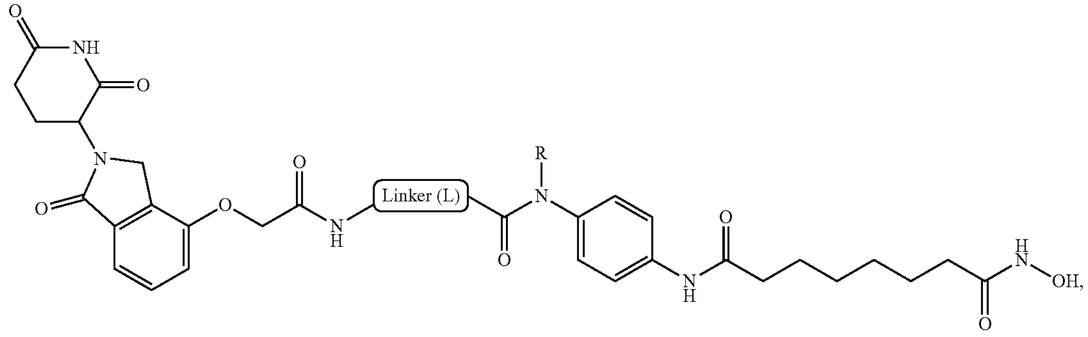

-continued
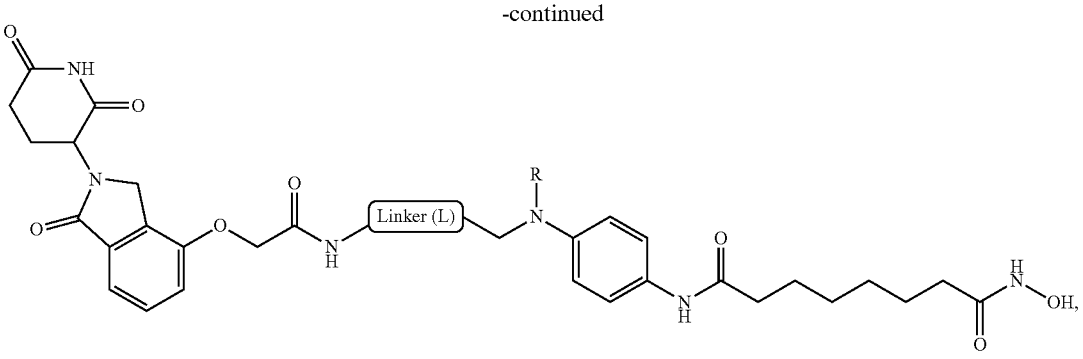
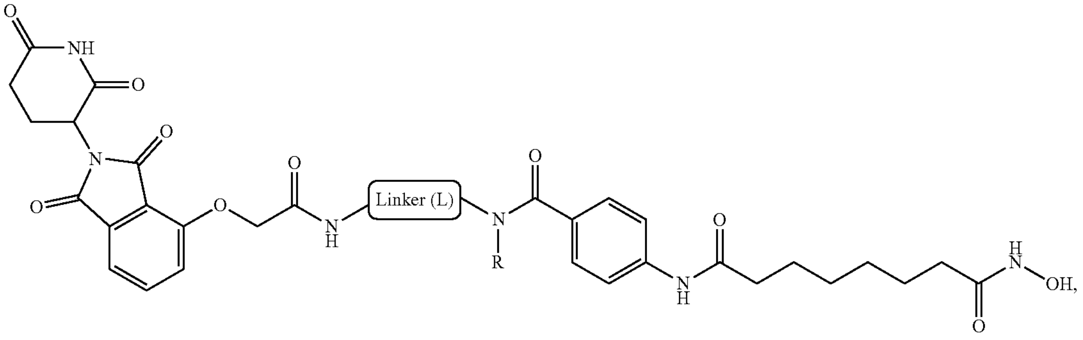
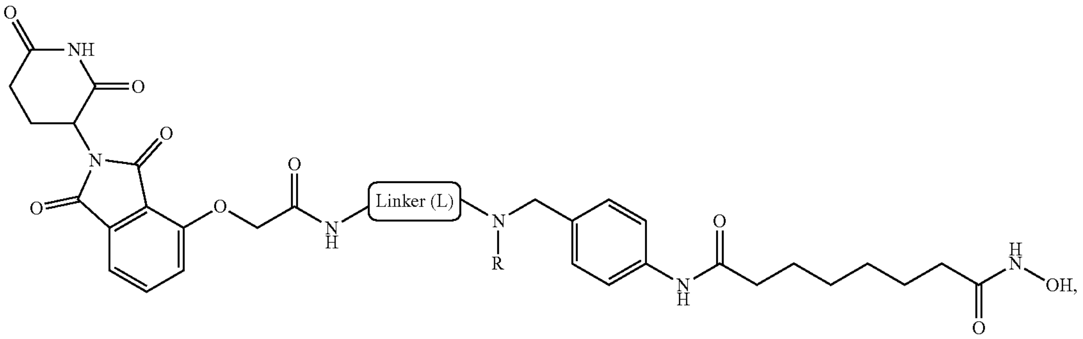
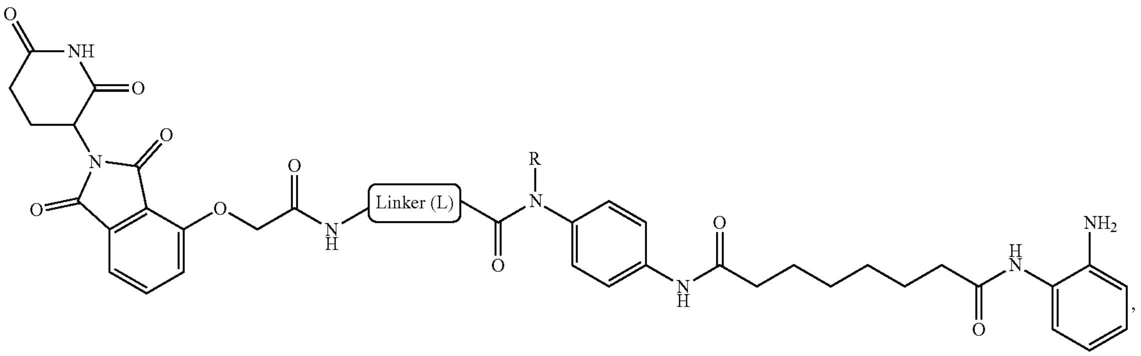

-continued
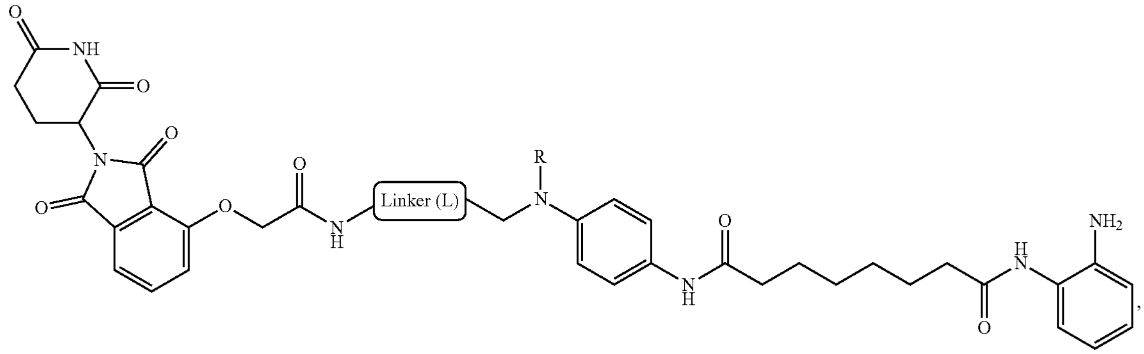
,
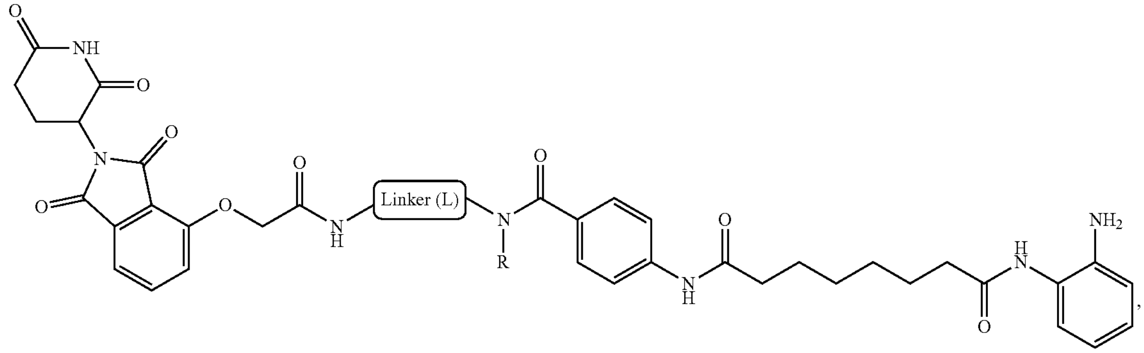
,
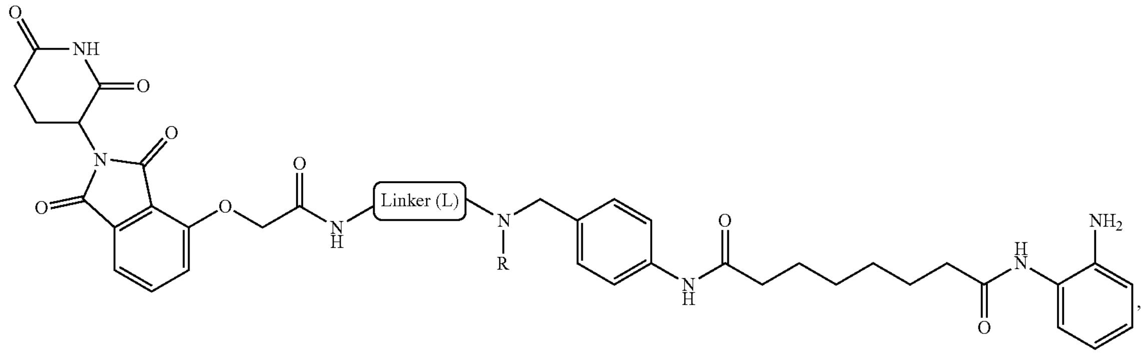
,
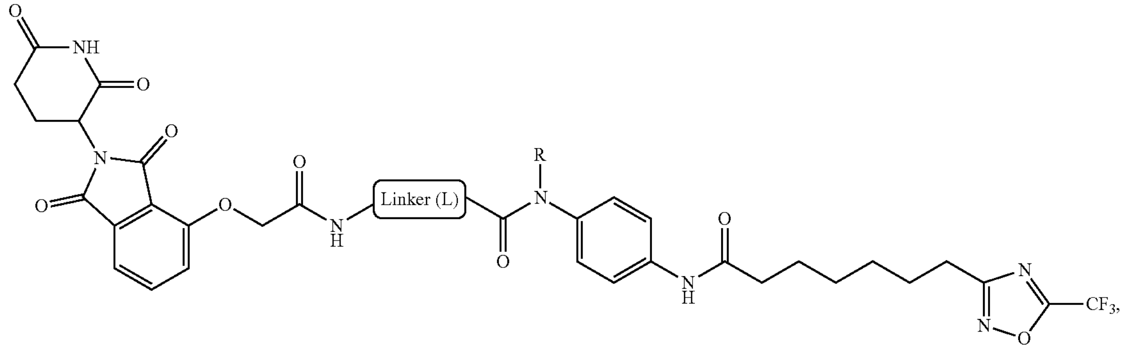
,

-continued
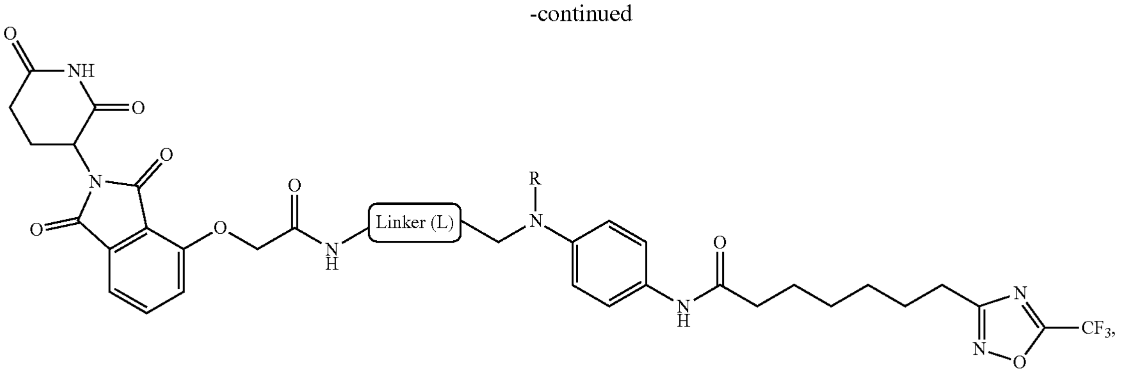
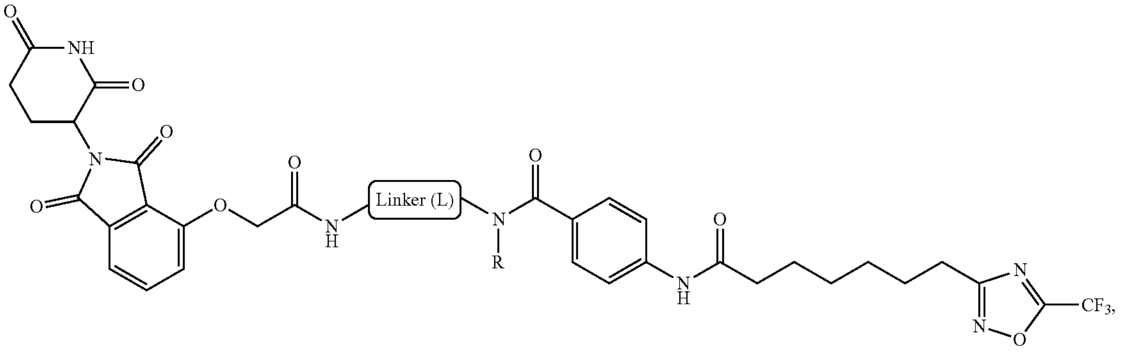
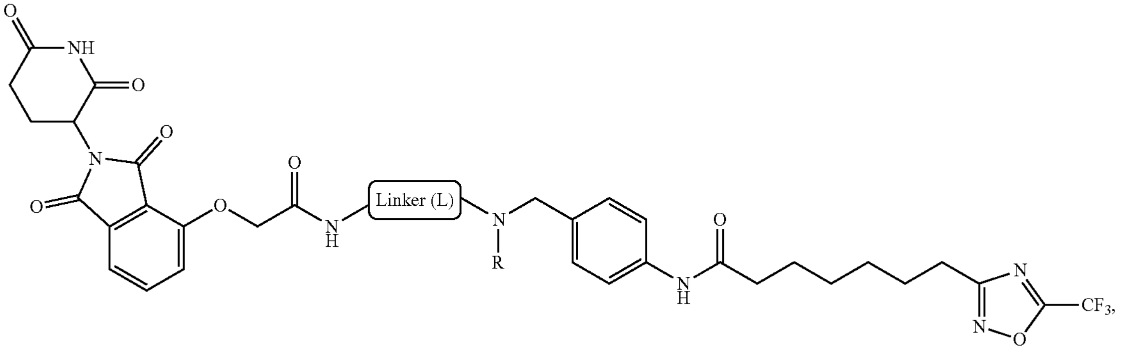
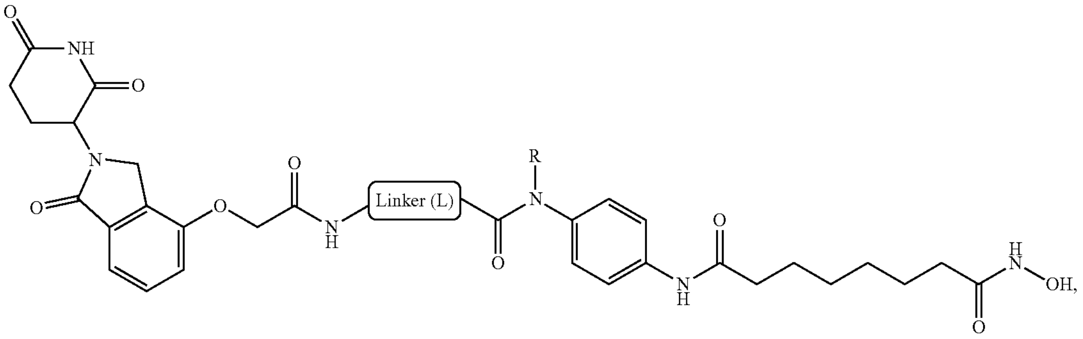
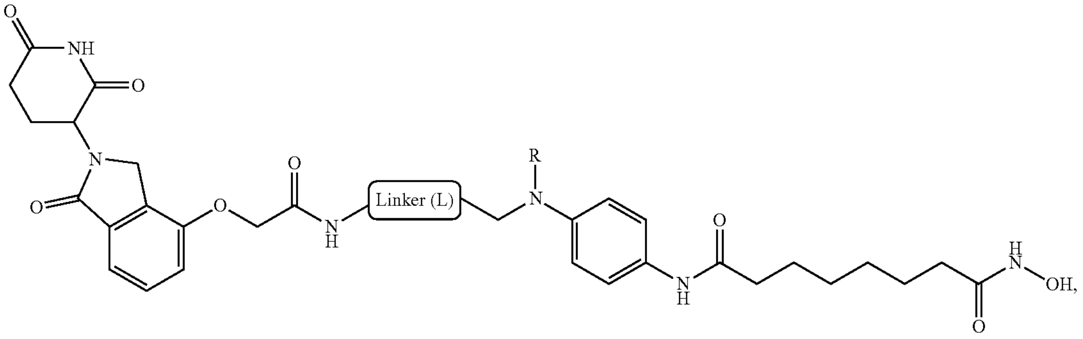

-continued
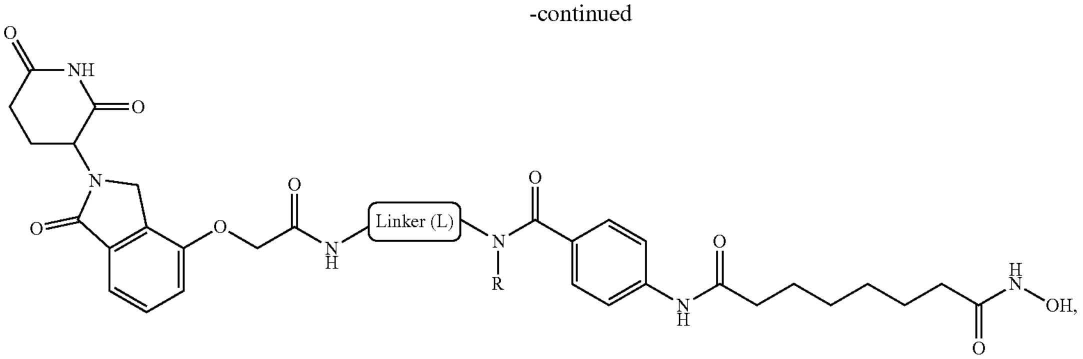
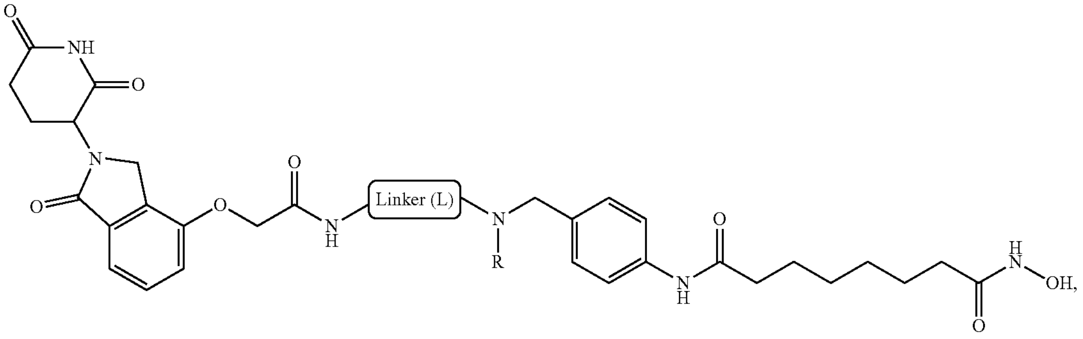
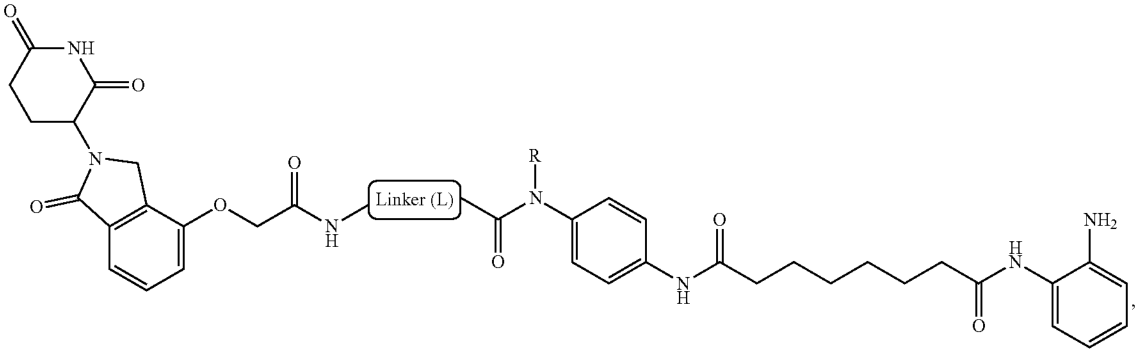
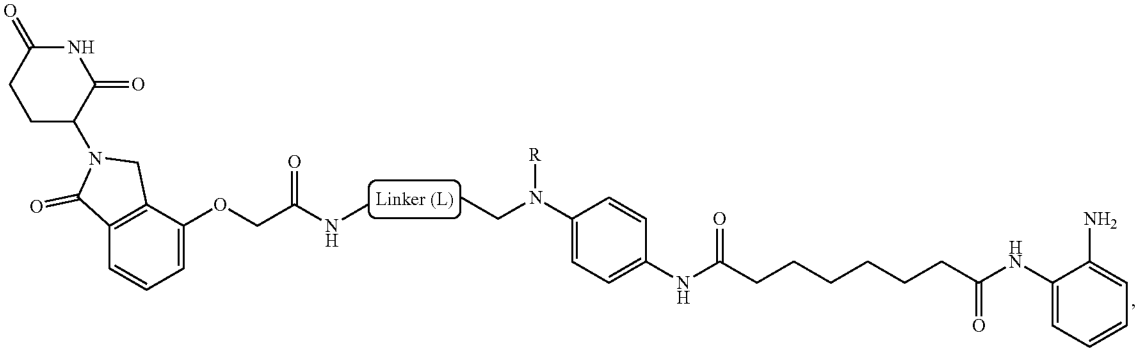
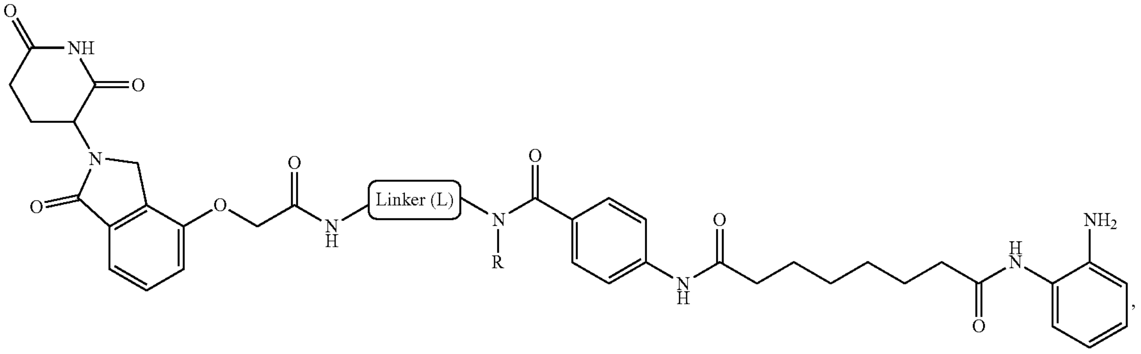

-continued
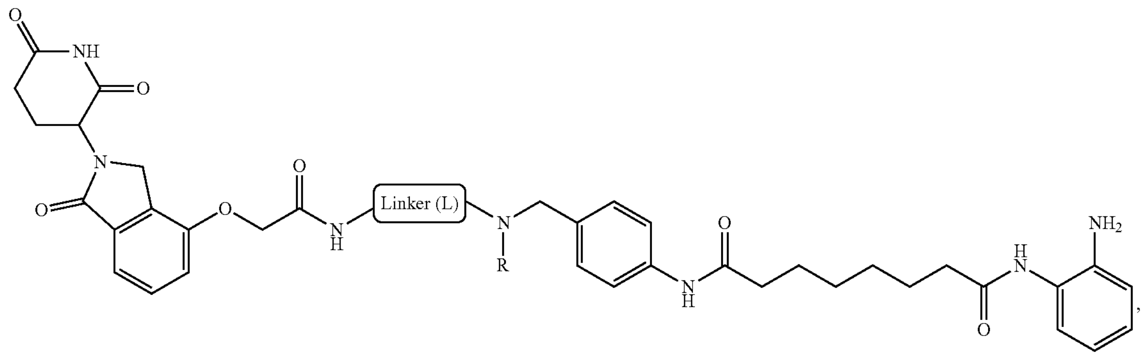
,
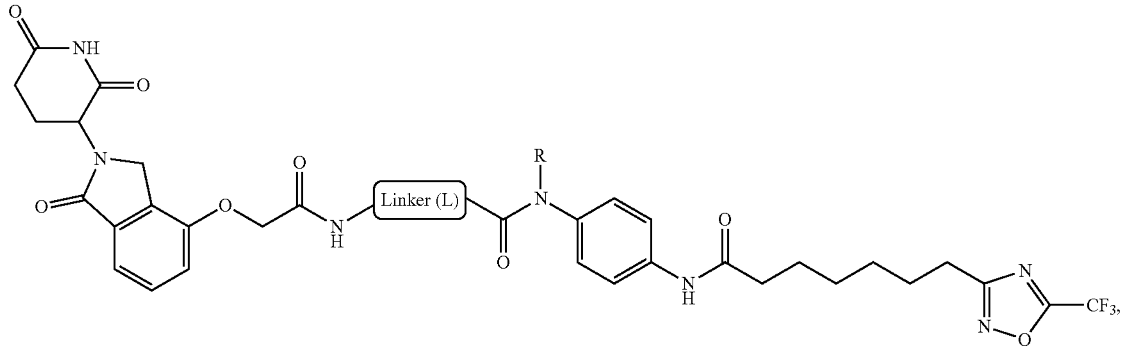
,
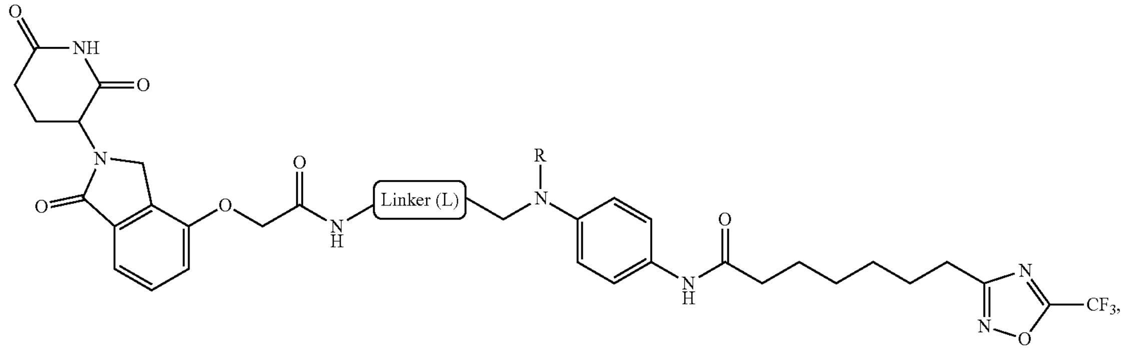
,
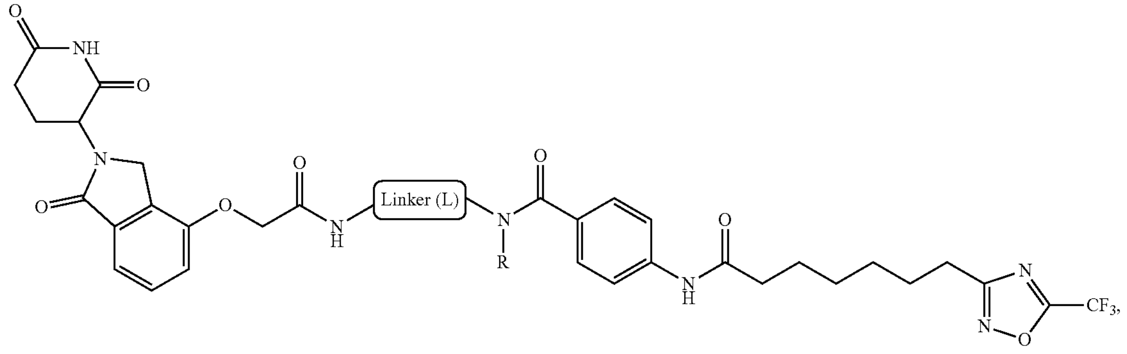
,

-continued
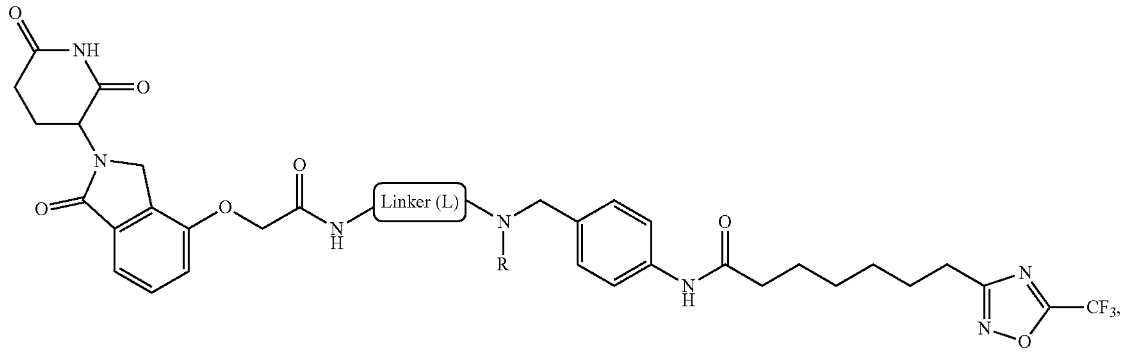
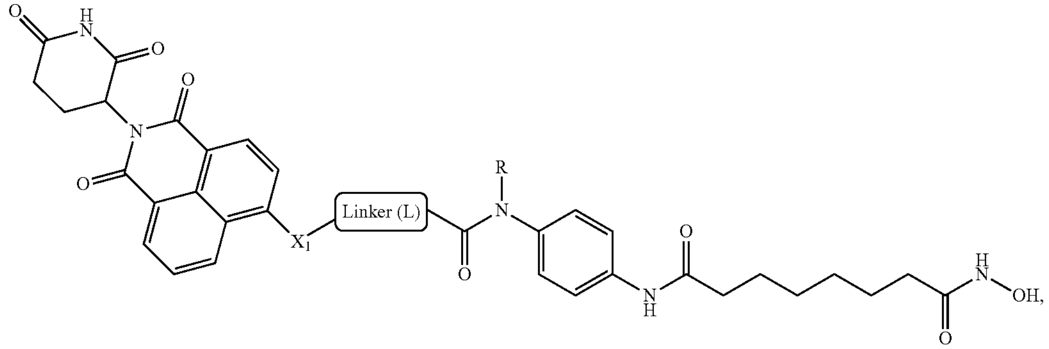
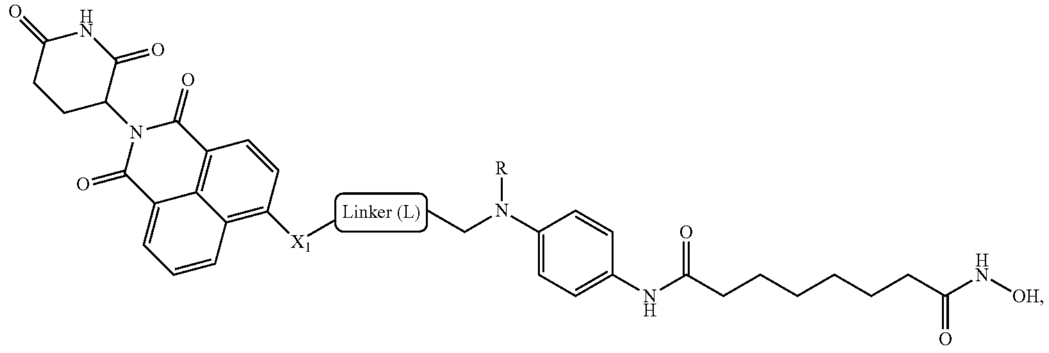
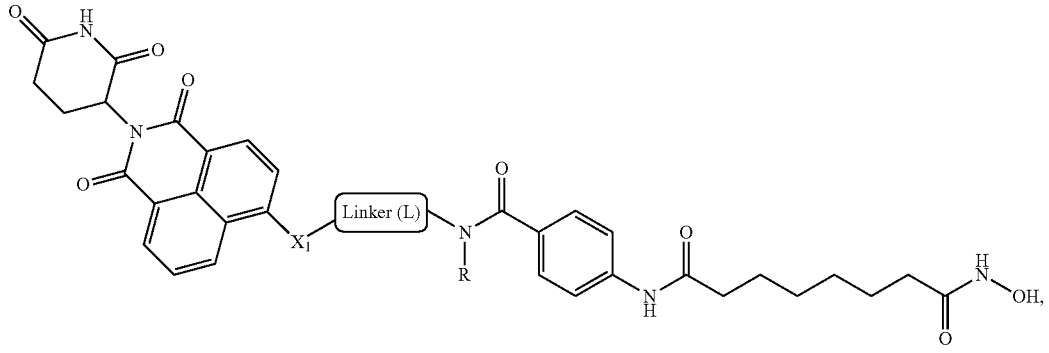

-continued
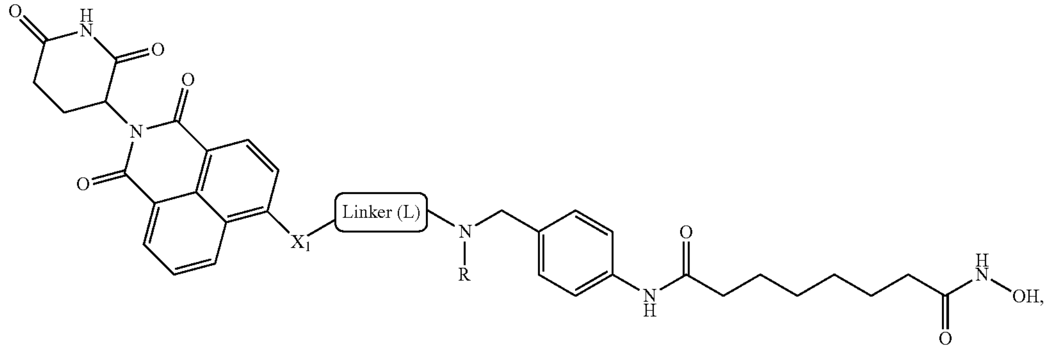
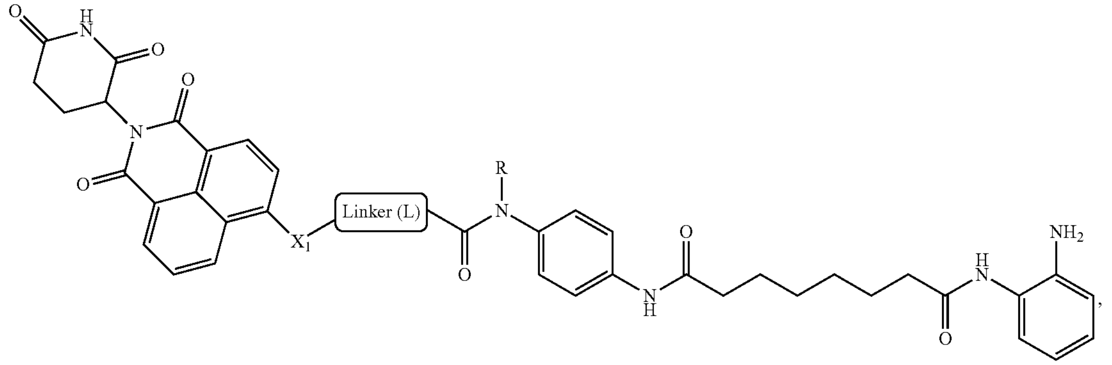
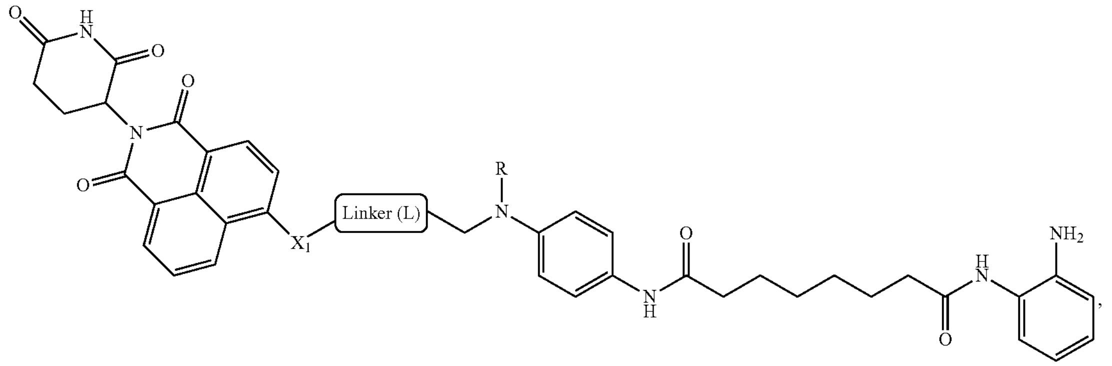
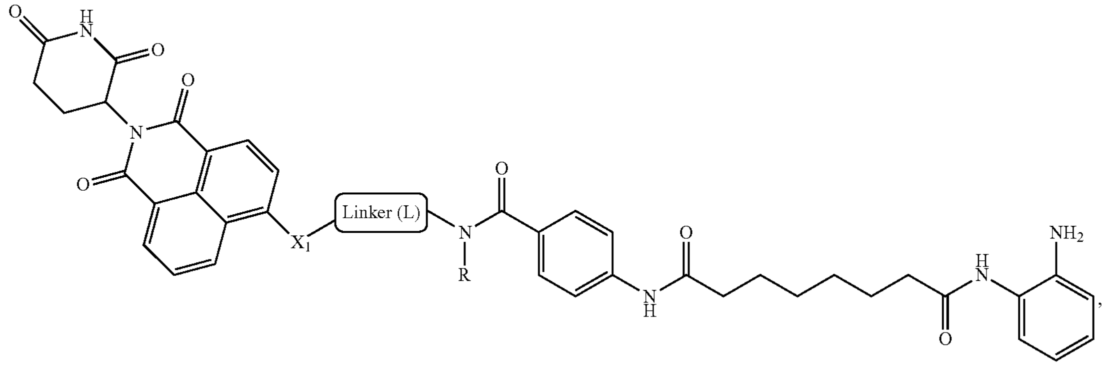

-continued
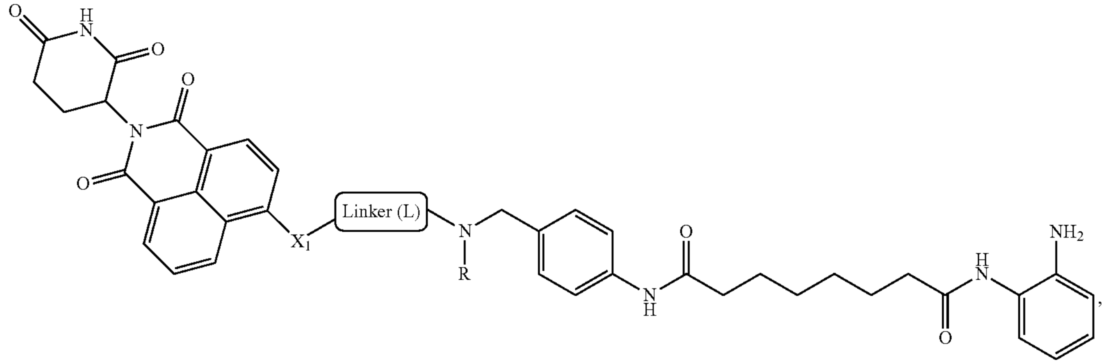
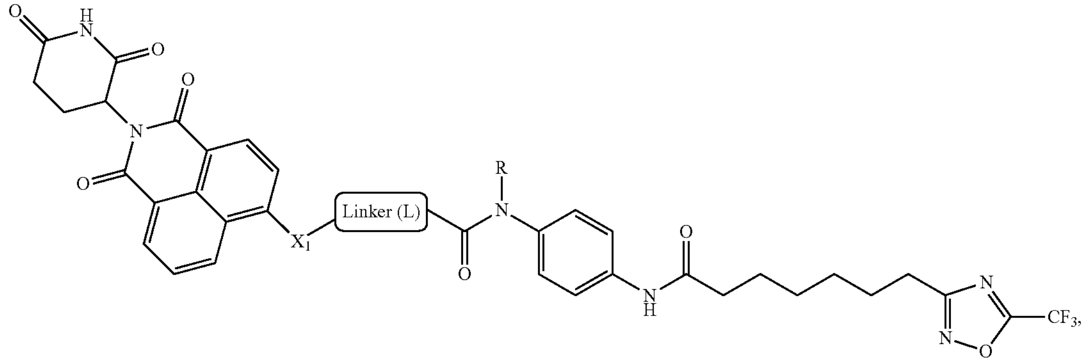
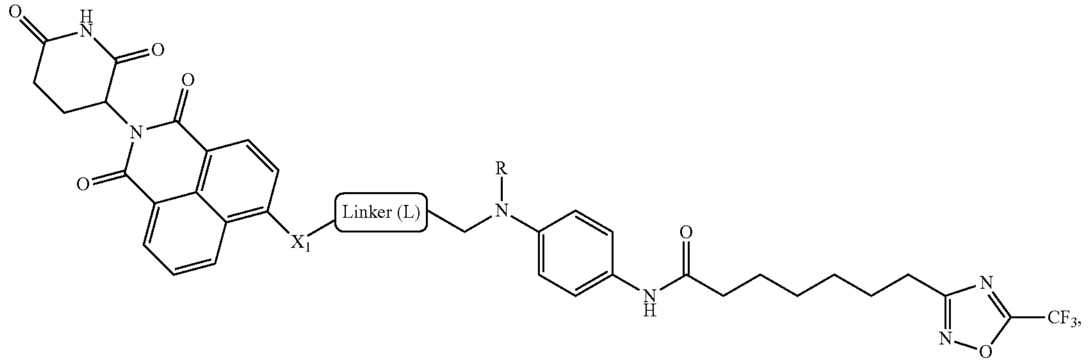
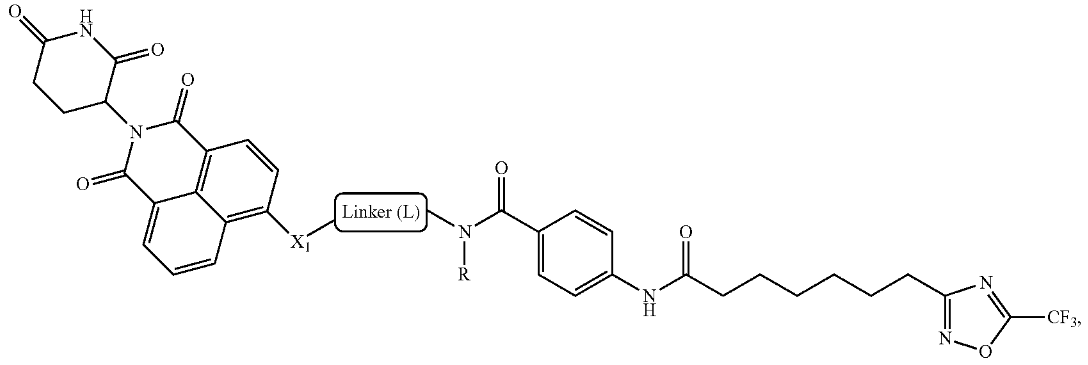

-continued
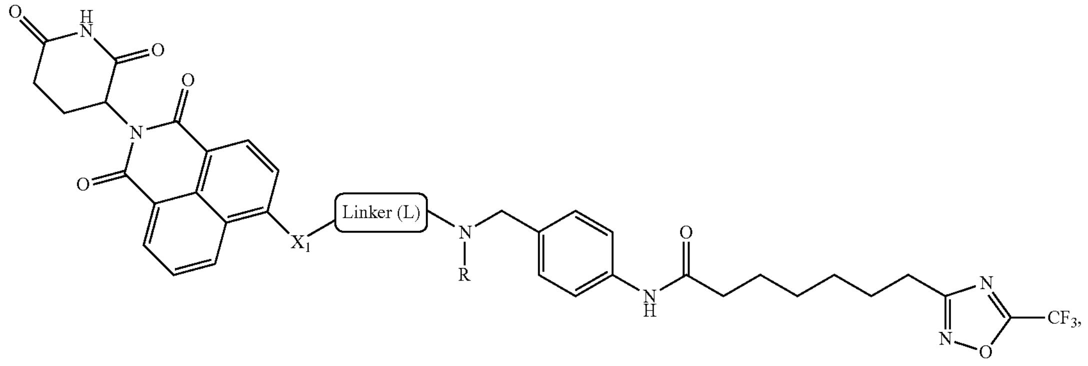
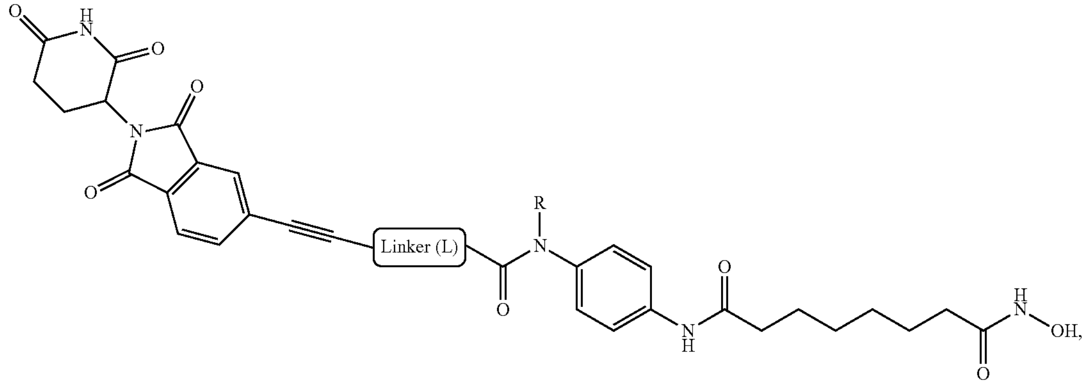
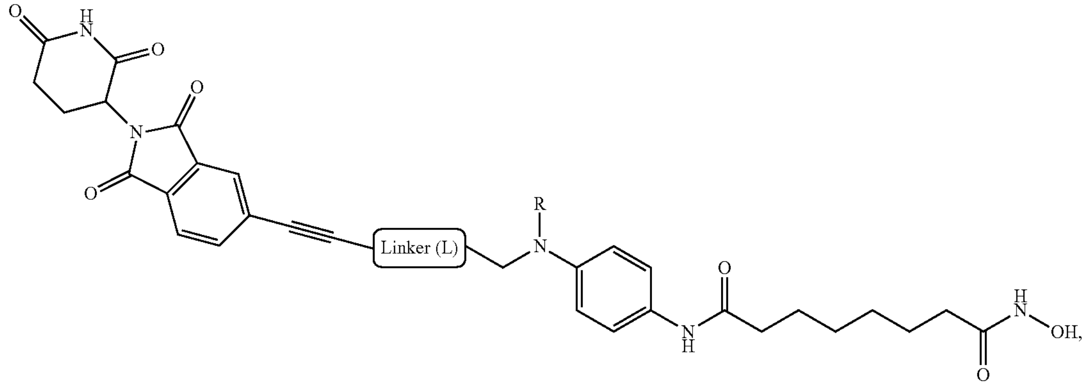
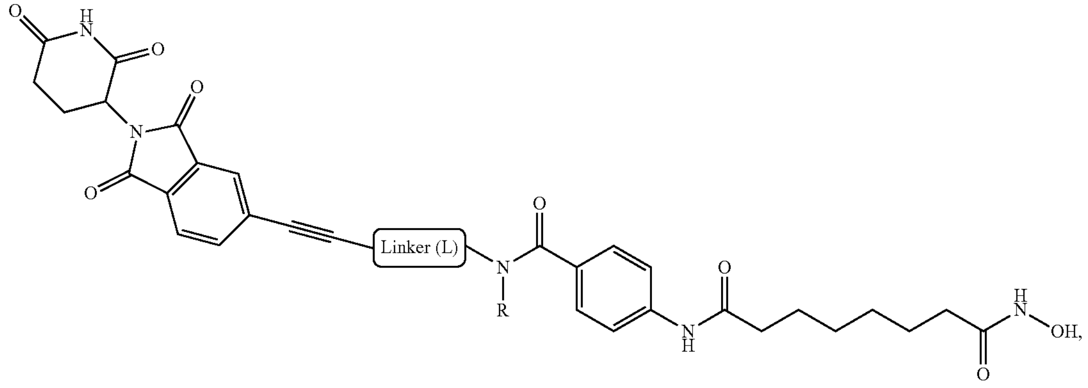

-continued
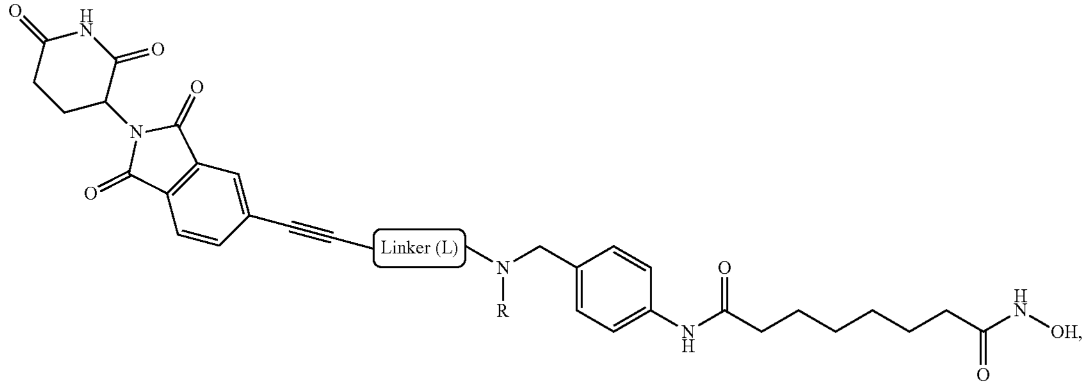
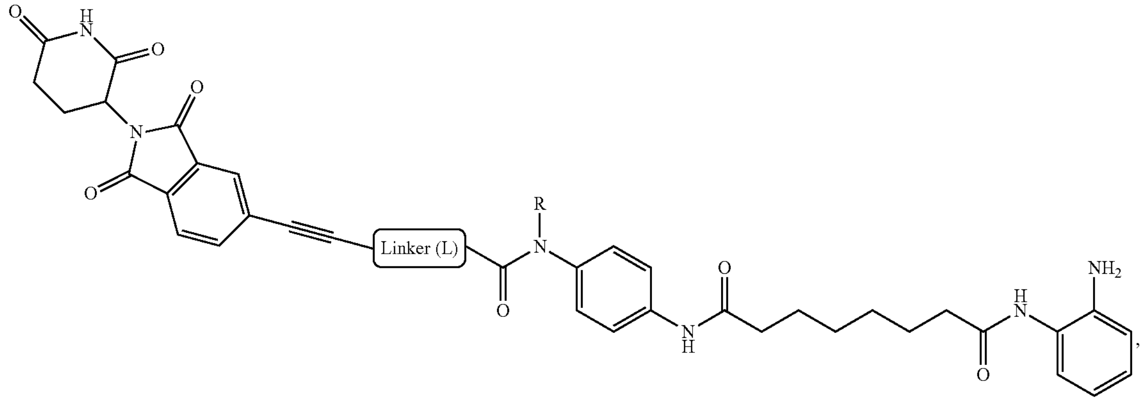
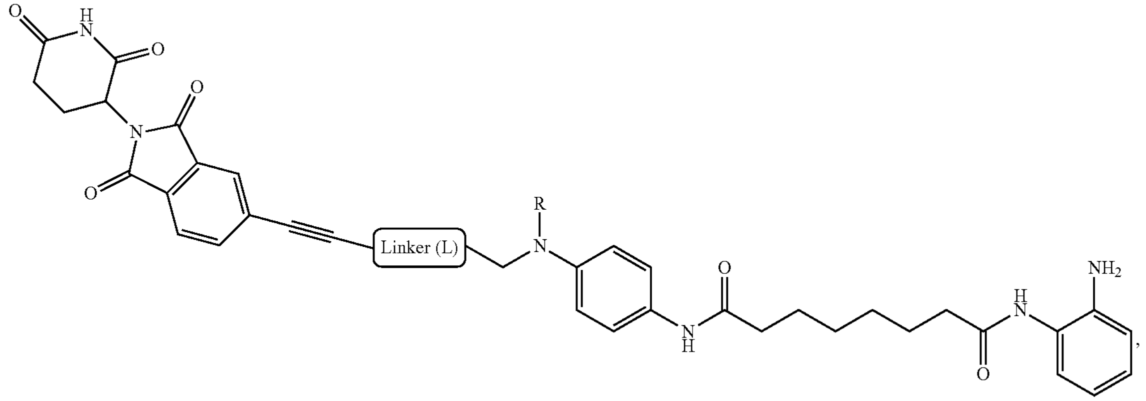
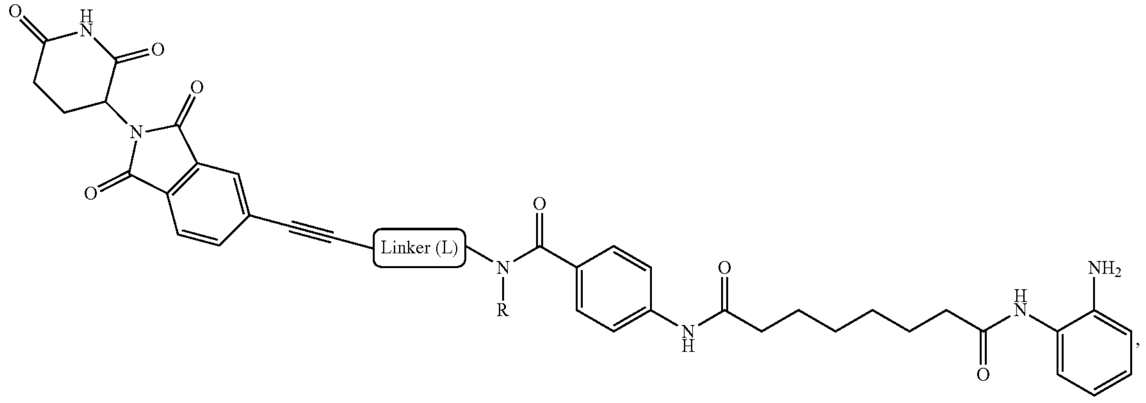

-continued
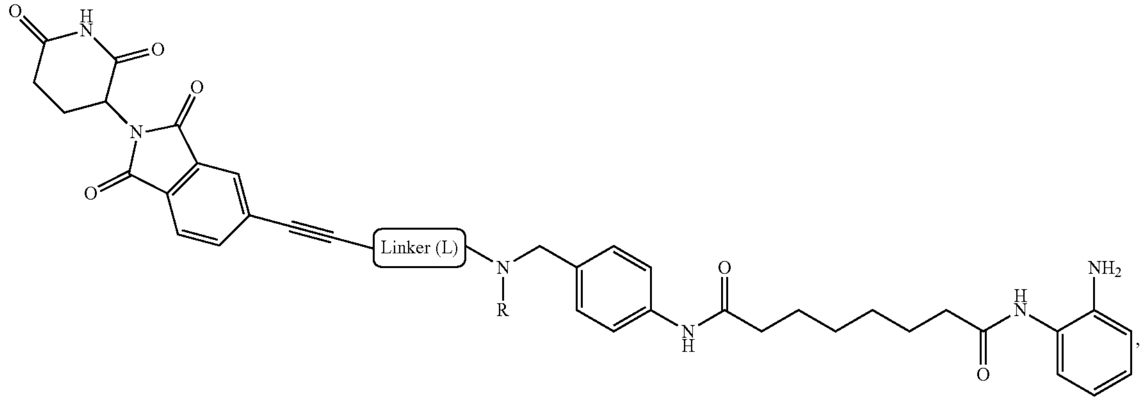
,
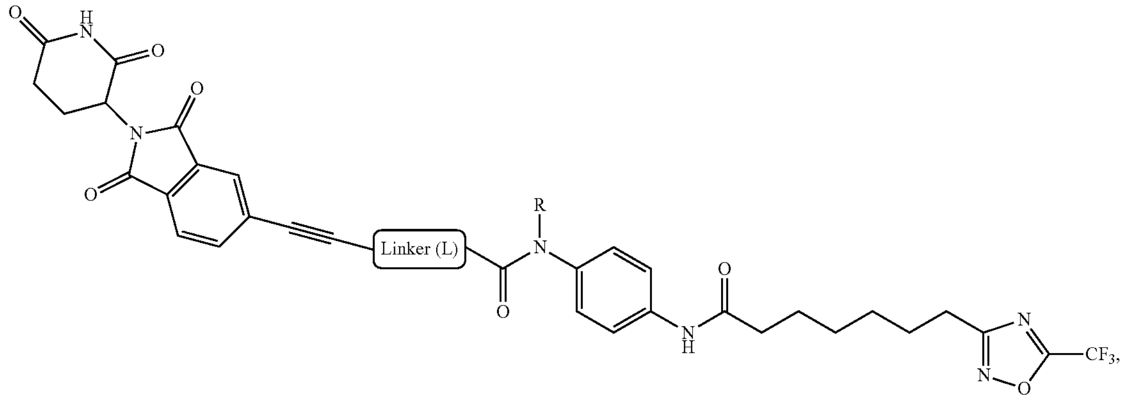
,
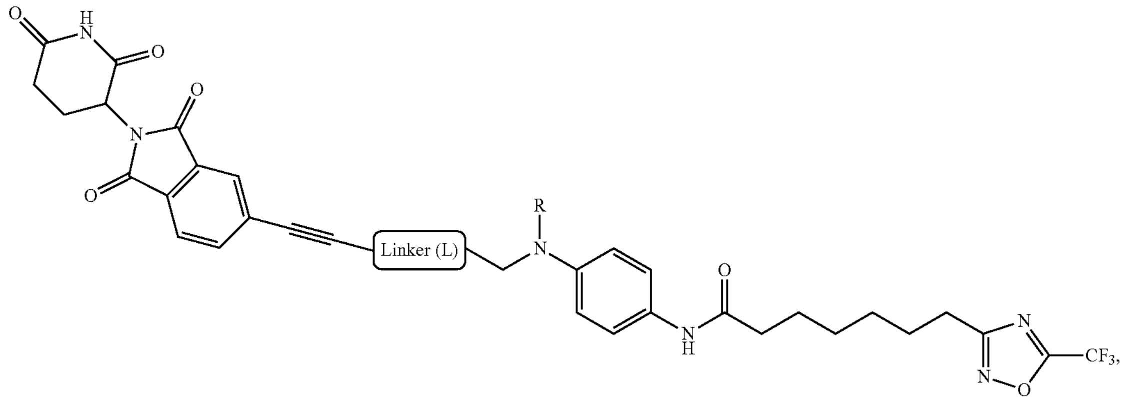
,
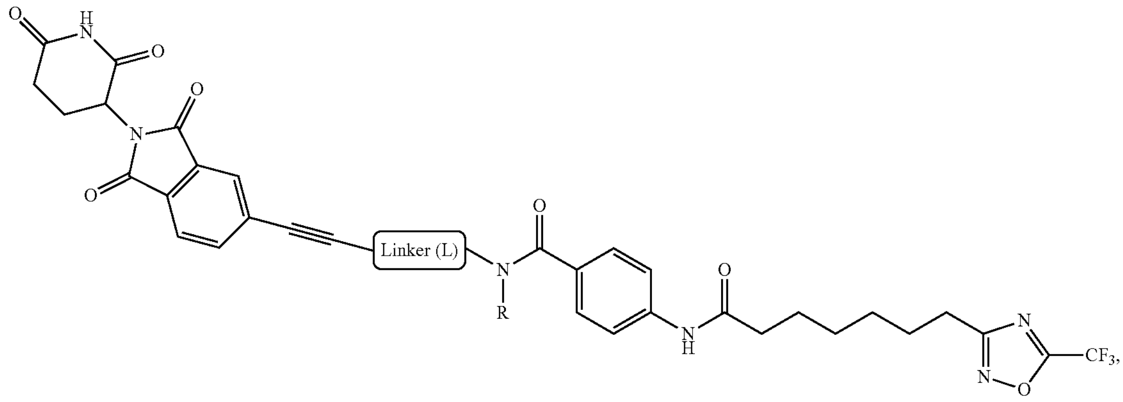
,

-continued
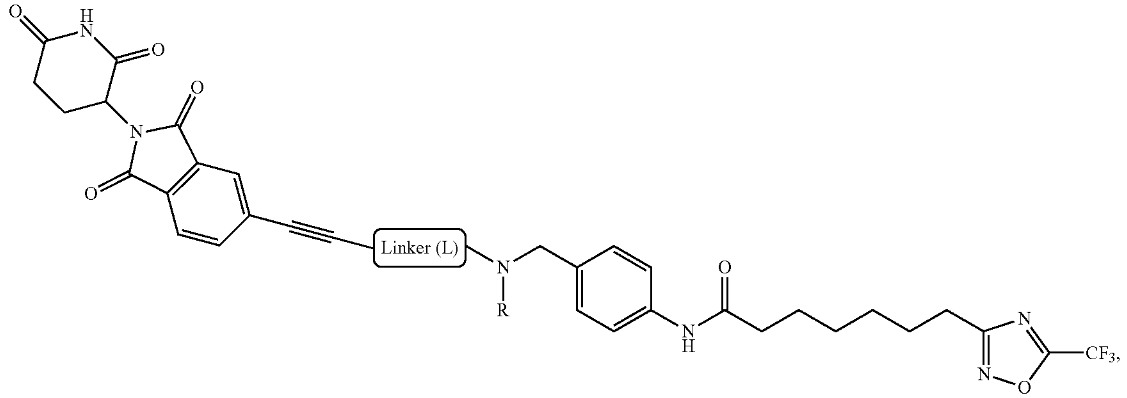
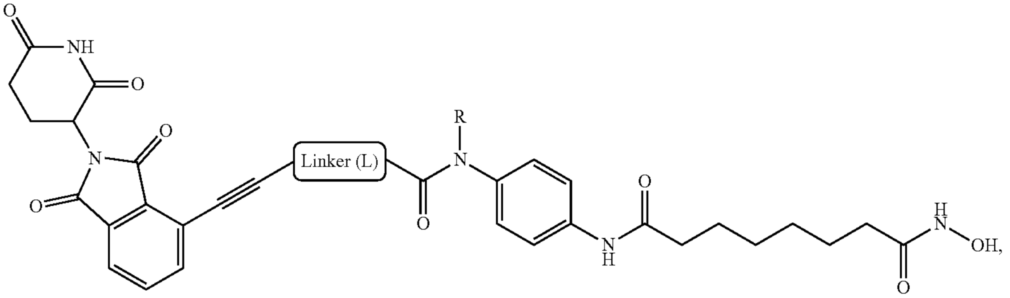
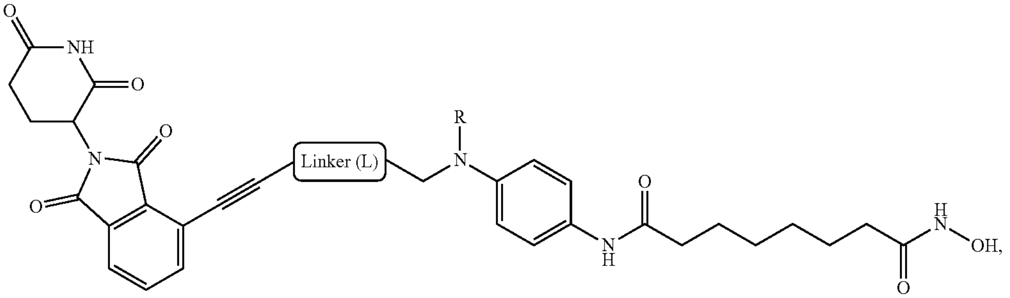
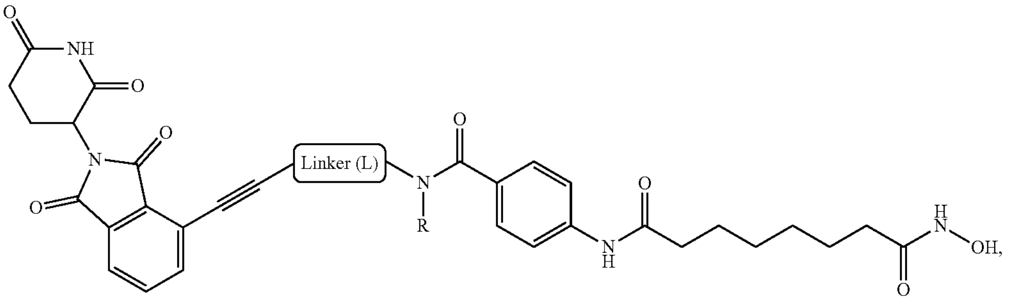
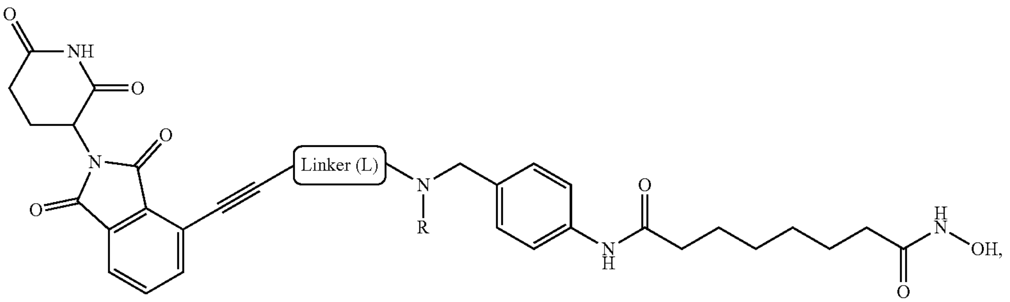

-continued
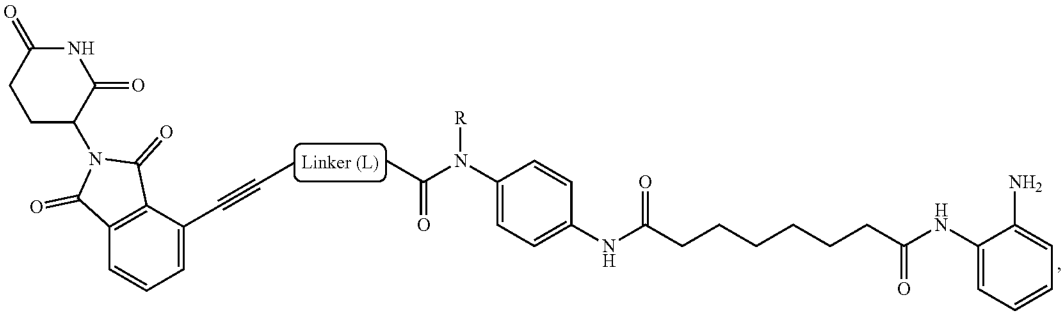
,
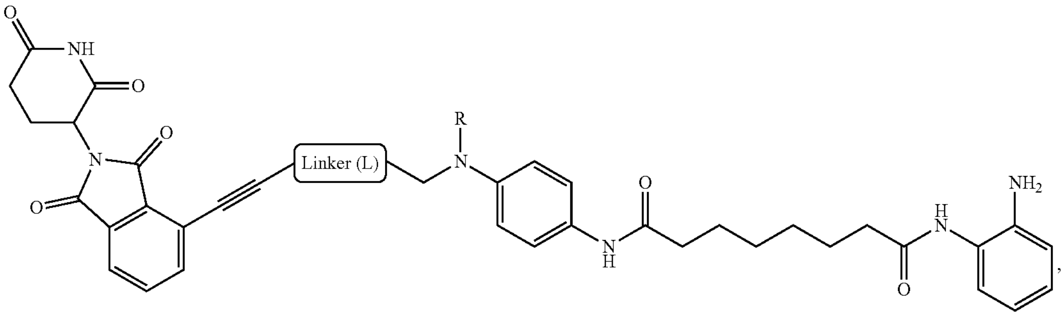
,
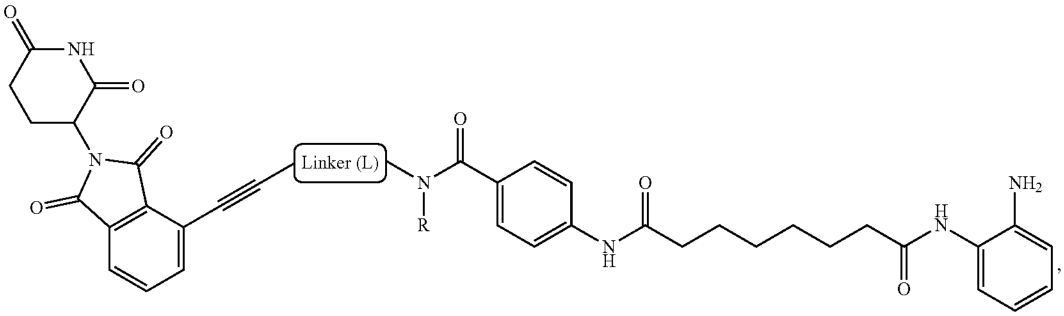
,
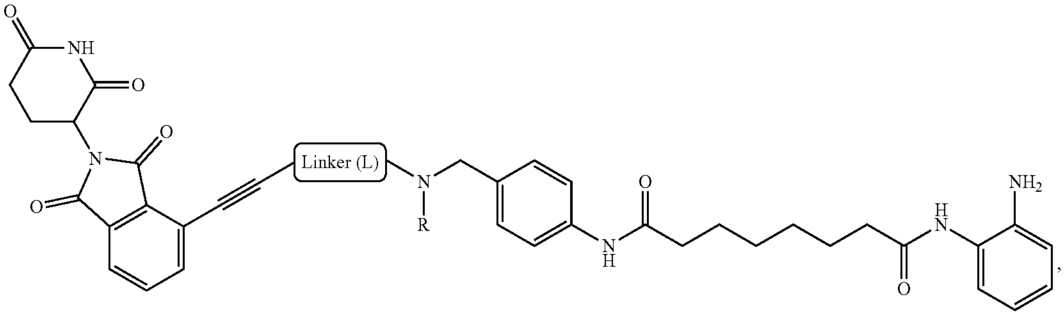
,
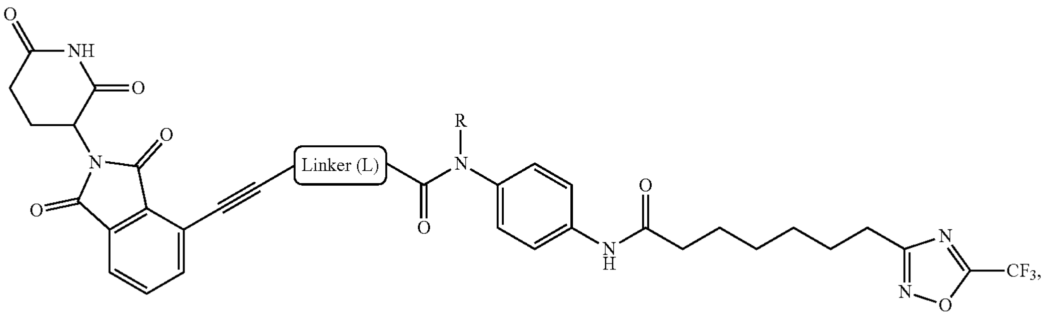
, -continued
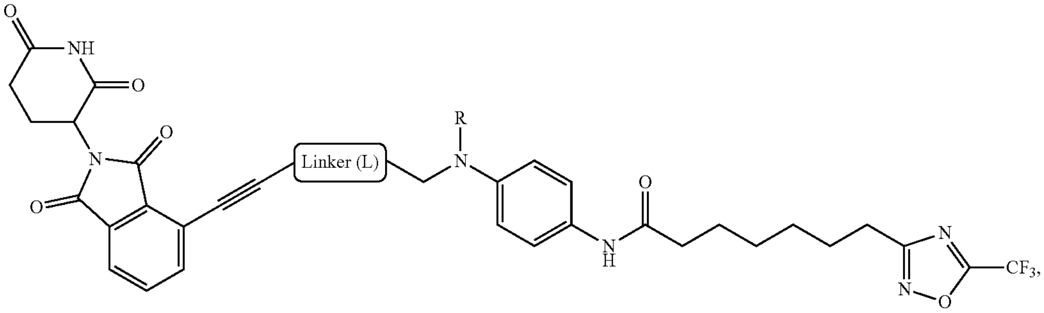
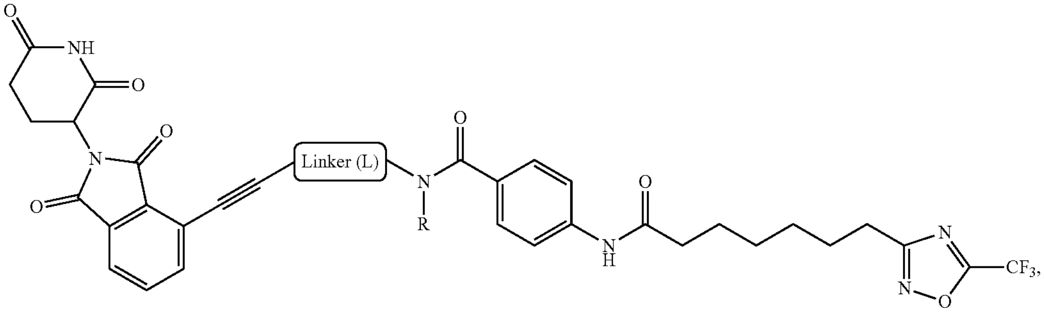
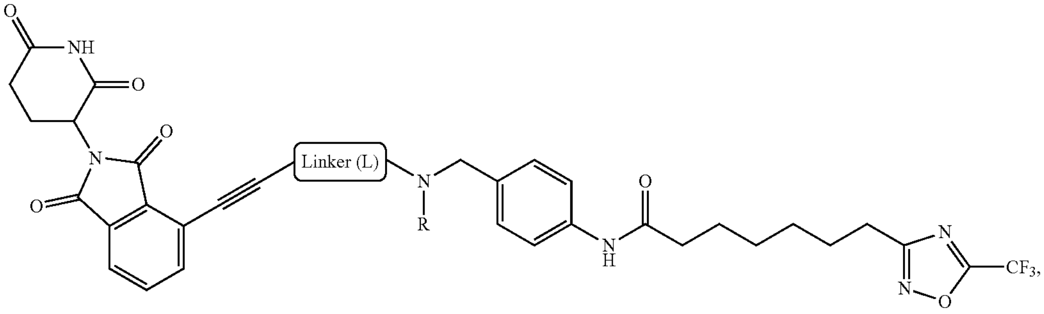
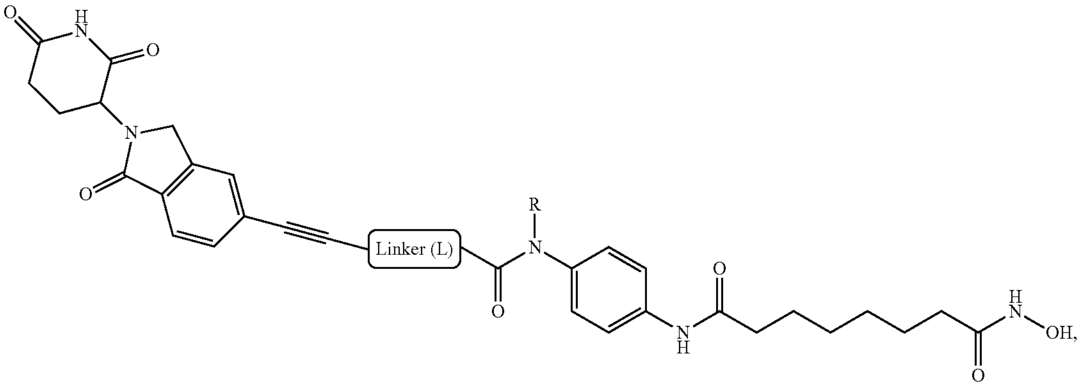
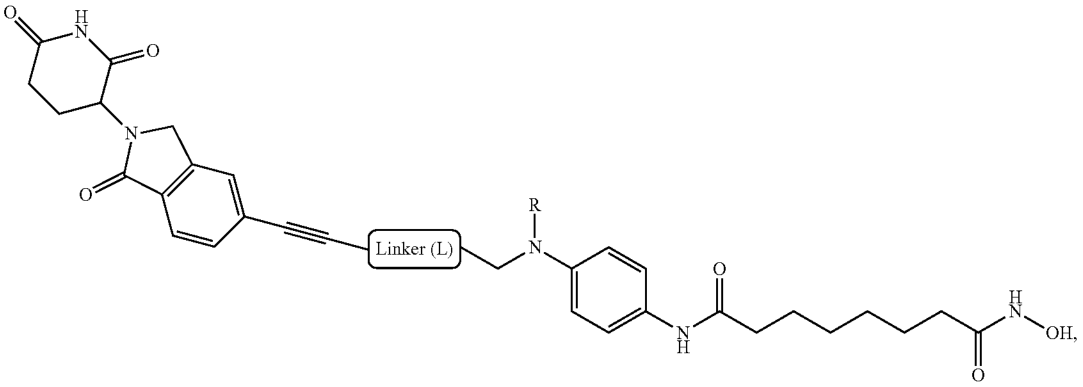

-continued
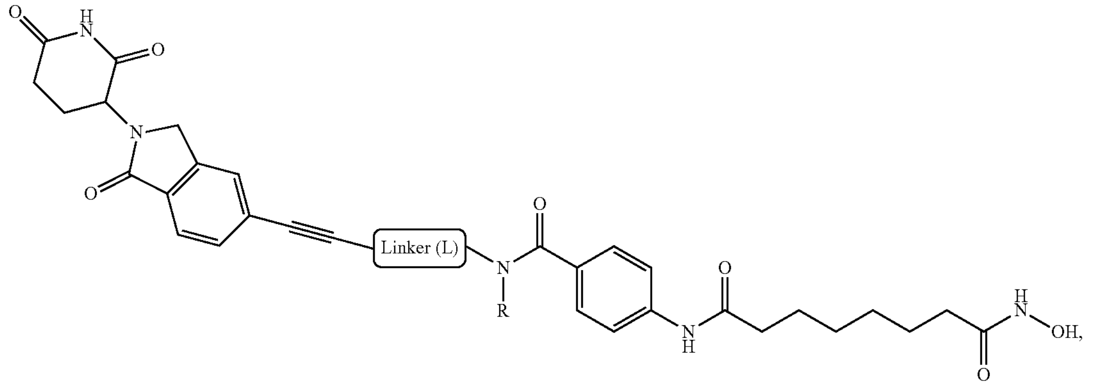
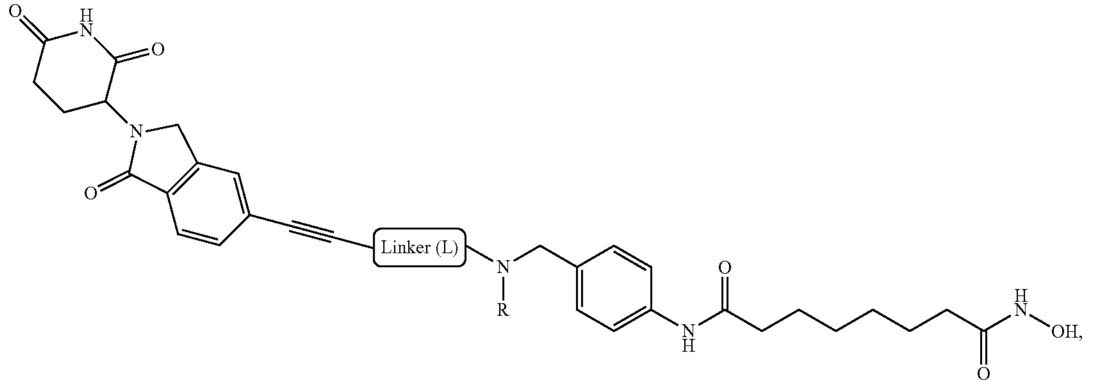
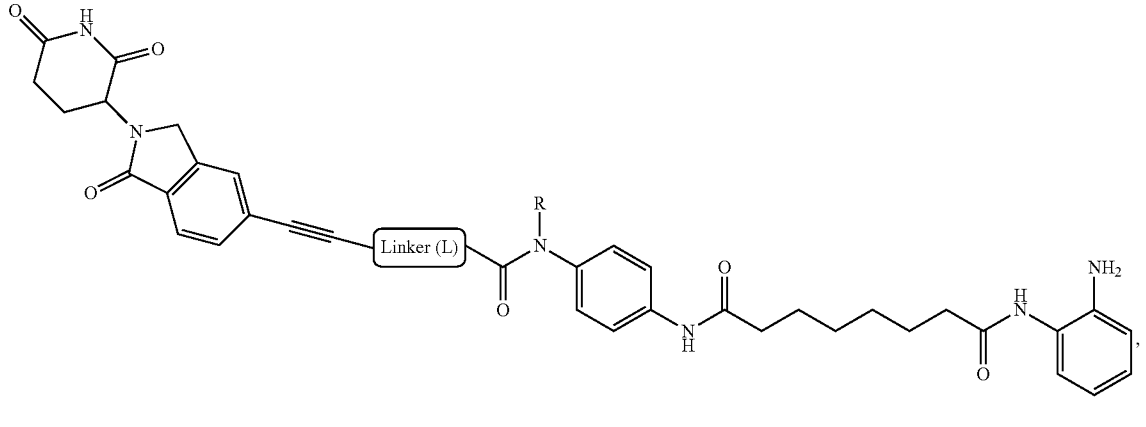
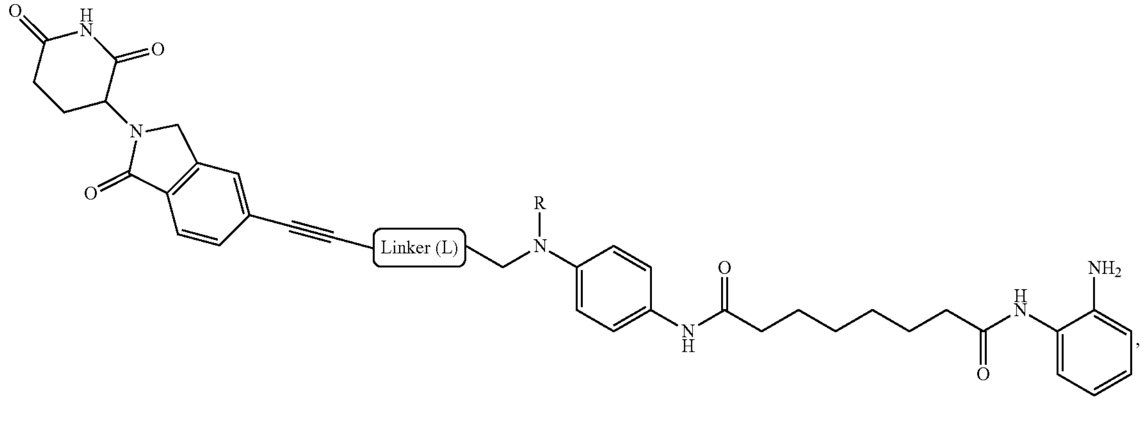

-continued
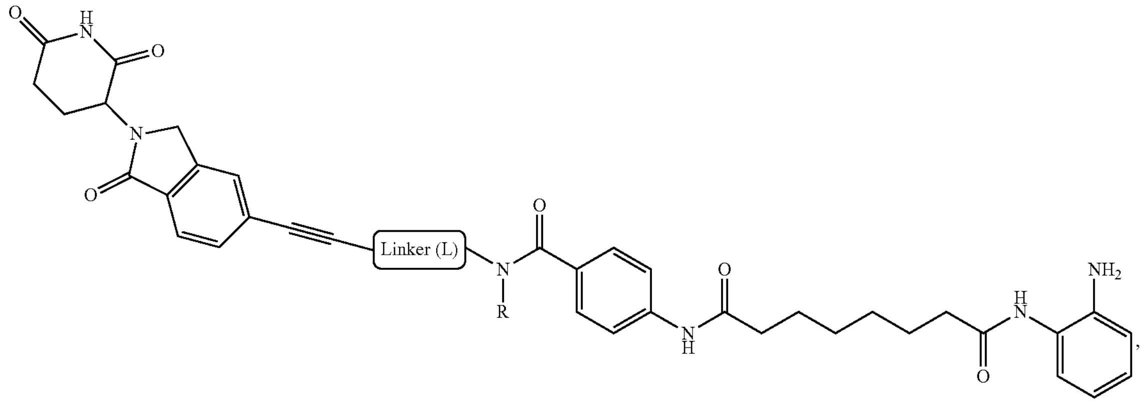
,
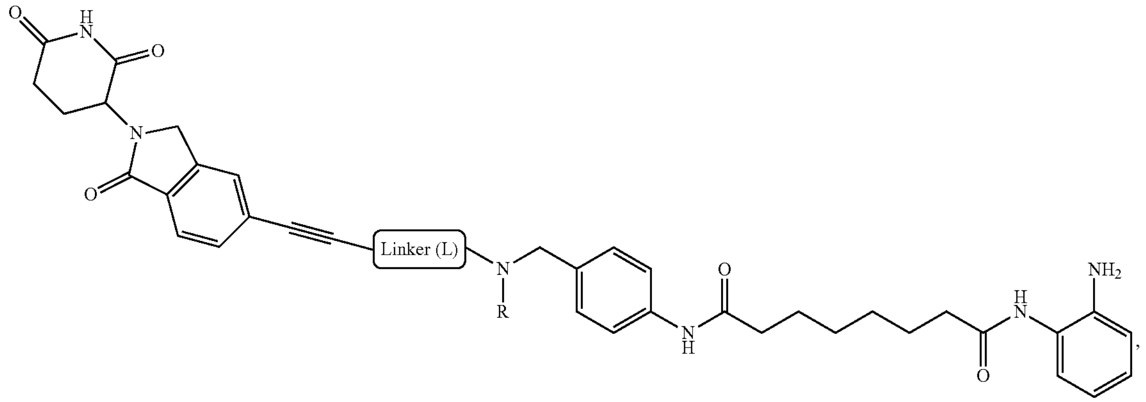
,
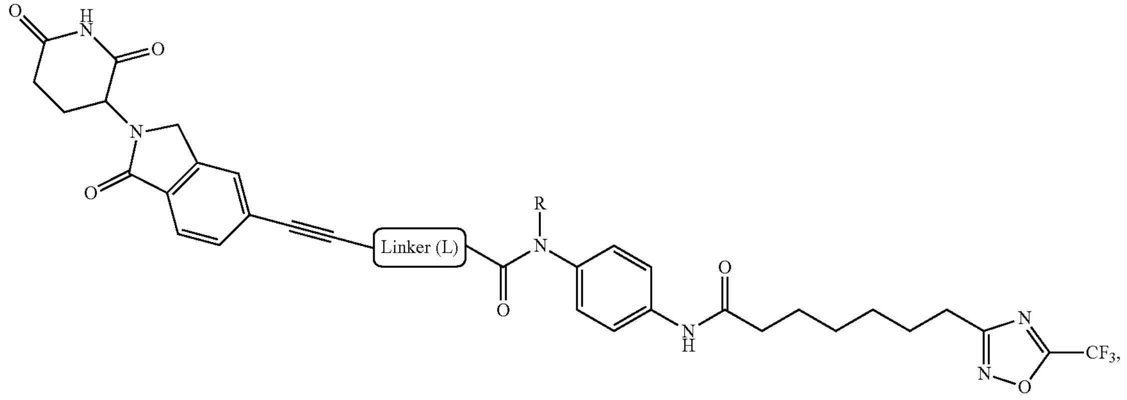
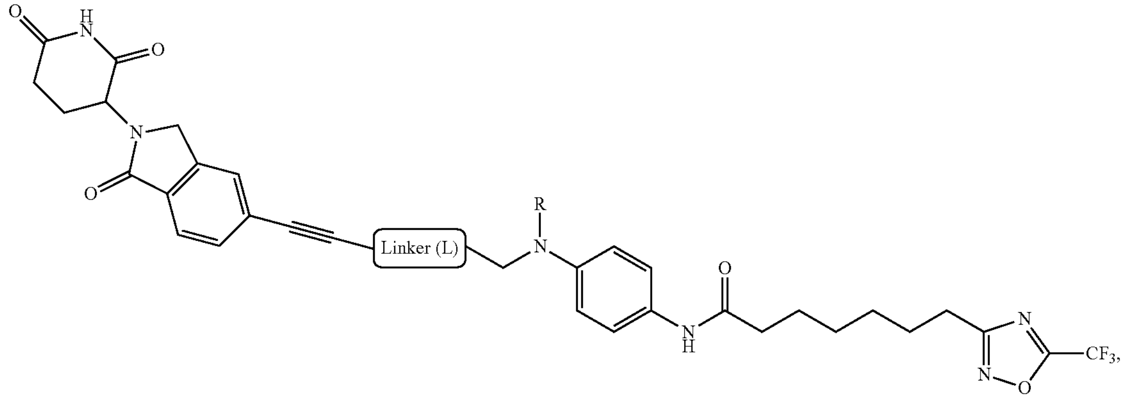

-continued
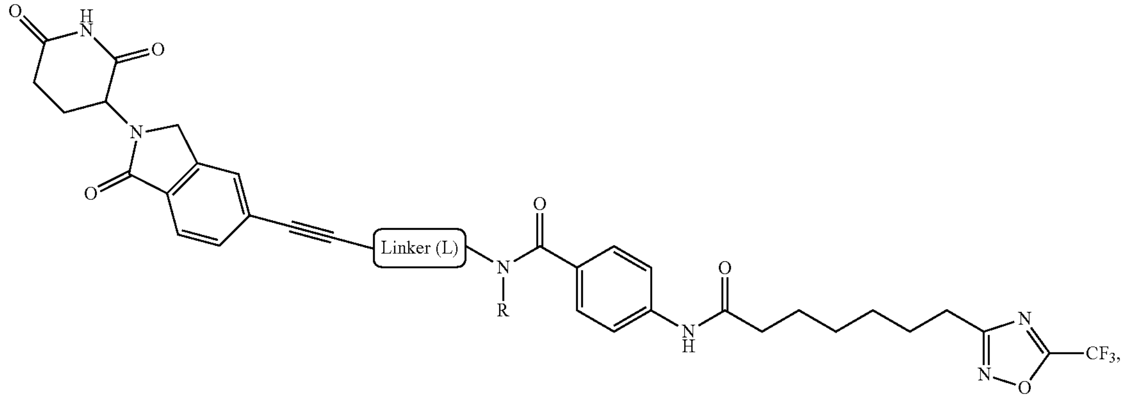
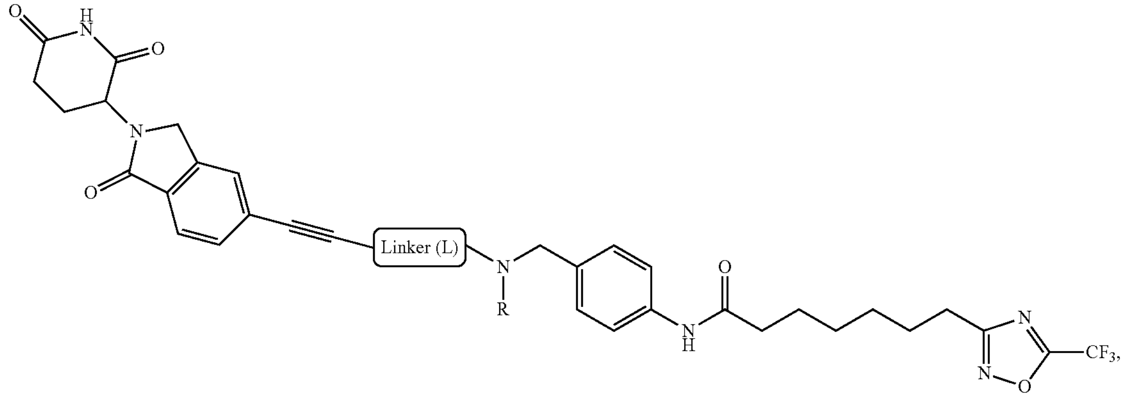
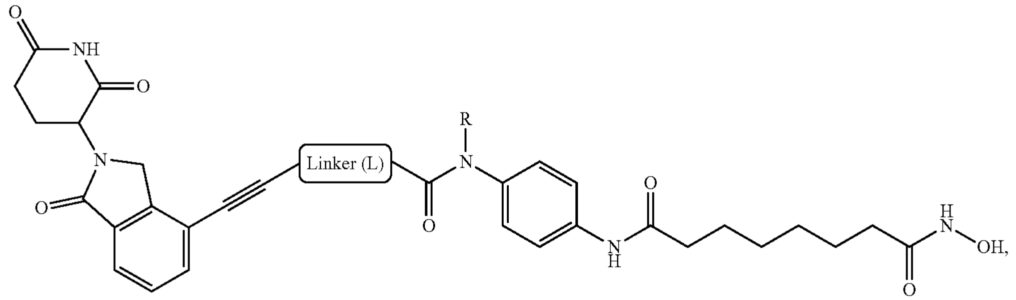
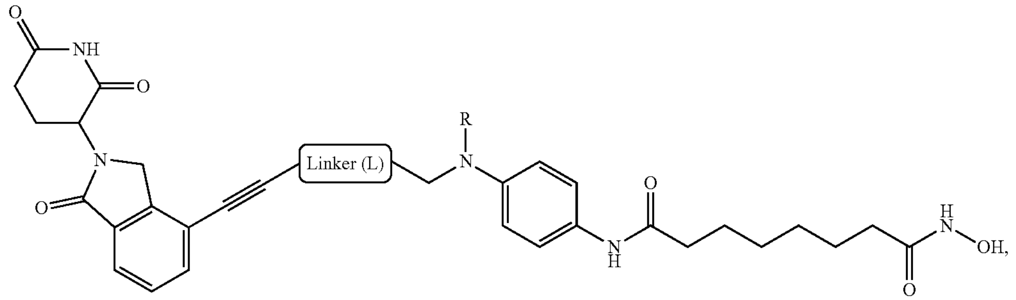
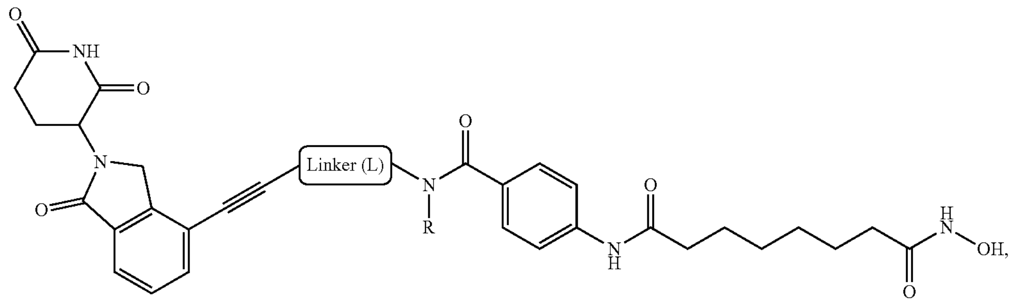

-continued
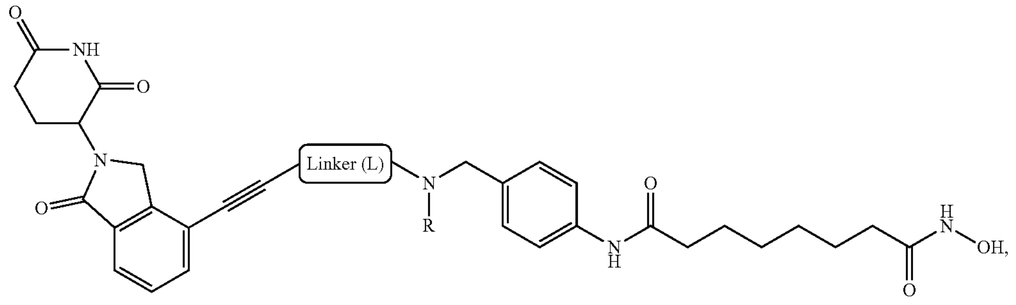
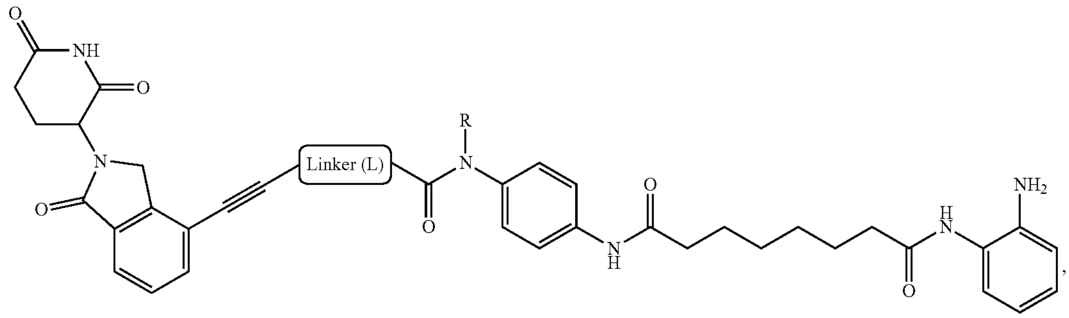
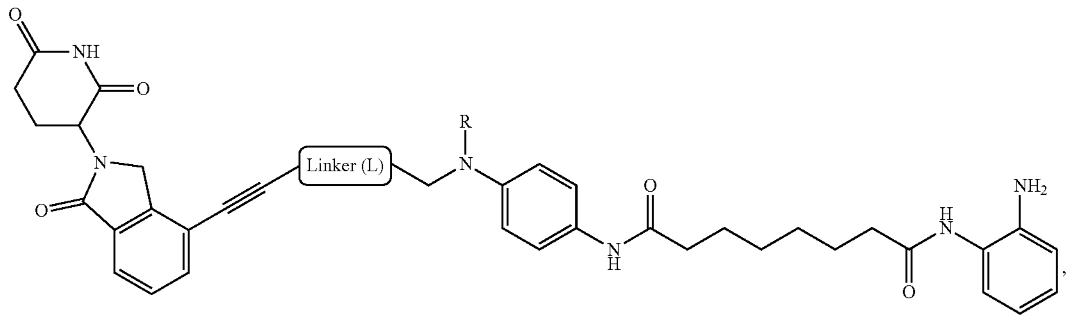
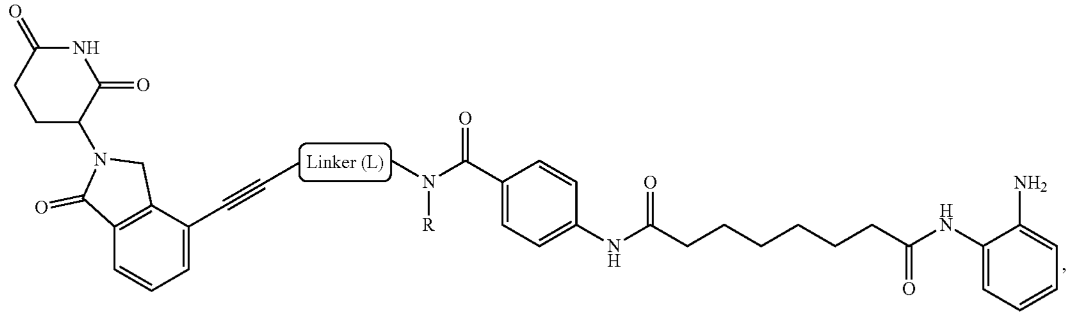
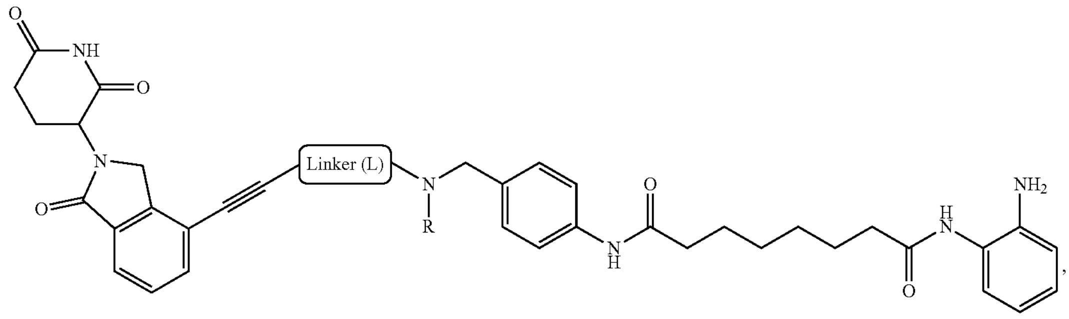

-continued

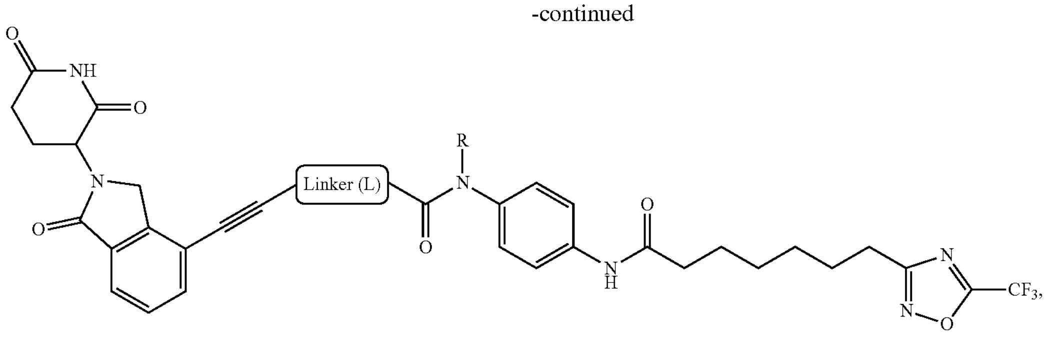

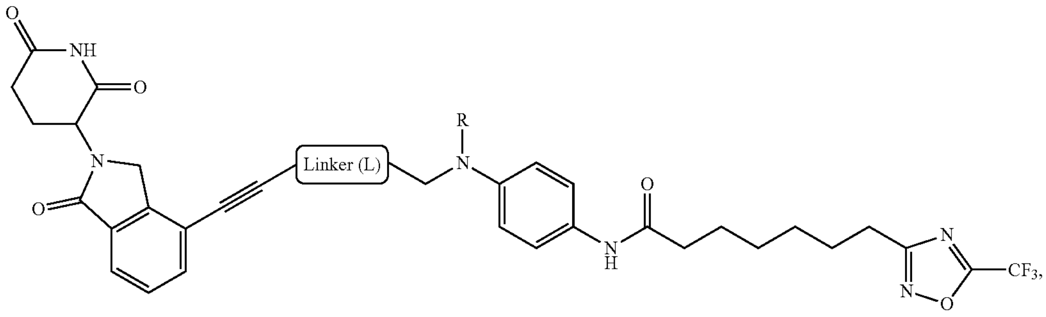

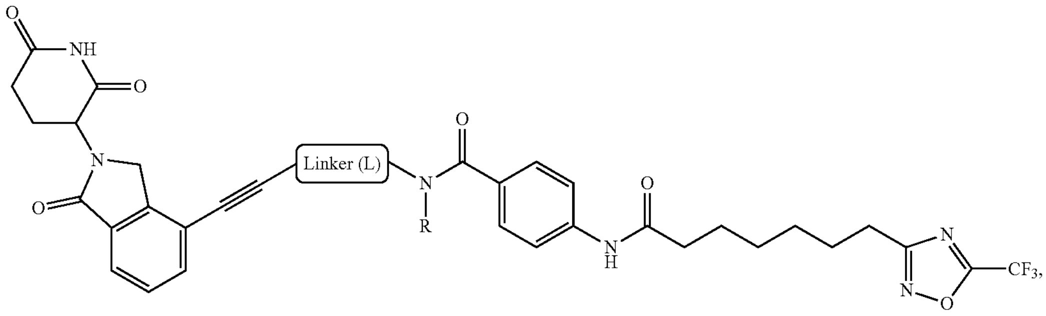

and

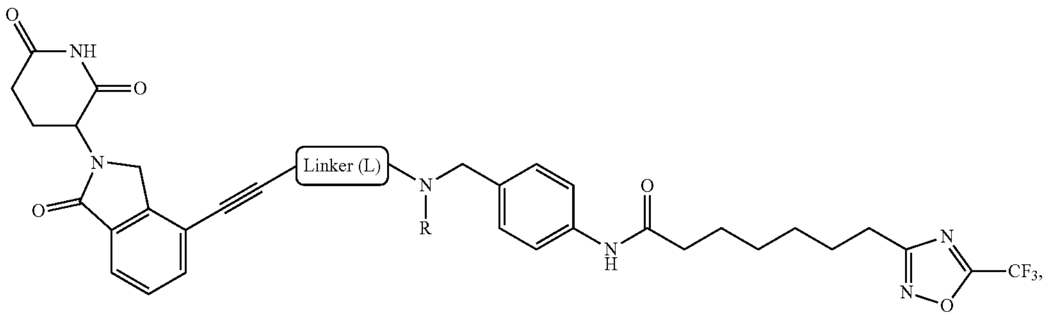

wherein $X_1$ is $CH_2$, NH, or O; and
R is H or Me;
or a pharmaceutically acceptable salt, or stereoisomer thereof.

Therefore, in some embodiments, bispecific compounds of this invention are represented by any structures generated by the combination of structures TL1 to TL2, Li to L10, and the structures of the degrons described herein, including D1 to D12, or a pharmaceutically acceptable salt or stereoisomer thereof.

In some embodiments, the bispecific compounds of the present invention have the following structures:

(1)
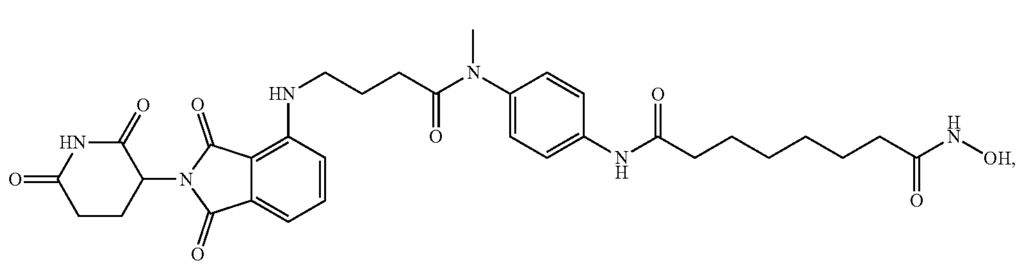
(2)
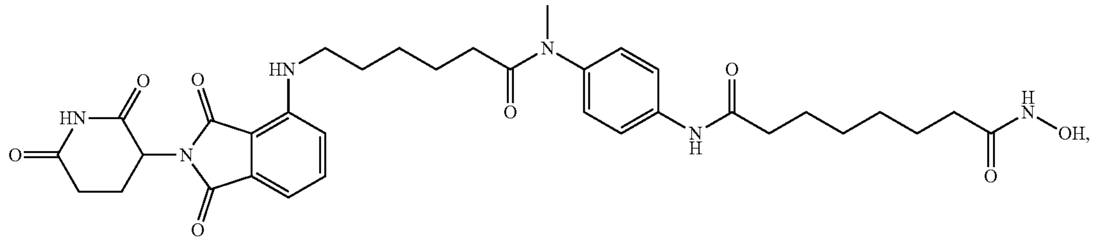
(3)
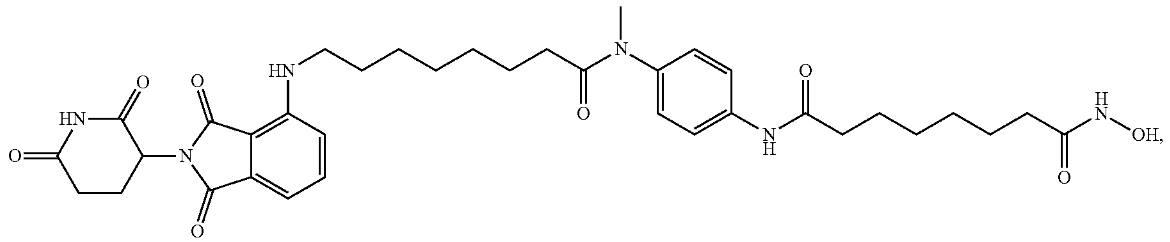
(4)
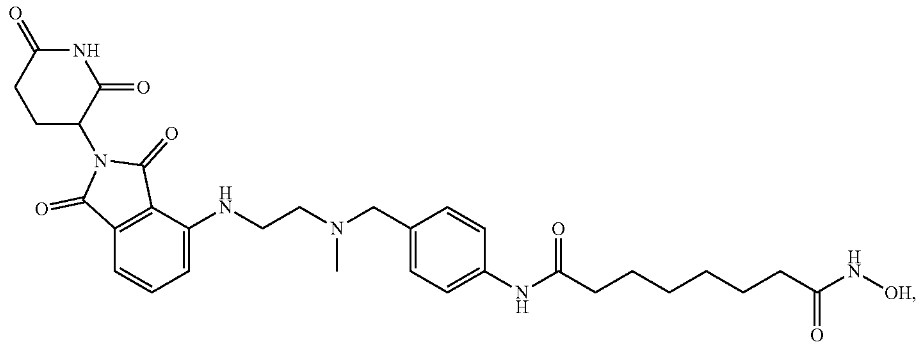
(5)
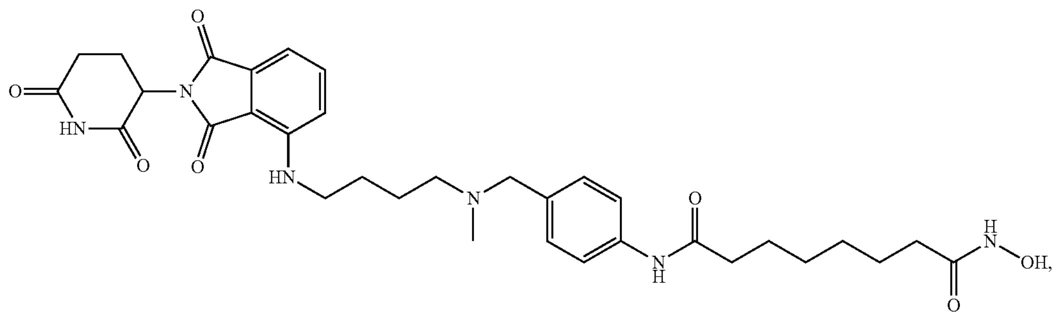

-continued (6)

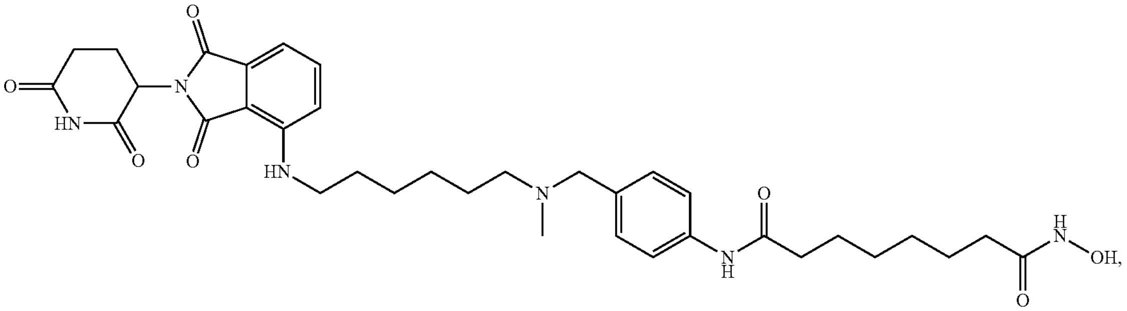

(7)

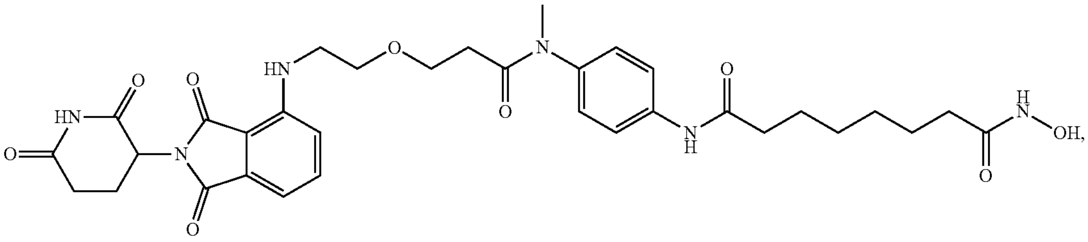

(8)

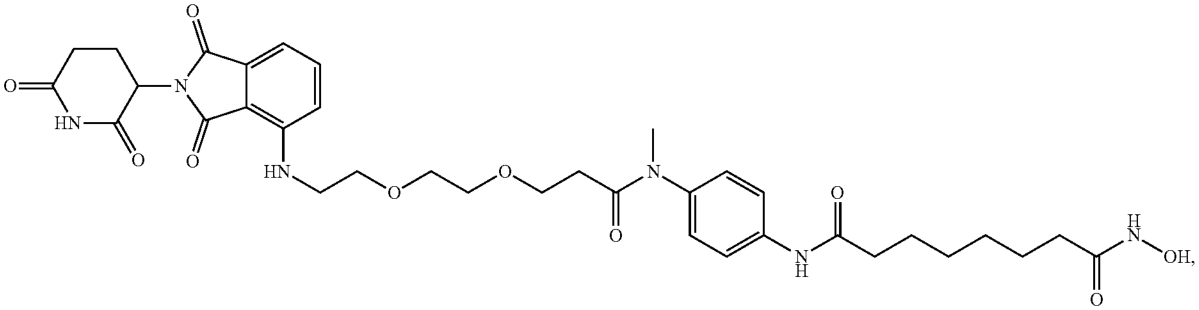

(9)

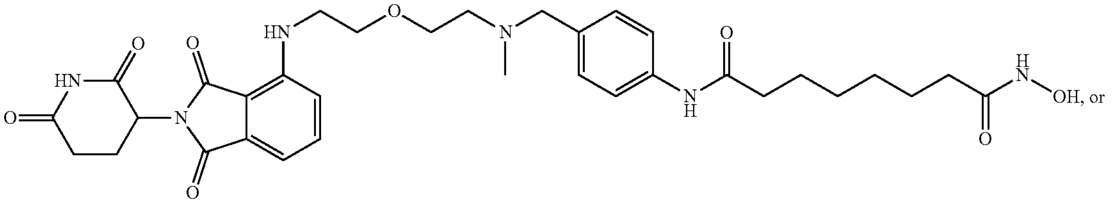

(10)

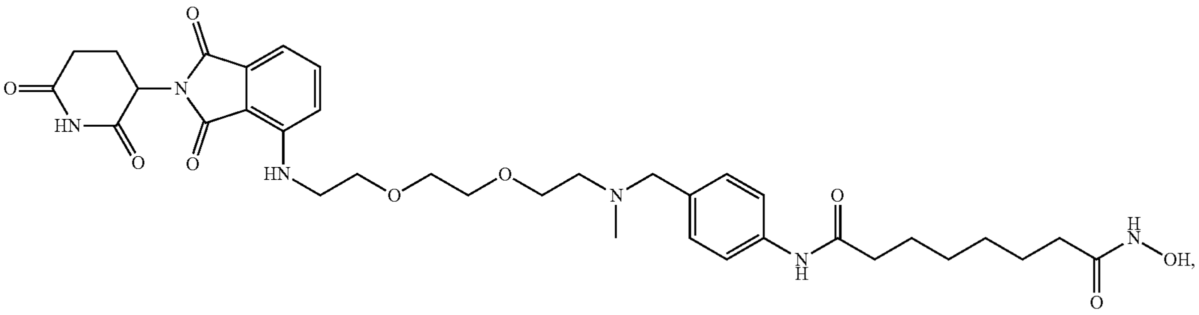

or a pharmaceutically acceptable salt or stereoisomer thereof.

Bispecific compounds of formula (I) may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

Bispecific compounds of formula (I) may have at least one chiral center and therefore may be in the form of a stereoisomer. As used herein, the term "stereoisomer" embraces all isomers of individual compounds that differ only in the orientation of their atoms in space. The term stereoisomer includes mirror image isomers (enantiomers which include the (R—) or (S—) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; therefore, for these compounds, administration of the compound in its (R—) form is considered equivalent to administration of the compound in its (S—) form. Accordingly, the compounds of the present invention may be made and used in the form of individual isomers and substantially free of other isomers, or in the form of a mixture of various isomers, e.g., racemic mixtures of stereoisomers.

In some embodiments, the bispecific compound of formula (I) is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^{2}H$, may afford certain therapeutic advantages resulting from greater metabolic stability, for example, increased in vivo half-life or reduced dosage requirements, and therefore may be advantageous in some circumstances.

In addition to the isotopic derivatives, the term "bispecific compounds of formula (I)" embraces N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the compounds presented herein are also considered to be disclosed herein.

Methods of Synthesis

In some embodiments, the present invention is directed to a method for making a bispecific compound of formula (I) or a pharmaceutically acceptable salt or stereoisomer thereof. Broadly, the inventive compounds or pharmaceutically-acceptable salts or stereoisomers thereof, may be prepared by any process known to be applicable to the preparation of chemically related compounds. Representative synthetic schemes are described in various working examples that illustrate non-limiting methods by which the bispecific compounds of the invention may be prepared.

Pharmaceutical Compositions

Another aspect of the present invention is directed to a pharmaceutical composition that includes a therapeutically effective amount of a bispecific compound of formula (I) or a pharmaceutically acceptable salt or stereoisomer thereof, and a pharmaceutically acceptable carrier. As known in the art, the term "pharmaceutically acceptable carrier" refers to a pharmaceutically acceptable material, composition or vehicle suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may further include one or more pharmaceutically acceptable excipients.

Broadly, bispecific compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, intradermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the bispecific compounds are formulated for oral or intravenous administration (e.g., systemic intravenous injection).

Accordingly, bispecific compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). The compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bispecific compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the bispecific compound is delivered in a targeted drug delivery system, for example, in a liposome coated with organ-specific antibody. In such embodiments, the liposomes are targeted to and taken up selectively by the organ.

The bispecific compounds may be formulated for buccal or sublingual administration, examples of which include tablets, lozenges and gels.

The bispecific compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bispecific compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bispecific compound of formula (I) or a pharmaceutically acceptable salt or a stereoisomer thereof; or a composition including a bispecific compound of formula (I) or a pharmaceutically acceptable salt or a stereoisomer thereof, that is effective in producing the desired therapeutic response in a particular patient suffering from a disease or disorder characterized or mediated by aberrant HDAC6 activity. The term "therapeutically effective amount" therefore includes the amount of a bispecific compound or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., neuroblastoma) cells, or reduces the amount of HDAC6 in diseased cells.

The total daily dosage of the compounds and usage thereof may be decided in accordance with standard medical practice, e.g., by the attending physician using sound medical judgment. The specific therapeutically effective dose for any particular subject may depend upon one or more of a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the compound; and like factors well known in the medical arts (see, for example, *Goodman and Gilman's. The Pharmacological Basis of Therapeutics,* 10th Edition, A. Gilman, J. Hardman and L. Limbird, eds., McGraw-Hill Press, 155-173, 2001).

Bispecific compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of the compound (e.g., 1, 2, 2.5, 3, 4, 5, 10, 15, 20, 25, 50, 100, 150, and 200 mg). In some embodiments, the compound may be administered at a dose in range from about 0.01 mg to about 200 mg/kg of body weight per day. In some embodiments, a dose of from 0.1 to 100, e.g., from 1 to 30 mg/kg per day in one or more dosages per day may be effective. By way of example, a suitable dose for oral administration may be in the range of 1-30 mg/kg of body weight per day, and a suitable dose for intravenous administration may be in the range of 1-10 mg/kg of body weight per day. In some embodiments, individual dosages may be formulated to contain the desired dosage amount depending upon the number of times the compound is administered per day.

Methods of Use

In some aspects, the present invention is directed to methods of treating diseases or disorders involving aberrant (e.g., dysfunctional or dysregulated) HDAC6 activity, that entails administration of a therapeutically effective amount of a bispecific compound formula (I) or a pharmaceutically acceptable salt or stereoisomer thereof, to a subject in need thereof.

The diseases or disorders may be said to be characterized or mediated by aberrant HDAC6 activity (e.g., elevated levels of HDAC6 or otherwise functionally abnormal HDAC6 relative to a non-pathological state). A "disease" is generally regarded as a state of health of a subject wherein the subject cannot maintain homeostasis. If the disease is not ameliorated then the subject's health continues to deteriorate. In contrast, a "disorder" (or "condition") in a subject is a state of health in which the subject is able to maintain homeostasis, but in which the subject's state of health is less favorable than it would be in the absence of the disorder. Left untreated, a disorder does not necessarily cause a further decrease in the animal's state of health.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" the treatment may be suffering from or suspected of suffering from a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Therefore, subjects suffering from a specific disease or disorder versus subjects suspected of suffering from a specific disease or disorder are not necessarily two distinct groups.

In some embodiments, the inventive bispecific compounds may be useful in the treatment of cell proliferative diseases and disorders (e.g., cancer or benign neoplasms). As used herein, the term "cell proliferative disease or disorder" refers to the conditions characterized by aberrant cell growth, or both, including noncancerous conditions such as neoplasms, precancerous conditions, benign tumors, and cancer.

Exemplary types of non-cancerous (e.g., cell proliferative) diseases or disorders that may be amenable to treatment with bispecific compounds of formula (I) include inflammatory diseases and conditions, autoimmune diseases, neurodegenerative diseases, heart diseases, viral diseases, chronic and acute kidney diseases or injuries, metabolic diseases, and allergic and genetic diseases.

In some embodiments, the bispecific compounds may be useful in the treatment of neurodegenerative diseases and disorders. As used herein, the term "neurodegenerative diseases and disorders" refers to the conditions characterized by progressive degeneration or death of nerve cells, or both, including problems with movement (ataxias), or mental functioning (dementias). Representative examples of such diseases and disorders include Alzheimer's disease (AD) and AD-related dementias, Parkinson's disease (PD) and PD-related dementias, prion disease, motor neuron diseases (MND), Huntington's disease (HD), Pick's syndrome, spinocerebellar ataxia (SCA), spinal muscular atrophy (SMA), primary progressive aphasia (PPA), amyotrophic lateral sclerosis (ALS), traumatic brain injury (TBI), multiple sclerosis (MS), dementias (e.g., vascular dementia (VaD), Lewy body dementia (LBD), semantic dementia, and frontotemporal lobar dementia (FTD).

In some embodiments, the bispecific compounds may be useful in the treatment of autoimmune diseases and disorders. As used herein, the term "autoimmune disease" refers to the condition where the immune system produces antibodies that attack normal body tissues. Representative examples of such diseases include Sjogren's syndrome, Hashimoto thyroiditis, rheumatoid arthritis, juvenile (type 1) diabetes, polymyositis, scleroderma, Addison disease, lupus including systemic lupus erythematosus, vitiligo, pernicious anemia, glomerulonephritis, pulmonary fibrosis, celiac disease, polymyalgia rheumatica, multiple sclerosis, ankylosing spondylitis, alopecia areata, vasculitis, and temporal arteritis.

In other embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors. In some embodiments, the cancer is a solid tumor.

Representative examples of cancers include adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with the compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver, brain, lung, colon, pancreas, prostate, ovary, breast, skin, and endometrium.

As used herein, "cell proliferative diseases or disorders of the hematological system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may therefore include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 rearrangement, lung adenocarcinoma, and squamous cell lung carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

In some embodiments, the cancer is breast cancer, prostate cancer, pancreatic cancer, laryngeal cancer, Hodgkin's lymphoma, neuroblastoma, polycythemia vera, T-cell lymphoma, multiple myeloma, leukemia, hepatocellular carcinoma, non-small cell lung cancer, or essential thrombocythemia.

Bispecific compounds of formula (I) may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which were unsuccessful or partially successful but who became unresponsive or intolerant to the particular treatment. Therapy may also be given as an adjuvant treatment, i.e., to prevent reoccurrence of cancer in patients with no currently detectable disease or after surgical removal of a tumor. Therefore, in some embodiments, the compounds may be administered to a patient who has received another therapy, such as chemotherapy, radioimmunotherapy, surgical therapy, immunotherapy, radiation therapy, targeted therapy or any combination thereof.

The methods of the present invention may entail administration of bispecific compounds of formula (I) or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails at least one 28-day cycle which includes daily administration for 3 weeks (21 days) followed by a 7-day "off" period. In other embodiments, the compound may be dosed twice a day (BID) over the course of two and a half days (for a total of 5 doses) or once a day (QD) over the course of two days (for a total of 2 doses). In other embodiments, the compound may be dosed once a day (QD) over the course of five days.

Combination Therapy

Bispecific compounds of formula (I) may be used in combination or concurrently with at least one other active agent, e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Therefore, if given sequentially, at the onset of administration of the second compound, the first of the two compounds is in some cases still detectable at effective concentrations at the site of treatment. The sequence and time interval may be determined such that they can act together (e.g., synergistically) to provide an increased benefit than if they were administered otherwise. For example, the therapeutics may be administered at the same time or sequentially in any order at different points in time; however, if not administered at the same time, they may be administered sufficiently close in time so as to provide the desired therapeutic effect, which may be in a synergistic fashion. Therefore, the terms are not limited to the administration of the active agents at exactly the same time.

In some embodiments, the treatment regimen may include administration of a bispecific compound of formula (I) in combination with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001*; Physician's Desk Reference 60th ed.,* 2006. For example, anti-cancer agents that may be suitable for use in combination with the inventive bispecific compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and chimeric antigen receptor T-cell (CAR-T) therapy.

In some embodiments, a bispecific compound of formula (I) and the additional (e.g., anticancer) therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more (e.g., anticancer) therapeutics may be administered within the same patient visit.

In some embodiments involving cancer treatment, the bispecific compound of formula (I) and the additional anticancer agent or therapeutic are cyclically administered. Cycling therapy involves the administration of one anticancer therapeutic for a period of time, followed by the administration of a second anticancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, a bispecific compound of the present invention may be used in combination other anticancer agents, examples of which include Durvalumab (e.g., for NSCLC), LEE011 (e.g., for NSCLC), Cisplatin, Gemcitabine Hydrochloride, or Paclitaxel Albumin-Stabilized Nanoparticle Formulation (e.g., for advanced malignant solid neoplasm, metastatic pancreatic adenocarcinoma, and Stage III and Stage IV pancreatic cancer), Trametinib (e.g., for NSCLC and neuroblastoma), Axitinib (e.g., for advanced solid tumors), Cobimetinib (e.g., for NSCLC), Brentuximab Vedotin (e.g., for ALK-Positive anaplastic large cell lymphoma, CD30-Positive neoplastic cells, and systemic anaplastic large cell lymphoma), Nivolumab (e.g., for ALK-positive NSCLC), Everolimus (e.g., for head and neck cancer), Pemetrexed, Cisplatin, and Carboplatin (e.g., for NSCLC), Pemetrexed, Cisplatin, and Docetaxel (e.g., for NSCLC), Pemetrexed and Docetaxel (e.g., for NSCLC), Bevacizumab (e.g., for NSCLC), and with Atezolizumab and Erlotinib (e.g., for NSCLC). In some embodiments, a bispecific compound of the present invention may be used alone or in combination with any one or more of Alectinib, Brigatinib, Crizotinib, and Ceritinib (e.g., for non-metastatic or metastatic lung cancer, NSCLC, ALK-positive NSCLC, NSCLC harboring ROS1 Rearrangement, Lung Adenocarcinoma, and Squamous Cell Lung Carcinoma).

Pharmaceutical Kits

The present compounds and/or compositions containing them may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a bispecific compound of formula (I) or a pharmaceutical composition thereof. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

These and other aspects of the present invention will be further appreciated upon consideration of the following Examples, which are intended to illustrate certain particular embodiments of the invention but are not intended to limit its scope, as defined by the claims.

Example 1: General

Unless otherwise noted, reagents and solvents were used as received from commercial suppliers. All reactions were monitored using a Waters® Acquity ultra performance liquid chromatography/mass spectrometry (UPLC/MS) system using Acquity UPLC® BEH C18 column (2.1×50 mm, 1.7 μm particle size). UPLC method A: solvent gradient=90% A at 0 min, 5% A at 1.8 min; method B: solvent gradient=85% A at 0 min, 1% A at 1.8 min; solvent A=0.1% formic acid in $H_2O$; solvent B=0.1% formic acid in acetonitrile; flow rate: 0.6 mL/min. Purification of reaction products was carried out by flash chromatography using CombiFlash®Rf with Teledyne ISCO RediSep® normal-phase silica flash columns; or Waters® high performance liquid chromatography (HPLC) system using SunFire™ C18 column (19×100 mm, 5 μm particle size): solvent gradient 0% to 99% acetonitrile in $H_2O$ (0.035% trifluoroacetic acid (TFA) as additive); flow rate: 20 mL/min, or SunFire™ C18 column (30×250 mm, 5 μm particle size): solvent gradient 0% to 99% acetonitrile in $H_2O$ (0.035% TFA as additive); flow rate: 40 mL/min. The purity of all compounds was over 95% and was analyzed with Waters® UPLC system. $^1H$ NMR and $^{13}C$ NMR spectra were obtained using Bruker Avance III spectrometers (500 MHz for $^1H$, and 125 MHz for $^{13}C$). Chemical shifts are reported relative to deuterated methanol (δ=3.31) or dimethyl sulfoxide (DMSO) (δ=2.50) for $^1H$ NMR. Spectra are given in ppm (δ) and as br=broad, s=singlet, d=doublet, t=triplet, q=quartet, m=multiplet and coupling constants J are reported in Hertz.

Example 2: General Procedure I

Synthesis of $N^1$-(4-(6-((2-(2,6-dioxopiperidin-3-yl)-1,3-dioxoisoindolin-4-yl)amino)-N-methylhexanamido)phenyl)-$N^8$-hydroxyoctanediamide (2)

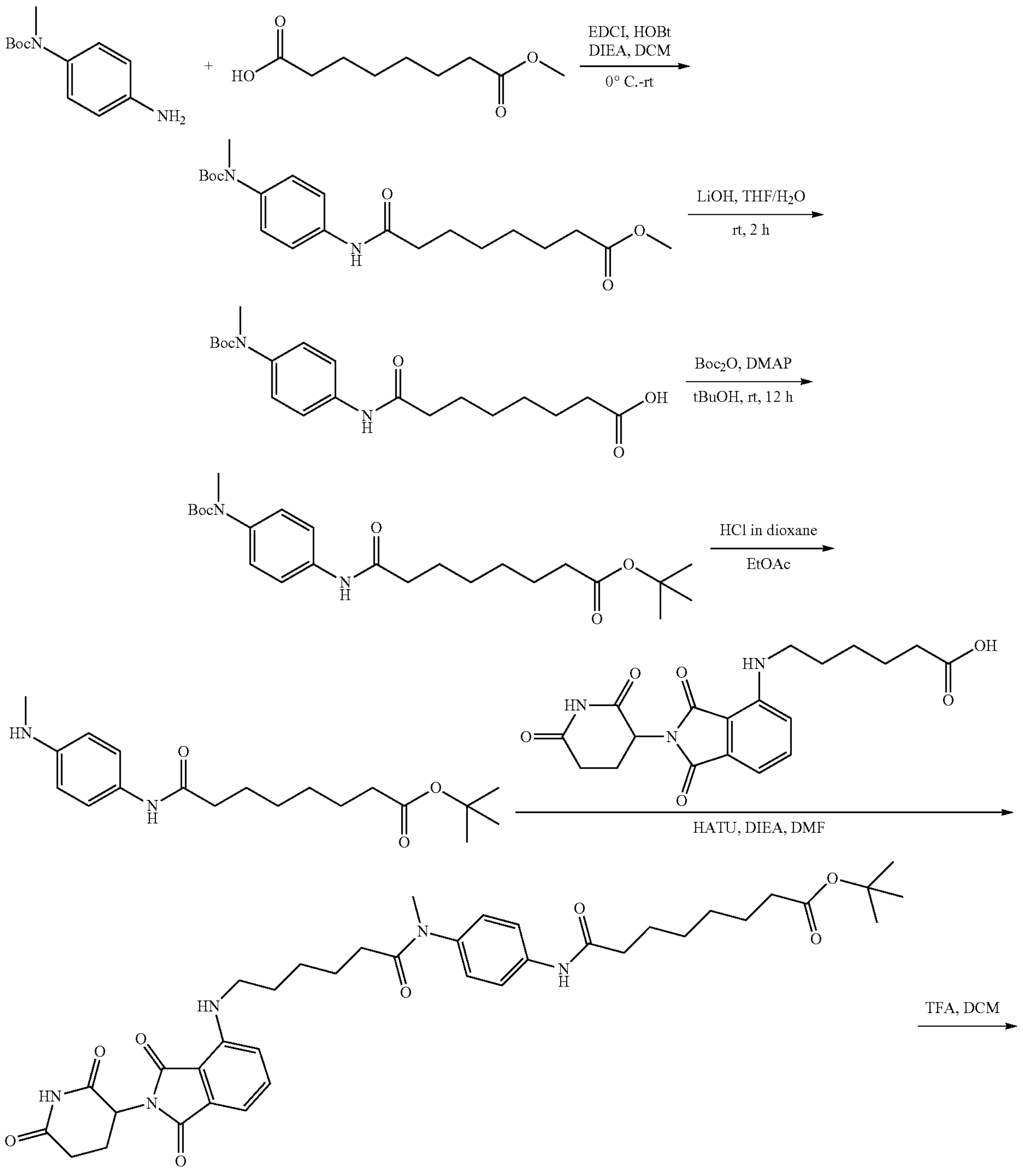

-continued

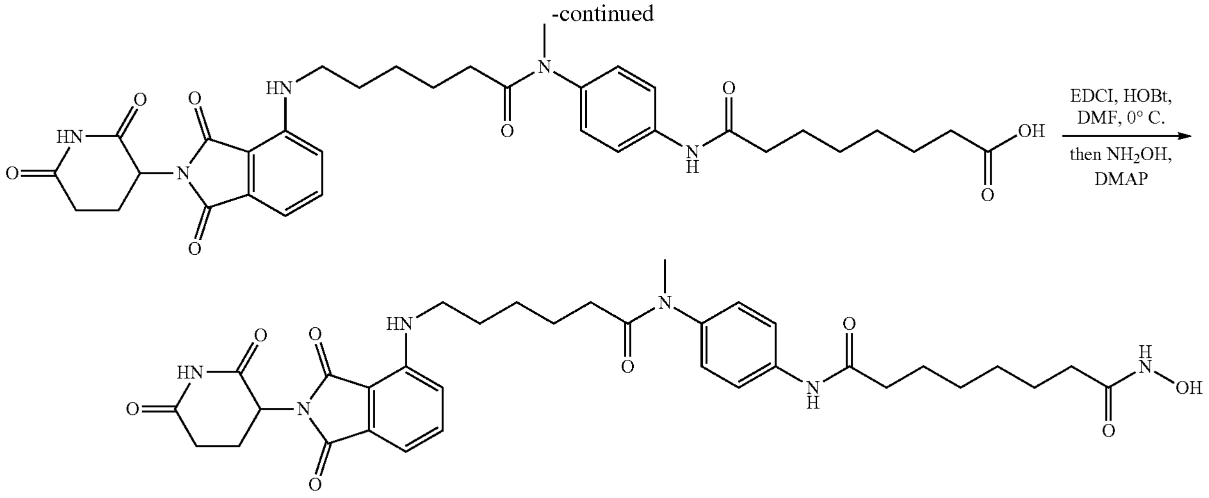

2

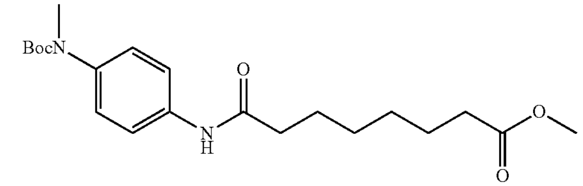 [SMILES: COC(=O)CCCCCCC(=O)Nc1ccc(N(C)C(=O)OC(C)(C)C)cc1]

Methyl 8-((4-((tert-butoxycarbonyl)(methyl)amino) phenyl)amino)-8-oxooctanoate To a mixture of tert-butyl (4-aminophenyl)(methyl)carbamate (1 eq, 1 g) and 8-methoxy-8-oxooctanoic acid (1 eq, 847 mg) in dichloromethane (18 mL) was added 1-Ethyl-3-(3-dimethylaminopropyl)carbodiimide (EDCI) (1.1 eq, 951 mg), hydroxybenzotriazole (HOBt) (1.1 eq, 669 mg) and N,N-diisopropylethylamine (DIEA) (1.5 eq, 1.17 mL) at 0° C. The mixture was warmed to room temperature and stirred for an additional 2 h. The reaction was monitored by UPLC-MS, once the reaction was completed, the mixture was quenched with $H_2O$ and extracted with three times with dichloromethane. The organic layer was combined and washed with brine, dried over $Na_2SO_4$, filtered and concentrated in vacuo. The residue was purified using ISCO (hexanes/ethyl acetate, 20%-80%) to yield the title compound (1.49 g, 84%). UPLC-MS RT: 1.45 min (Method A), Mass m/z: (393.37, M+1).

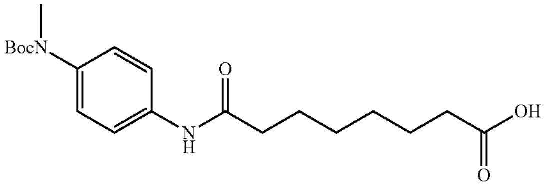 [SMILES: CN(C(=O)OC(C)(C)C)c1ccc(NC(=O)CCCCCCC(=O)O)cc1]

8-((4-((tert-butoxycarbonyl)(methyl)amino)phenyl) amino)-8-oxooctanoic acid

Methyl 8-((4-((tert-butoxycarbonyl)(methyl)amino)phenyl)amino)-8-oxooctanoate (1 eq, 1.34 g) was dissolved in a mixture of tetrahydrofuran (THF) and $H_2O$ (1:1, 30 mL, 0.1 M), the mixture was treated with LiOH (2 eq, 287 mg) and was stirred at room temperature for 4 h. Once the reaction was completed, the mixture was acidified with 2N HCl. The precipitate was filtered, washed with cold $H_2O$ and dried with a stream of nitrogen. The residue was used without further purification (1.07 g, 83%). UPLC-MS RT: 1.23 min (Method A), Mass m/z: (322.87, M-tBu+1).

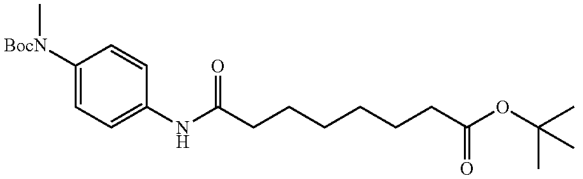 [SMILES: CN(C(=O)OC(C)(C)C)c1ccc(NC(=O)CCCCCCC(=O)OC(C)(C)C)cc1]

tert-Butyl 8-((4-((tert-butoxycarbonyl)(methyl) amino)phenyl)amino)-8-oxooctanoate A solution of 8-((4-((tert-butoxycarbonyl)(methyl)amino) phenyl)amino)-8-oxooctanoic acid (1 eq, 500 mg) in tert-butanol (7 mL, 0.2 M) was treated with $Boc_2O$ (2 eq, 577 mg) and a catalytic amount of 4-dimethylaminopyridine (DMAP) (0.15 eq, 24 mg). The mixture was stirred at room temperature for 12 h. The reaction was monitored by UPLC-MS. Once the reaction was completed, the mixture was concentrated in vacuo and passed through a silica plug. The eluent was collected, concentrated and used without further purification. UPLC-MS RT: 1.71 min (Method A), Mass m/z: (378.97, M-tBu+1).

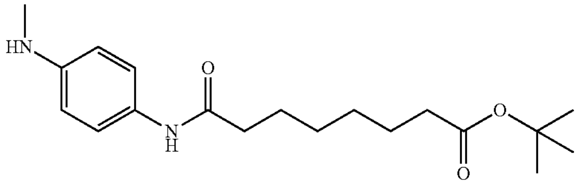 [SMILES: CNc1ccc(NC(=O)CCCCCCC(=O)OC(C)(C)C)cc1]

tert-Butyl 8-((4-(methylamino)phenyl)amino)-8-oxooctanoate

To a solution of tert-butyl 8-((4-((tert-butoxycarbonyl)(methyl)amino)phenyl)amino)-8-oxooctanoate in ethyl acetate (13 mL) was added 4N HCl in dioxane (5 eq, 1.63 mL). The mixture was stirred at room temperature for 20 h. Additional HCl (2.5 eq, 0.82 mL) was added, and the mixture was stirred for an additional 2 h. Once the reaction was completed, solvent was removed in vacuo to yield the title compound (150 mg, 34% over 2 steps). UPLC-MS RT: 1.11 min (Method A), Mass m/z: (334.97, M+1).

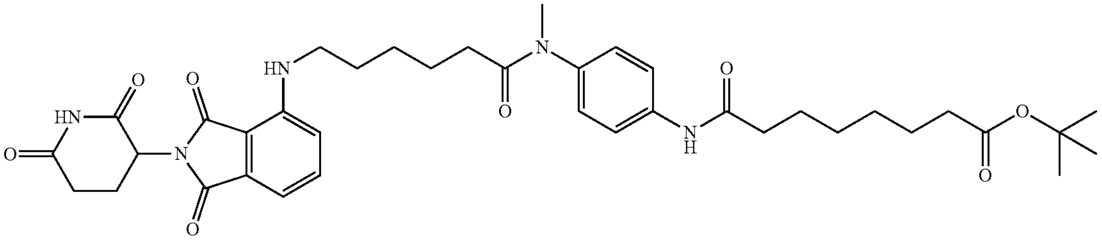 [SMILES: CN(C(=O)CCCCCNc1cccc2c1C(=O)N(C1CCC(=O)NC1=O)C2=O)c1ccc(NC(=O)CCCCCCC(=O)OC(C)(C)C)cc1]

tert-Butyl 8-((4-(6-((2-(2,6-dioxopiperidin-3-yl)-1,3-dioxoisoindolin-4-yl)amino)-N-methylhexanamido)phenyl)amino)-8-oxooctanoate To a solution of tert-butyl 8-((4-(methylamino)phenyl)amino)-8-oxooctanoate (1 eq, 30 mg) in dimethylformamide (DMF) (1 mL, 0.1M) was added 6-((2-(2,6-dioxopiperidin-3-yl)-1,3-dioxoisoindolin-4-yl)amino)hexanoic acid (1 eq, 35 mg). The mixture was treated with 1-[Bis(dimethylamino)methylene]-1H-1,2,3-triazolo[4,5-b]pyridinium 3-oxid hexafluorophosphate (HATU) (1.2 eq, 41 mg) and DIEA (2 eq, 31 μL). The reaction mixture was stirred at room temperature for 1 h. The reaction was monitored by UPLC-MS. Once the reaction was completed, the mixture was quenched with $H_2O$ and extract three times with ethyl acetate. The organic layers were combined and washed with brine, dried over $Na_2SO_4$, filtered and concentrated in vacuo. The residue was purified using ISCO (dichloromethane/methanol, 0%-10%) to yield the title compound. UPLC-MS RT: 1.54 min (Method A), Mass m/z: (647.90, M-tBu+1).

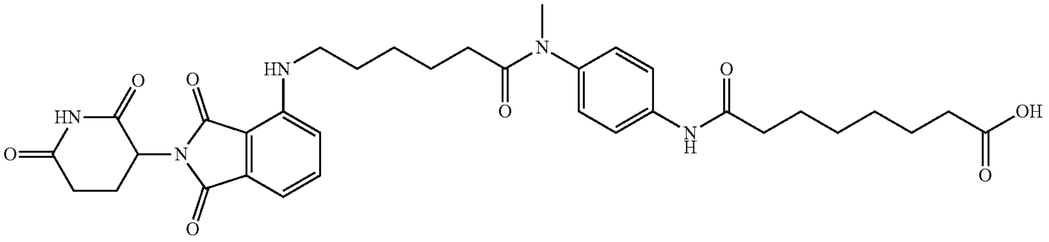 [SMILES: CN(C(=O)CCCCCNc1cccc2c1C(=O)N(C1CCC(=O)NC1=O)C2=O)c1ccc(NC(=O)CCCCCCC(=O)O)cc1]

8-((4-(6-((2-(2,6-dioxopiperidin-3-yl)-1,3-dioxoisoindolin-4-yl)amino)-N-methylhexanamido)phenyl)amino)-8-oxooctanoic acid tert-Butyl 8-((4-(6-((2-(2,6-dioxopiperidin-3-yl)-1,3-dioxoisoindolin-4-yl)amino)-N-methylhexanamido)phenyl)amino)-8-oxooctanoate was treated with a mixture of TFA/dichloromethane (1:5 mixture). The mixture was stirred at room temperature for 2 h. The reaction was monitored by UPLC-MS. Once the reaction was completed, the solvent was removed in vacuo, and the residue was used in the next step without further purification. UPLC-MS RT: 1.13 min (Method A), Mass m/z: (647.90, M+1).

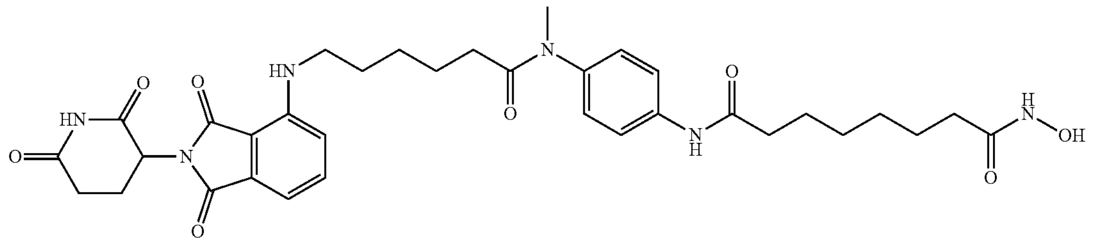 [SMILES: CN(C(=O)CCCCCNc1cccc2c1C(=O)N(C1CCC(=O)NC1=O)C2=O)c1ccc(NC(=O)CCCCCCC(=O)NO)cc1]

$N^1$-(4-(6-((2-(2,6-dioxopiperidin-3-yl)-1,3-dioxoisoindolin-4-yl)amino)-N-methylhexanamido)phenyl)-$N^8$-hydroxyoctanediamide (2)

To a solution of 8-((4-(6-((2-(2,6-dioxopiperidin-3-yl)-1,3-dioxoisoindolin-4-yl)amino)-N-methylhexanamido)phenyl)amino)-8-oxooctanoic acid (1 eq, 17 mg) in DMF (0.5 mL) was added EDCI (1.1 eq, 5.6 mg) and HOBt (1.1 eq, 3.9 mg) at 0° C. The mixture was stirred at 0° C. for 1 h, then freshly made $NH_2OH$ in methanol (2 eq) was added, followed by DMAP (cat. 1 crystal). The reaction was gradually warmed to room temperature, and stirred for 1 h. Once the reaction was completed, the solvent was removed and the residue was purified using HPLC ($H_2O$/acetonitrile, 0%-100%) to yield the title compound as a yellow solid (3.2 mg, 19%). UPLC-MS RT: 1.00 min (Method A), Mass m/z: (662.90, M+1).

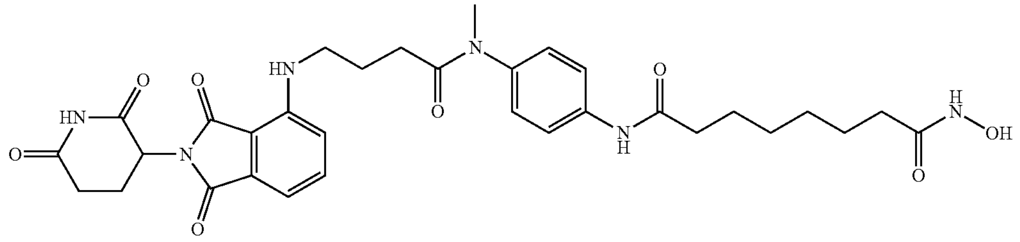 [SMILES: CN(C(=O)CCCNc1cccc2c1C(=O)N(C1CCC(=O)NC1=O)C2=O)c1ccc(NC(=O)CCCCCCC(=O)NO)cc1]

$N^1$-(4-(4-((2-(2,6-dioxopiperidin-3-yl)-1,3-dioxoisoindolin-4-yl)amino)-N-methylbutanamido)phenyl)-$N^8$-hydroxyoctanediamide (1)

Compound 1 was synthesized from tert-butyl 8-((4-(methylamino)phenyl)amino)-8-oxooctanoate and 4-((2-(2,6-dioxopiperidin-3-yl)-1,3-dioxoisoindolin-4-yl)amino)butanoic acid according to General Procedure I. UPLC-MS RT: 0.76 min (Method B), Mass m/z: (635.32, M+1).

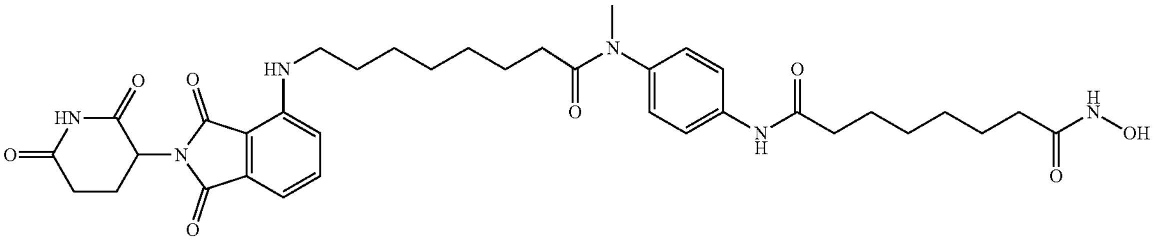 [SMILES: CN(C(=O)CCCCCCCNc1cccc2c1C(=O)N(C1CCC(=O)NC1=O)C2=O)c1ccc(NC(=O)CCCCCCC(=O)NO)cc1]

N[1]-(4-(8-((2-(2,6-dioxopiperidin-3-yl)-1,3-dioxoisoindolin-4-yl)amino)-N-methyloctanamido)phenyl)-N[8]-hydroxyoctanediamide (3)

Compound 3 was synthesized from tert-butyl 8-((4-(methylamino)phenyl)amino)-8-oxooctanoate and 8-((2-(2,6-dioxopiperidin-3-yl)-1,3-dioxoisoindolin-4-yl)amino)octanoic acid according to General procedure I. UPLC-MS RT: 1.12 min (Method A), Mass m/z: (690.80, M+1).

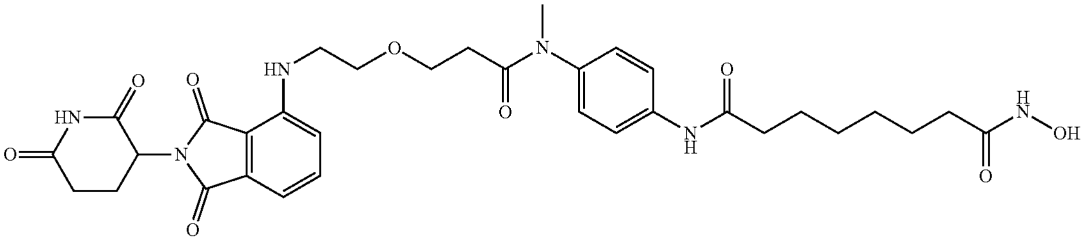 [SMILES: CN(C(=O)CCOCCNc1cccc2c1C(=O)N(C1CCC(=O)NC1=O)C2=O)c1ccc(NC(=O)CCCCCCC(=O)NO)cc1]

N[1]-(4-(3-(2-((2-(2,6-dioxopiperidin-3-yl)-1,3-dioxoisoindolin-4-yl)amino)ethoxy)-N-methylpropanamido)phenyl)-N[8]-hydroxyoctanediamide (7)

Compound 7 was synthesized from tert-butyl 8-((4-(methylamino)phenyl)amino)-8-oxooctanoate and 3-(2-((2-(2,6-dioxopiperidin-3-yl)-1,3-dioxoisoindolin-4-yl)amino)ethoxy)propanoic acid according to General procedure I. UPLC-MS RT: 0.91 min (Method A), Mass m/z: (664.80, M+1). $^1$H NMR (500 MHz, Methanol-$d_4$) δ 9.82 (s, 1H), 7.60 (d, J=8.2 Hz, 2H), 7.54 (dd, J=8.5, 7.1 Hz, 1H), 7.20 (d, J=8.3 Hz, 2H), 7.09-7.03 (m, 2H), 5.09 (dd, J=12.4, 5.4 Hz, 1H), 3.70 (t, J=5.9 Hz, 2H), 3.61 (t, J=5.1 Hz, 2H), 3.46 (t, J=5.3 Hz, 2H), 3.22 (s, 3H), 2.88 (ddd, J=18.6, 13.7, 5.3 Hz, 1H), 2.79-2.68 (m, 2H), 2.41-2.33 (m, 4H), 2.16-2.06 (m, 3H), 1.74-1.59 (m, 4H), 1.46-1.34 (m, 4H).

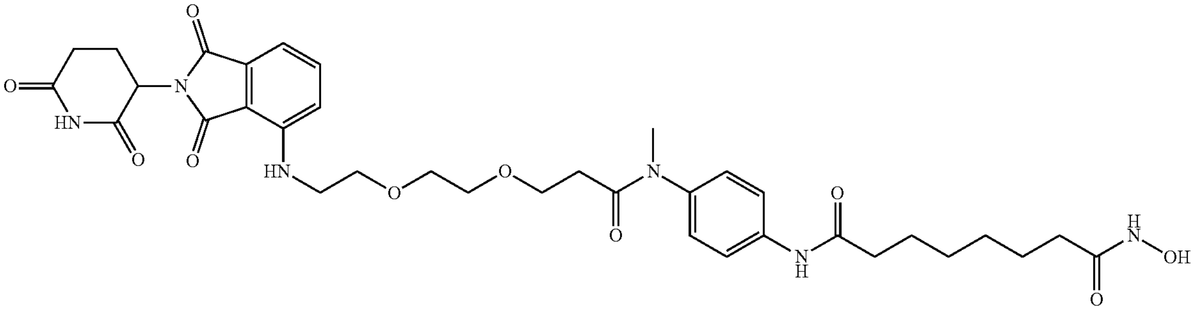 [SMILES: CN(C(=O)CCOCCOCCNc1cccc2c1C(=O)N(C1CCC(=O)NC1=O)C2=O)c1ccc(NC(=O)CCCCCCC(=O)NO)cc1]

$N^1$-(4-(3-(2-(2-((2-(2,6-dioxopiperidin-3-yl)-1,3-dioxoisoindolin-4-yl)amino)ethoxy)ethoxy)-$N^8$-methylpropanamido)phenyl)-NP-hydroxyoctanediamide (8)

Compound 8 was synthesized from tert-butyl 8-((4-(methylamino)phenyl)amino)-8-oxooctanoate and 3-(2-(2-((2-(2,6-dioxopiperidin-3-yl)-1,3-dioxoisoindolin-4-yl)amino)ethoxy)ethoxy)propanoic acid according to General procedure I. UPLC-MS RT: 0.91 min (Method A), Mass m/z: (708.80, M+1).

Example 3: General Procedure II

Synthesis of tert-butyl 8-((4-((methylamino)methyl)phenyl)amino)-8-oxooctanoate

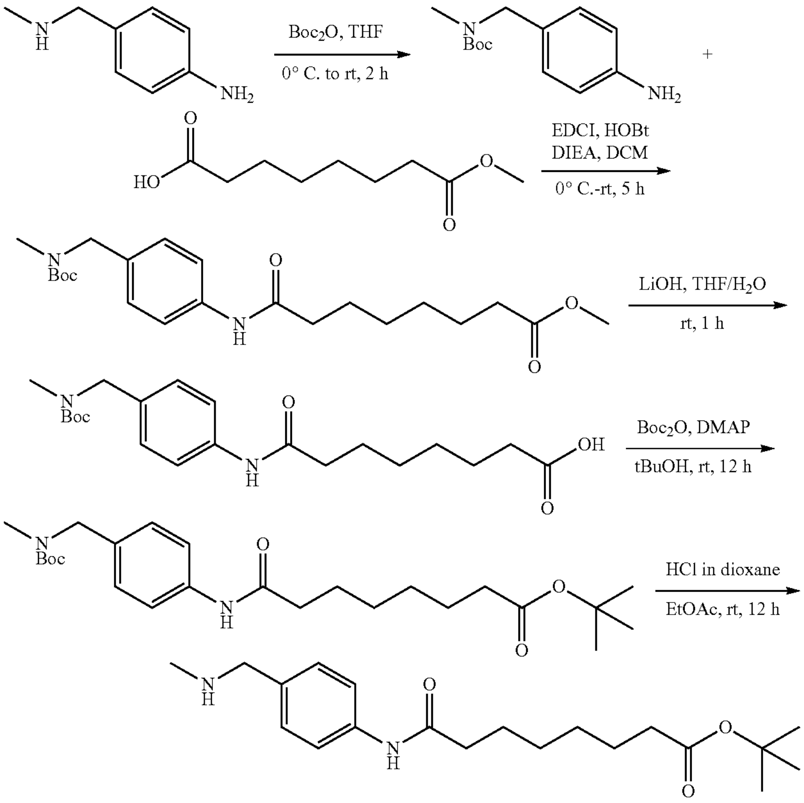

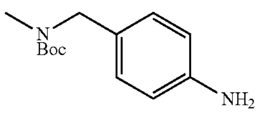 [SMILES: CN(Cc1ccc(N)cc1)C(=O)OC(C)(C)C]

tert-Butyl (4-aminobenzyl)(methyl)carbamate

To a solution of 4-((methylamino)methyl)aniline (1 eq, 1 g) in THF (37 mL) was added $Boc_2O$ (1.2 eq, 1.9 g) at 0° C. The reaction mixture was warmed to room temperature and stirred for 2 h. When the starting material was consumed, the solvent was removed in vacuo, and the residue was purified using ISCO (hexanes/ethyl acetate, 0%-45%) to yield the title compound (1.68 g, 97%). UPLC-MS RT: 0.83 min (Method A), Mass m/z: (105.92, M-NBocMe-1).

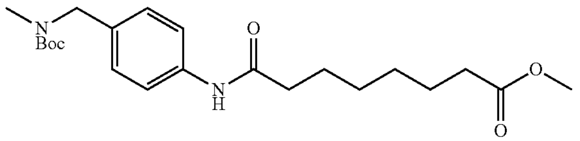

Methyl 8-((4-(((tert-butoxycarbonyl)(methyl)amino)methyl)phenyl)amino)-8-oxooctanoate To a mixture of tert-butyl (4-aminobenzyl)(methyl)carbamate (1 eq, 1.43 g) and 8-methoxy-8-oxooctanoic acid (1 eq, 1.14 g) in dichloromethane (30 mL, 0.2 M) was added EDCI (1.1 eq, 1.28 g), HOBt (1.1 eq, 900 mg) and DIEA (1.5 eq, 1.58 mL) at 0° C. The reaction mixture was warmed to room temperature and stirred for 5 h. When the starting material was consumed, the mixture was quenched with $H_2O$ and extracted three times with dichloromethane. The organic layers were combined and washed with brine, dried over $Na_2SO_4$, filtered and concentrated in vacuo. The residue was purified using ISCO (dichloromethane/ethyl acetate, 0%-40%) to yield the title compound (2.28 g, 93%). UPLC-MS RT: 1.49 min (Method A), Mass m/z: (407.37, M+1).

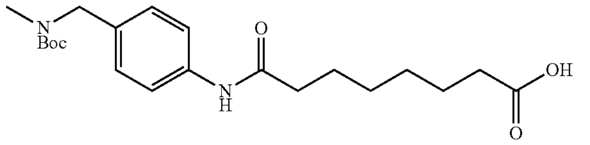 [SMILES: CN(Cc1ccc(NC(=O)CCCCCCC(=O)O)cc1)C(=O)OC(C)(C)C]

8-((4-(((tert-butoxycarbonyl)(methyl)amino)methyl) phenyl)amino)-8-oxooctanoic acid Methyl 8-((4-(((tert-butoxycarbonyl)(methyl)amino) methyl)phenyl)amino)-8-oxooctanoate (1 eq, 1.14 g) was dissolved in a mixture of THF and $H_2O$ (1:1 mixture, 15 mL, 0.2 M) and the reaction mixture was treated with LiOH (2 eq, 236 mg) and stirred at room temperature for 1 h. When the starting material was consumed, the mixture was acidified with 2N HCl and extract three times with ethyl acetate. The organic layers were combined and washed with brine, dried over $Na_2SO_4$, filtered and concentrated in vacuo. The residue was used in the next step without further purification. UPLC-MS RT: 1.28 min (Method A), Mass m/z: (393.17, M−Boc+1).

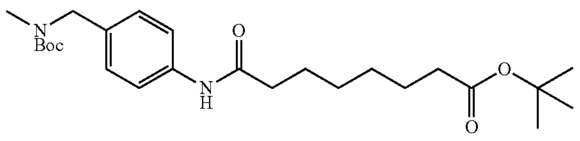 [SMILES: CN(Cc1ccc(NC(=O)CCCCCCC(=O)OC(C)(C)C)cc1)C(=O)OC(C)(C)C]

tert-Butyl 8-((4-(((tert-butoxycarbonyl)(methyl) amino)methyl)phenyl)amino)-8-oxooctanoate To a solution of 8-((4-(((tert-butoxycarbonyl)(methyl) amino)methyl)phenyl)amino)-8-oxooctanoic acid (1 eq, 1.10 g, crude) in tert-butanol (14 mL, 0.2 M) was added $Boc_2I$ (1.5 eq, 918 mg) and DMAP (0.2 eq, 69 mg). The reaction mixture was stirred at room temperature for 24 h. When the starting material was consumed, the solvent was removed in vacuo, and the residue was purified using ISCO (dichloromethane/ethyl acetate, 0%-30%) to yield the title compound (670 mg, 53%). UPLC-MS RT: 1.75 min (Method A), Mass m/z: (349.17, M−Boc+1).

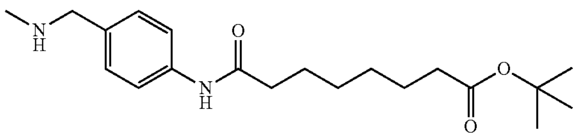 [SMILES: CNCc1ccc(NC(=O)CCCCCCC(=O)OC(C)(C)C)cc1]

tert-Butyl 8-((4-((methylamino)methyl)phenyl) amino)-8-oxooctanoate

A solution of 8-((4-(((tert-butoxycarbonyl)(methyl) amino)methyl)phenyl)amino)-8-oxooctanoate (1 eq, 670 mg) in ethyl acetate (7.5 mL, 0.2 M) was treated with 4N HCl in dioxane (8 eq, 3 mL), the reaction mixture was stirred at room temperature for 12 h. When the starting material was consumed, the mixture was basified with 2N NaOH and extracted three times with ethyl acetate. The organic layer was combined and washed with brine, dried over $Na_2SO_4$, filtered and concentrated in vacuo. The residue was purified using ISCO (dichloromethane/methanol, 0%-10%) to yield the title compound (350 mg, 67%). UPLC-MS RT: 0.93 min (Method A), Mass m/z: (349.17, M+1).

Synthesis of $N^1$-(4-(((6-((2-(2,6-dioxopiperidin-3-yl)-1,3-dioxoisoindolin-4-yl)amino)hexyl)(methyl) amino)methyl)phenyl)-$N^8$-hydroxyoctanediamide (6)

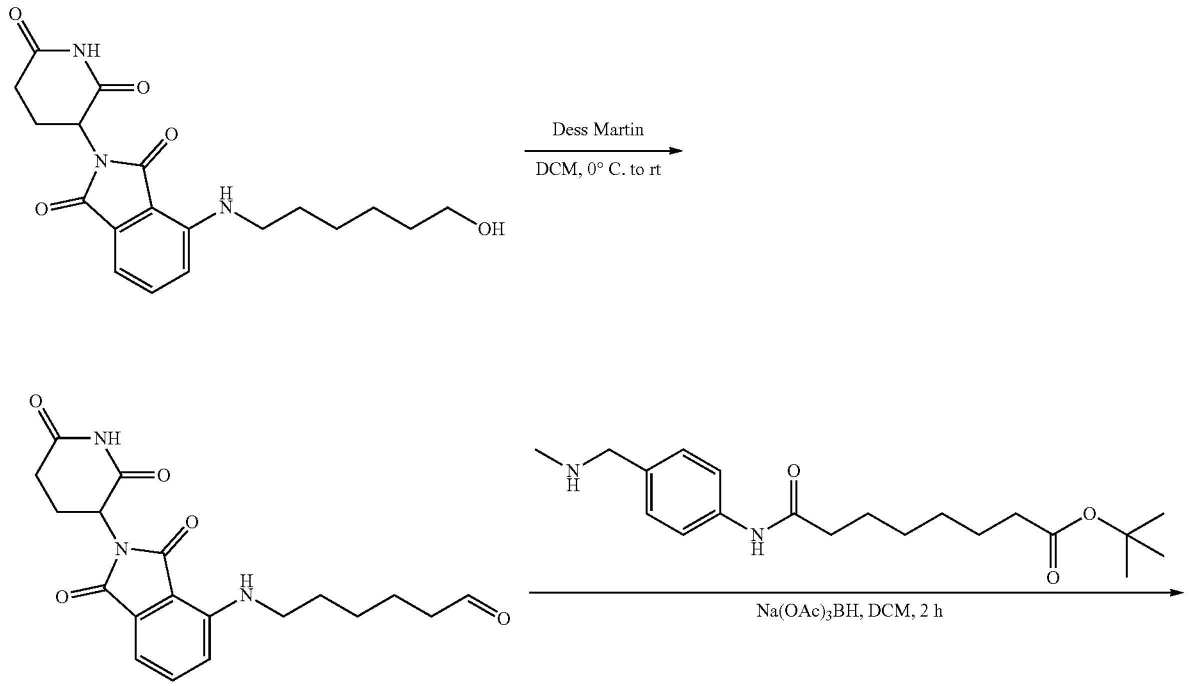

-continued
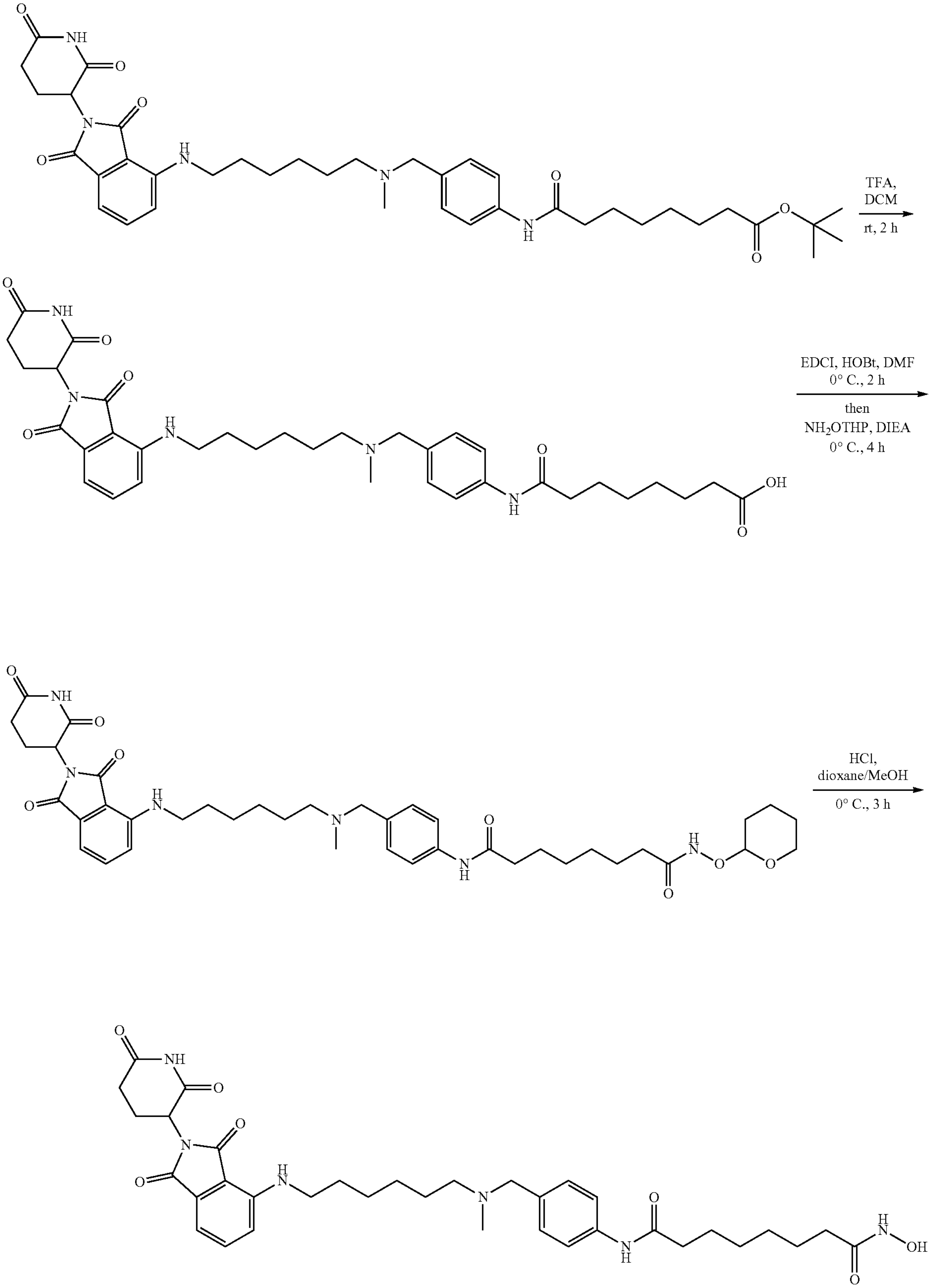

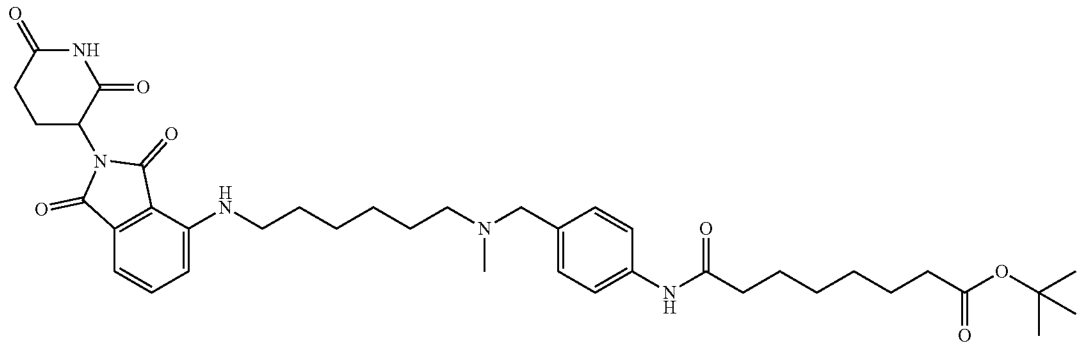 [SMILES: CN(CCCCCCNc1cccc2c1C(=O)N(C1CCC(=O)NC1=O)C2=O)Cc1ccc(NC(=O)CCCCCCC(=O)OC(C)(C)C)cc1]

tert-Butyl 8-((4-(((6-((2-(2,6-dioxopiperidin-3-yl)-1,3-dioxoisoindolin-4-yl)amino)hexyl)(methyl)amino)methyl)phenyl)amino)-8-oxooctanoate A solution of 2-(2,6-dioxopiperidin-3-yl)-4-((6-hydroxyhexyl)amino)isoindoline-1,3-dione (1 eq, 40 mg) in dichloromethane (1 mL, 0.1 M) was treated with Dess-Martin periodinane (1.05 eq, 48 mg) at 0° C. The reaction mixture was warmed gradually to room temperature and stirred for 2 h. When the starting material was consumed, the reaction mixture was quenched with $H_2O$ and extracted three times with dichloromethane. The organic layers were combined and washed with brine, dried over $Na_2SO_4$, filtered and concentrated in vacuo. The residue was passed through a short column and the eluent was collected and concentrated in vacuo. The crude residue was used in the next step without further purification. UPLC-MS RT: 1.14 min (Method A), Mass m/z: (354.17, M−$H_2O$+1).

The crude residue (1 eq, 30 mg) was dissolved in dichloromethane (2 mL), and tert-butyl 8-((4-((methylamino)methyl)phenyl)amino)-8-oxooctanoate (1 eq, 28.2 mg) was added at room temperature, followed by $NaBH(OAc)_3$ (1.5 eq, 25.8 mg). The reaction mixture was stirred at room temperature for 2 h. When the starting material was consumed, the reaction was quenched with aqueous $NaHCO_3$ and extracted three times with dichloromethane. The organic layers were combined and washed with brine, dried over $Na_2SO_4$, filtered and concentrated in vacuo. The residue was purified using ISCO (dichloromethane/methanol, 0%-10%) to yield the title compound (40 mg, 53%). UPLC-MS RT: 1.29 min (Method A), Mass m/z: (704.60, M+1).

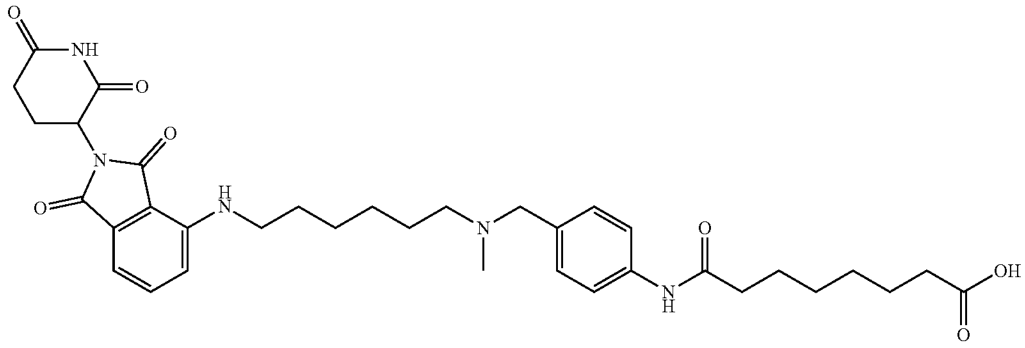 [SMILES: CN(CCCCCCNc1cccc2c1C(=O)N(C1CCC(=O)NC1=O)C2=O)Cc1ccc(NC(=O)CCCCCCC(=O)O)cc1]

8-((4-(((6-((2-(2,6-dioxopiperidin-3-yl)-1,3-dioxoisoindolin-4-yl)amino)hexyl)(methyl)amino)methyl)phenyl)amino)-8-oxooctanoic acid tert-butyl 8-((4-(((6-((2-(2,6-dioxopiperidin-3-yl)-1,3-dioxoisoindolin-4-yl)amino)hexyl)(methyl)amino)methyl)phenyl)amino)-8-oxooctanoate (1 eq, 40 mg) was treated with a mixture of TFA/dichloromethane (1:5) at room temperature. The reaction mixture was stirred for 2 h. When the starting material was consumed, the solvent was removed in vacuo, and the residue was used without further purification. UPLC-MS RT: 0.95 min (Method A), Mass m/z: (647.90, M+1).

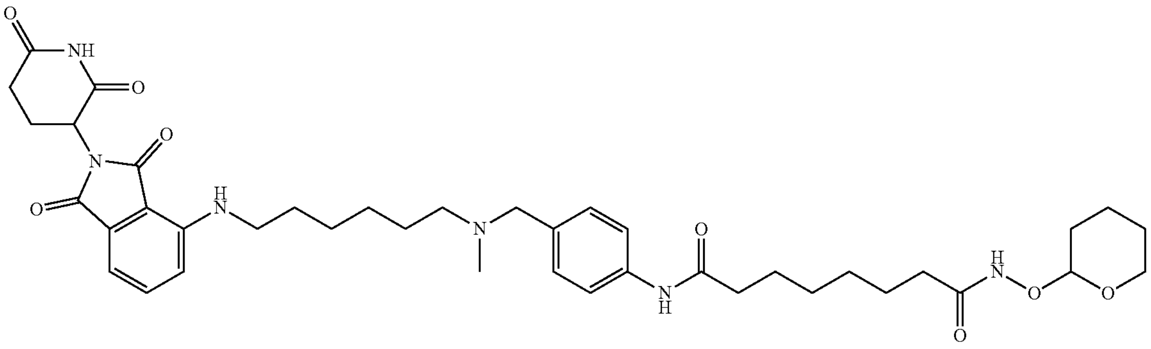 [SMILES: CN(CCCCCCNc1cccc2c1C(=O)N(C1CCC(=O)NC1=O)C2=O)Cc1ccc(NC(=O)CCCCCCC(=O)NOC2CCCCO2)cc1]

$N^1$-(4-(((6-((2-(2,6-dioxopiperidin-3-yl)-1,3-dioxoisoindolin-4-yl)amino)hexyl)(methyl)amino)methyl)phenyl)-$N^8$-((tetrahydro-2H-pyran-2-yl)oxy)octanediamide To a solution of 8-((4-(((6-((2-(2,6-dioxopiperidin-3-yl)-1,3-dioxoisoindolin-4-yl)amino)hexyl)(methyl)amino)methyl)phenyl)amino)-8-oxooctanoic acid (1 eq, 18 mg) in DMF (0.5 mL, 0.06 M) was added EDCI (1.2 eq, 6.4 mg) and HOBt (1.2 eq, 4.5 mg) at 0° C. The mixture was stirred at 0° C. for 2 h, then $NH_2OTHP$ (1.5 eq, 4.9 mg) and DIEA (2 eq, 9.7 μL) were added at 0° C. The reaction mixture stirred at 0° C. and gradually warmed to room temperature and stirred for another 4 h. The solvent was removed in vacuo, and the residue was purified using HPLC ($H_2O$/acetonitrile, 0%-100%) to yield the title compound. UPLC-MS RT: 1.00 min (Method A), Mass m/z: (747.01, M+1).

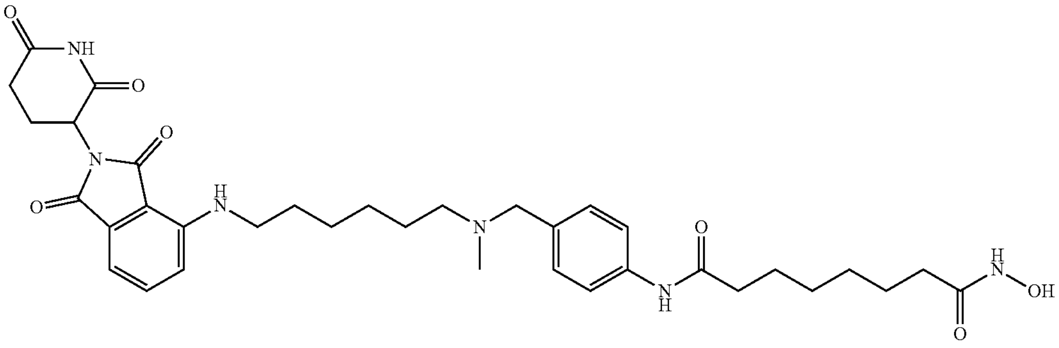 [SMILES: CN(CCCCCCNc1cccc2c1C(=O)N(C1CCC(=O)NC1=O)C2=O)Cc1ccc(NC(=O)CCCCCCC(=O)NO)cc1]

N[1]-(4-(((6-((2-(2,6-dioxopiperidin-3-yl)-1,3-dioxoisoindolin-4-yl)amino)hexyl)(methyl)amino)methyl)phenyl)-N[8]-hydroxyoctanediamide (6)

A solution of N[1]-(4-(((6-((2-(2,6-dioxopiperidin-3-yl)-1,3-dioxoisoindolin-4-yl)amino)hexyl)(methyl)amino)methyl)phenyl)-N[8]-((tetrahydro-2H-pyran-2-yl)oxy)octanediamide (1 eq) in solvent mixture of dioxane and methanol (1:1, 1 mL) was treated with 4N HCl in dioxane (10 eq, 70 μL) at 0° C. The reaction mixture was warmed to room temperature and stirred for 3 h. When the starting material was consumed, the solvent was removed in vacuo, and the residue was purified using HPLC ($H_2O$/acetonitrile, 0%-100%) to yield the title compound (3.4 mg, 18% over 2 steps). UPLC-MS RT: 0.83 min (Method A), Mass m/z: (662.90, M+1).

Example 4: General Procedure III

Synthesis of N[1]-(4-(((4-((2-(2,6-dioxopiperidin-3-yl)-1,3-dioxoisoindolin-4-yl)amino)butyl)(methyl)amino)methyl)phenyl)-N-hydroxyoctanediamide (5)

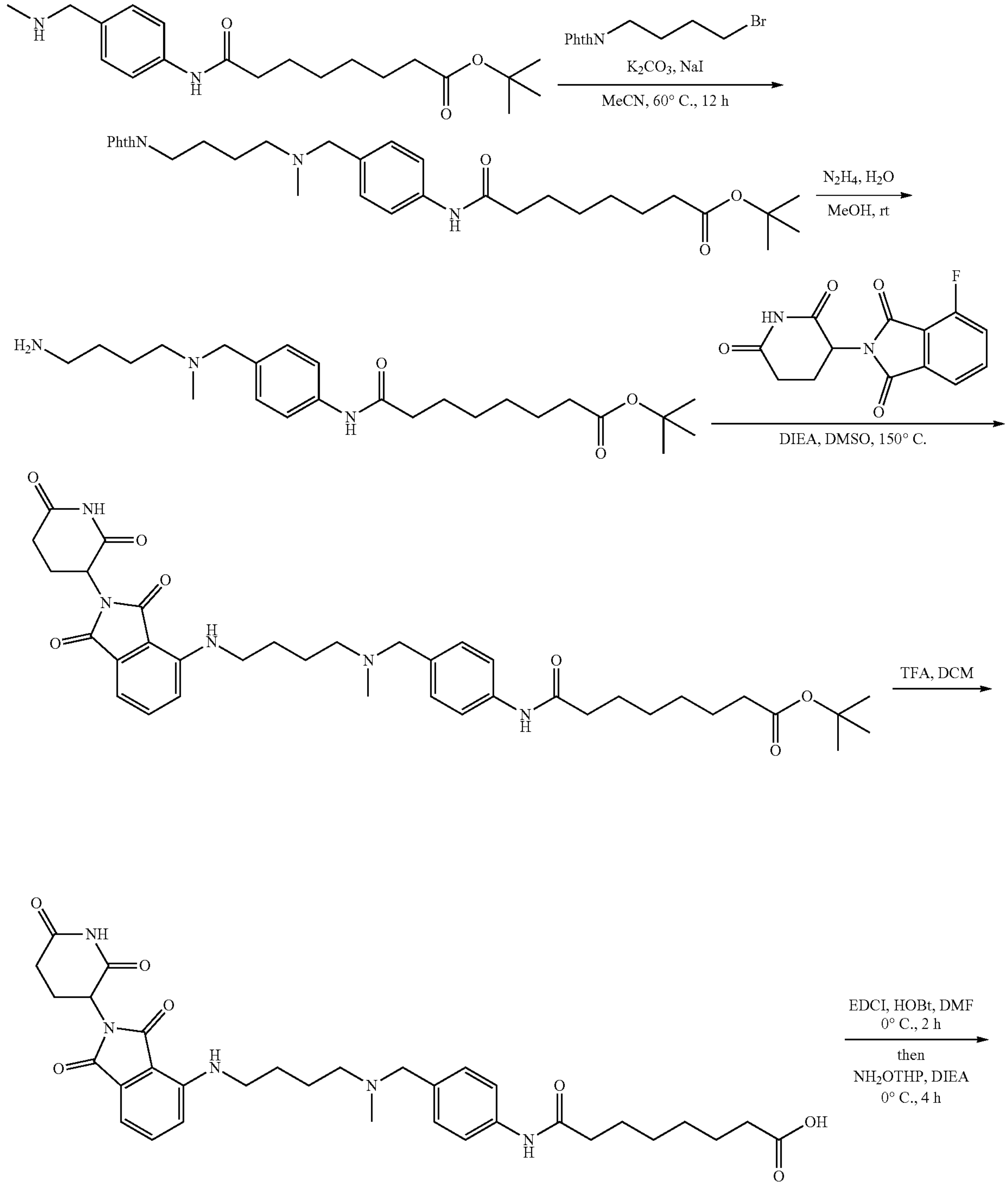

-continued

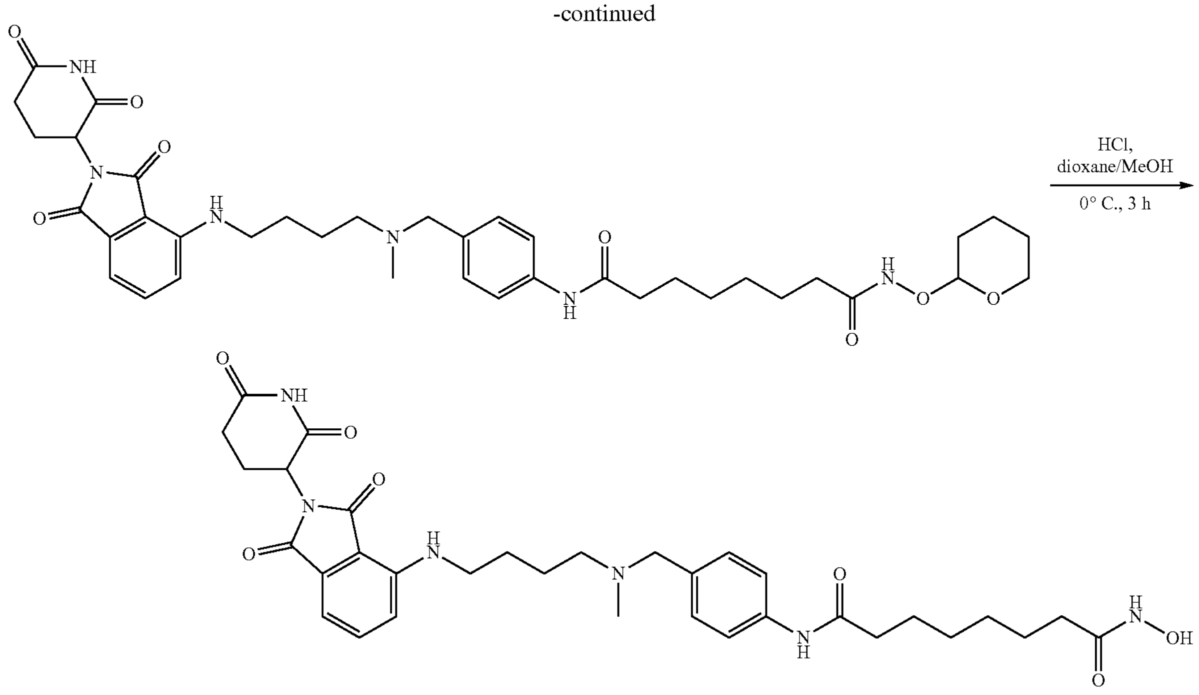

5

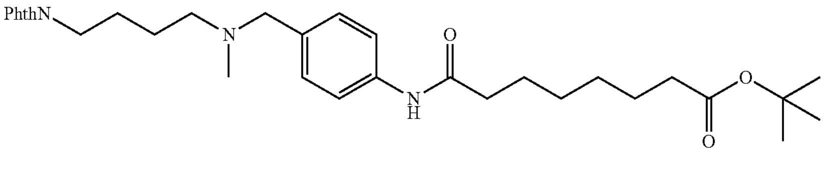

tert-Butyl 8-((4-(((4-(1,3-dioxoisoindolin-2-yl)butyl)(methyl)amino)methyl)phenyl)amino)-8-oxooctanoate To a solution of tert-butyl 8-((4-((methylamino)methyl)phenyl)amino)-8-oxooctanoate (1 eq, 92 mg) and 2-(4-bromobutyl)isoindoline-1,3-dione (1.5 eq, 112 mg) in acetonitrile (2.6 mL, 0.1 M) was added $K_2CO_3$ (2 eq, 73 mg) and NaI (0.1 eq, 4 mg) in one portion. The reaction mixture was heated to 65° C. and stirred for 12 h. When the starting material was consumed, the mixture was filtered through a pad of Celite®, concentrated in vacuo, and the residue was purified using ISCO (dichloromethane/ethyl acetate, 0%-75%) to yield the title compound (112 mg, 77%). UPLC-MS RT: 1.24 min (Method A), Mass m/z: (549.89, M+1).

tert-Butyl 8-((4-(((4-aminobutyl)(methyl)amino)methyl)phenyl)amino)-8-oxooctanoate A solution of tert-butyl 8-((4-(((4-(1,3-dioxoisoindolin-2-yl)butyl)(methyl)amino)methyl)phenyl)amino)-8-oxooctanoate (1 eq, 112 mg) in methanol (2 mL, 0.1 M) was treated with $N_2H_4 \cdot H_2O$ (5 eq, 50 μL). The reaction mixture was stirred at room temperature for 12 h. When the starting material was consumed, the mixture was acidified with 2N HCl to pH 1, and washed twice with diethyl ether. The aqueous layer was basified with 2N NaOH to pH>10, and back-extracted three times with ethyl acetate. The organic layers were combined and washed with brine, dried over $Na_2SO_4$, filtered and concentrated in vacuo. The residue was purified using ISCO (dichloromethane/methanol/$NH_3$, 0%-15%) to yield the title compound (85 mg, quant.). UPLC-MS RT: 0.73 min (Method A), Mass m/z: (420.17, M+1).

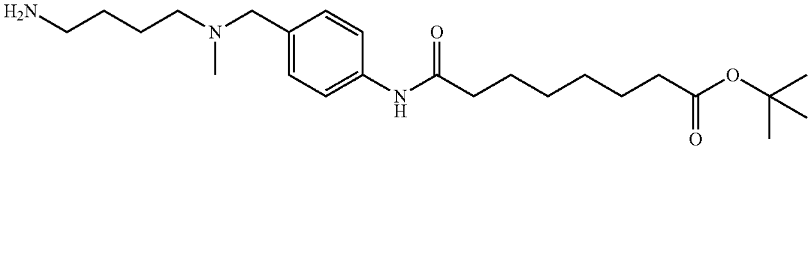 [SMILES: CN(CCCCN)Cc1ccc(NC(=O)CCCCCCC(=O)OC(C)(C)C)cc1]

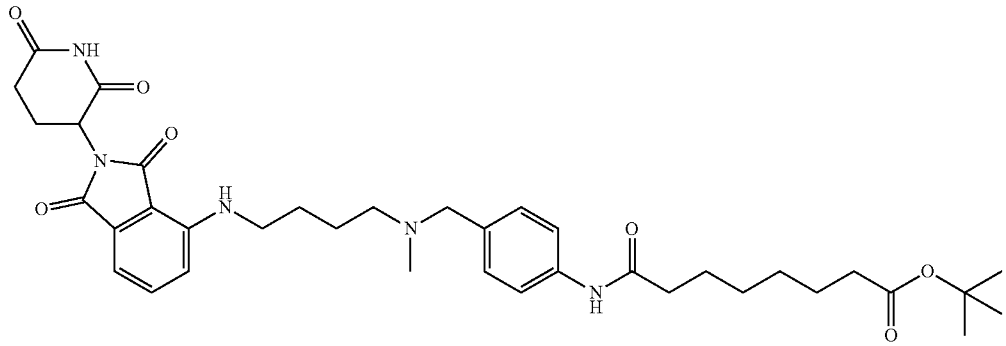 [SMILES: CN(CCCCNc1cccc2c1C(=O)N(C1CCC(=O)NC1=O)C2=O)Cc1ccc(NC(=O)CCCCCCC(=O)OC(C)(C)C)cc1]

tert-Butyl 8-((4-(((4-((2-(2,6-dioxopiperidin-3-yl)-1,3-dioxoisoindolin-4-yl)amino)butyl)(methyl)amino)methyl)phenyl)amino)-8-oxooctanoate To a solution of tert-butyl 8-((4-(((4-aminobutyl)(methyl)amino)methyl)phenyl)amino)-8-oxooctanoate (1 eq, 85 mg) and 2-(2,6-dioxopiperidin-3-yl)-4-fluoroisoindoline-1,3-dione (1.2 eq, 67 mg) in DMSO (2 mL, 0.1 M) was added DIEA (3 eq, 106 μL). The reaction mixture was heated to 150° C. and stirred for 1 h. When the starting material was consumed, the residue was purified first using HPLC ($H_2O$/acetonitrile, 0%-100%), and then with ISCO (dichloromethane/methanol, 0%-10%) to yield the title compound. UPLC-MS RT: 1.23 min (Method A), Mass m/z: (676.00, M+1).

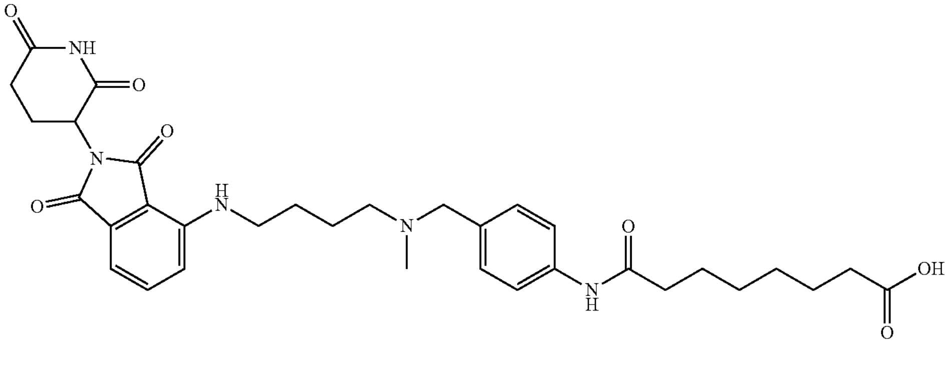 [SMILES: CN(CCCCNc1cccc2c1C(=O)N(C1CCC(=O)NC1=O)C2=O)Cc1ccc(NC(=O)CCCCCCC(=O)O)cc1]

8-((4-(((4-((2-(2,6-dioxopiperidin-3-yl)-1,3-dioxoisoindolin-4-yl)amino)butyl)(methyl)amino)methyl)phenyl)amino)-8-oxooctanoic acid tert-butyl 8-((4-(((4-((2-(2,6-dioxopiperidin-3-yl)-1,3-dioxoisoindolin-4-yl)amino)butyl)(methyl)amino)methyl)phenyl)amino)-8-oxooctanoate (1 eq, 80 mg) was treated with a mixture of TFA/dichloromethane (1:5), the reaction mixture stirred at room temperature for 6 h. When the starting material was consumed, the solvent was removed in vacuo, and the residue was used in the next step without further purification (30 mg, 24% over 2 steps). UPLC-MS RT: 0.88 min (Method A), Mass m/z: (619.99, M+1).

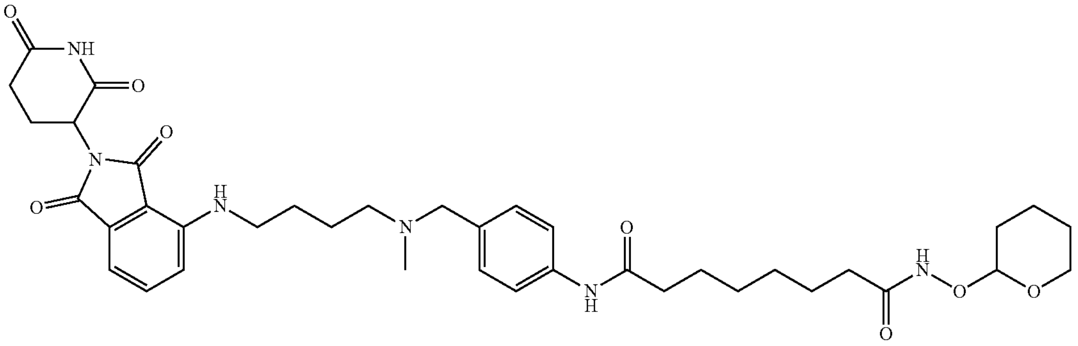 [SMILES: CN(CCCCNc1cccc2c1C(=O)N(C1CCC(=O)NC1=O)C2=O)Cc1ccc(NC(=O)CCCCCCC(=O)NOC2CCCCO2)cc1]

N[1]-(4-(((4-((2-(2,6-dioxopiperidin-3-yl)-1,3-dioxoisoindolin-4-yl)amino)butyl)(methyl)amino)methyl)phenyl)-N[8]-((tetrahydro-2H-pyran-2-yl)oxy)octanediamide To a solution of 8-((4-(((4-((2-(2,6-dioxopiperidin-3-yl)-1,3-dioxoisoindolin-4-yl)amino)butyl)(methyl)amino)methyl)phenyl)amino)-8-oxooctanoic acid (1 eq, 30 mg) in DMF (0.5 mL, 0.1 M) was added EDCI (1.2 eq, 10.2 mg), HOBt (1.2 eq, 7.2 mg) at 0° C., and the reaction mixture stirred at 0° C. for 2 h, then $NH_2OTHP$ (1.5 eq, 7.8 mg) and DIEA (2 eq, 15 μL) were added at 0° C. The reaction mixture was stirred at 0° C. and gradually warmed to room temperature and stirred for another 4 h. Solvent was removed in vacuo, and the residue was purified using HPLC ($H_2O$/acetonitrile, 0%-100%) to yield the title compound. UPLC-MS RT: 0.86 min (Method A), Mass m/z: (718.90, M+1).

N[1]-(4-(((4-((2-(2,6-dioxopiperidin-3-yl)-1,3-dioxoisoindolin-4-yl)amino)butyl)(methyl)amino)methyl)phenyl)-N[8]-hydroxyoctanediamide (5)

A solution of N[1]-(4-(((4-((2-(2,6-dioxopiperidin-3-yl)-1,3-dioxoisoindolin-4-yl)amino)butyl)(methyl)amino)methyl)phenyl)-N[8]-((tetrahydro-2H-pyran-2-yl)oxy)octanediamide (1 eq) in a solvent mixture of dioxane and methanol (1:1, 1 mL) was treated with 4N HCl in dioxane (10 eq, 121 μL) at 0° C. The reaction mixture was warmed to room temperature and stirred for 3 h. When the starting material was consumed, the solvent was removed in vacuo, and the residue was purified using HPLC ($H_2O$/acetonitrile, 0%-100%) to yield the title compound (14.9 mg, 49% over 2 steps). UPLC-MS RT: 0.70 min (Method A), Mass m/z: (635.00, M+1). $^1H$ NMR (500 MHz, DMSO-$d_6$, as a TFA salt) δ 11.09 (s, 1H), 10.32 (s, 1H), 10.03 (s, 1H), 9.40 (s, 1H), 8.64 (s, 1H), 7.66 (d, J=8.5 Hz, 2H), 7.60 (dd, J=8.6, 7.1 Hz, 1H), 7.40 (d, J=8.5 Hz, 2H), 7.11 (d, J=8.6 Hz, 1H), 7.05 (d, J=7.0 Hz, 1H), 6.63 (t, J=6.1 Hz, 1H), 5.05 (dd, J=12.8, 5.5 Hz, 1H), 4.30 (dd, J=13.0, 4.1 Hz, 1H), 4.14 (dd, J=13.1, 6.0 Hz, 1H), 3.37-3.31 (m, 2H), 3.18-3.09 (m, 1H), 3.00 (tt, J=11.3, 5.6 Hz, 1H), 2.89 (ddd, J=17.0, 13.8, 5.4 Hz, 1H), 2.64 (d, J=4.8 Hz, 3H), 2.62-2.55 (m, 1H), 2.54-2.52 (m, 1H), 2.30 (t, J=7.4 Hz, 2H), 2.06-1.99 (m, 1H), 1.93 (t, J=7.4 Hz, 2H), 1.83-1.67 (m, 2H), 1.64-1.52 (m, 4H), 1.48 (p, J=7.2 Hz, 2H), 1.34-1.20 (m, 4H).

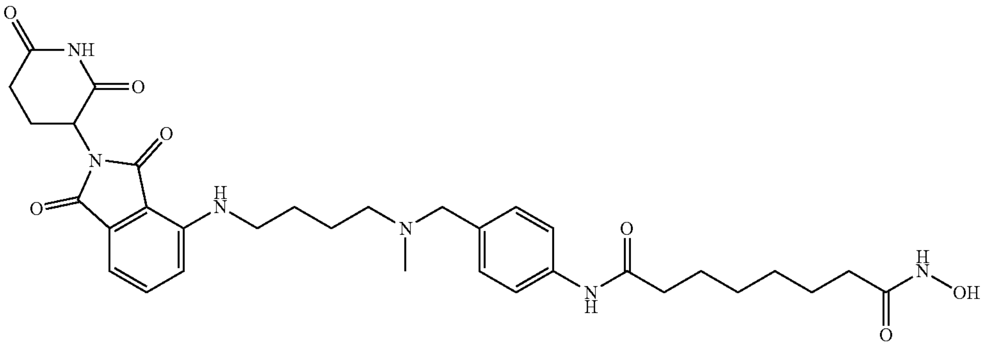 [SMILES: CN(CCCCNc1cccc2c1C(=O)N(C1CCC(=O)NC1=O)C2=O)Cc1ccc(NC(=O)CCCCCCC(=O)NO)cc1]

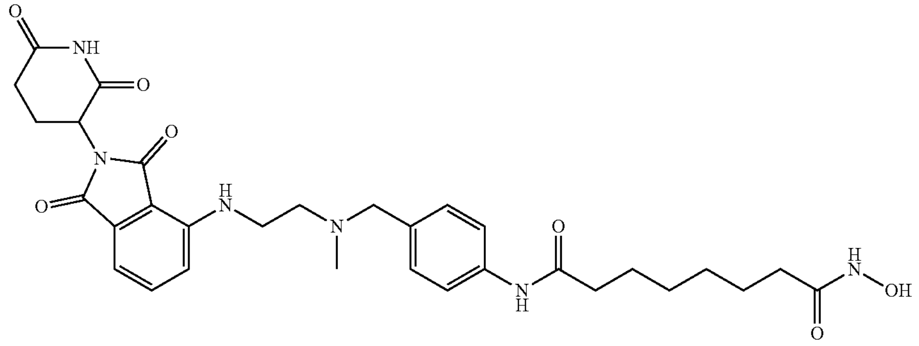 [SMILES: CN(CCNc1cccc2c1C(=O)N(C1CCC(=O)NC1=O)C2=O)Cc1ccc(NC(=O)CCCCCCC(=O)NO)cc1]

N[1]-(4-(((2-((2-(2,6-dioxopiperidin-3-yl)-1,3-dioxoisoindolin-4-yl)amino)ethyl)(methyl)amino)methyl)phenyl)-N-hydroxyoctanediamide (4)

Compound 4 was synthesized from tert-butyl 8-((4-((methylamino)methyl)phenyl)amino)-8-oxooctanoate and 2-(2-bromoethyl)isoindoline-1,3-dione, according to General procedure III. UPLC-MS RT: 0.58 min (Method A), Mass m/z: (606.99, M+1). $^1$H NMR (500 MHz, DMSO-$d_6$, as a TFA salt) δ 11.11 (d, J=4.4 Hz, 1H), 10.32 (s, 1H), 9.96 (d, J=21.8 Hz, 1H), 9.52 (d, J=22.7 Hz, 1H), 8.65 (s, 1H), 7.66-7.55 (m, 3H), 7.38 (dd, J=11.1, 8.3 Hz, 2H), 7.14-7.04 (m, 2H), 6.86 (q, J=7.2 Hz, 1H), 5.07 (dd, J=12.8, 5.4 Hz, 1H), 4.40-4.30 (m, 1H), 4.29-4.20 (m, 1H), 3.81-3.63 (m, 2H), 3.36-3.28 (m, 1H), 3.23-3.11 (m, 1H), 2.90 (ddd, J=17.1, 13.8, 5.4 Hz, 1H), 2.78 (dd, J=10.1, 4.6 Hz, 3H), 2.65-2.56 (m, 1H), 2.56-2.51 (m, 1H), 2.29 (t, J=7.6 Hz, 2H), 2.12-2.01 (m, 1H), 1.94 (t, J=7.4 Hz, 2H), 1.57 (p, J=7.3 Hz, 2H), 1.49 (p, J=7.2 Hz, 2H), 1.33-1.19 (m, 4H).

Example 5: Biochemical Profiling

Compounds 1 and 3 were tested in a HDAC assay from Reaction Biology® against 10 different HDACs.

HDAC Assay Protocol

Reagents

Base Reaction buffer: 50 mM Tris-HCl, pH8.0, 137 mM NaCl, 2.7 mM KCl, and 1 mM $MgCl_2$, Add fresh: 1 mg/ml BSA, 1% DMSO Substrate Fluorogenic HDAC General Substrate (HDAC1, HDAC2, HDAC3, HDAC6, HDAC10, and HDAC11): 50 μM, Arg-His-Lys-Lys(Ac)-AMC (HDAC8 only substrate: 50 μM, Arg-His-Lys(Ac)-Lys(Ac))-AMC Class2A Substrate (HDAC4, HDAC5, HDAC7, and HDAC9): Boc-Lys(trifluoroacetyl)-AMC For SIRTs 1-3, general Class1 HDAC substrate and 500 μM NAD+

For SIRT5, Ac-Lys-succ and 500 μM NAD+

Reaction Procedure

Deacetylation Step

1. Delivered 2× enzyme in wells of reaction plate except in the control wells and added buffer to control wells.
2. Delivered compounds in 100% DMSO into the enzyme mixture by Acoustic technology (Echo550; nanoliter range). Spin down and pre-incubation.
3. Delivered 2× Substrate Mixture (Fluorogenic HDAC Substrate and co-factor if applicable) in all reaction wells to initiate the reaction. Spin and shake.
4. Incubated for 30 min for Class 2A, 1 hr for HDAC1, 2, 3, and 6, and 2 hr for the rest of HDACs and SIRTs at 30° C. with seal.

Development Step

5. Added Developer with Trichostatin A (or Nicotinamide for SIRTs) to stop the reaction and to generate fluorescent color.
6. The fluorescence that was generated was detected with excitation (Ex) at 360 nM and emission (Em) at 460 nM by the EnVision Multilabel Plate Reader (PerkinElmer®, Santa Clara, CA, USA).
7. $IC_{50}$ values, presented in Table 1, were derived from a 10-dose response curve. The results show that the addition of a linker and CRBN targeting group altered the isoform selectivity of the SAHA-based degrader compounds.

TABLE 1

Biochemical selectivity of compounds 1 and 3.

| | Compound $IC_{50}$ (M) | | |
|---|---|---|---|
| Target | SAHA* | Compound 3 | Compound 1 |
| HDAC1 | 3.06E−07 | 4.41E−06 | 1.04E−06 |
| HDAC2 | 2.42E−07 | 1.44E−05 | 2.47E−06 |
| HDAC3 | 1.32E−07 | 3.43E−06 | 1.44E−06 |
| HDAC4 | 7.60E−05 | — | — |
| HDAC5 | 2.72E−05 | 7.83E−06 | 5.75E−06 |
| HDAC6 | 1.98E−08 | 4.01E−08 | 4.85E−08 |
| HDAC7 | 1.05E−04 | — | — |
| HDAC8 | 3.06E−07 | 4.00E−07 | 6.21E−07 |
| HDAC9 | 1.41E−04 | — | — |
| HDAC10 | 4.32E−07 | 6.58E−06 | NT** |

*from Reaction Biology ®

**NT, not tested

Example 6: Cellular CRBN Engagement Assay

The cellular CRBN engagement assay measures the cellular binding affinity which is the combination of the compound's cell permeability and their binding affinity to CRBN. This is done by measuring the ability of thalidomide-based degrader molecules to compete with pan-BET bromodomain degrader dBET6 (Nowak et al., Nat. Chem. Biol. 14:706-714 (2018)) for CRBN binding in cells. If no degrader compound is present in the cell, $BRD4_{BRD2}$-eGFP is degraded by dBET6 via the proteasome system. Therefore, treatment with an increasing concentration of cell-permeable thalidomide-based degrader results in competition with dBET6 for CRBN occupancy, thereby recovering GRP signal and provides a measure of inhibition for deriving the $IC_{50}$.

$BRD4_{BD2}$ were subcloned into mammalian pcDNA5/FRT Vector (Ampicillin and Hygromycin B resistant) modified to contain MCS-eGFP-P2A-mCherry. Stable cell lines expressing eGFP-protein fusion and mCherry reporter were generated using Flip-In 293 system. Plasmid (0.3 μg) and pOG44 (4.7 μg) DNA were preincubated in 100 μL of Opti-MEM I (Gibco, Life Technologies™) media containing 0.05 mg/ml Lipofectamine 2000 (Invitrogen™) for 20 min and added to Flip-In 293 cells containing 1.9 ml of DMEM media (Gibco, Life Technologies™) per well in a 6-well plate format (Falcon, 353046). Cells were propagated after 48 h and transferred into a 10 $cm^2$ plate (Corning, 430165) in DMEM media containing 50 μg/ml of Hygromycin B (REF 10687010, Invitrogen™) as a selection marker. Following 2-3 passage cycles, FACS (FACSAria II, BD) was used to enrich for cells expressing eGFP and mCherry.

Cells were seeded at 30-50% confluency in either 24, 48 or 96 well plates (3524, 3548, 3596 respectively, Costar) a day before compound treatment. The inventive compounds were titrated in the presence of 100 nM dBET6 and then were incubated with cells for 5 h following trypsinization and resuspension in DMEM media, transferred into 96-well plates (353910, Falcon®) and analyzed by flow cytometer (Guava® easyCyte™ HT, Millipore®). Signal from at least 3000 events per well was acquired and the eGFP and mCherry florescence monitored. Data was analyzed using FlowJo® (FlowJo®, LCC). Forward and side scatter outliers, frequently associated with cell debris, were removed leaving >90% of total cells, followed by removal of eGFP and mCherry signal outliers, leaving 88-90% of total cells creating the set used for quantification. The eGFP protein abundance relative to mCherry was then quantified as a 10-fold amplified ratio for each individual cell using the formula: 10×eGFP/mCherry. The median of the ratio was then calculated per set, normalized to the median of the DMSO ratio.

The results of the cellular CRBN engagement assay are shown in FIG. 1A-FIG. 1E. Compounds 2 and 3 exhibited $IC_{50}$ values of 5.37 μM and 1.63 μM, respectively.

Example 7: Multiplexed Mass Spectrometry-Based Proteomics

Lysis buffer (8 M Urea, 50 mM NaCl, 50 mM 4-(2hydroxyethyl)-1-piperazineethanesulfonic acid (EPPS) pH 8.5, protease and phosphatase inhibitors from Roche®) were added to the cell pellets and homogenized by 20 passes through a 21 gauge (1.25 in. long) needle to achieve a cell lysate with a protein concentration between 1-4 mg $mL^{-1}$. A micro-BCA assay (Pierce™) was used to determine the final protein concentration in the cell lysate. 200 μg of protein for each sample were reduced and alkylated as described above.

Proteins were precipitated using methanol/chloroform. Four volumes of methanol were added to the cell lysate, followed by one volume of chloroform, and finally three volumes of water. The mixture was vortexed and centrifuged to separate the chloroform phase from the aqueous phase. The precipitated protein was washed with three volumes of methanol, centrifuged and the resulting washed precipitated protein was allowed to air dry. The precipitated protein was resuspended in 4 M Urea, 50 mM HEPES pH 7.4, followed by dilution to 1 M urea with the addition of 200 mM EPPS, pH 8. Proteins were first digested with LysC (1:50; enzyme: protein) for 12 hours at room temperature. The LysC digestion was diluted to 0.5 M Urea with 200 mM EPPS pH 8 followed by digestion with trypsin (1:50; enzyme:protein) for 6 hours at 37° C. Tandem mass tag (TMT) reagents (Thermo Fisher Scientific™) were dissolved in anhydrous acetonitrile (ACN) according to manufacturer's instructions.

Anhydrous ACN was added to each peptide sample to a final concentration of 30% v/v, and labeling was induced with the addition of TMT reagent to each sample at a ratio of 1:4 peptide:TMT label. The 10-plex labeling reactions were performed for 1.5 hours at room temperature and the reaction quenched by the addition of hydroxylamine to a final concentration of 0.3% for 15 minutes at room temperature. The sample channels were combined at a 1:1:1:1:1:1: 1:1:1:1:1 ratio, desalted using Cis solid phase extraction cartridges (Waters) and analyzed by LC-MS for channel ratio comparison. Samples were then combined using the adjusted volumes determined in the channel ratio analysis and dried down in a speed vacuum. The combined sample was then resuspended in 1% formic acid, and acidified (pH 2-3) before being subjected to desalting with C18 SPE (Sep-Pak®, Waters). Samples were then offline fractionated into 96 fractions by high pH reverse-phase HPLC (Agilent® LC1260) through an aeris peptide xb-c18 column (Phenomenex®) with mobile phase A containing 5% acetonitrile and 10 mM $NH_4HCO_3$ in LC-MS grade $H_2O$, and mobile phase B containing 90% acetonitrile and 10 mM $NH_4HCO_3$ in LC-MS grade $H_2O$ (both pH 8.0). The 96 resulting fractions were then pooled in a non-continuous manner into 24 fractions and these fractions were used for subsequent mass spectrometry analysis.

Data were collected using an Orbitrap Fusion™ Lumos™ mass spectrometer (Thermo Fisher Scientific™, San Jose, CA, USA) coupled with a Proxeon EASY-nLC™ 1200 LC pump (Thermo Fisher Scientific™). Peptides were separated on an EasySpray™ ES803 75 μm inner diameter microcapillary column (ThermoFisher Scientific™). Peptides were separated using a 190 min gradient of 6-27% acetonitrile in 1.0% formic acid with a flow rate of 350 nL/min.

Each analysis used an MS3-based TMT method as described previously. The data were acquired using a mass range of m/z 340-1350, resolution 120,000, AGC target $1\times10^6$, maximum injection time 100 ms, dynamic exclusion of 120 seconds for the peptide measurements in the Orbitrap. Data dependent MS2 spectra were acquired in the ion trap with a normalized collision energy (NCE) set at 55%, AGC target set to $1.5\times10^5$ and a maximum injection time of 150 ms. MS3 scans were acquired in the Orbitrap with a HCD collision energy set to 55%, AGC target set to $1.5\times10^5$, maximum injection time of 150 ms, resolution at 50,000 and with a maximum synchronous precursor selection (SPS) precursors set to 10.

Proteome Discoverer™ 2.2 (Thermo Fisher Scientific™) was used for RAW file processing and controlling peptide and protein level false discovery rates, assembling proteins from peptides, and protein quantification from peptides. MS/MS spectra were searched against a Uniprot human database (September 2016) with both the forward and reverse sequences. Database search criteria was the following: tryptic with two missed cleavages, a precursor mass tolerance of 20 ppm, fragment ion mass tolerance of 0.6 Da, static alkylation of cysteine (57.02146 Da), static TMT labelling of lysine residues and N-termini of peptides (229.16293 Da), and variable oxidation of methionine (15.99491 Da). TMT reporter ion intensities were measured using a 0.003 Da window around the theoretical m/z for each reporter ion in the MS3 scan. Peptide spectral matches with poor quality MS3 spectra were excluded from quantitation (summed signal-to-noise across 10 channels<200 and precursor isolation specificity<0.5), and resulting data was filtered to only include proteins that had a minimum of 2 unique peptides identified. Reporter ion intensities were normalized and scaled using in-house scripts in the R framework. Statistical analysis was carried out using the limma package within the R framework.

The scatterplots in FIG. 2A-FIG. 2E show the change of cellular protein abundance in response to treatment of Kelly cells with 1 μM of compounds 1-5, 7, and 8 compared to DMSO control treated cells. Treatment with each of these bispecific compounds induced a significant reduction in HDAC6 protein levels when compared to the DMSO treated cells. The protein abundance measurements were made using multiplexed TMT quantitative mass spectrometry. Significant changes were assessed by moderated t-test comparing each of the bispecific compound treated cells to the DMSO control treated cells. The log 2-fold change (log 2 FC) is shown on the y-axis and the negative $\log_{10}$ p value ($-\log_{10}$ p value) is displayed on the x-axis for one independent biological replicate of the bispecific compound treatment and three independent biological replicates of the DMSO control treatment.

Figure 3:
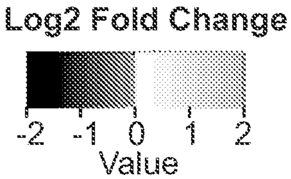
FIG. 3 is a heat map that shows the change in relative protein abundance of HDAC's identified in the experiment with treatment of Kelly cells with inventive bifunctional compounds 1-3, 7, and 8, (1 μM, 5 hours), compared to DMSO control. Significant changes were assessed by moderated t-test and colored according to movement and the log 2-fold change value displayed in the box for one independent biological replicates of treatment and three independent biological replicates of DMSO.
Figure 4A:
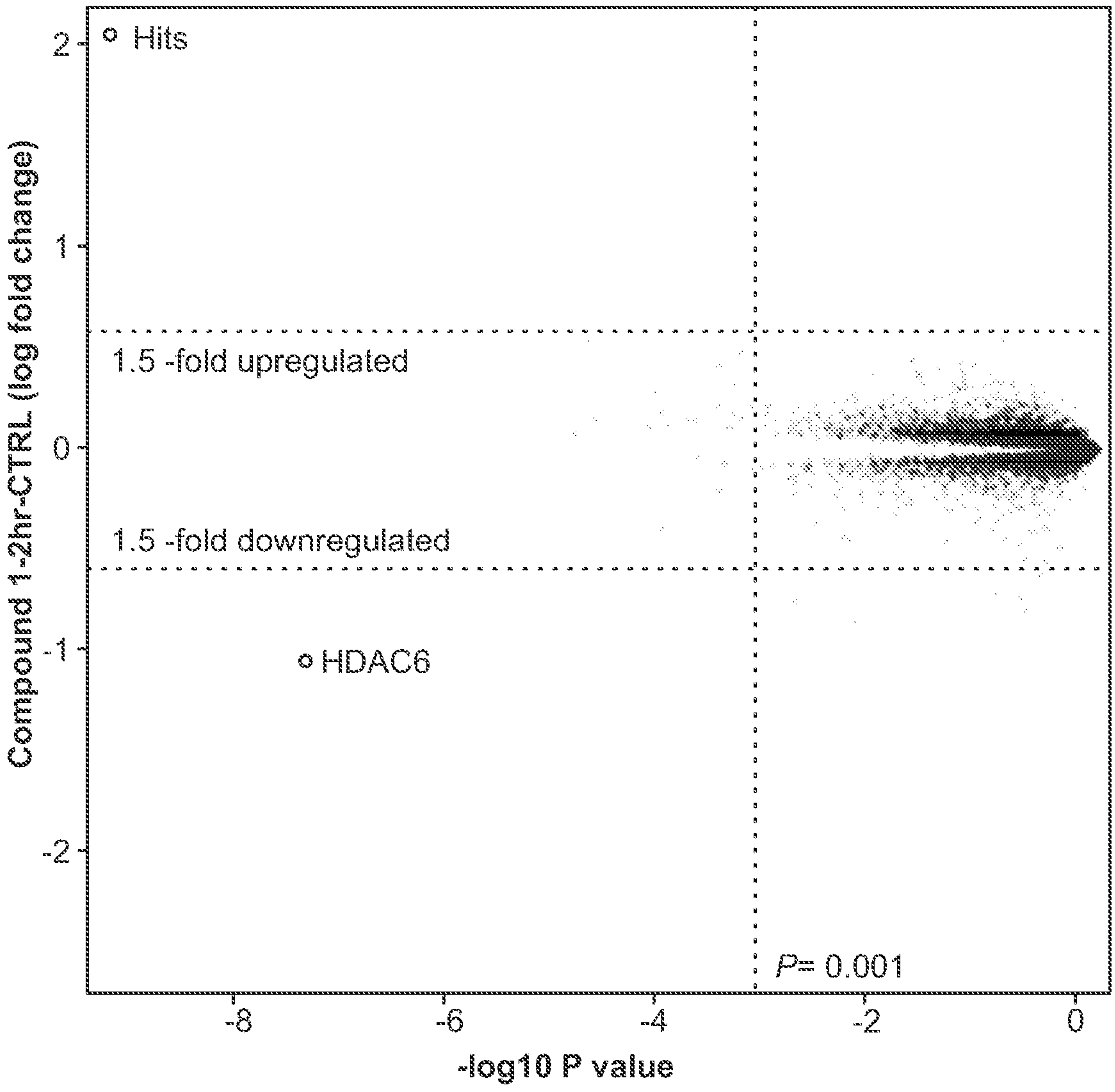
FIG. 4A-FIG. 4D are scatter plots that show the change in relative protein abundance with treatment of Kelly cells with inventive bifunctional compound 1 at 1 μM over a course of time (2, 4, 8, and 16 hours), compared to DMSO control. Significant changes were assessed by moderated t-test and displayed with log 2 fold change on the y-axis and negative $\log_{10}$ P values on the x-axis for two independent biological replicates of bifunctional compound 1 and three independent biological replicates of DMSO.
Figure 4B:
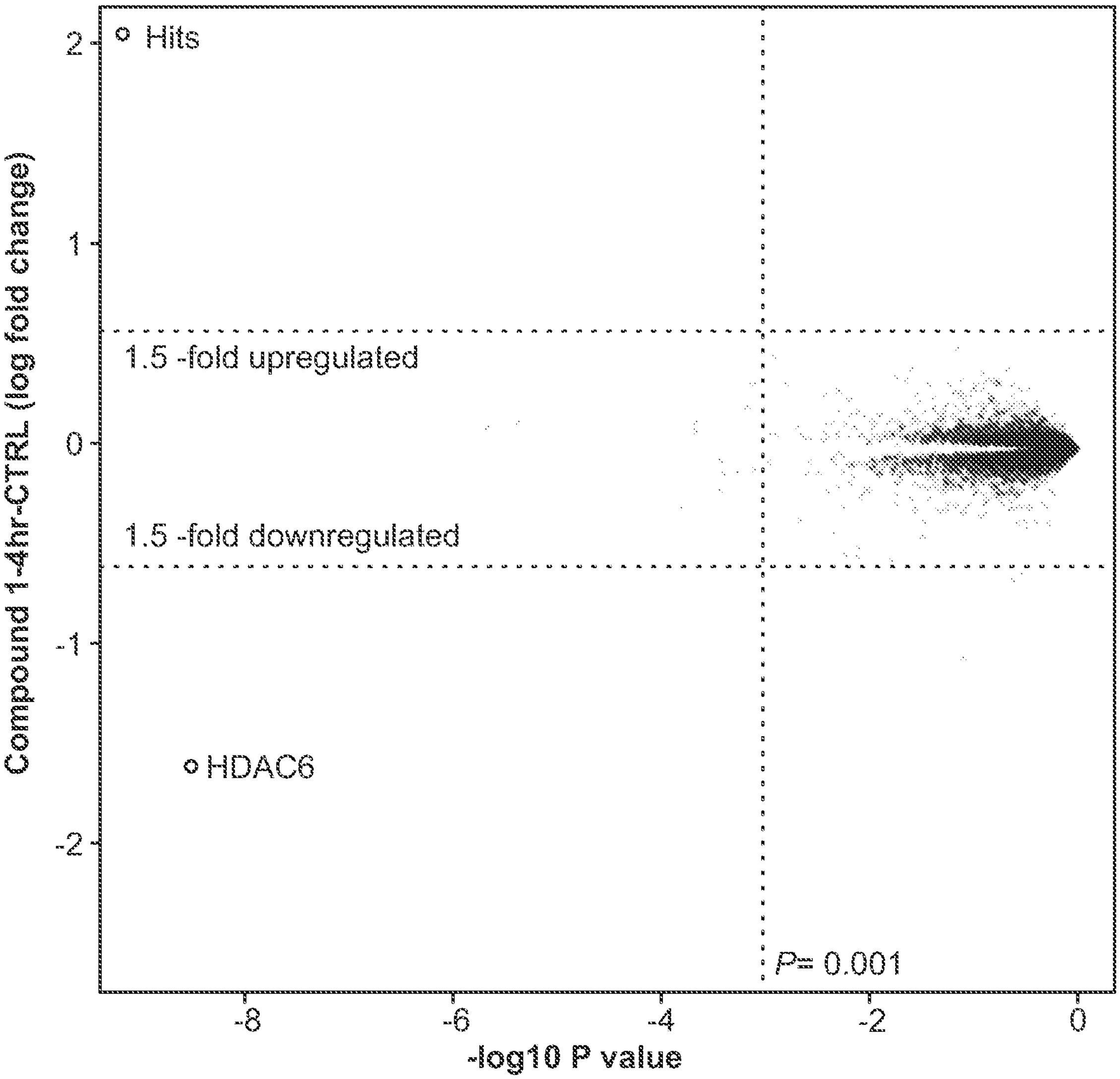
Figure 4C:
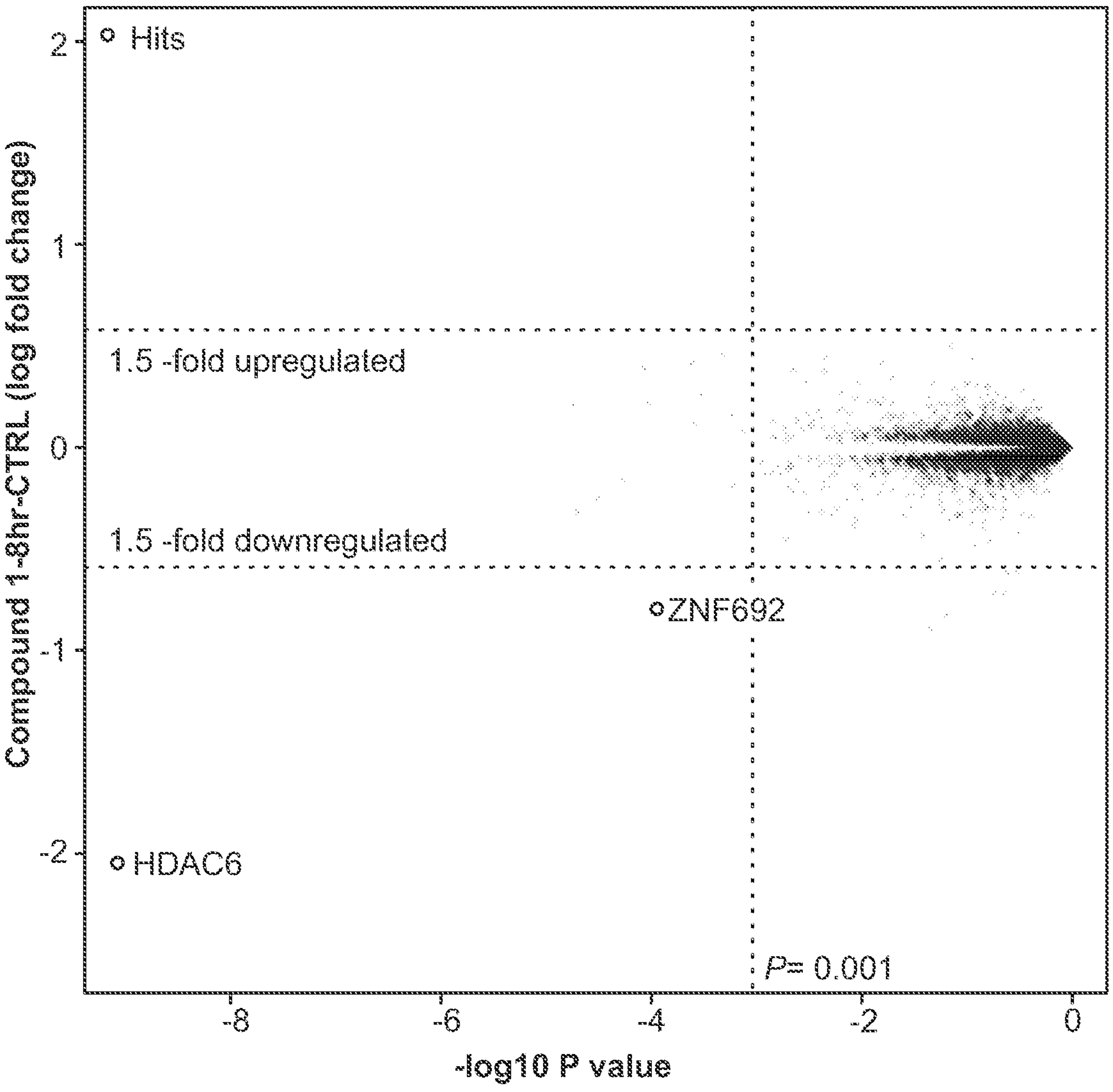
Figure 4D:
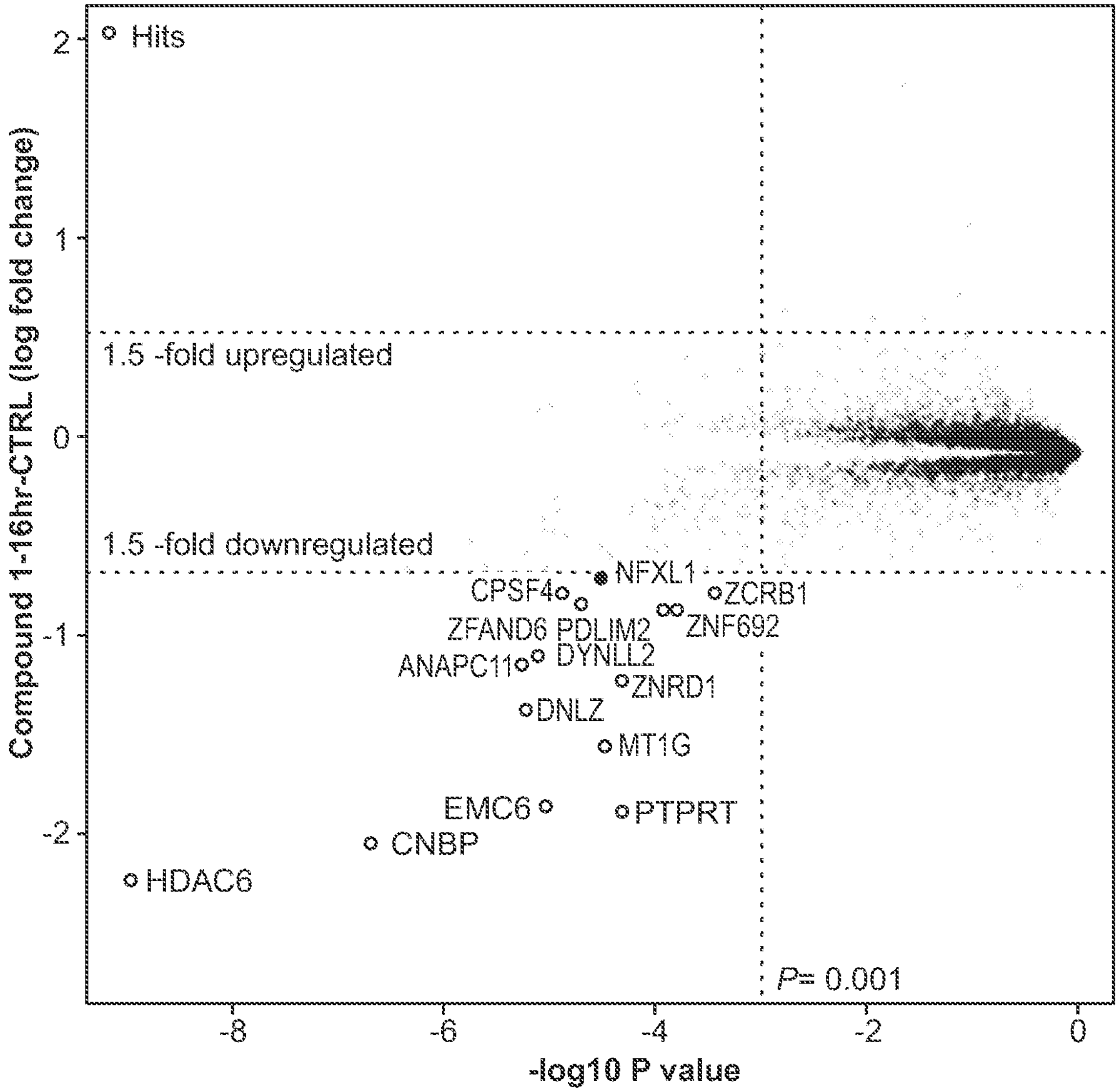

The heat map in FIG. 3 displays the change in cellular HDAC abundance in response to treatment of Kelly cells with 1 μM of compounds 1-3, 7, and 8 compared to DMSO control treated cells. This figure shows that these bispecific compounds induced down-regulation of cellular HDAC6 protein levels, but did not affect the cellular protein levels of the other identified HDAC proteins. The protein abundance measurements were made using multiplexed TMT quantitative mass spectrometry and significant changes were assessed by moderated t-test, as described above.

The scatterplots in FIG. 4A-FIG. 4D show the change of cellular protein abundance in response to treatment of Kelly cells with 1 μM of compound 1 over a course of time (2, 4, 8, and 16 hours) compared to DMSO control treated cells. Treatment with compound 1 induced a significant reduction in HDAC6 protein levels after just 2 hours when compared to the DMSO treated cells and the HDAC6 protein levels continued to decrease over the course of 16 hours. The protein abundance measurements were made using multiplexed TMT quantitative mass spectrometry and significant changes were assessed by moderated t-test, as described above.

Figure 5:
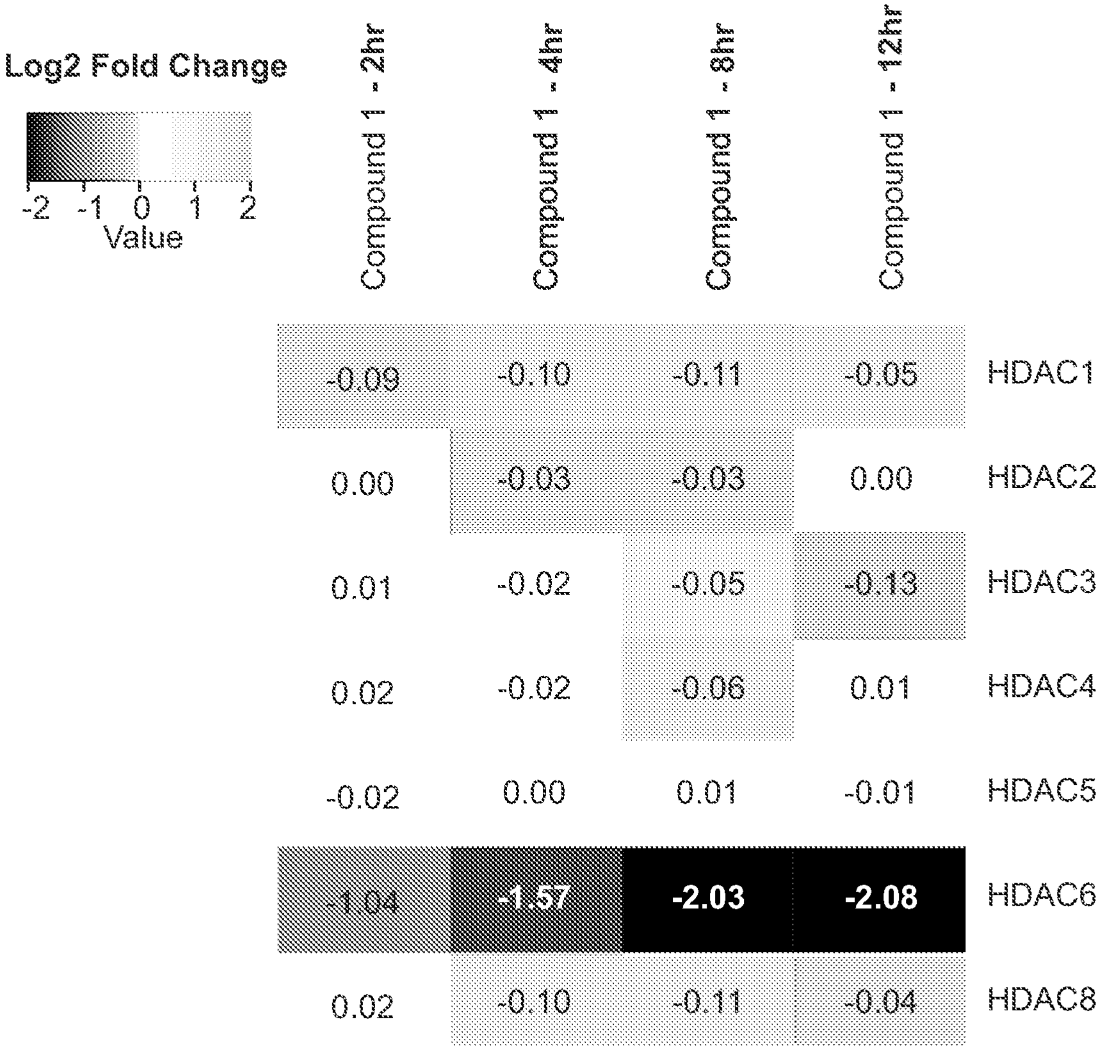
FIG. 5 is a heat map that shows the change in relative protein abundance of HDACs identified in the experiment with treatment of Kelly cells with inventive bifunctional compound 1 at 1 μM over a course of time (2, 4, 8, and 16 hours), compared to DMSO control. Significant changes were assessed by moderated t-test and colored according to movement and the log 2 fold change value displayed in the box for two independent biological replicates of treatment and three independent biological replicates of DMSO.

The heat map in FIG. 5 displays the change in cellular HDAC abundance in response to treatment of Kelly cells with 1 μM of compound 1 over the course of time (2, 4, 8, and 16 hours) compared to DMSO control treated cells. The figure shows that compound 1 induced down regulation of cellular HDAC6 protein levels, but did not affect the cellular protein levels of the other identified HDAC proteins. The protein abundance measurements were made using multiplexed TMT quantitative mass spectrometry and significant changes were assessed by moderated t-test, as described above.

All patent publications and non-patent publications are indicative of the level of skill of those skilled in the art to which this invention pertains. All these publications (including any specific portions thereof that are referenced) are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A bispecific compound having a structure represented by formula (I):

(I)

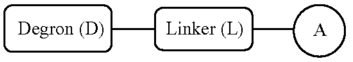

, or a pharmaceutically acceptable salt or stereoisomer thereof, wherein

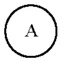

is a moiety represented by formula TL1 or TL2:

(TL1)

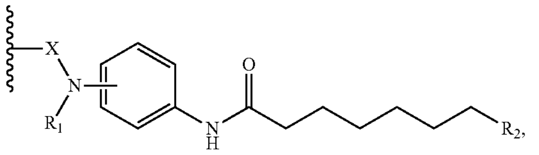

or (TL2)

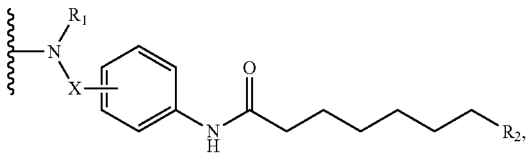

wherein

X is $CH_2$ or C═O;

$R_1$ is H or Me; and $R_2$ is

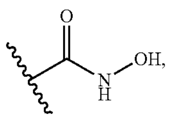

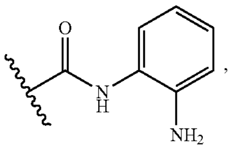

or

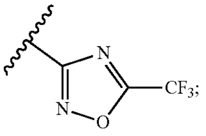 [SMILES: *c1noc(C(F)(F)F)n1]

the degron is represented by any one of the formulas (D1-D12):
(D1)
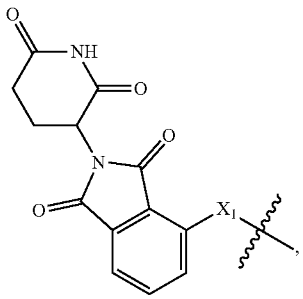
(D2)
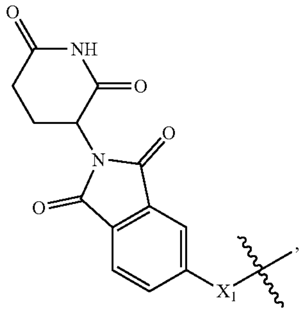
(D3)
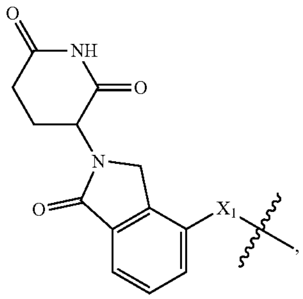
(D4)
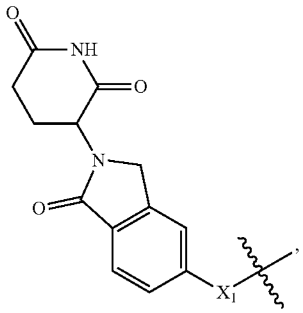
-continued
(D5)
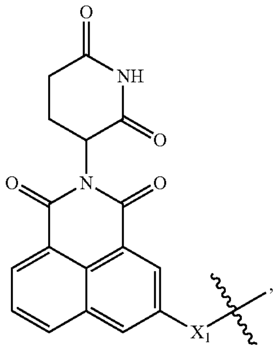
(D6)
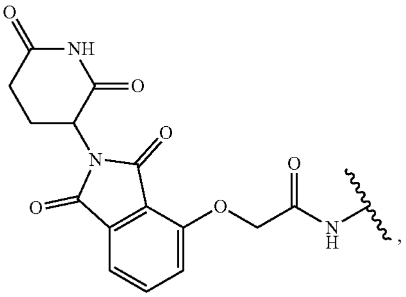
(D7)
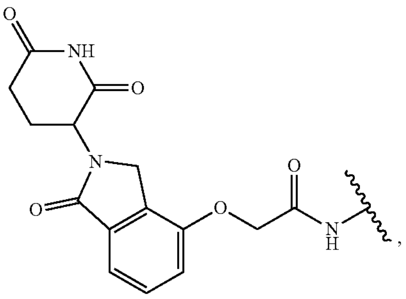
(D8)
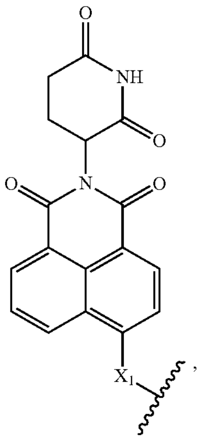

-continued (D9)

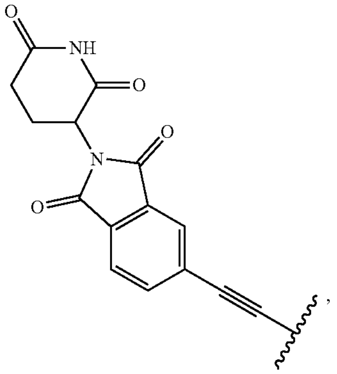

(D10)

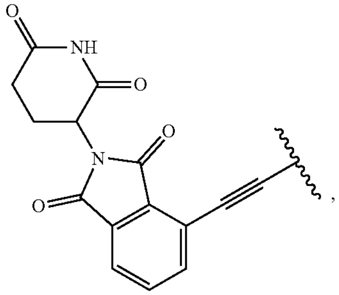

(D11)

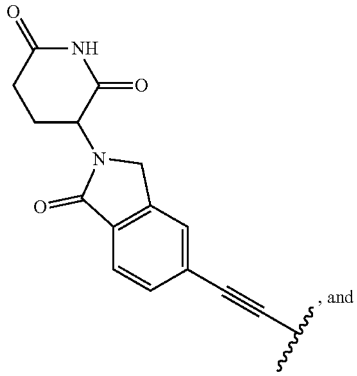

, and (D12)

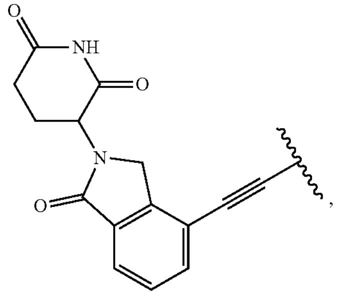

wherein $X_1$ is $CH_2$, NH, or O, and the linker is an alkylene chain which may be interrupted by, and/or terminate at either or both termini in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, $—S(O)_2—$, —OS(O)—, —S(O)O—, —S(O)—, $—OS(O)_2—$, $—S(O)_2O—$, $—N(R')S(O)_2—$, $—S(O)_2N(R')—$, —N(R')S(O)—, —S(O)N(R')—, $—N(R')S(O)_2N(R')—$, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different, or a polyethylene glycol chain which may terminate at either or both termini in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, $—S(O)_2—$, —OS(O)—, —S(O)O—, —S(O)—, $—OS(O)_2—$, $—S(O)_2O—$, $—N(R')S(O)_2—$, $—S(O)_2N(R')—$, —N(R')S(O)—, —S(O)N(R')—, $—N(R')S(O)_2N(R')—$, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

2. The bispecific compound of claim 1, wherein $R_2$ is

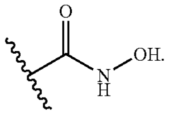 [SMILES: *C(=O)NO]

3. The bispecific compound of claim 1, wherein

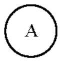

is selected from the group consisting of:

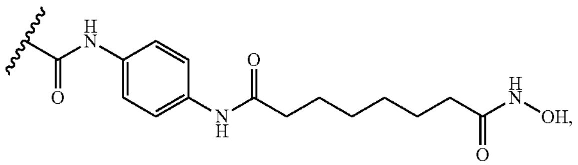

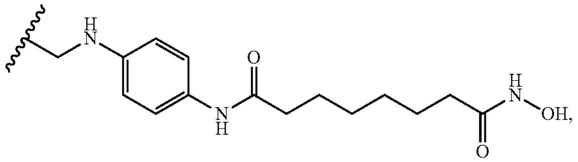

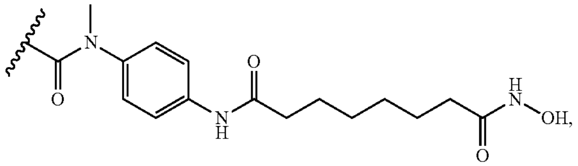

-continued
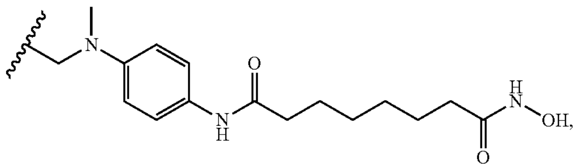,
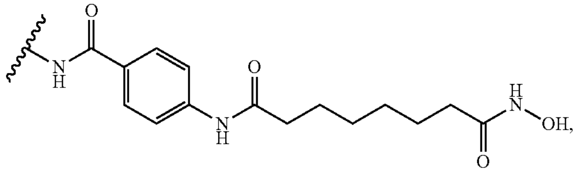,
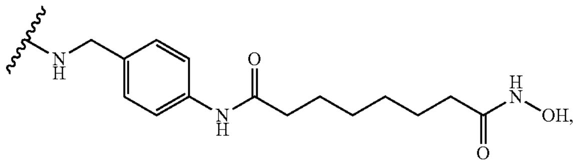,
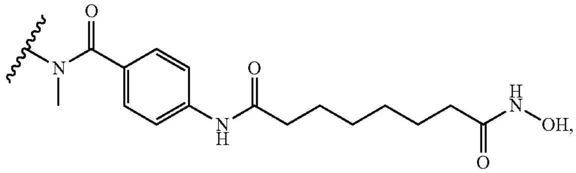,
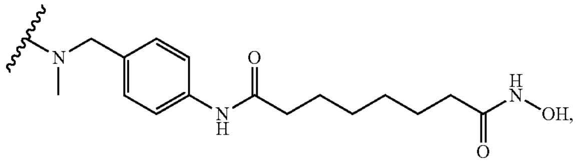,
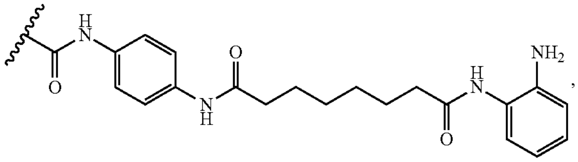,
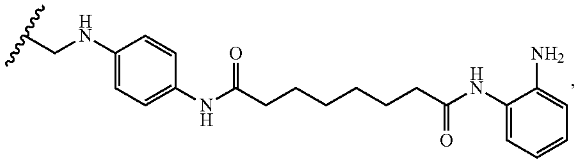,
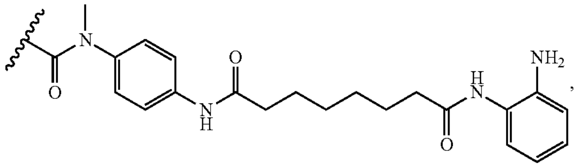,
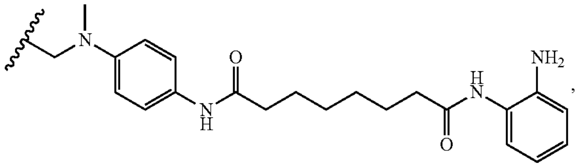,
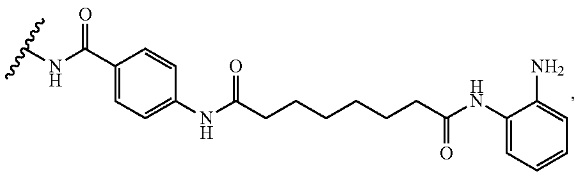,
-continued
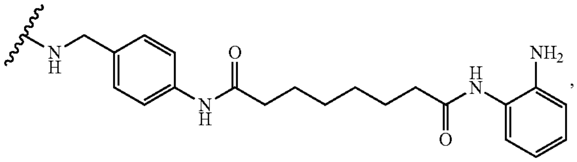,
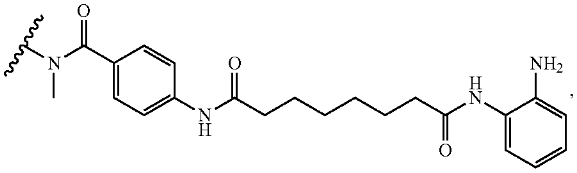,
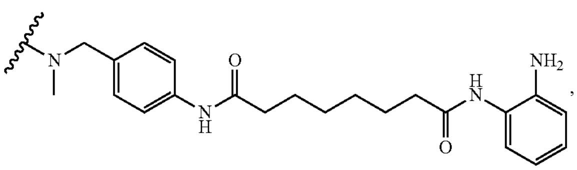,
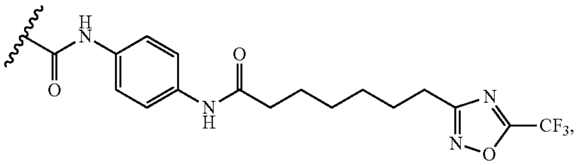,
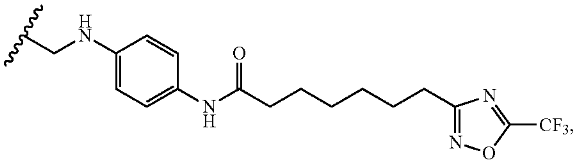,
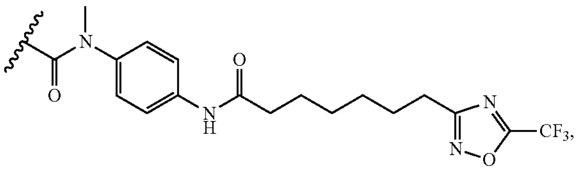,
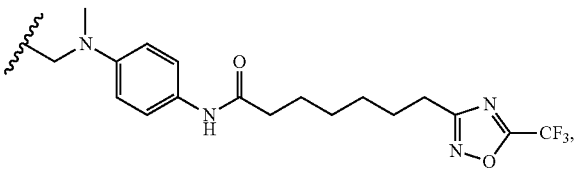,
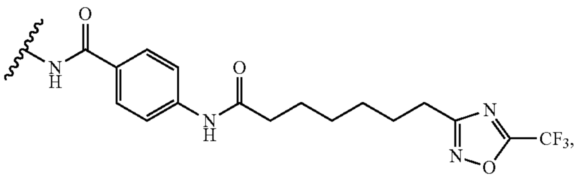,
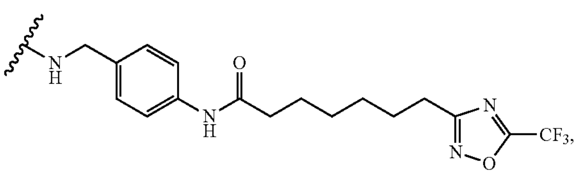,
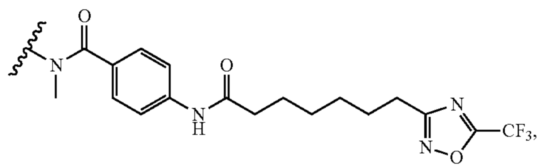 and -continued

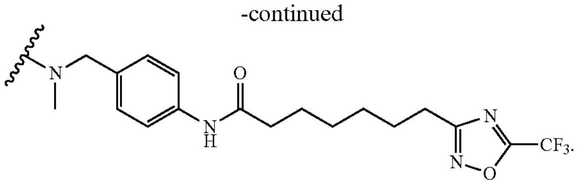

4. The bispecific compound of claim 1, wherein the linker is an alkylene chain which may be interrupted by, and/or terminate at either or both termini in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

5. The bispecific compound of claim 4, wherein the linker is an alkylene chain having 2-8 alkylene units.

6. The bispecific compound of claim 1, wherein the linker is a polyethylene glycol (PEG) chain which may terminate at either or both termini in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, N(R')C(O)N(R')—, —N(R')C(O)O—, —OC(O)N(R')—, —C(NR')—, —N(R')C(NR)—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

7. The bispecific compound of claim 6, wherein the linker is a polyethylene glycol chain having 2-6 PEG units.

8. The bispecific compound of claim 1, which is represented by any one of the following structures:

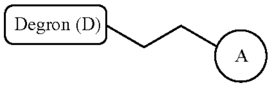
,

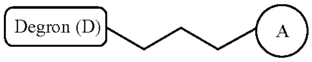
,

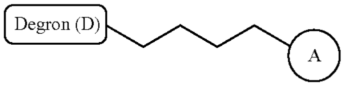
,

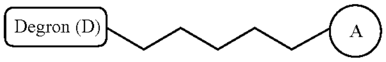
,

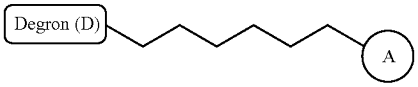
,

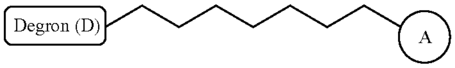
,

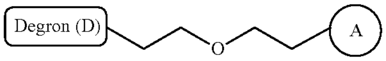
, or

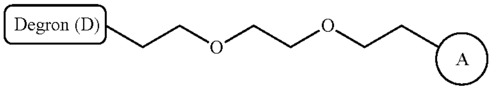
, or a pharmaceutically acceptable salt or stereoisomer thereof.

9. The bispecific compound of claim 1, which is represented by any one of the following structures:

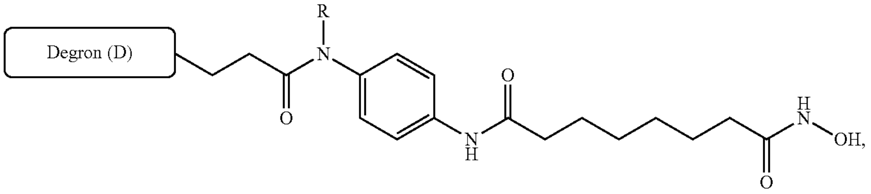

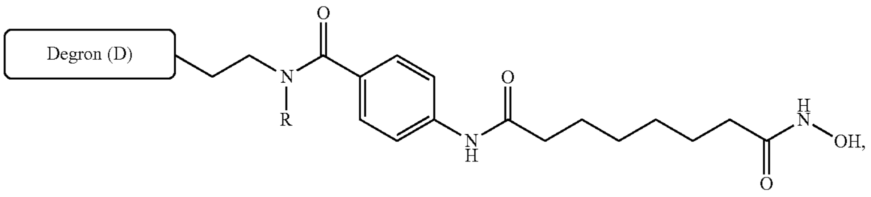

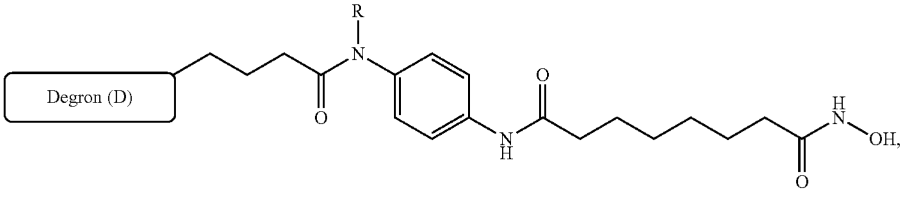

-continued
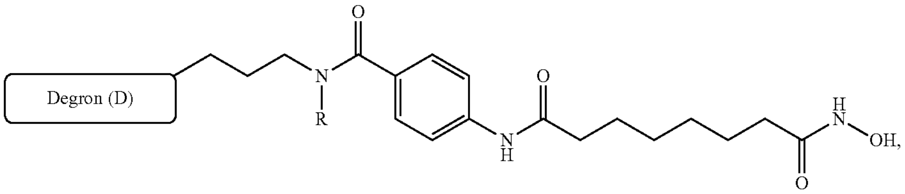
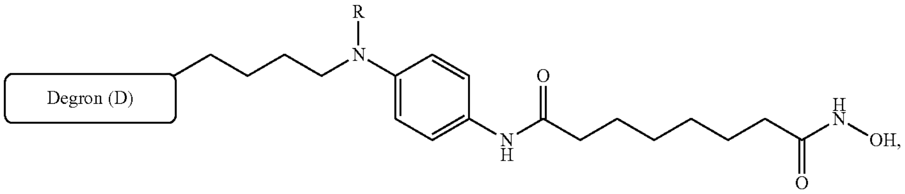
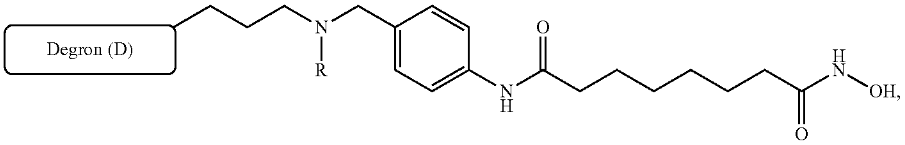
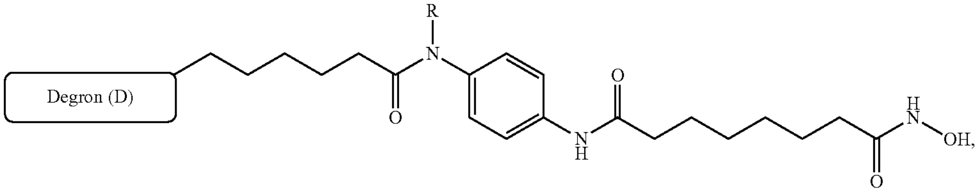
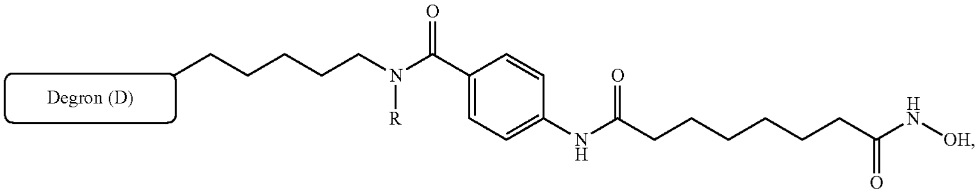
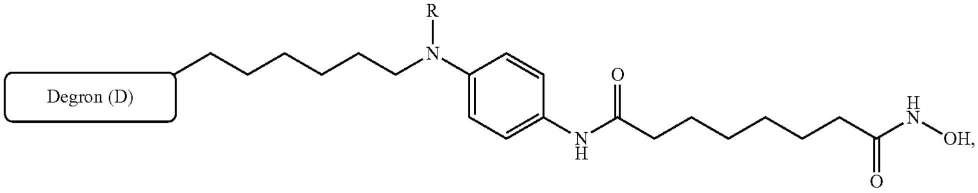
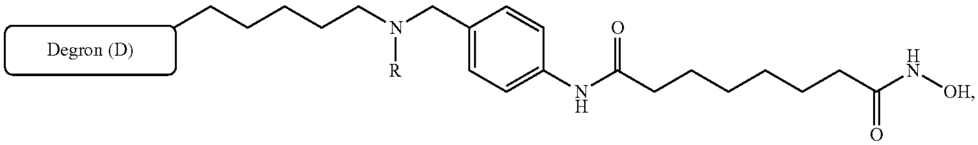
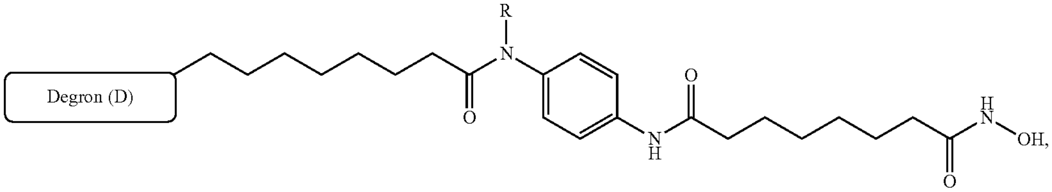
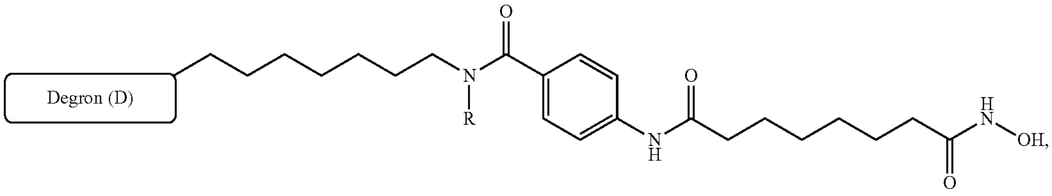

-continued
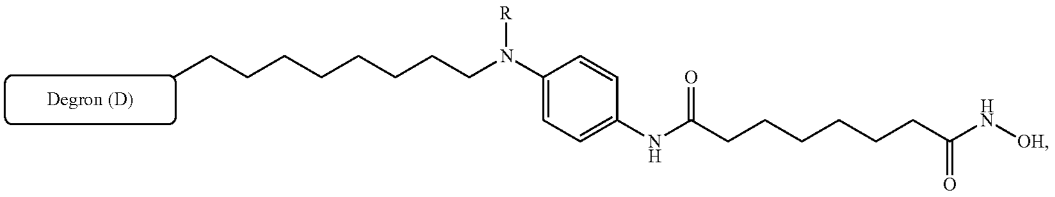
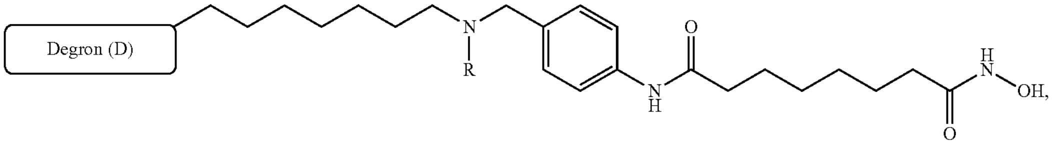
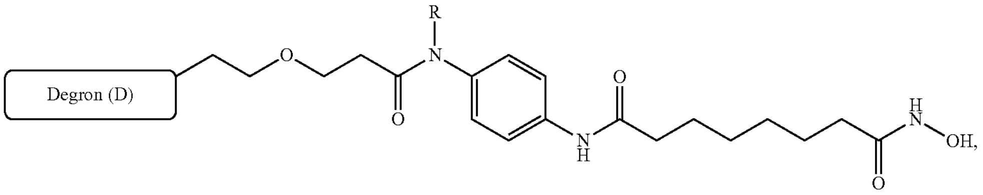
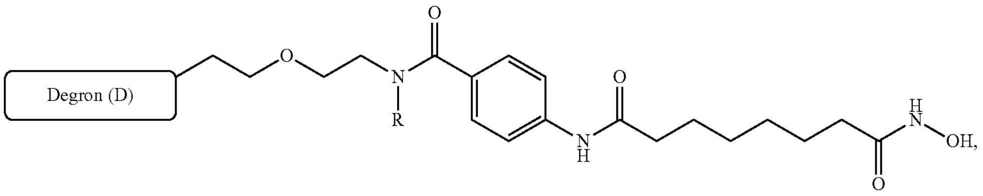
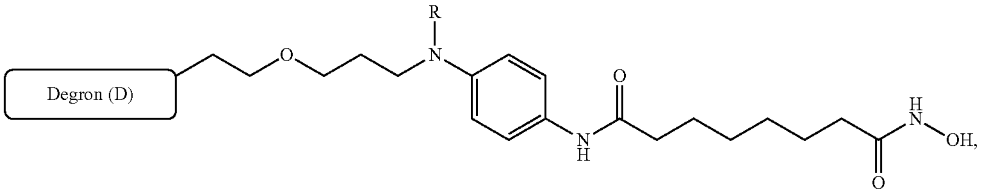
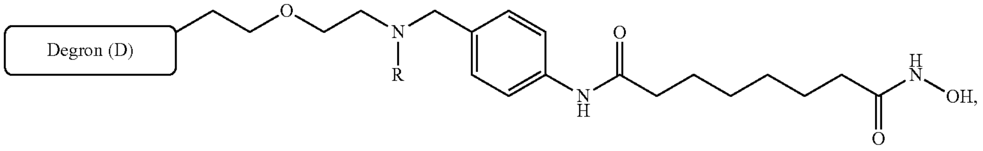
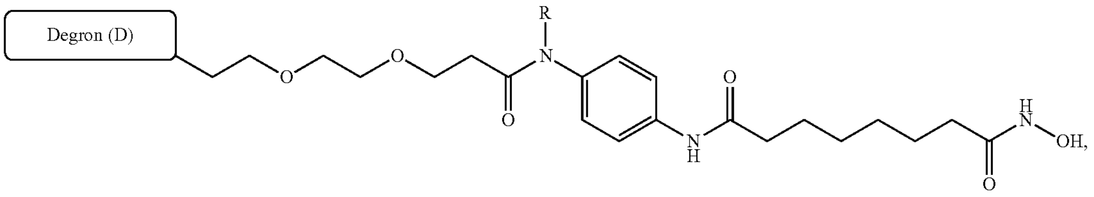
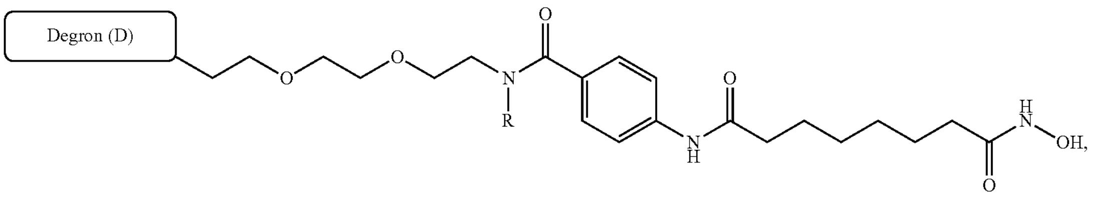
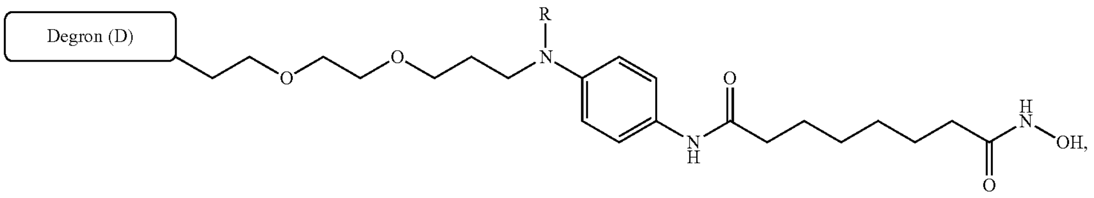

-continued
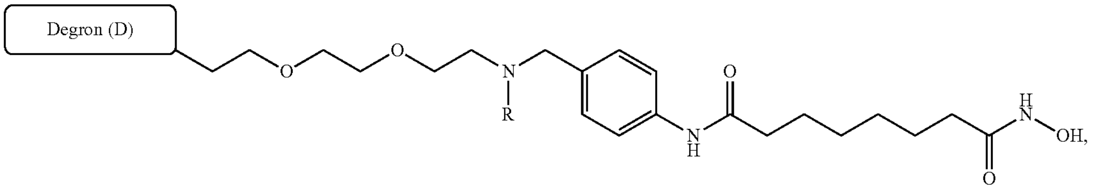
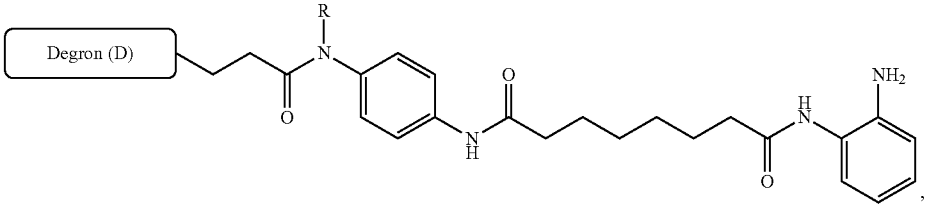
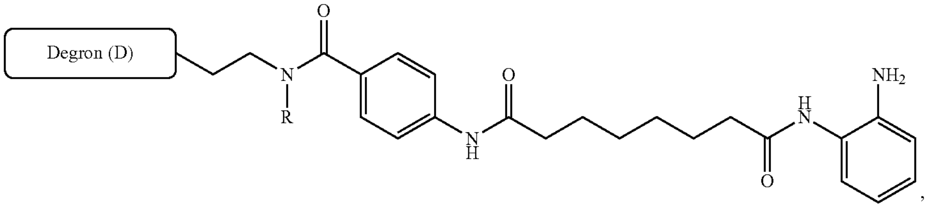
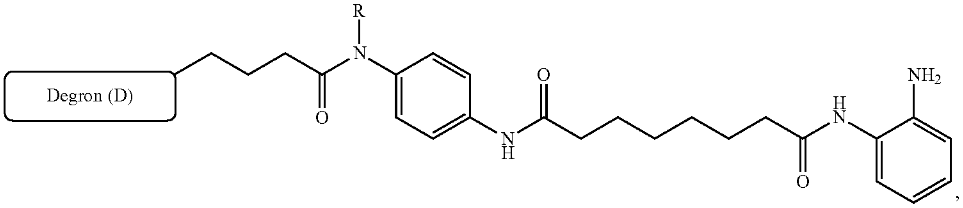
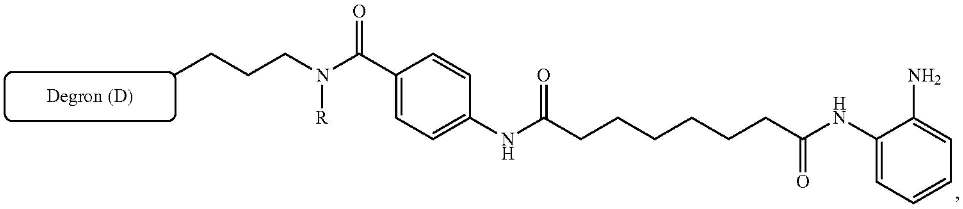
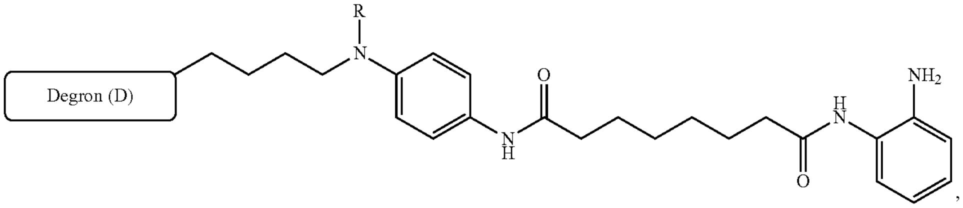
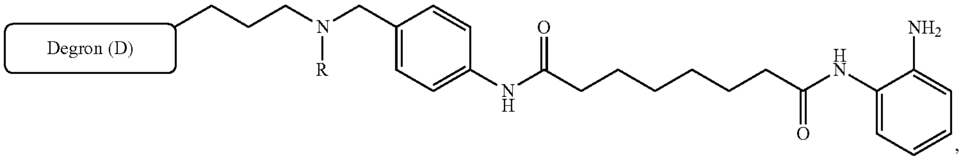
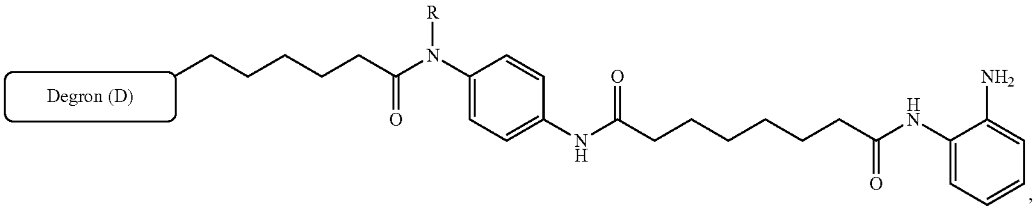

-continued
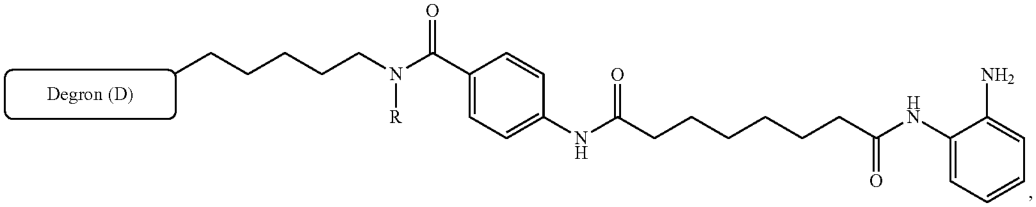
,
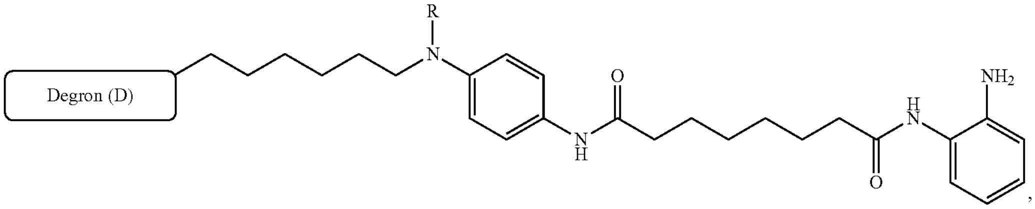
,
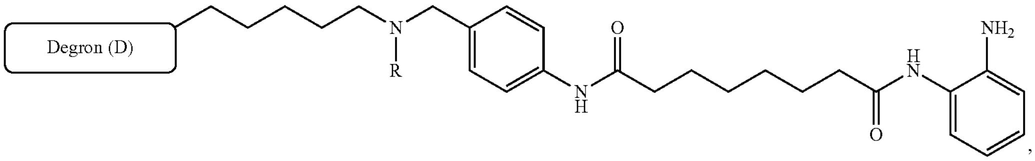
,
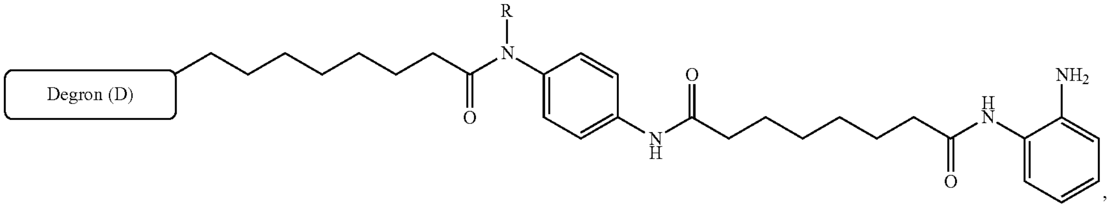
,
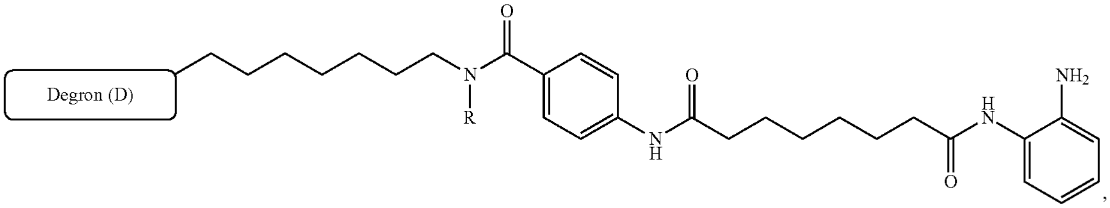
,
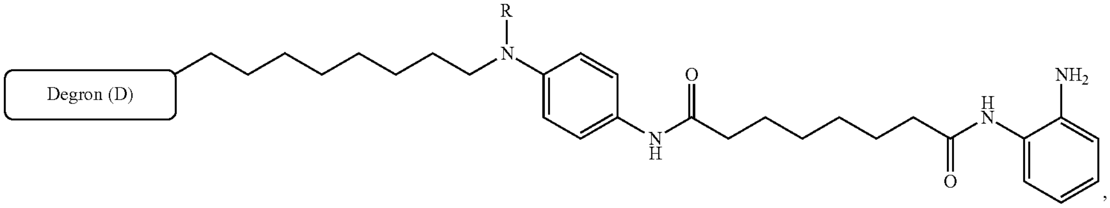
,
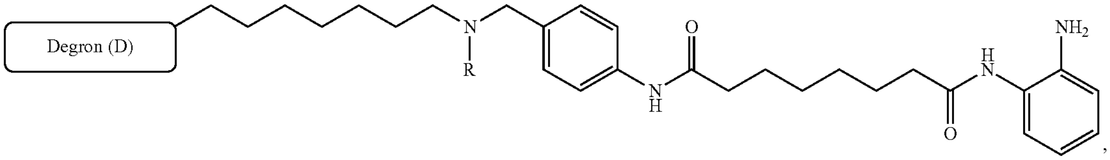
,
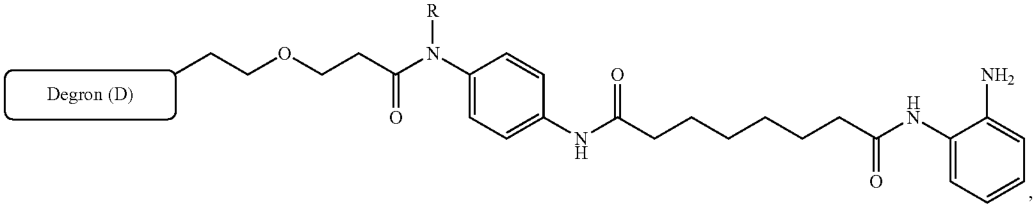
, -continued
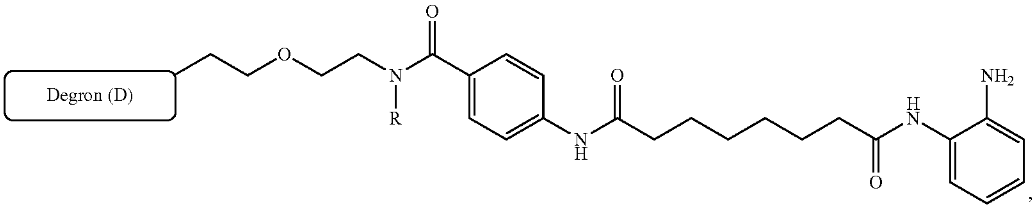
,
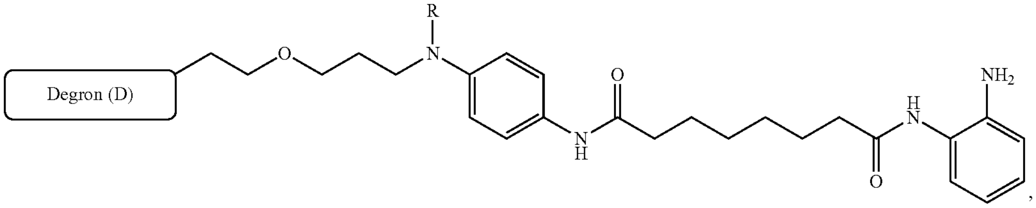
,
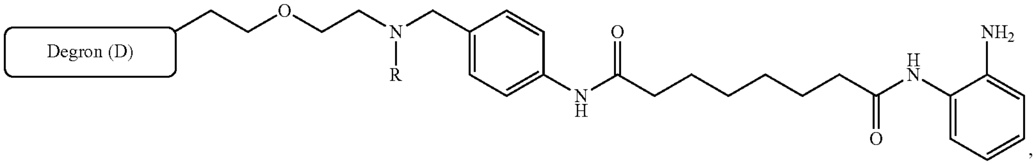
,
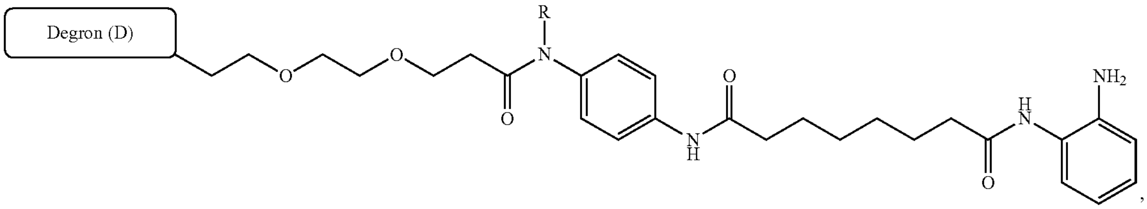
,
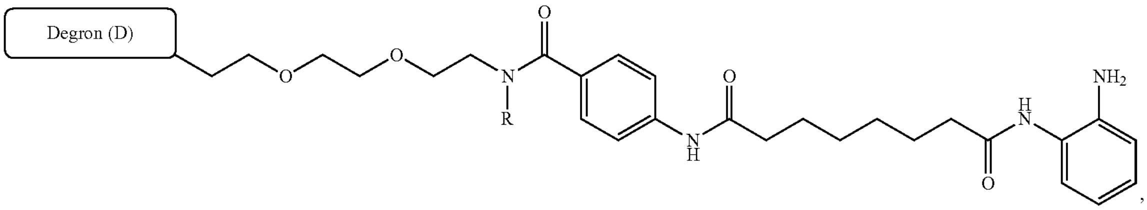
,
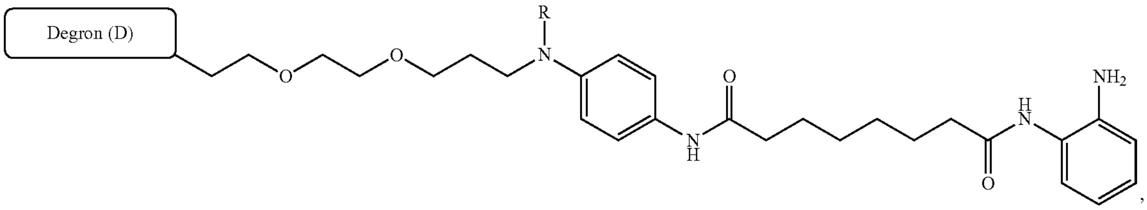
,
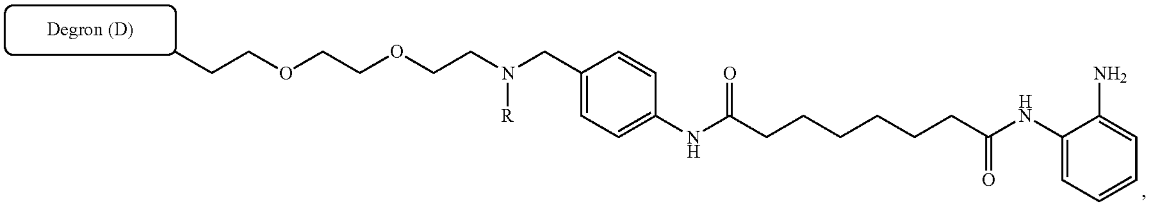
,
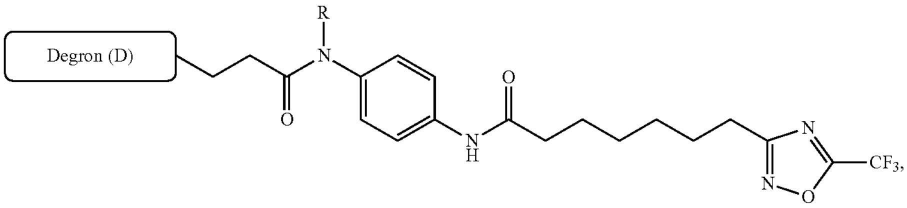
, -continued
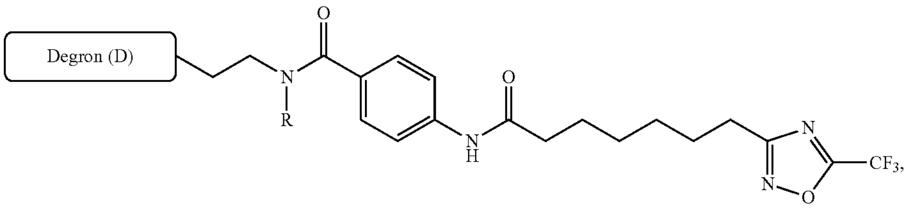
,
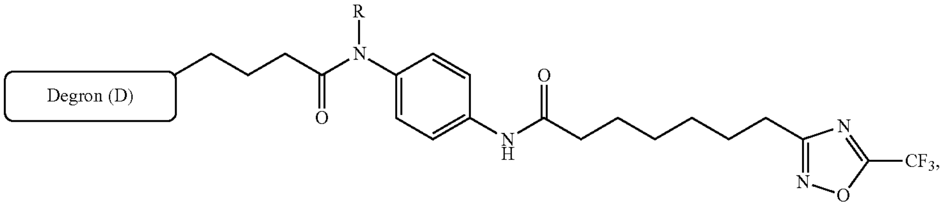
,
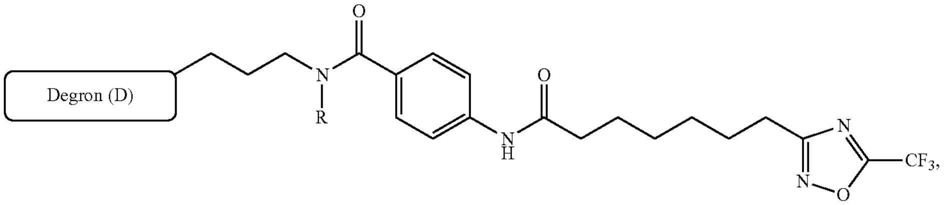
,
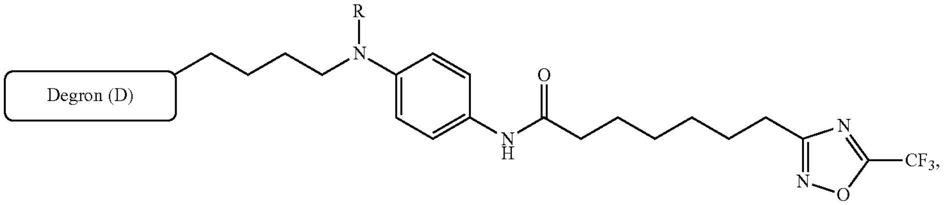
,
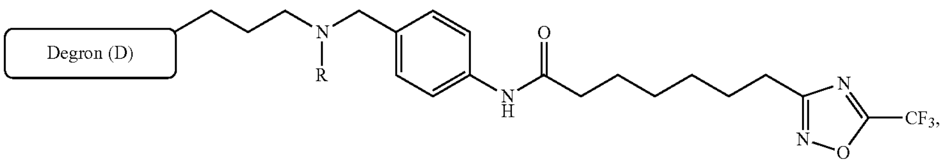
,
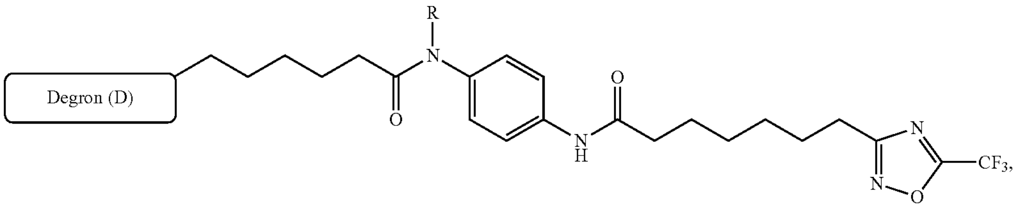
,
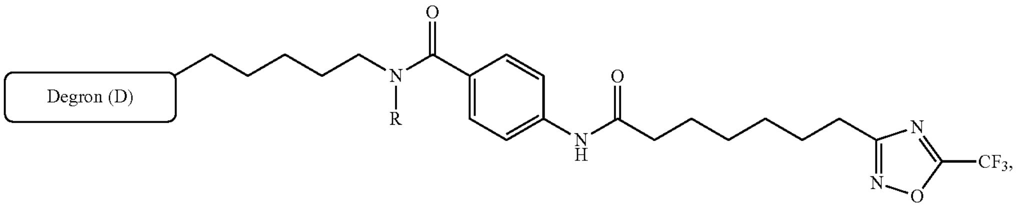
,
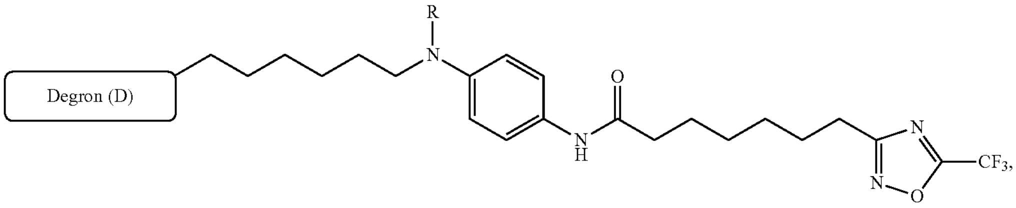
, -continued
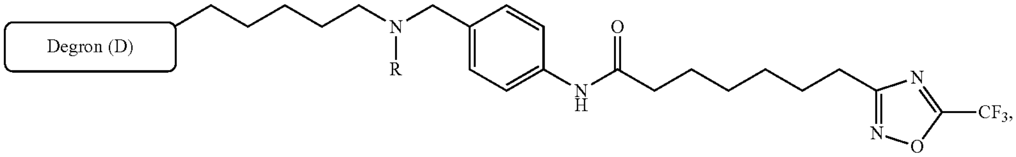,
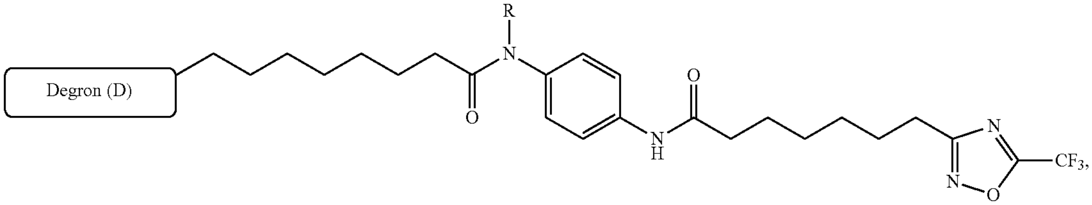,
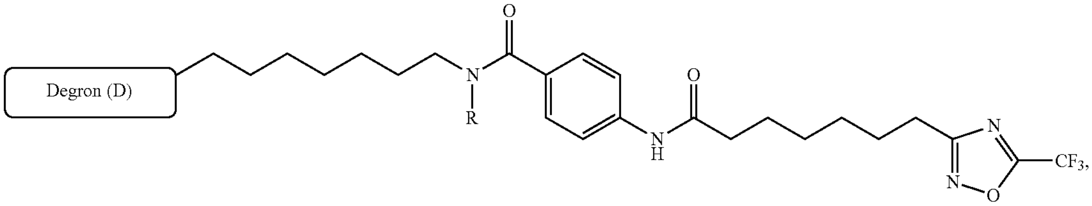,
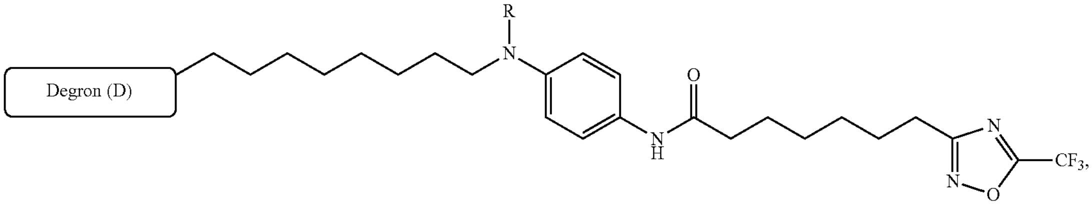,
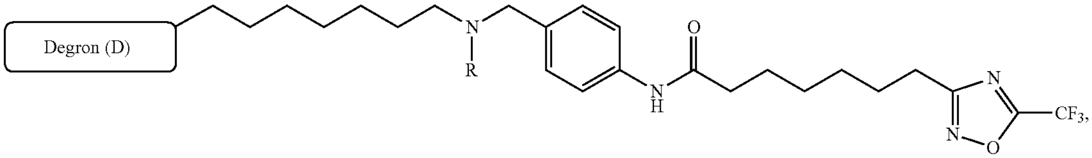,
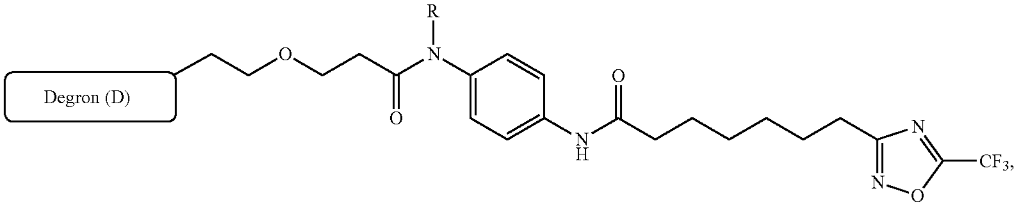,
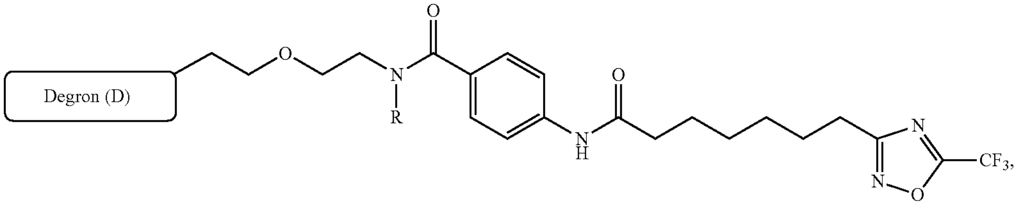,
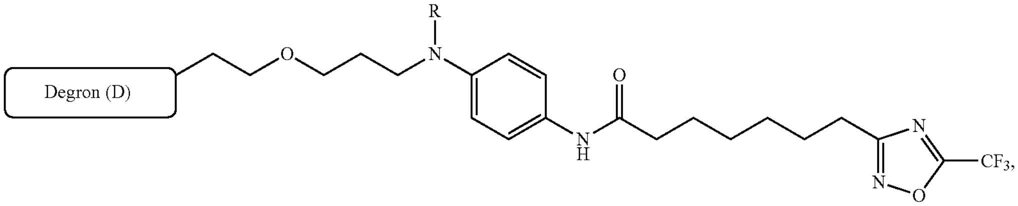,
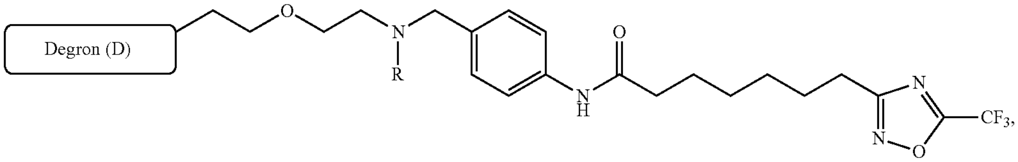, -continued
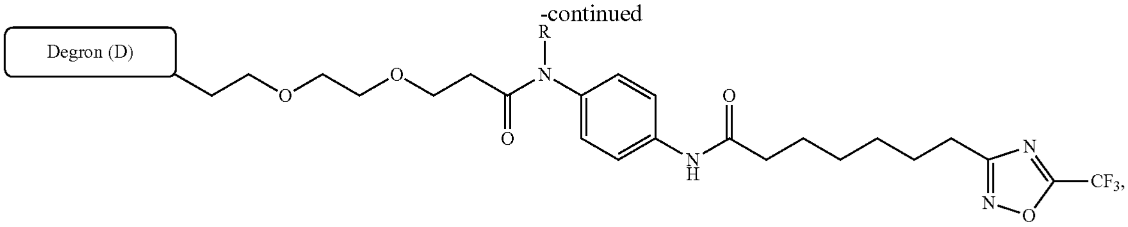
,
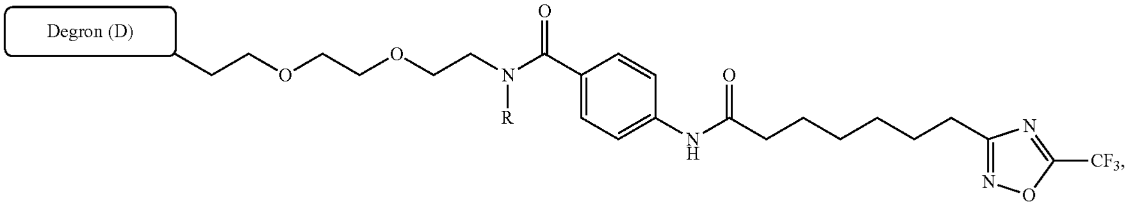
,
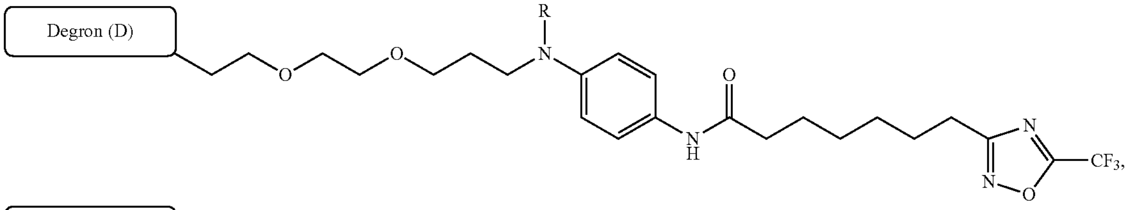
, or
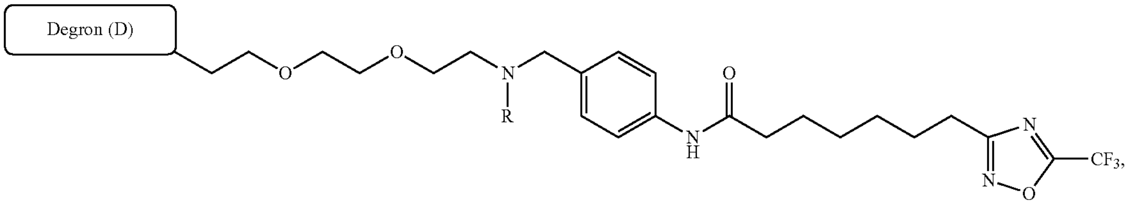
,
wherein R is H or Me,
or a pharmaceutically acceptable salt or stereoisomer thereof.
10. The bispecific compound of claim 1, wherein the degron is represented by any one of the formulas (D1-D4):
(D1)
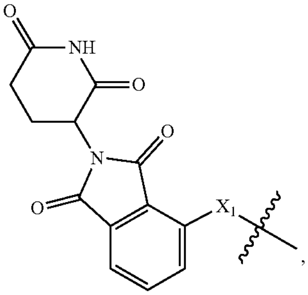
,
(D2)
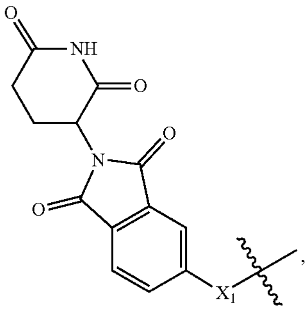
,
-continued
(D3)
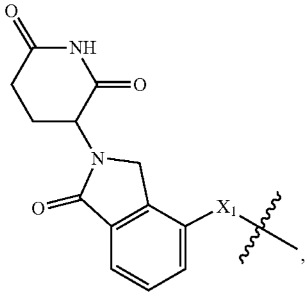
, and
(D4)
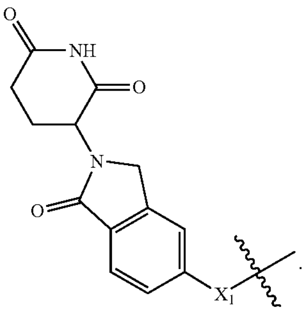
.

11. The bispecific compound of claim 1, which is represented by any one of the following structures:
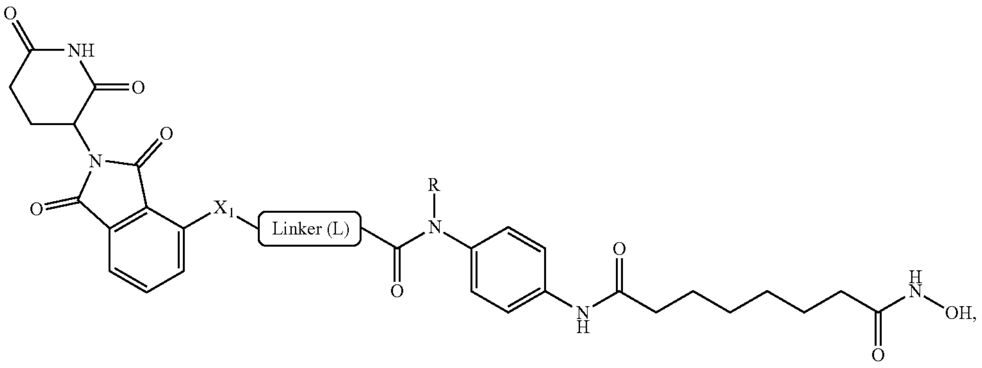
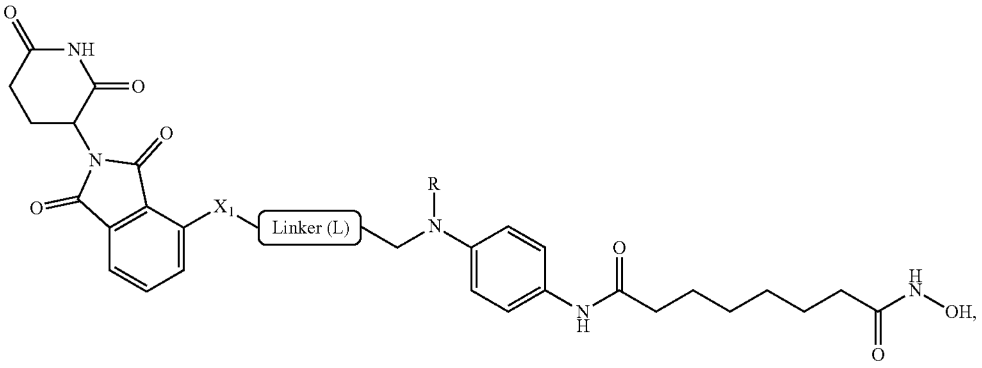
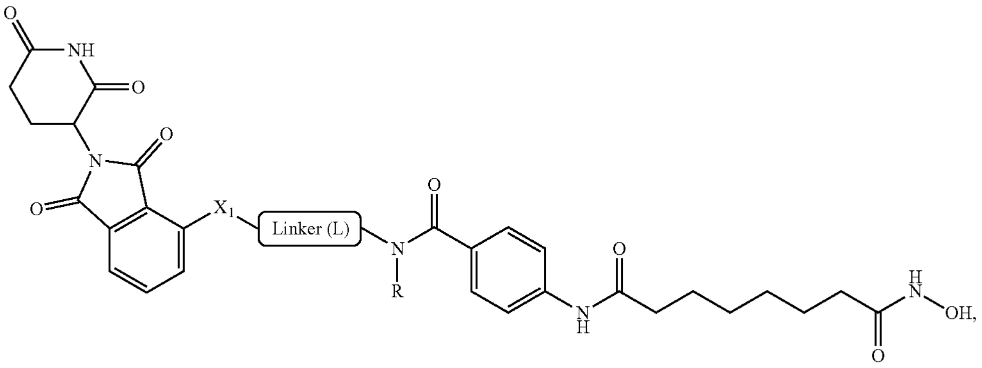
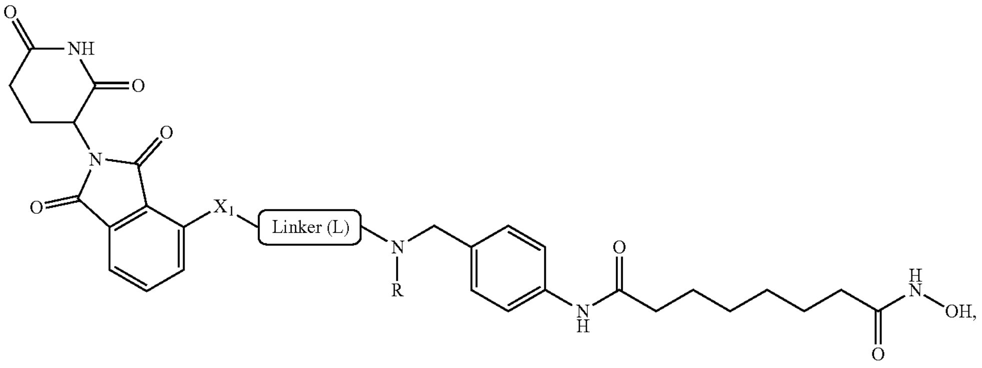

-continued
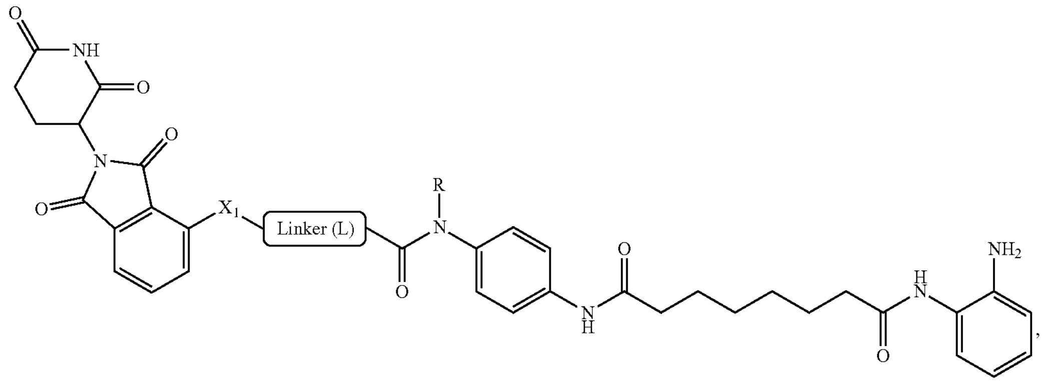
,
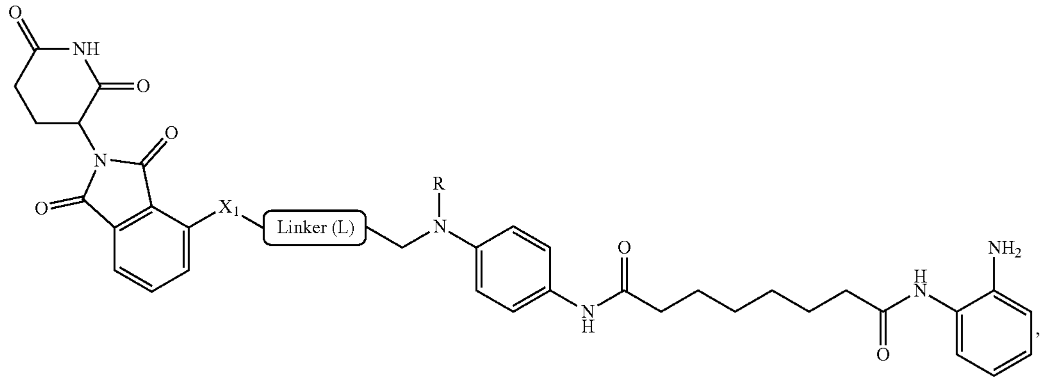
,
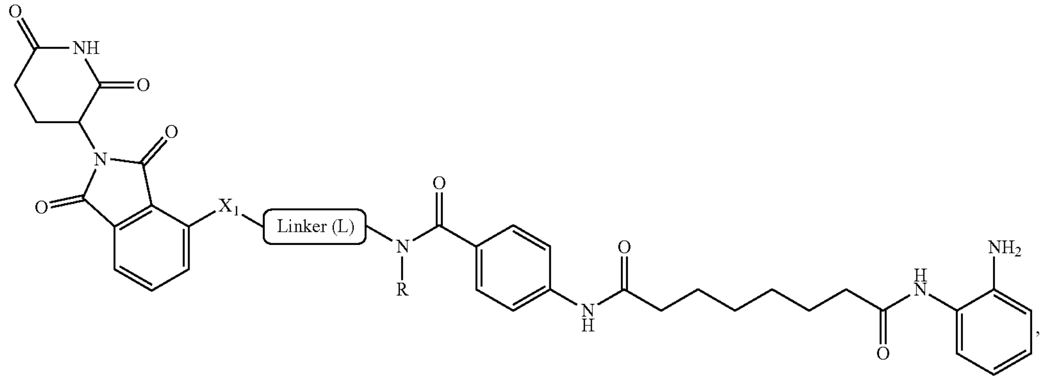
,
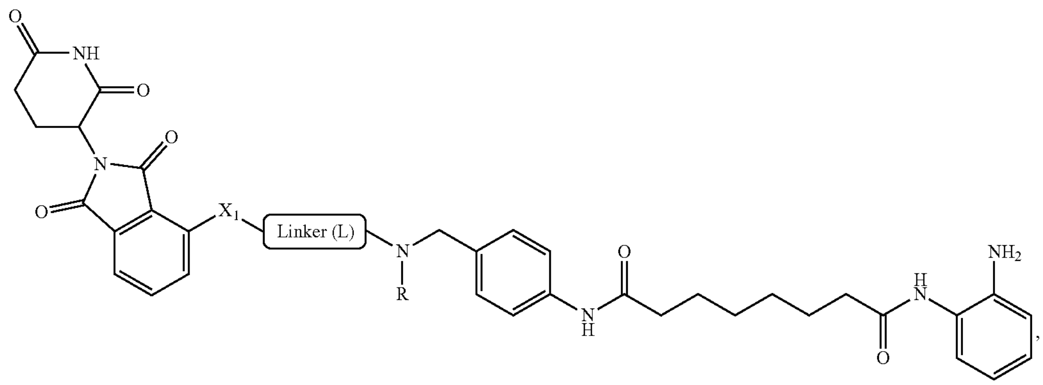
,

-continued
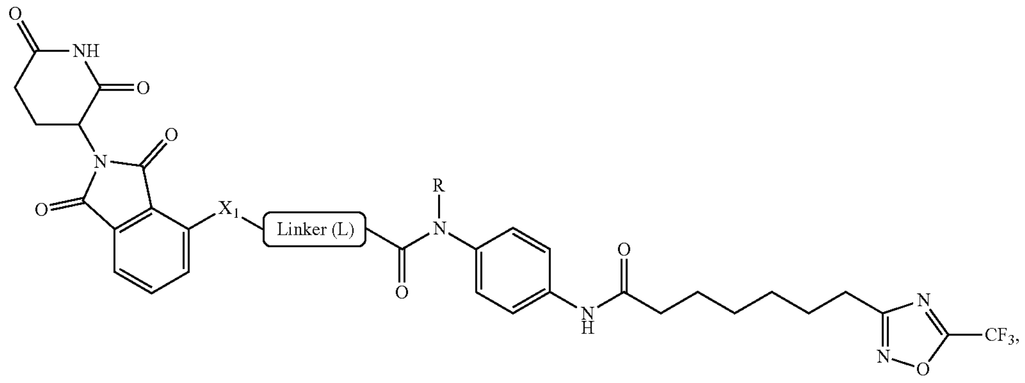
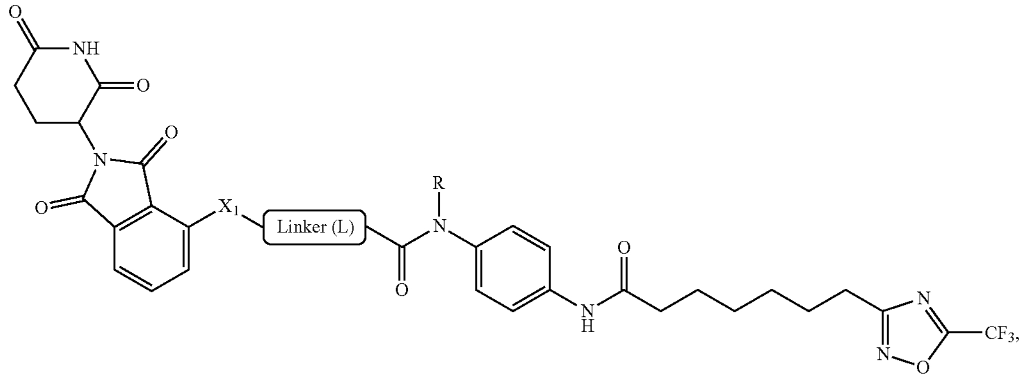
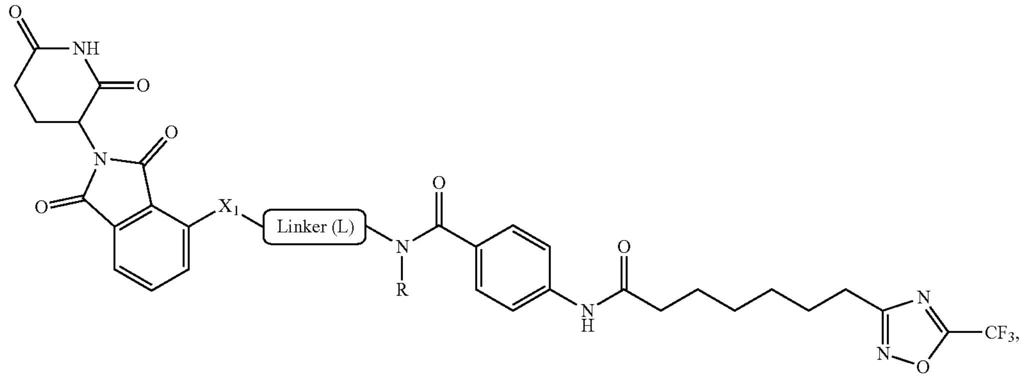
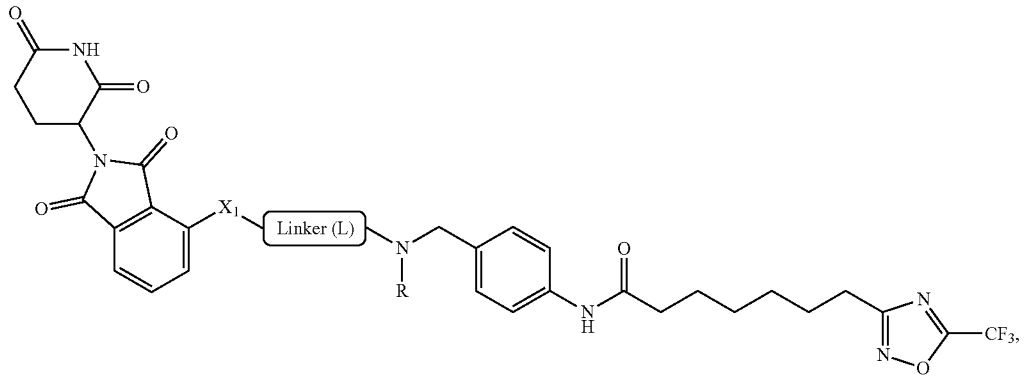

-continued
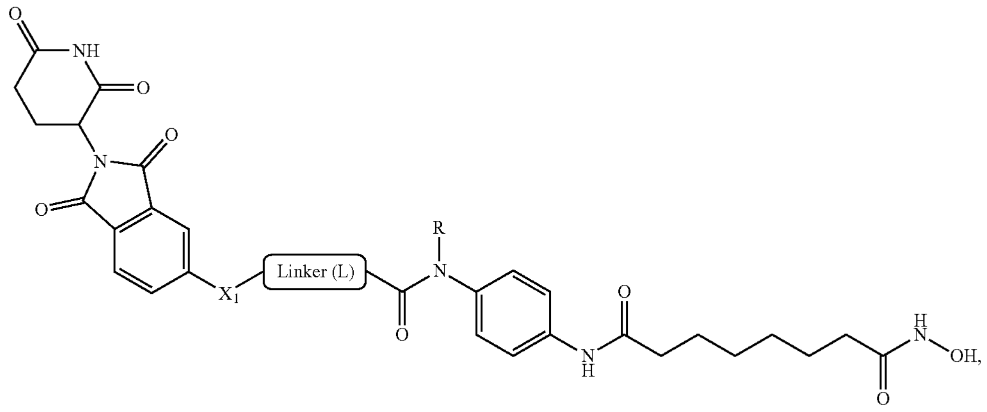
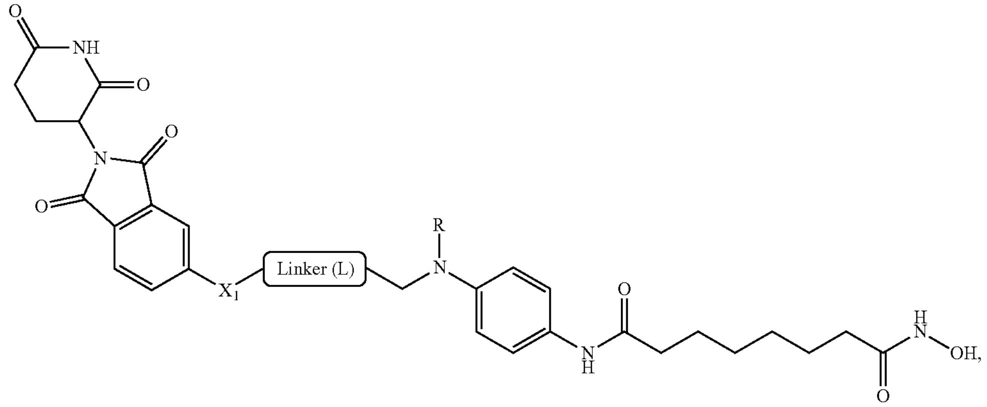
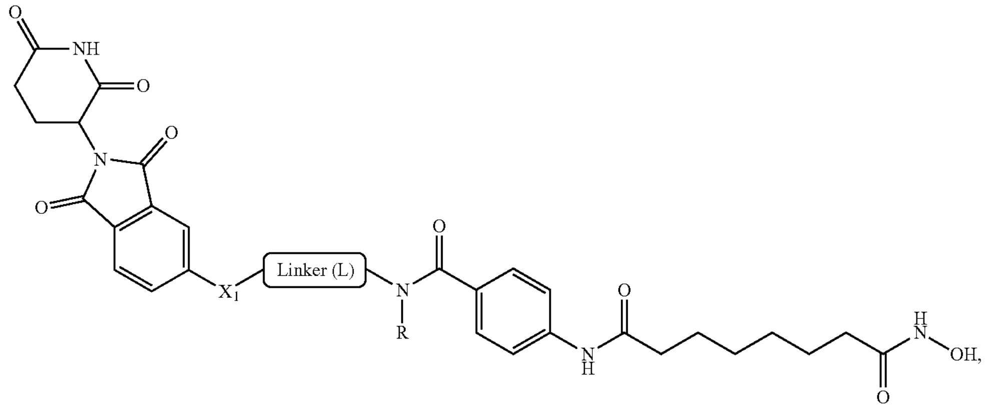
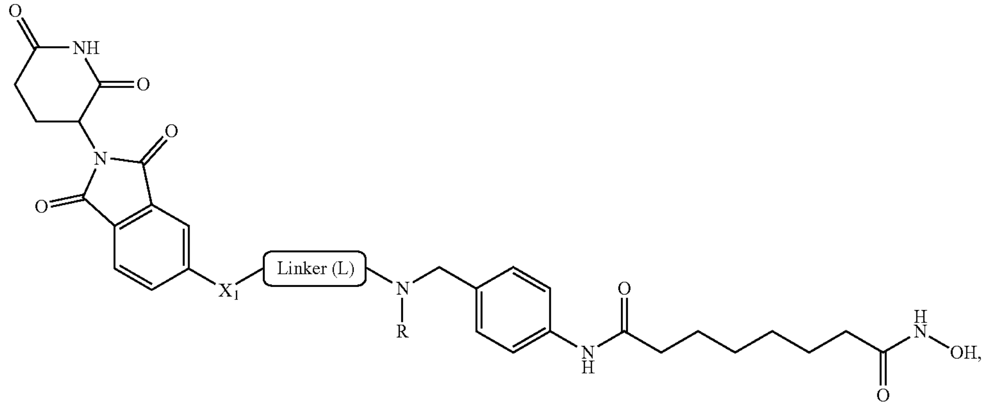

-continued
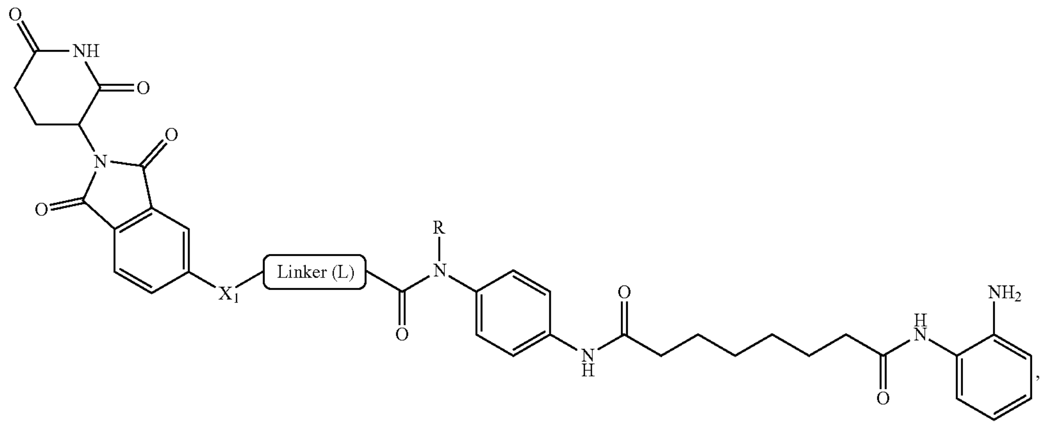
,
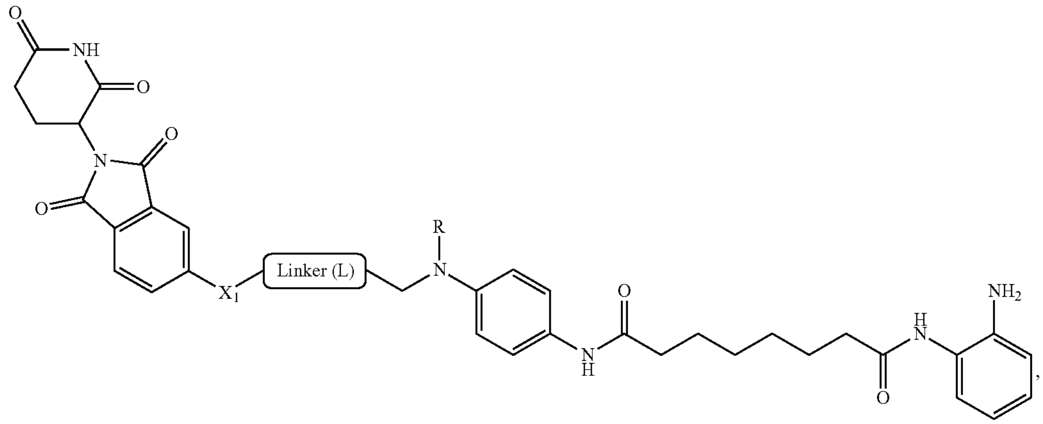
,
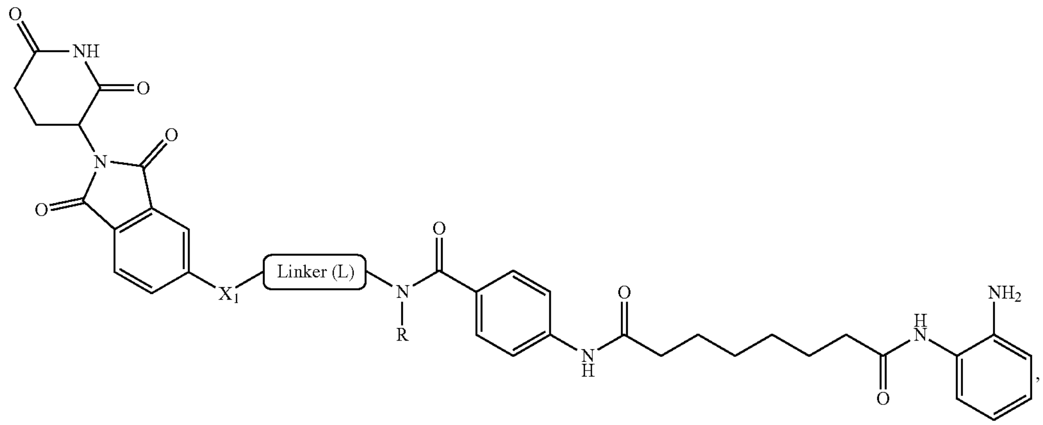
,
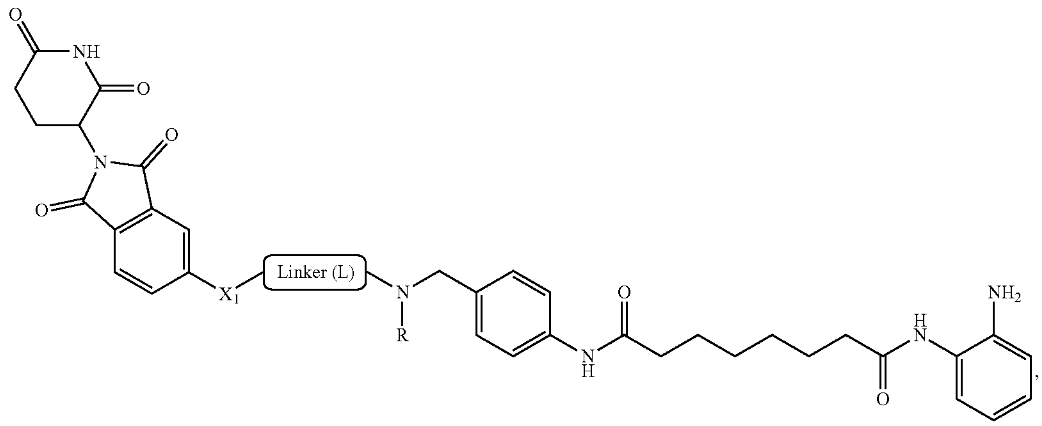
,

-continued
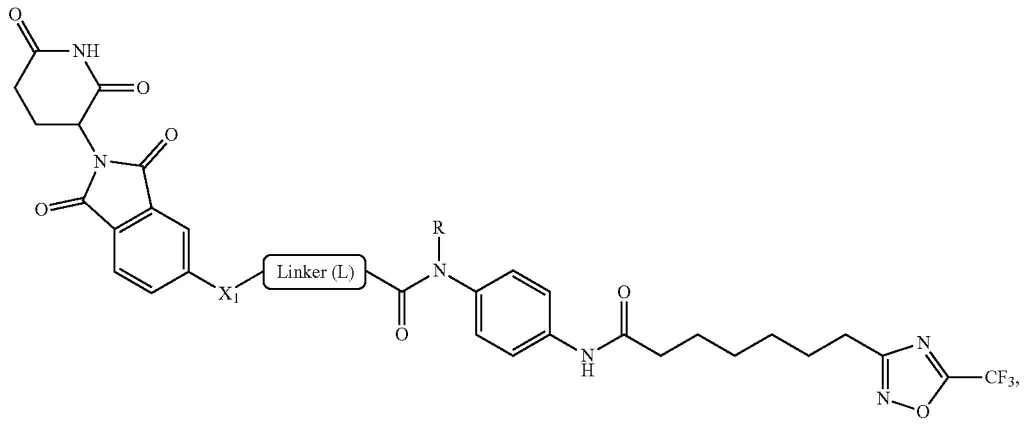
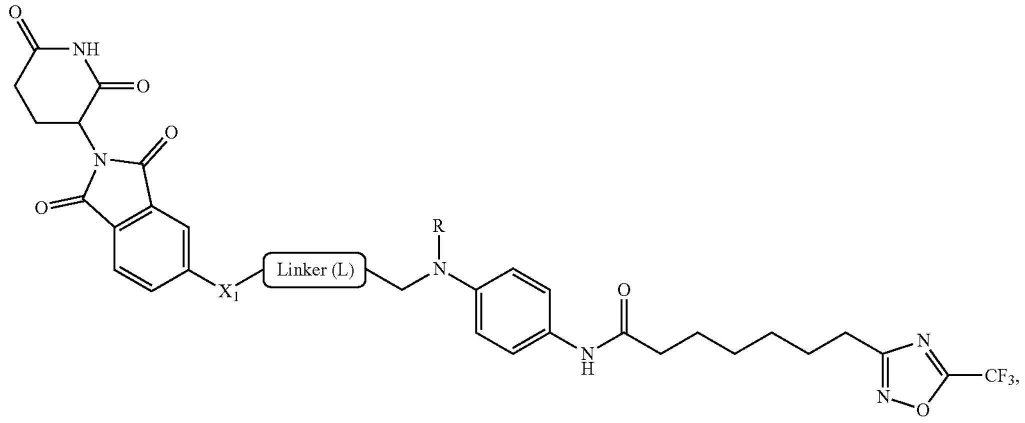
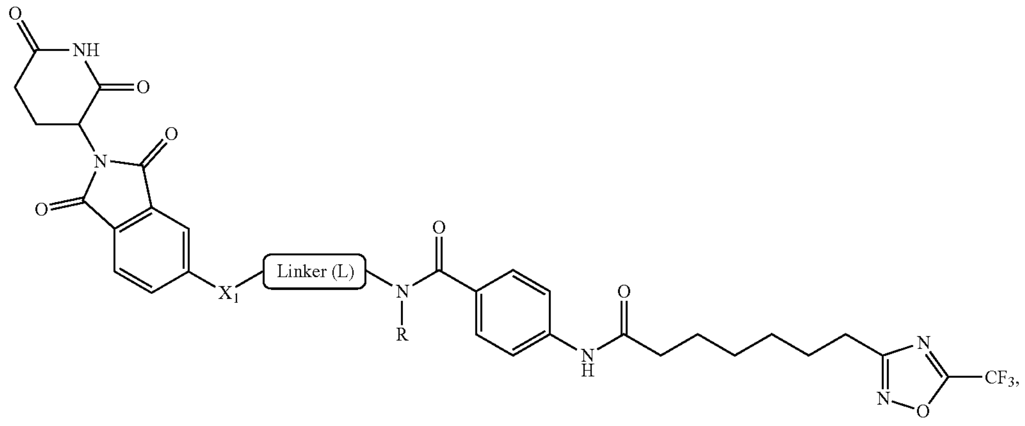
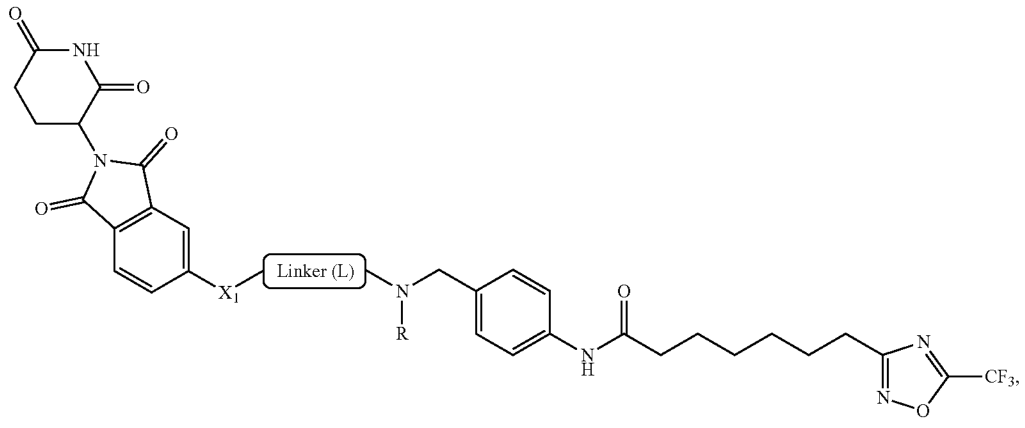

-continued
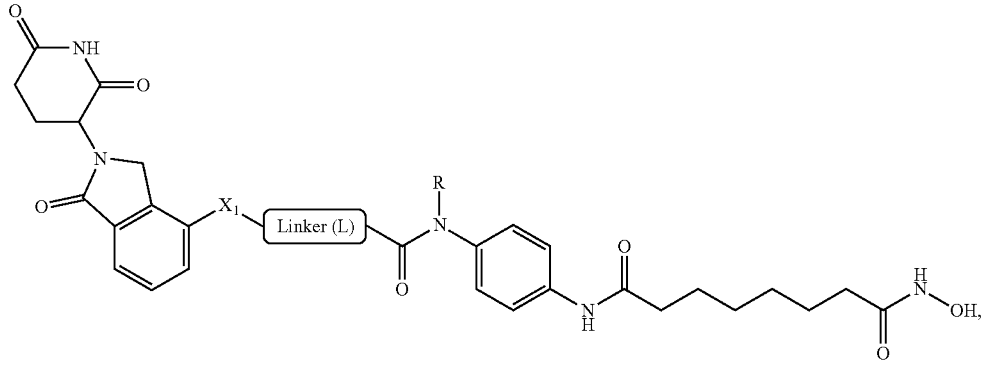
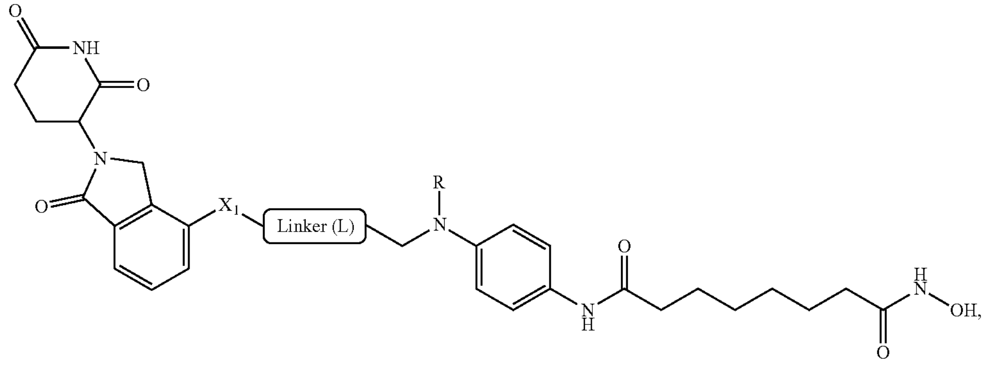
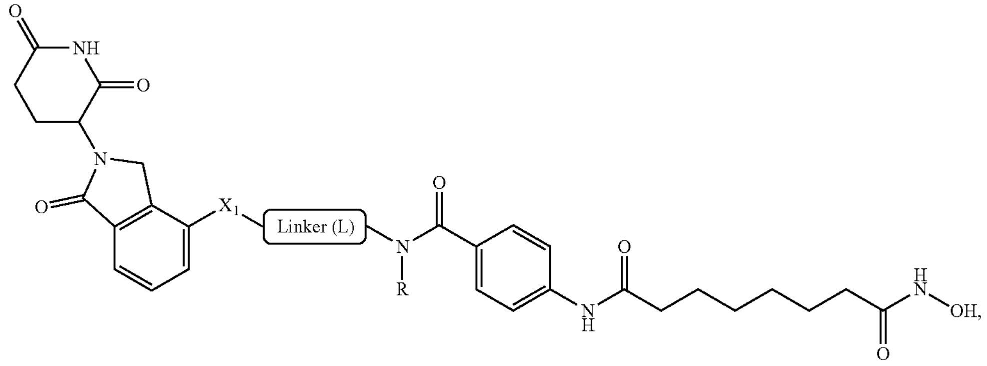
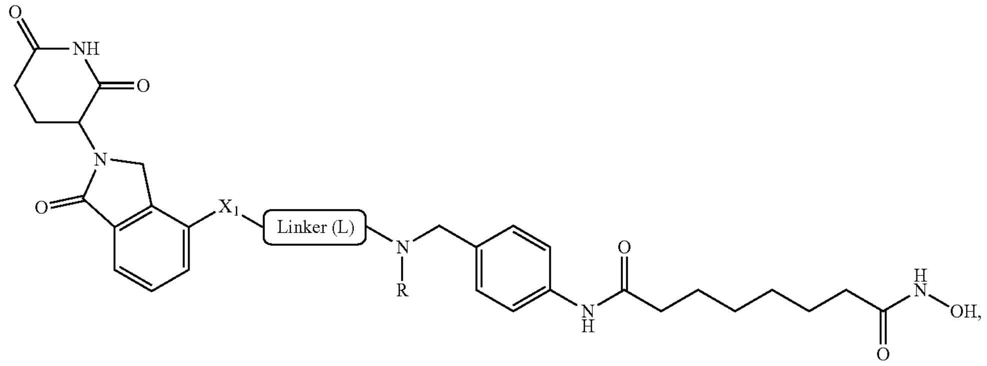

-continued
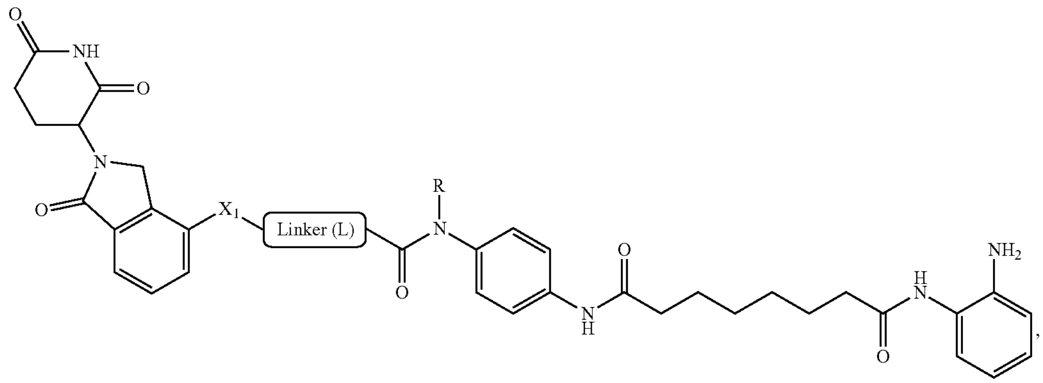
,
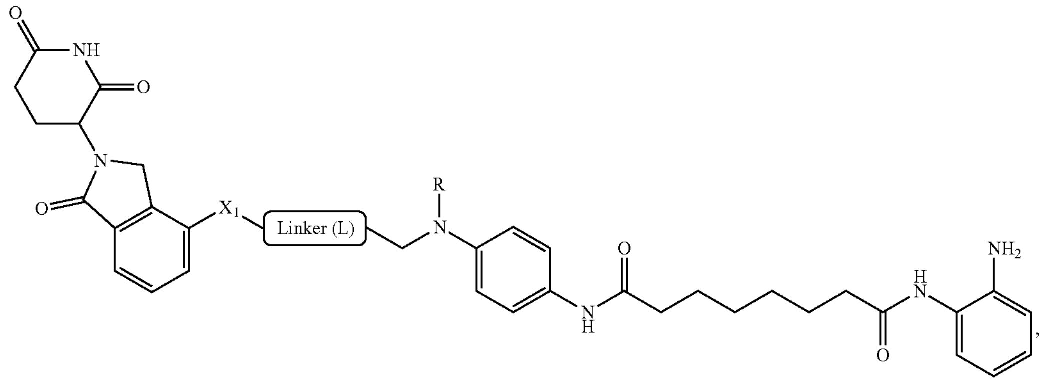
,
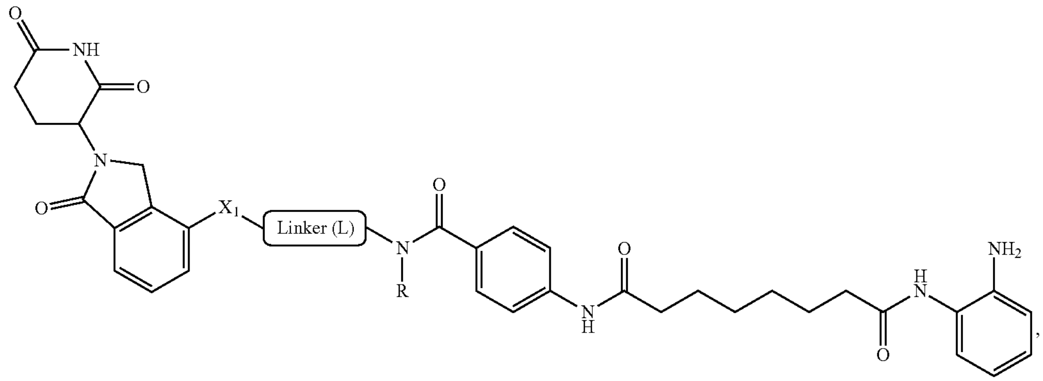
,
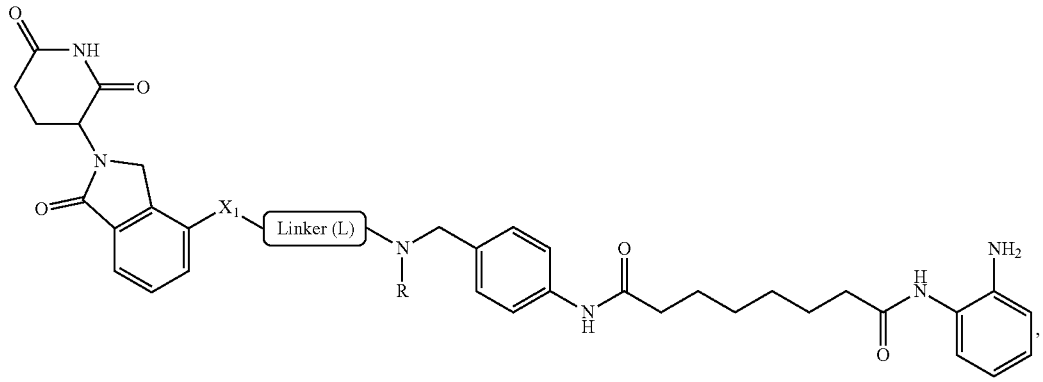
,

-continued
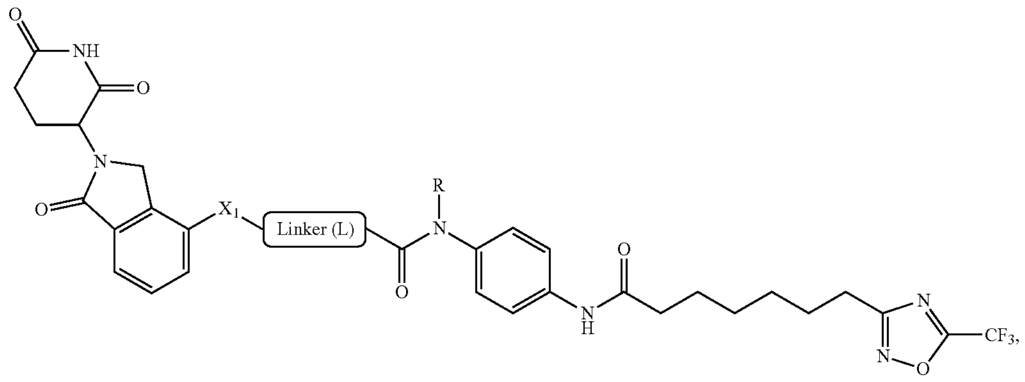
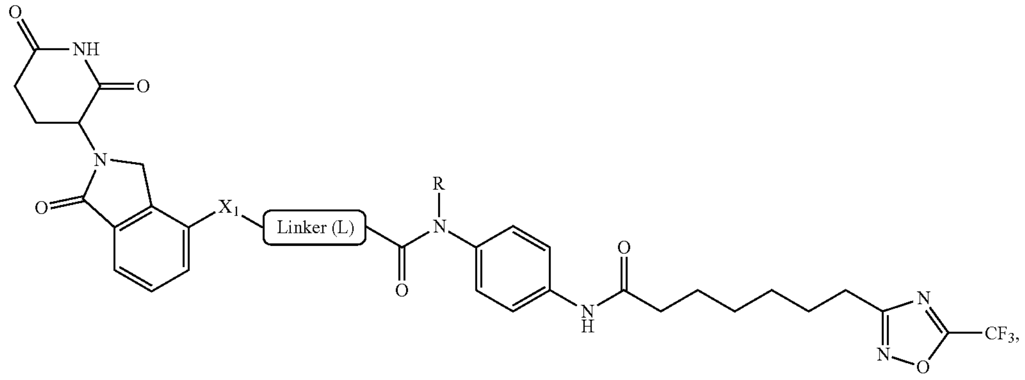
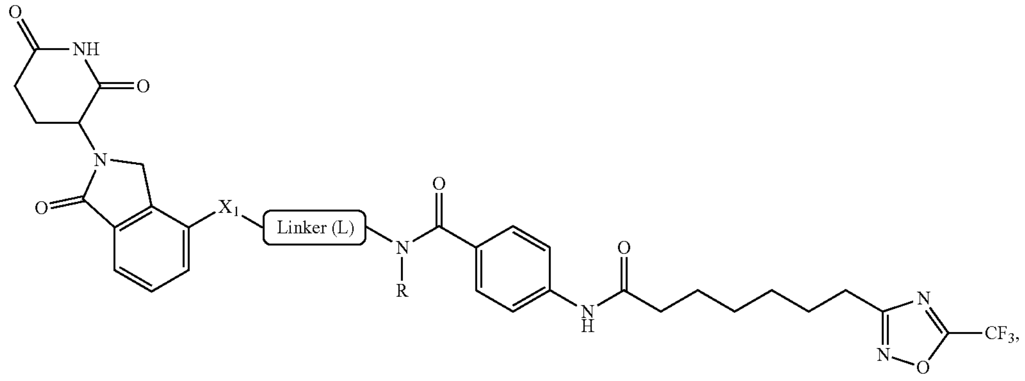
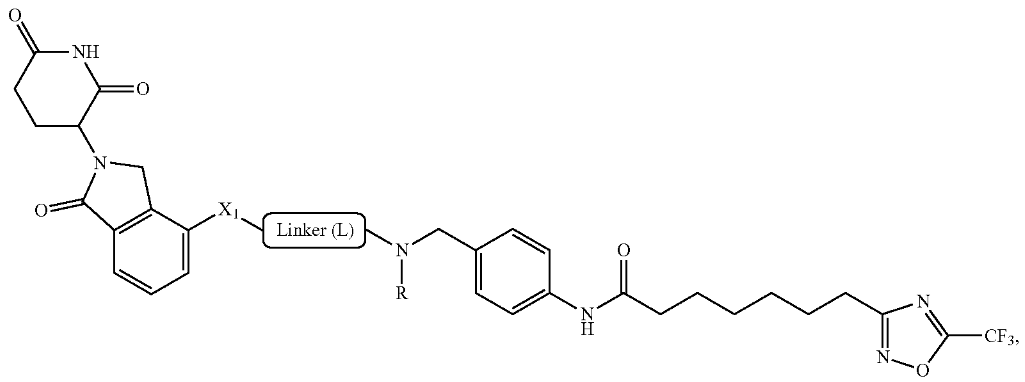

-continued
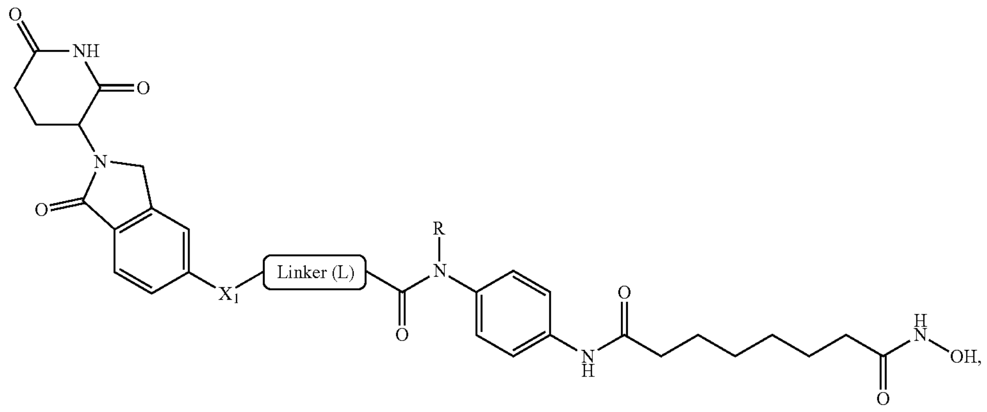
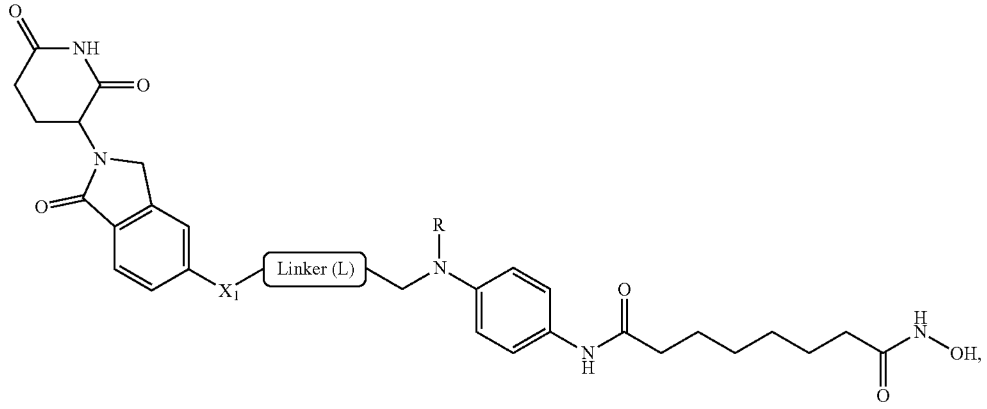
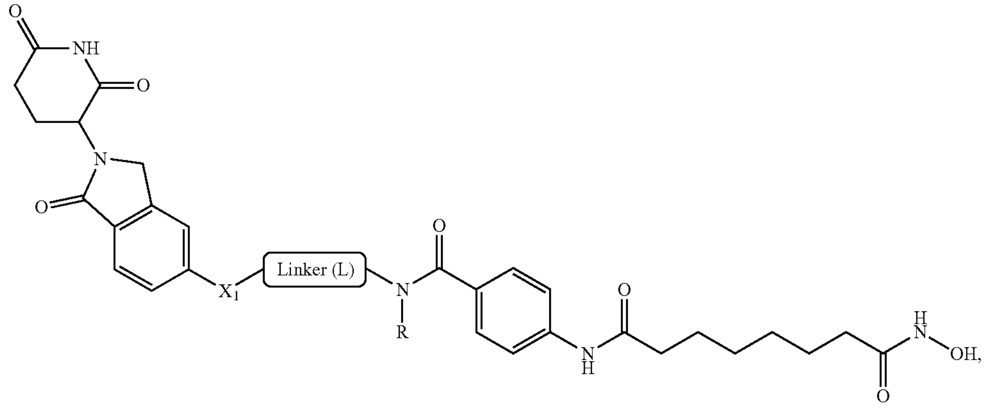
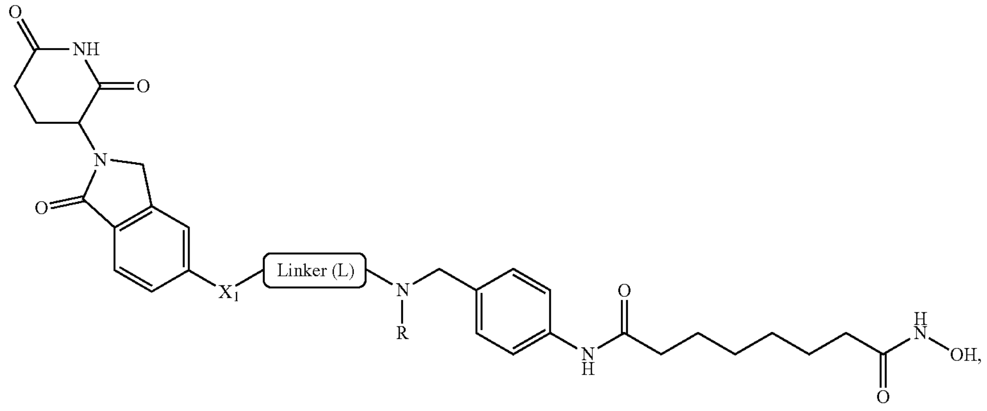

-continued
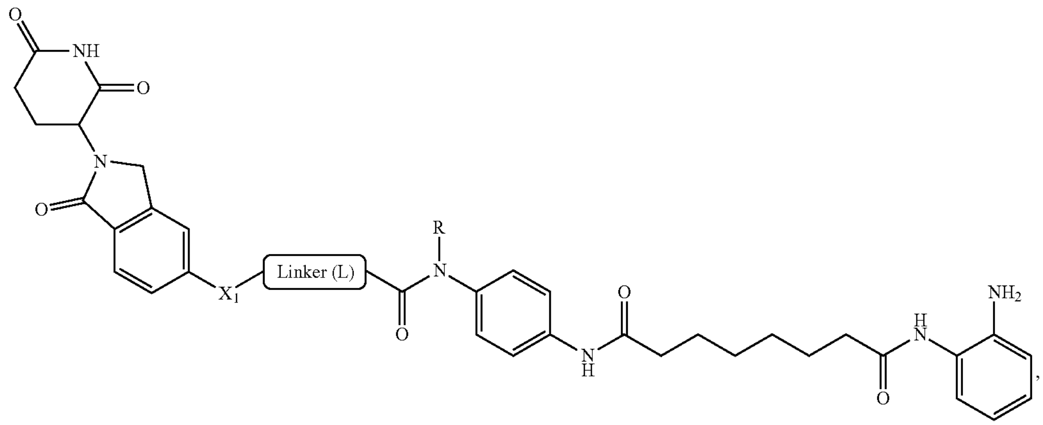
,
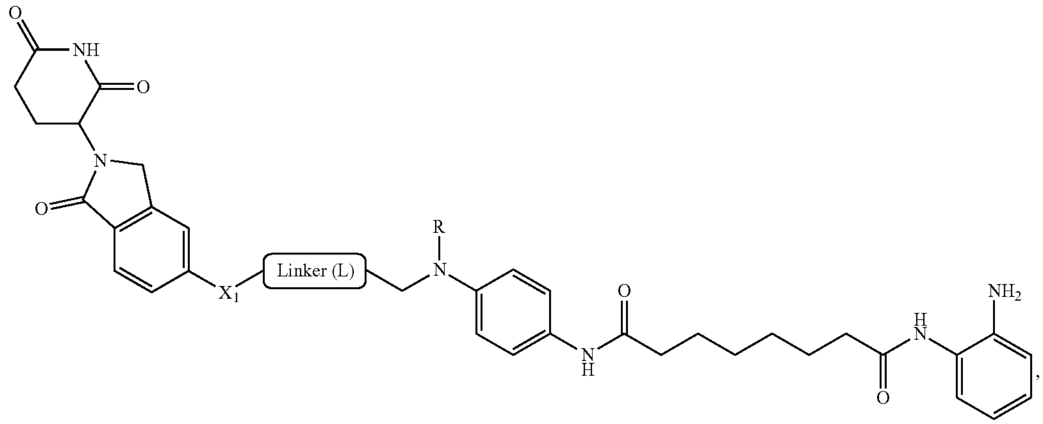
,
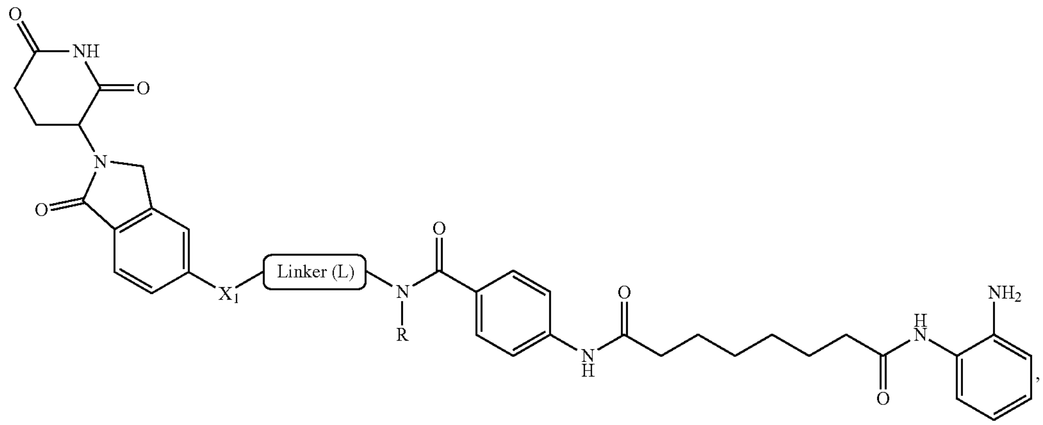
,
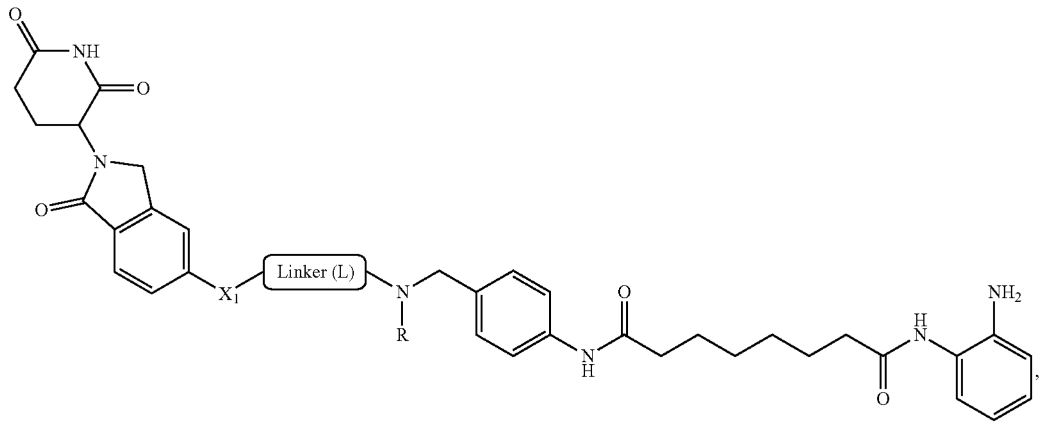
,

-continued
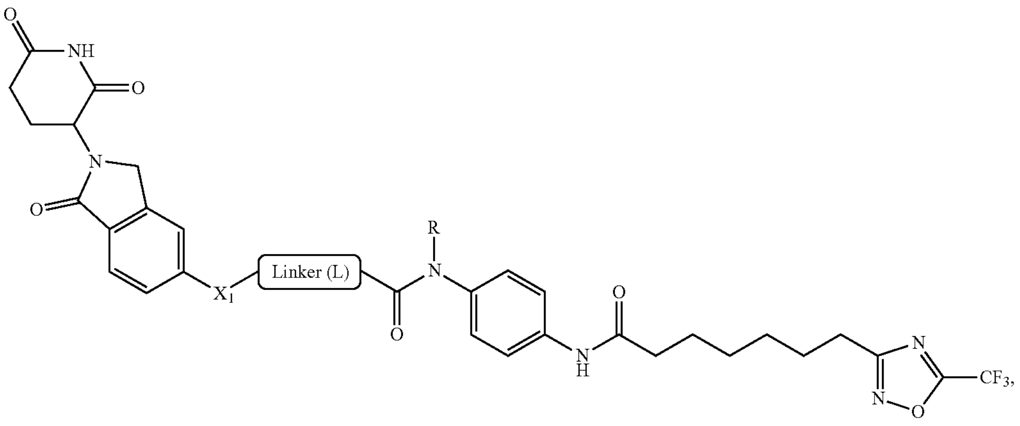
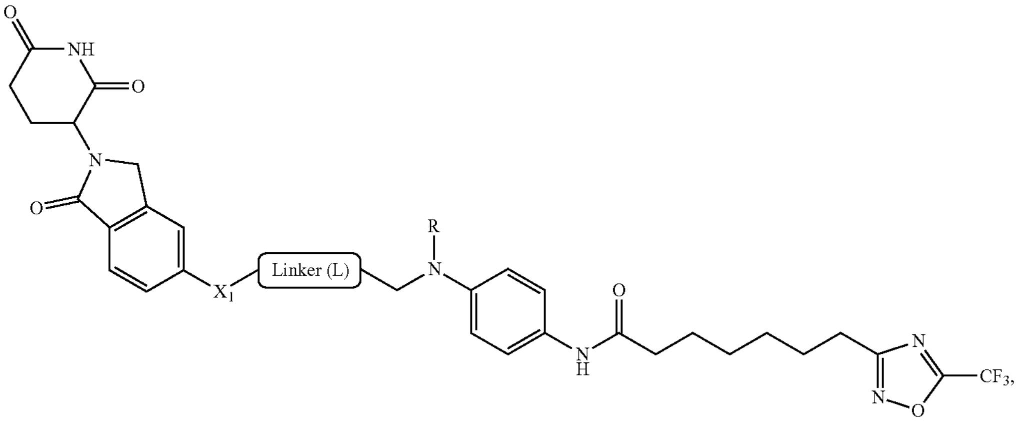
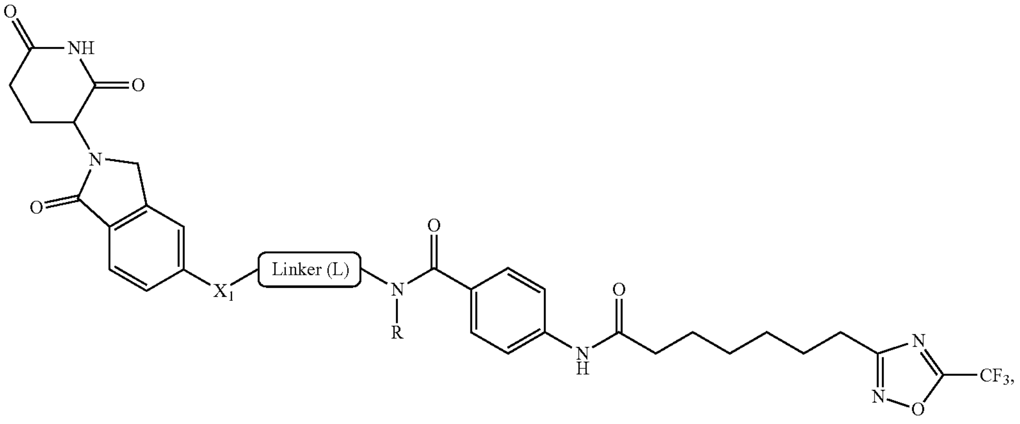
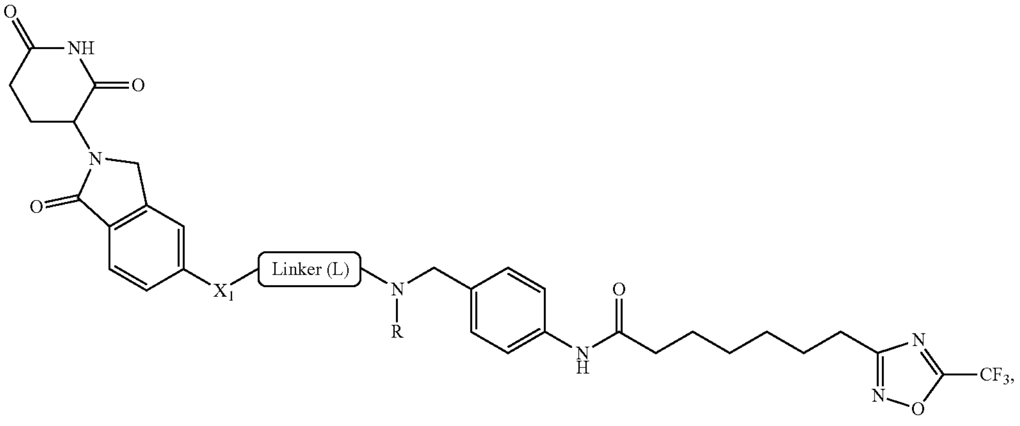

-continued
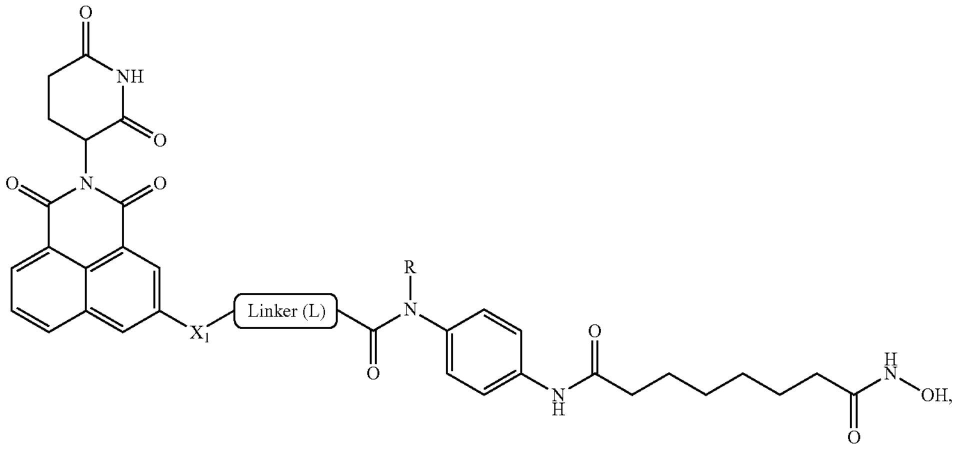
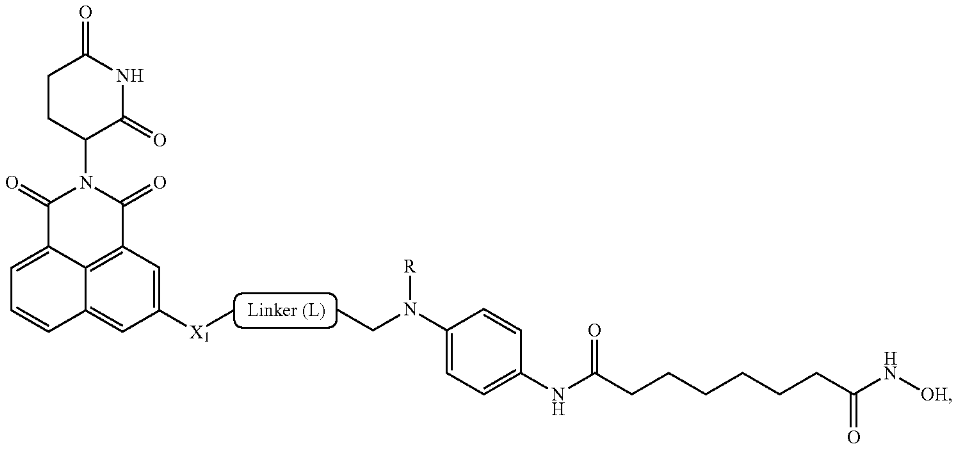
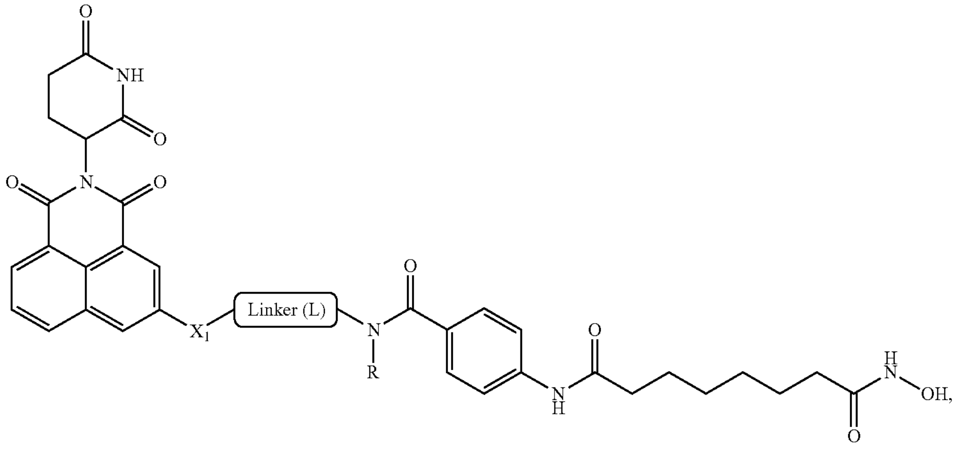

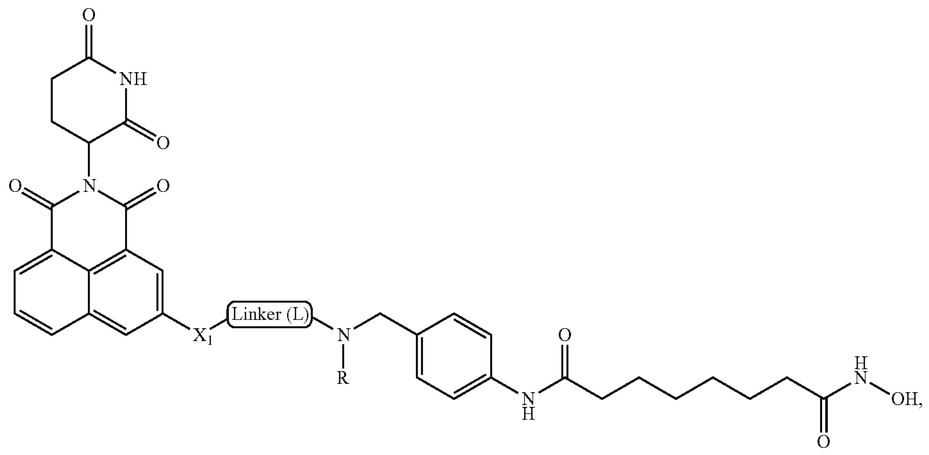
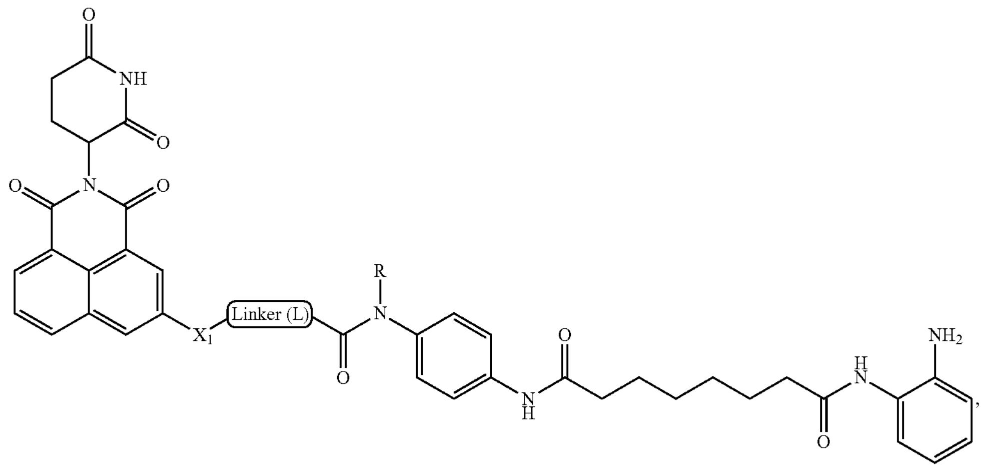
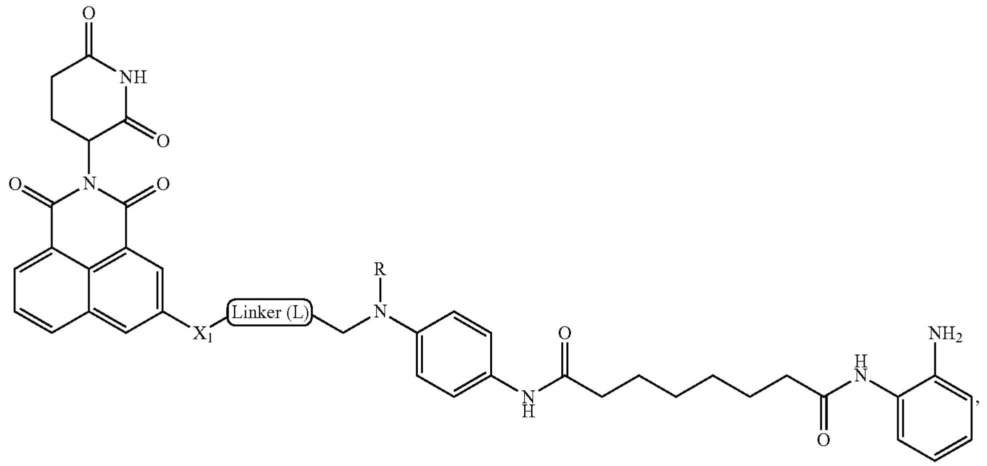

-continued
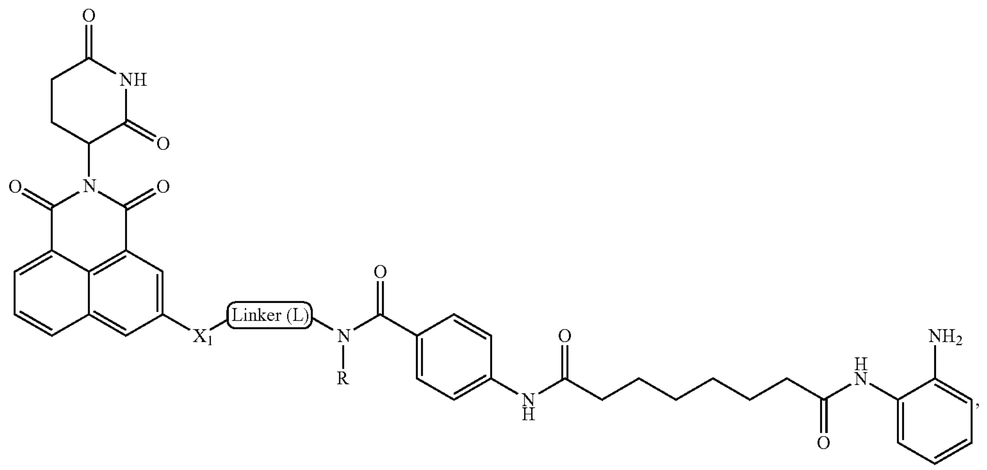
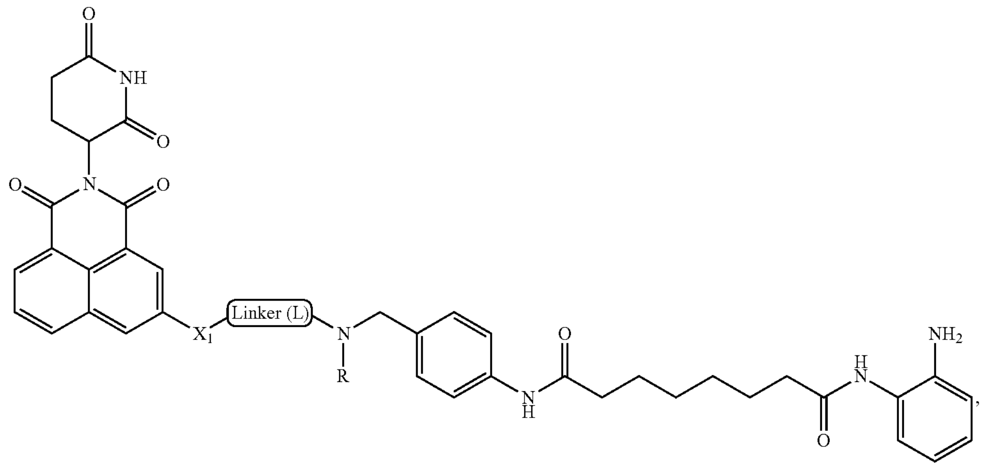
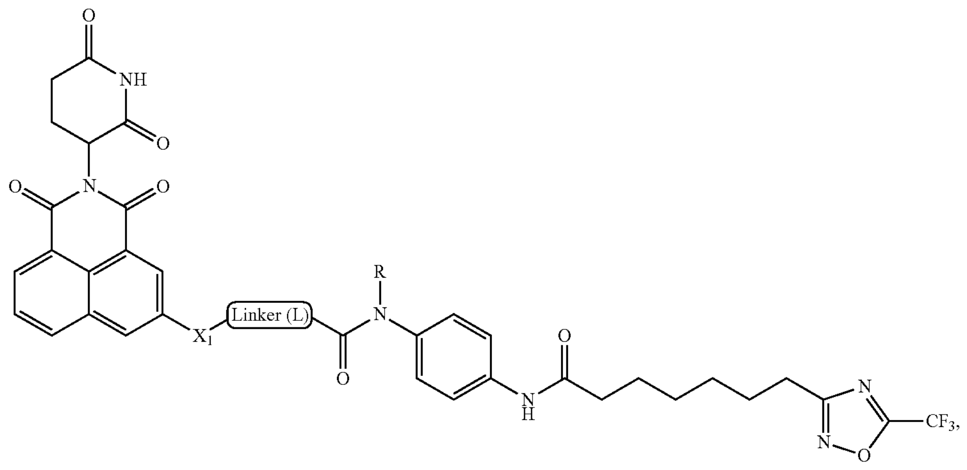

-continued
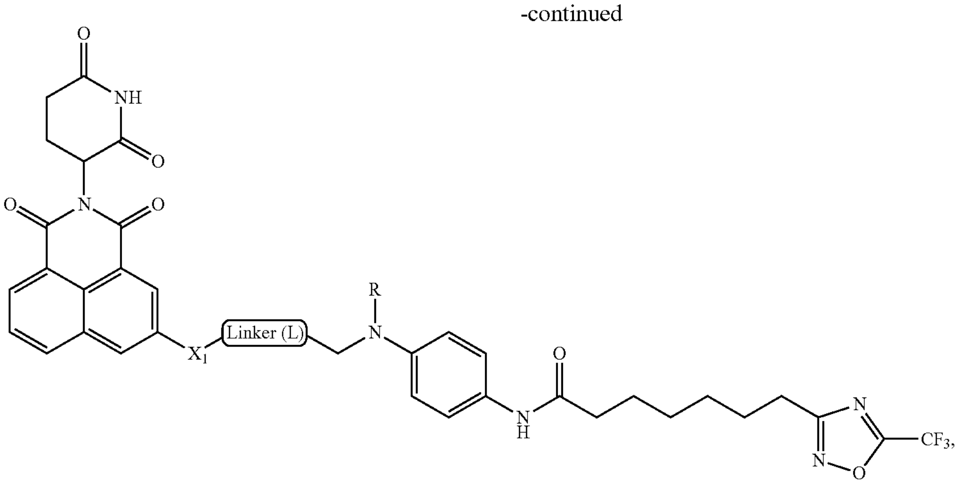
,
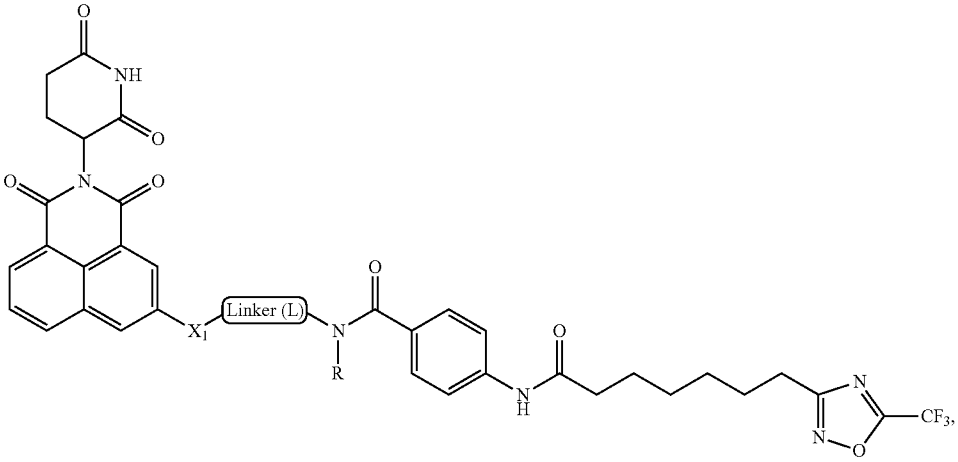
,
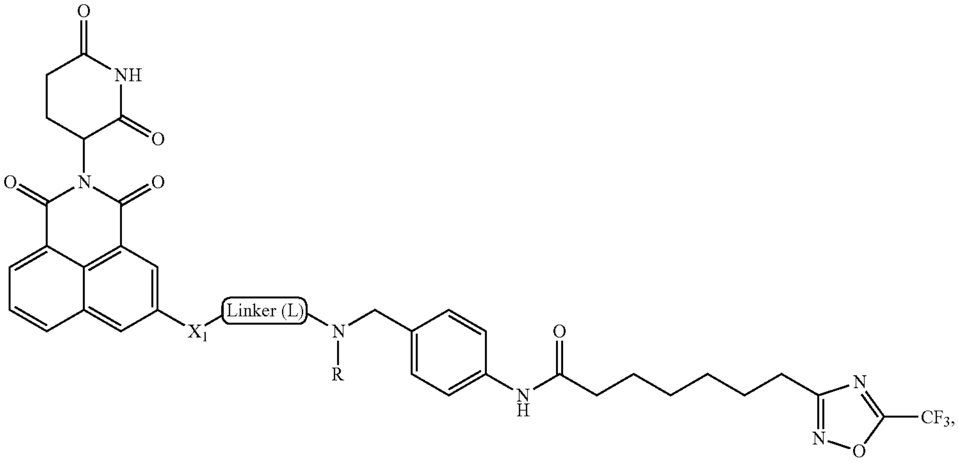
,
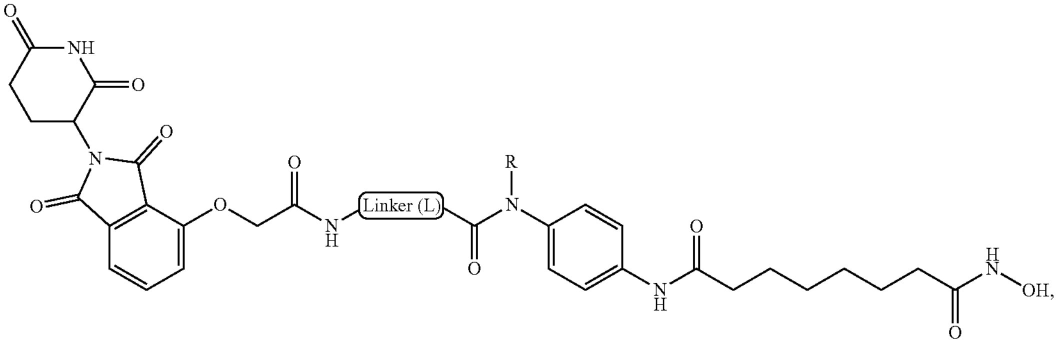
,

-continued
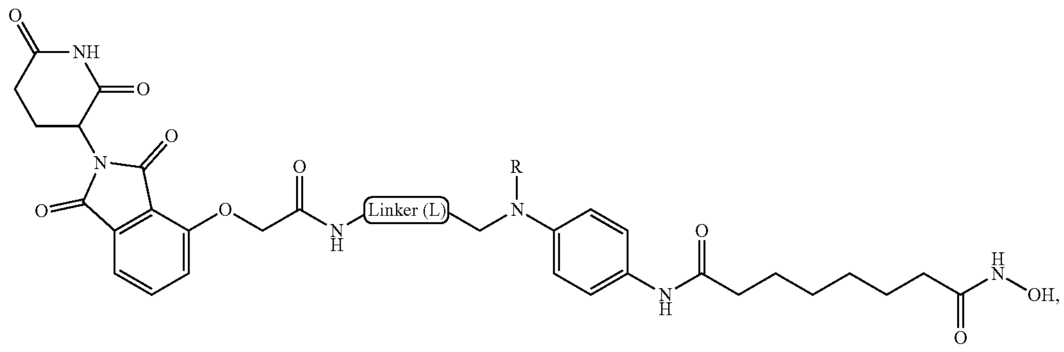
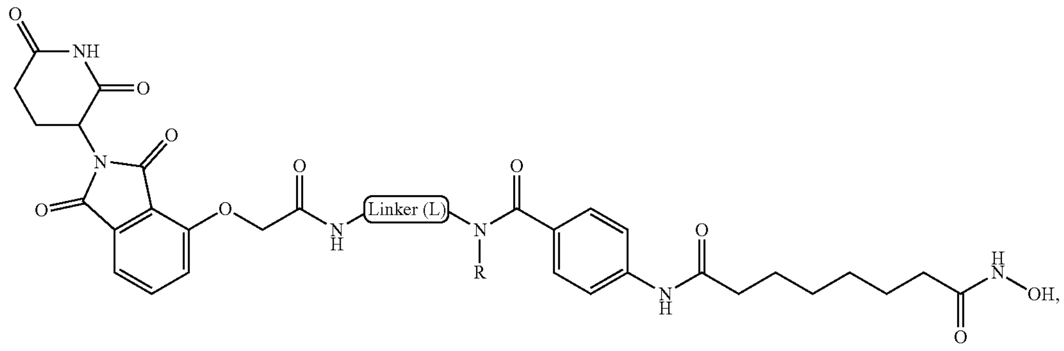
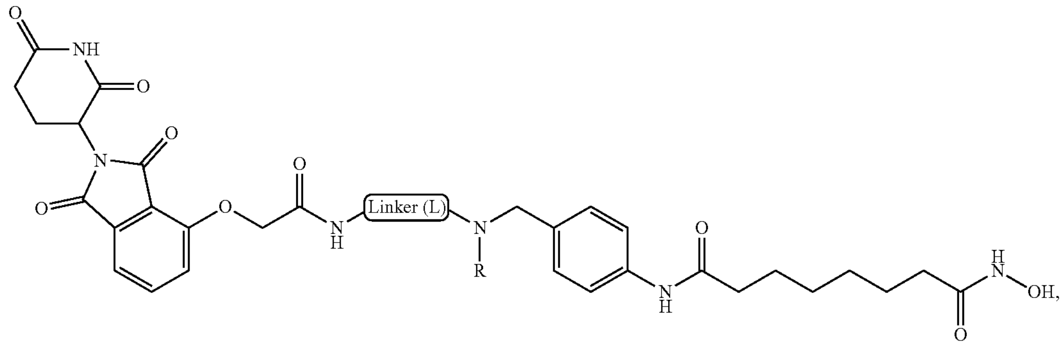
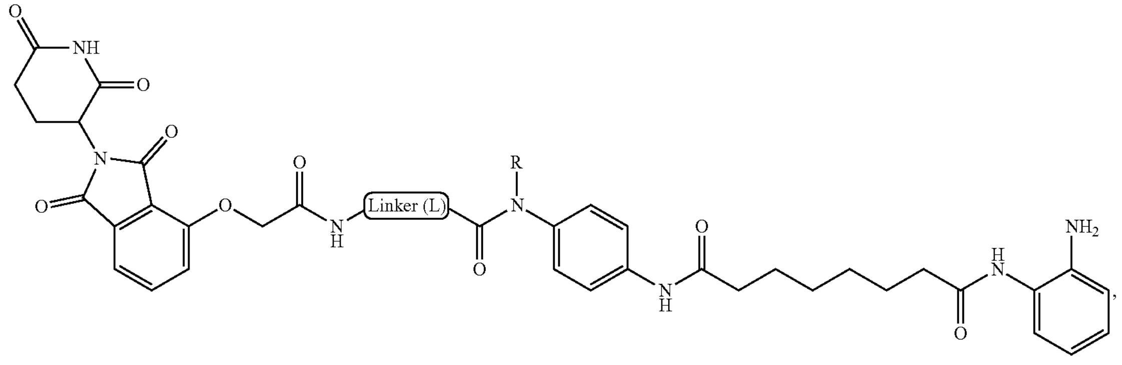

-continued
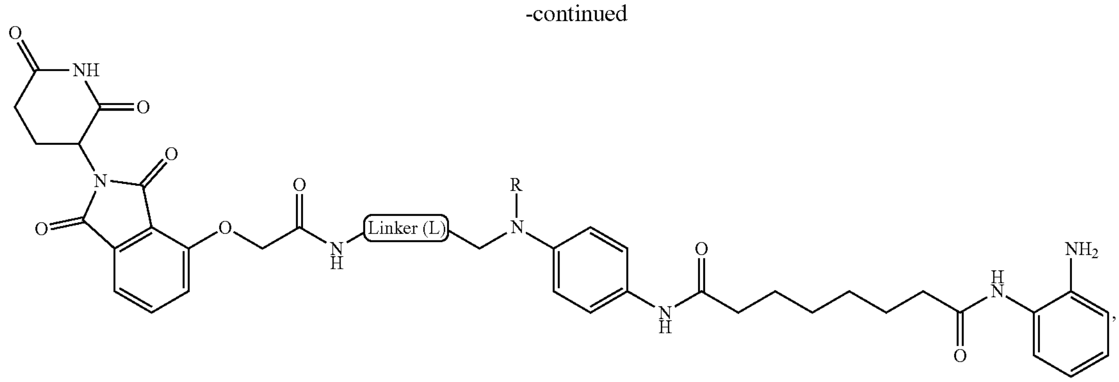
,
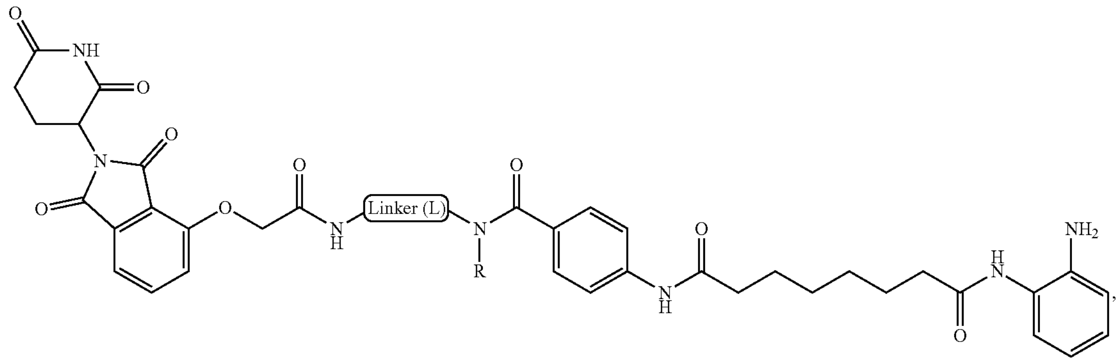
,
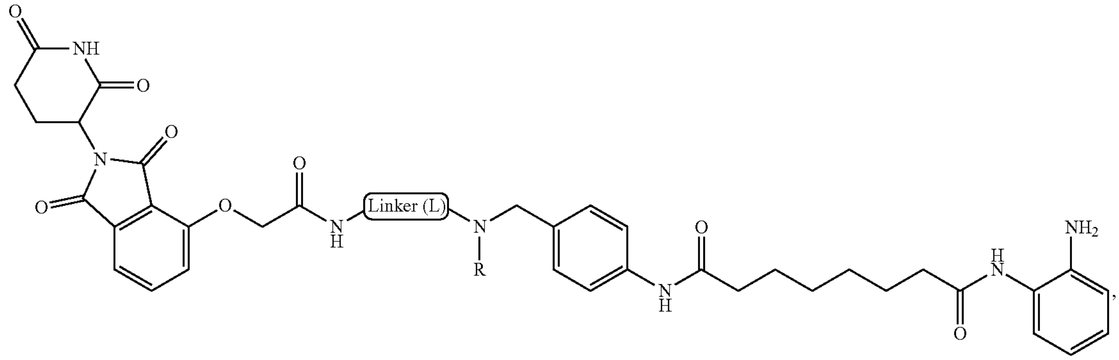
,
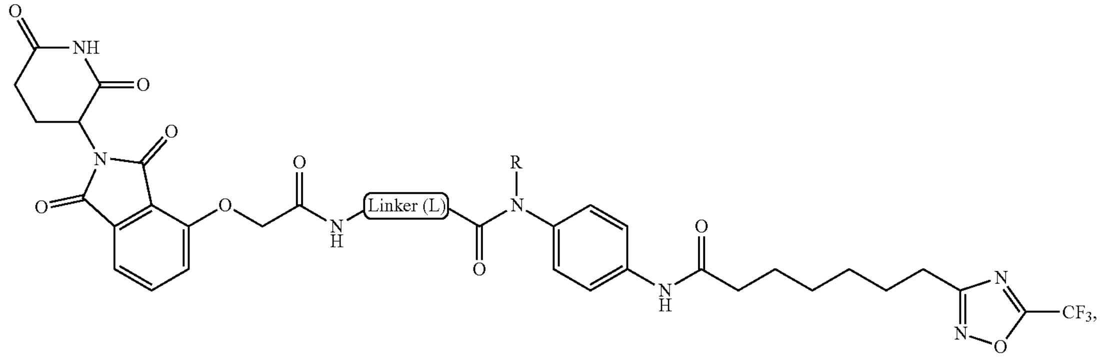
,

-continued
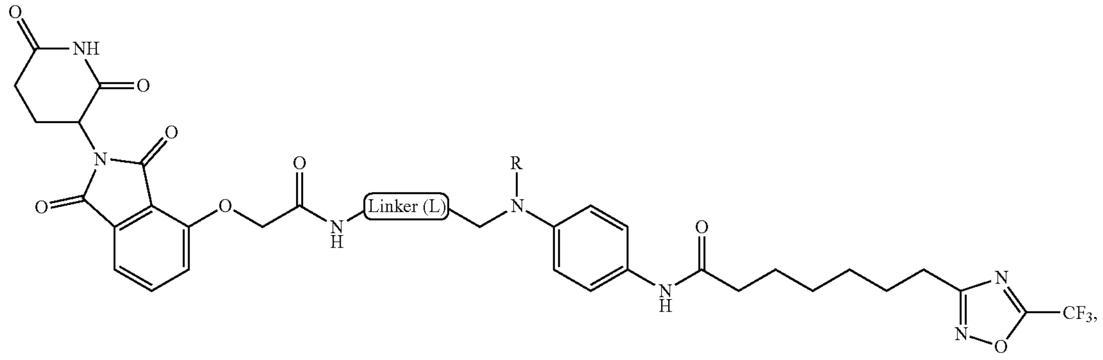
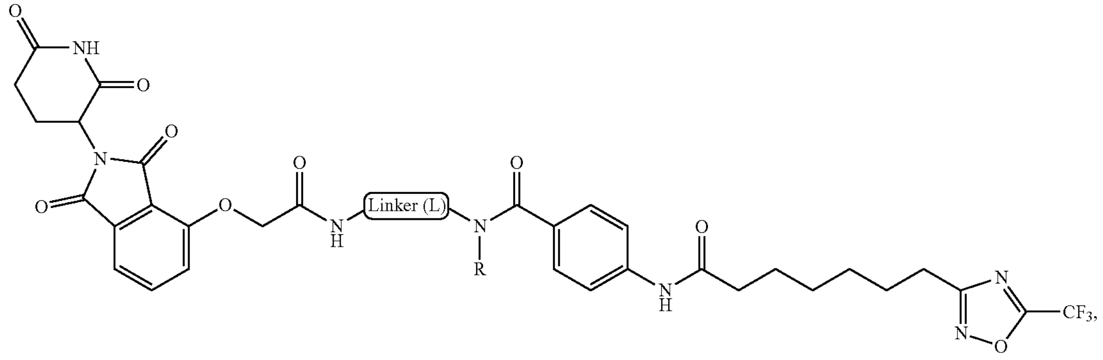
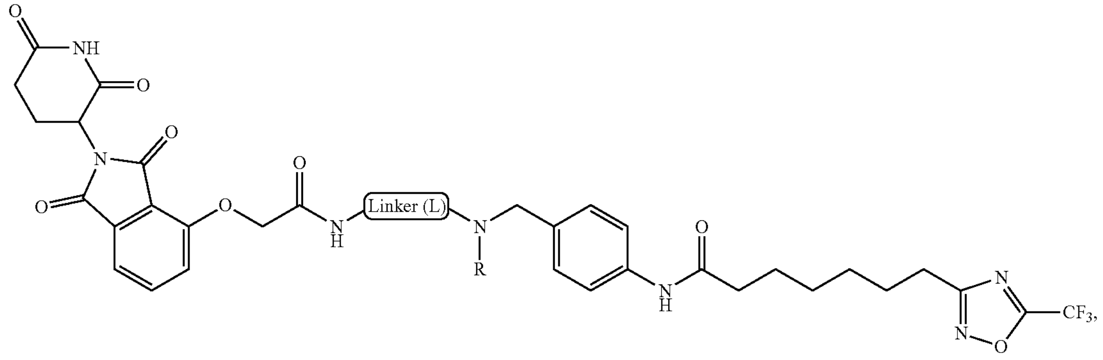
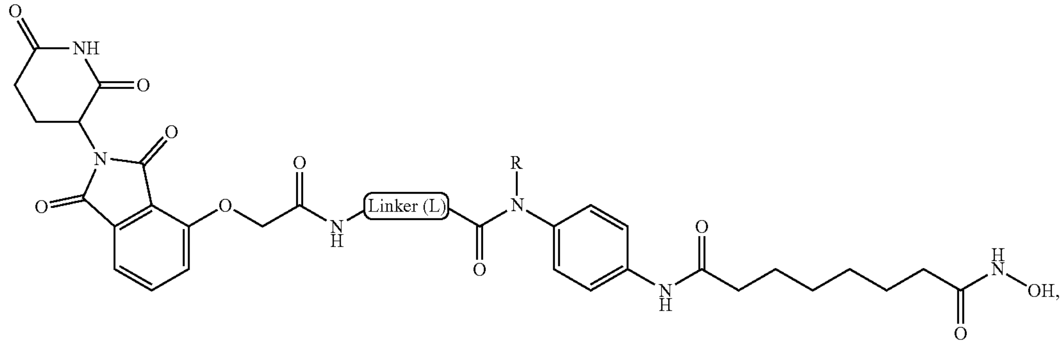

-continued
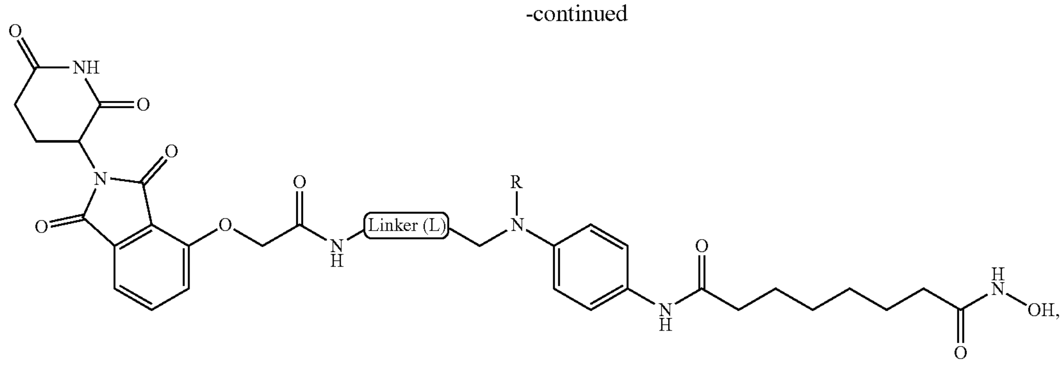
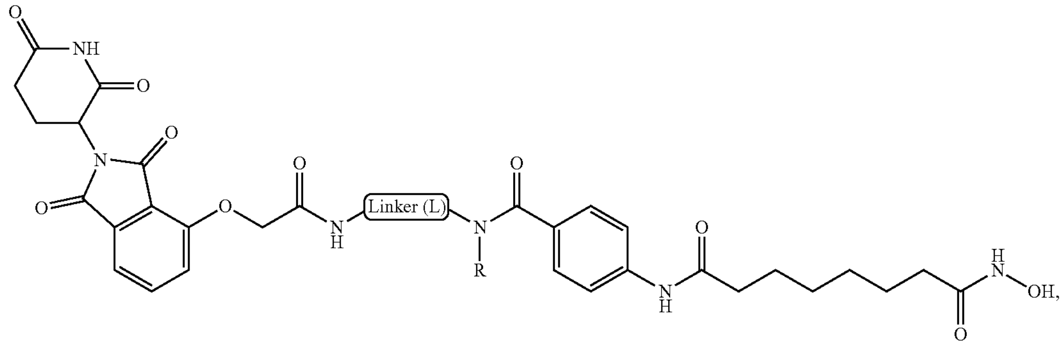
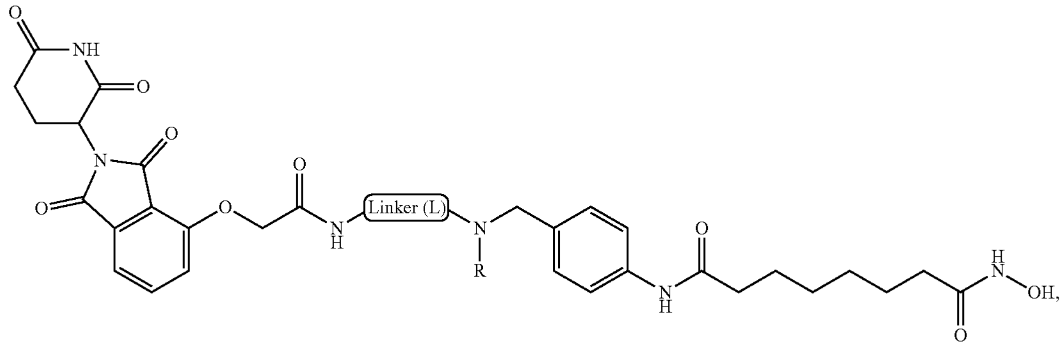
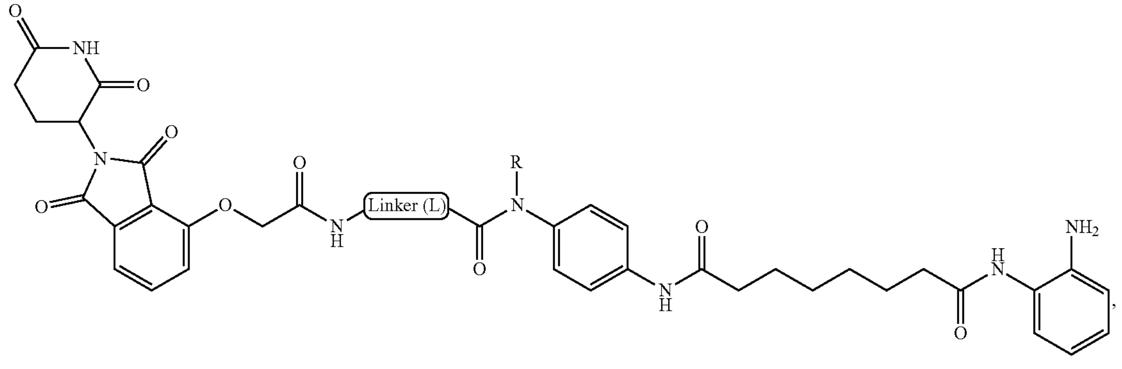

-continued
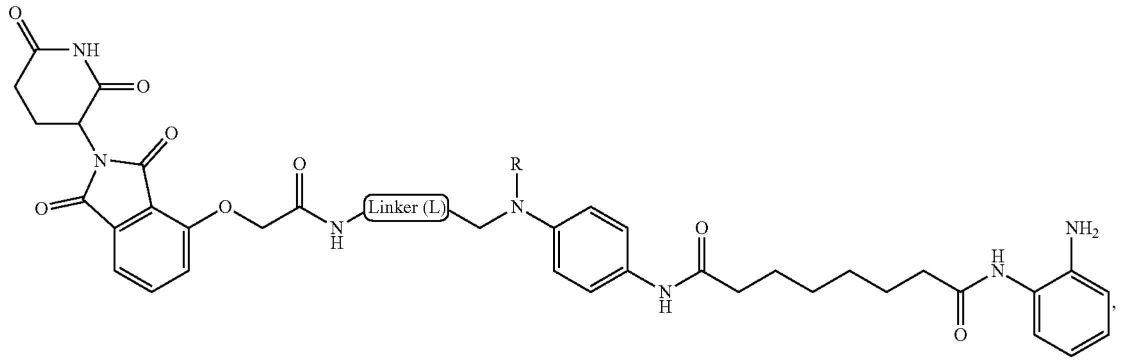
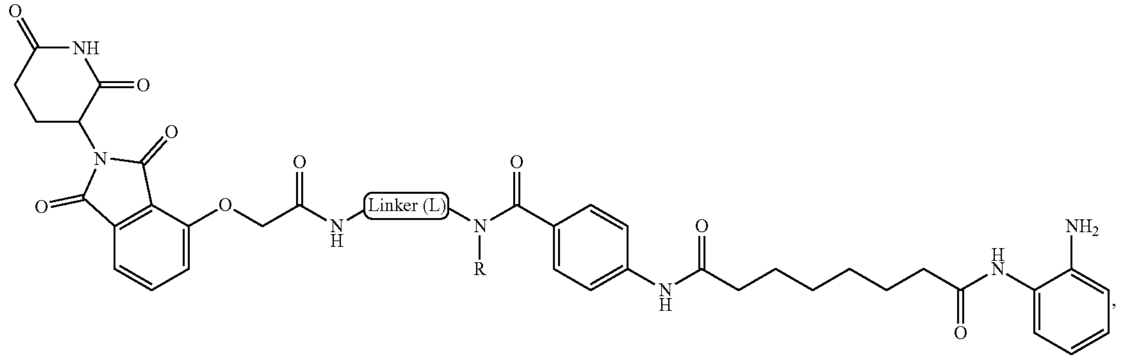
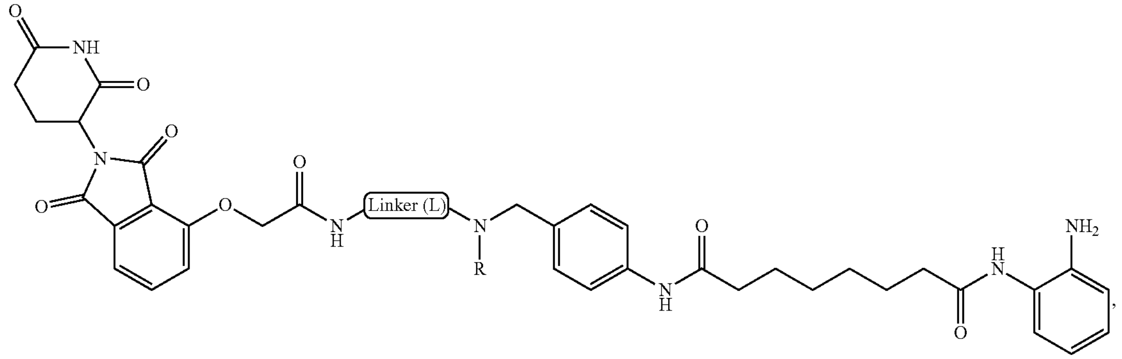
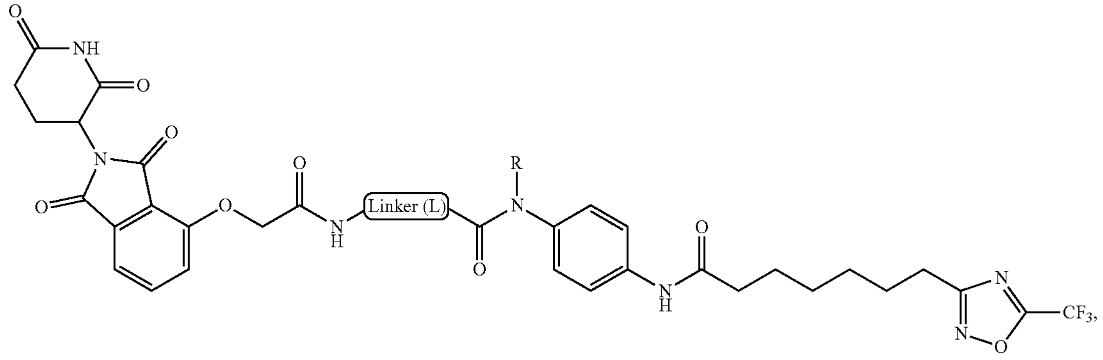

-continued
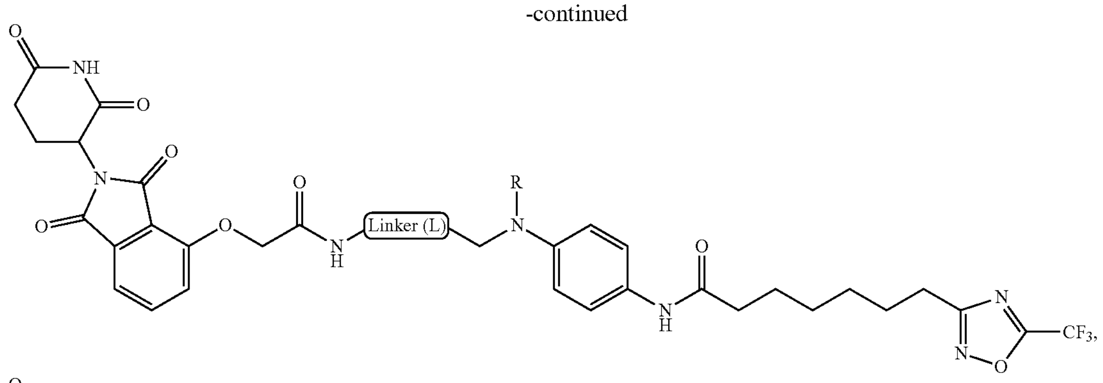
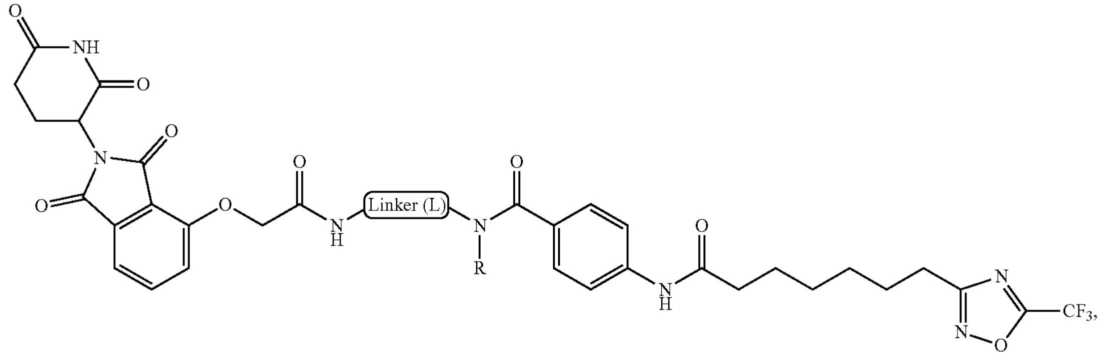
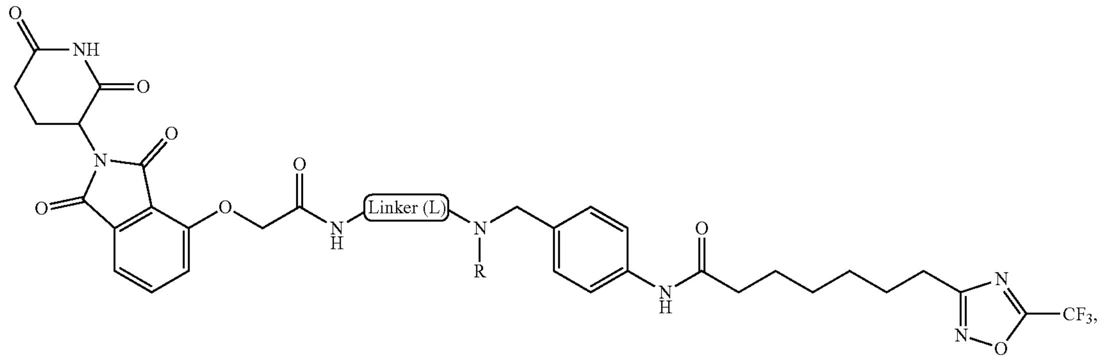
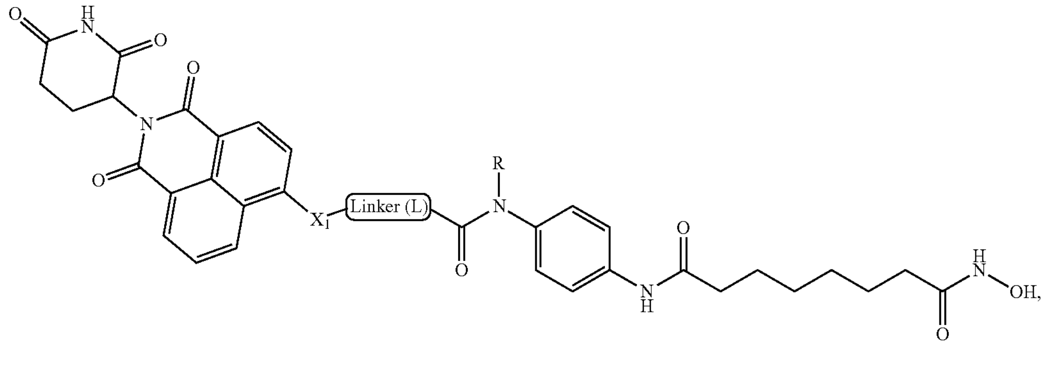

-continued
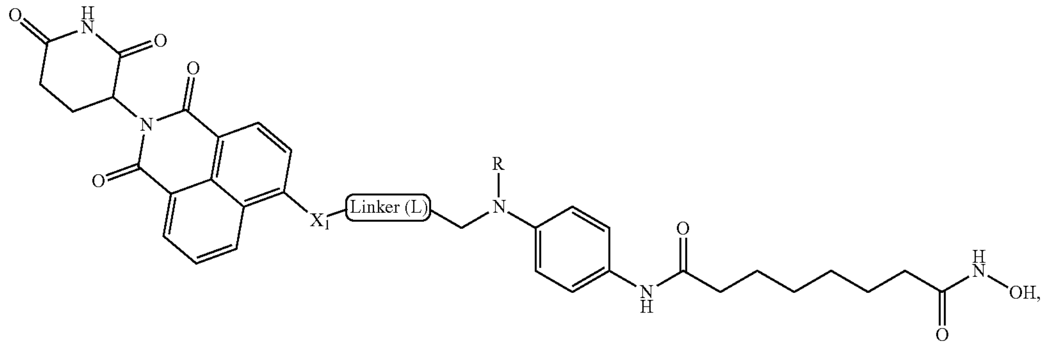
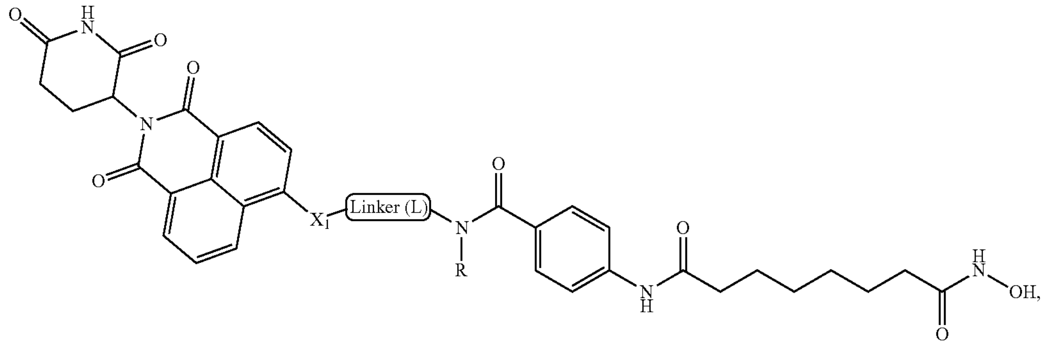
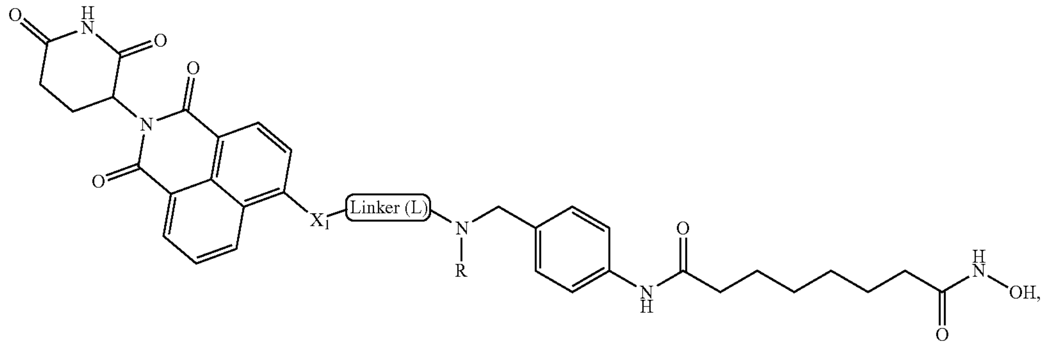
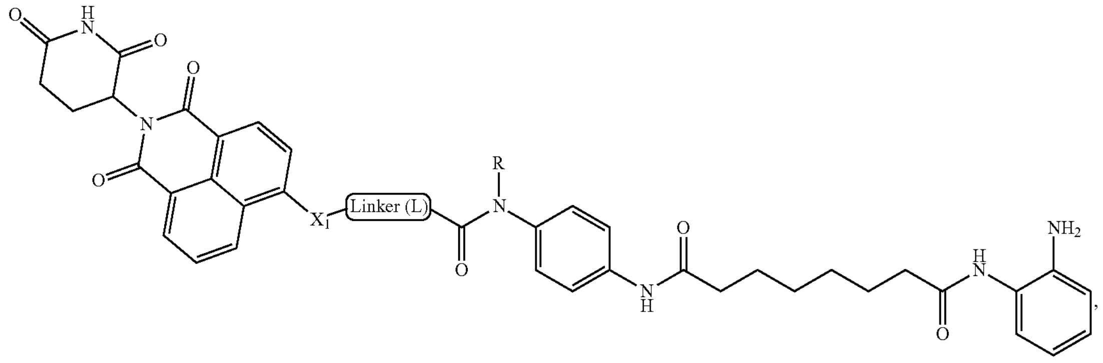

-continued
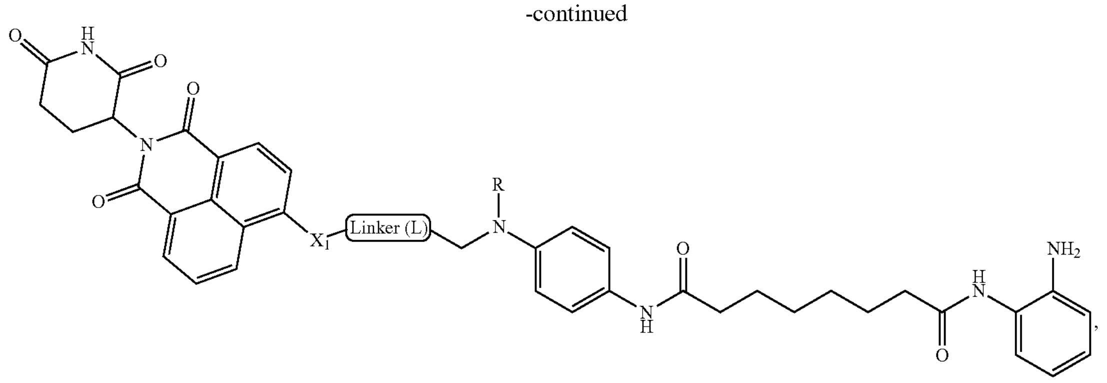
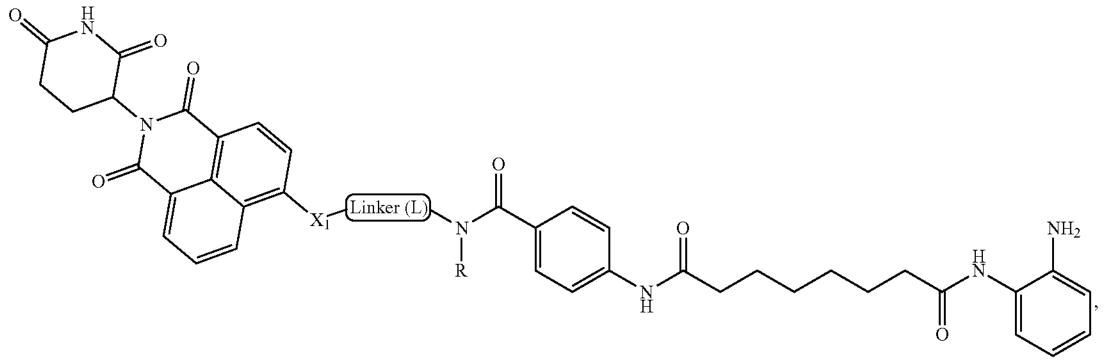
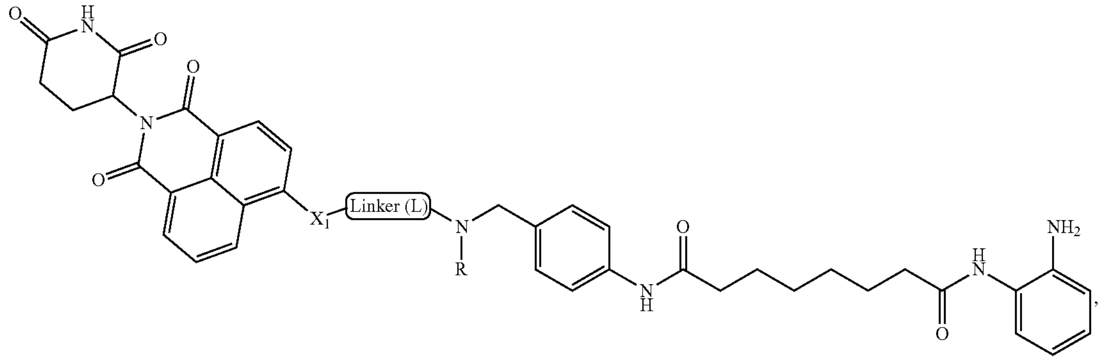
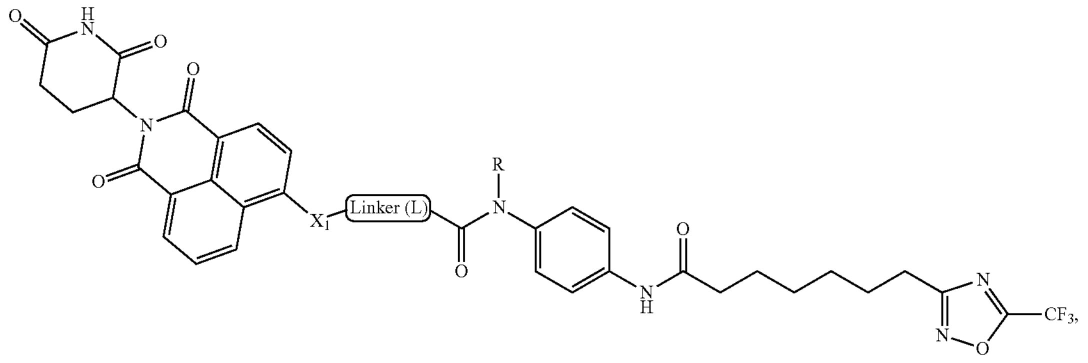

-continued
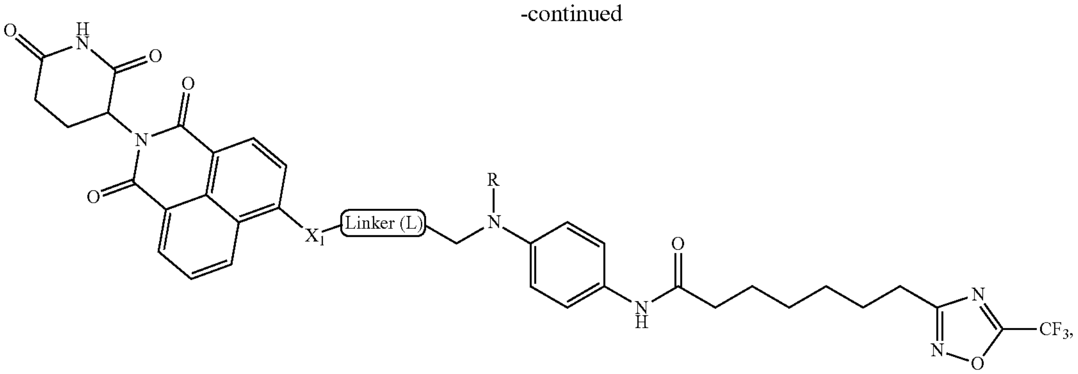
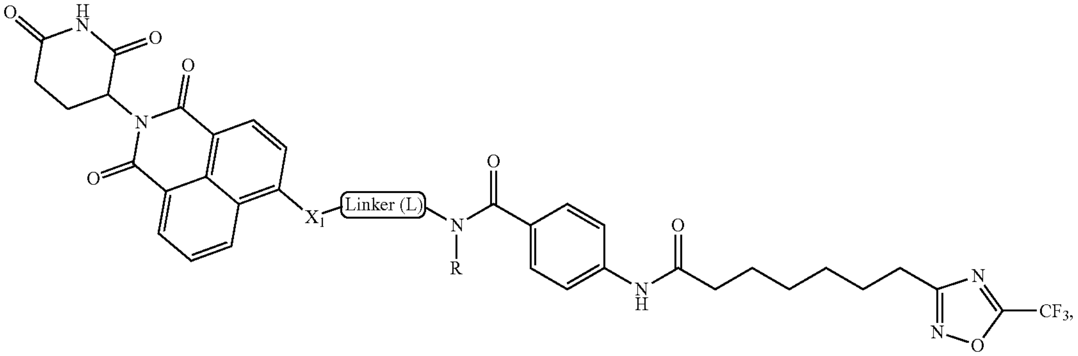
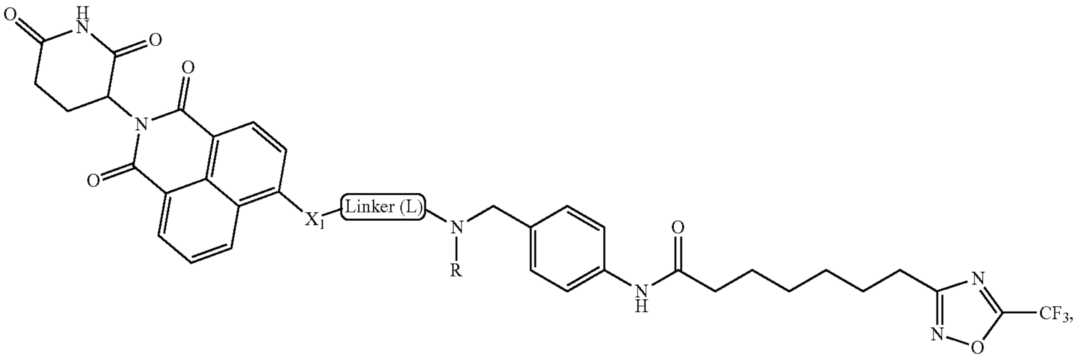
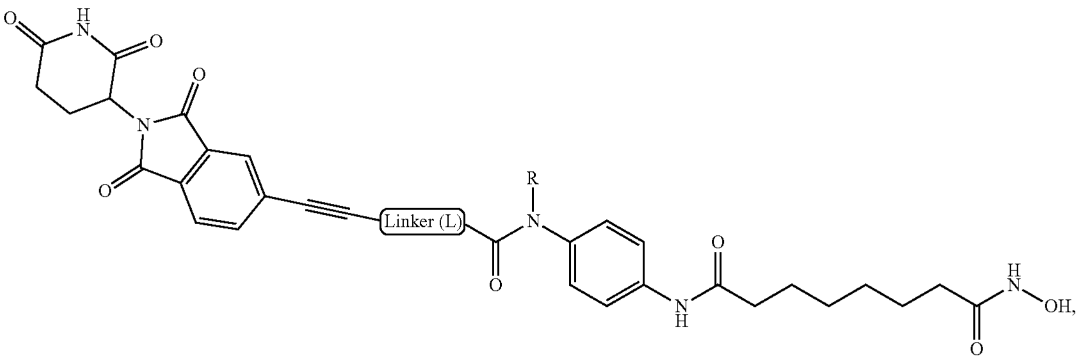

-continued
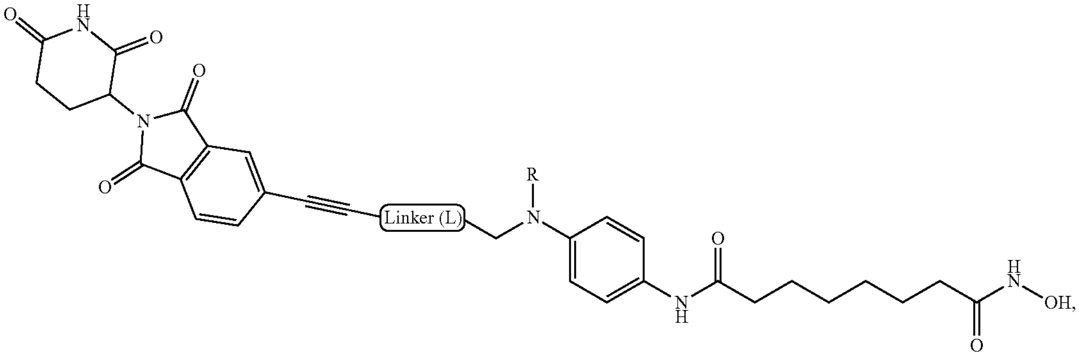
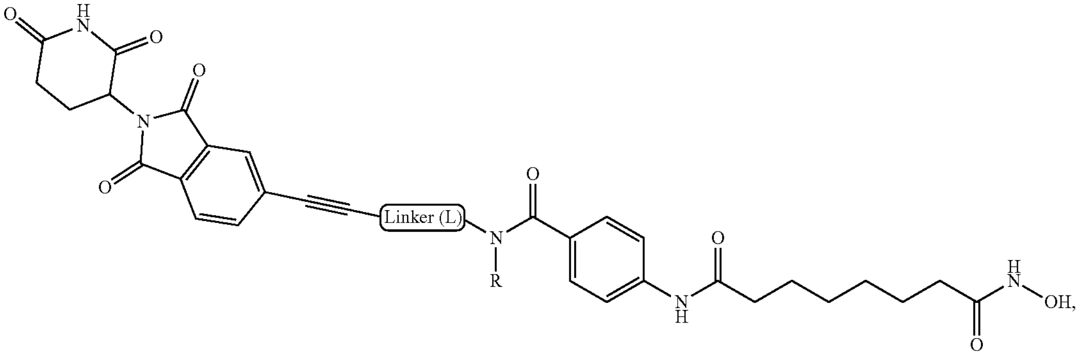
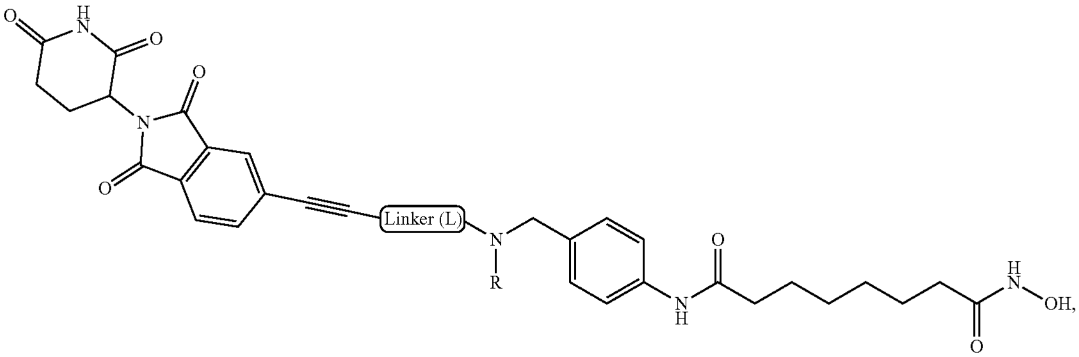
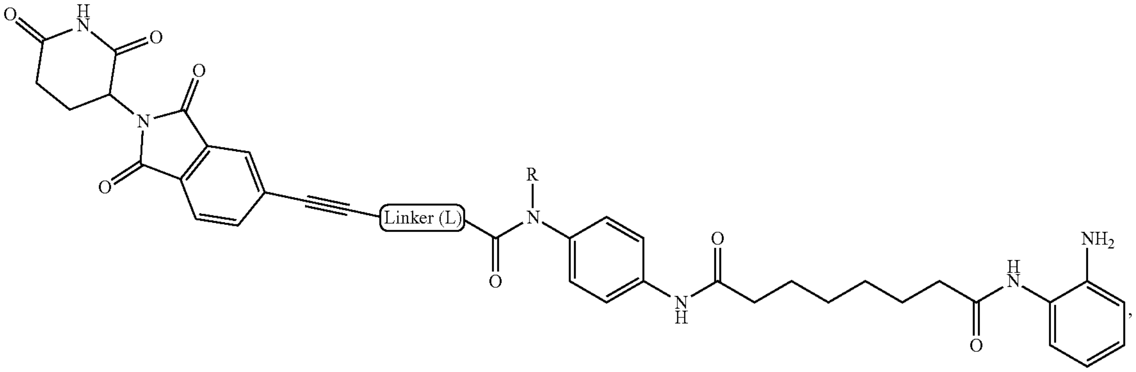

-continued
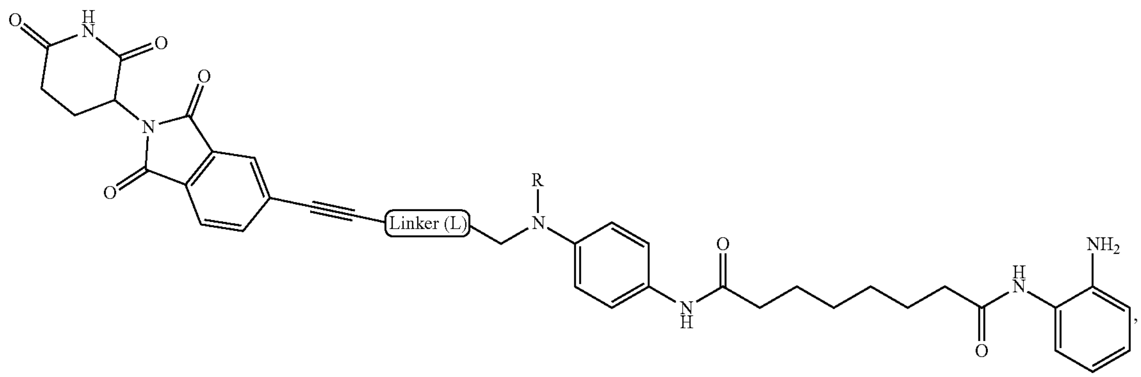
,
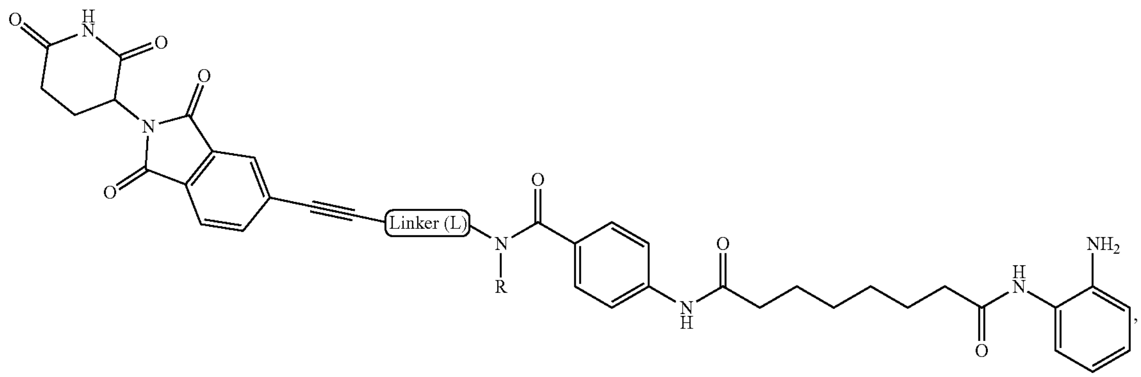
,
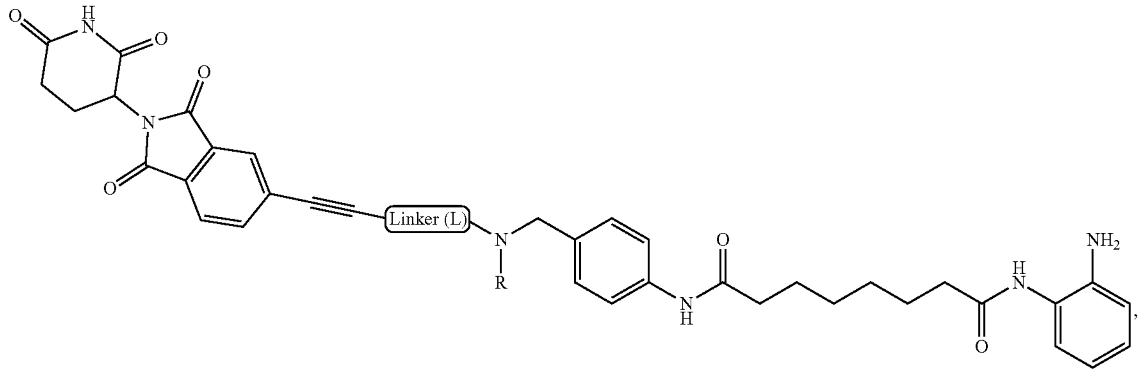
,
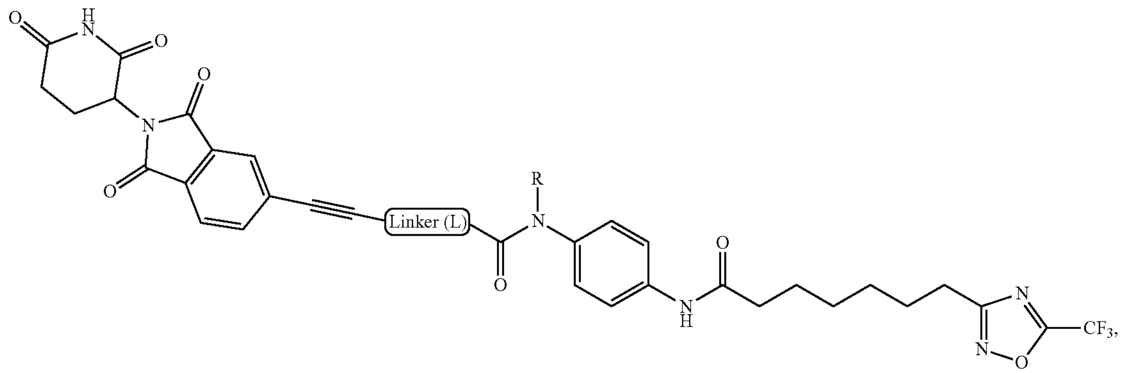
,

-continued
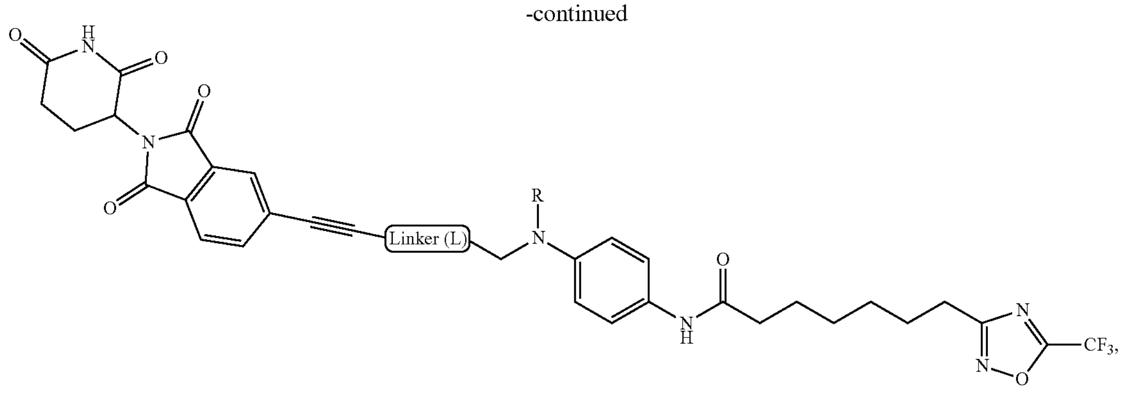
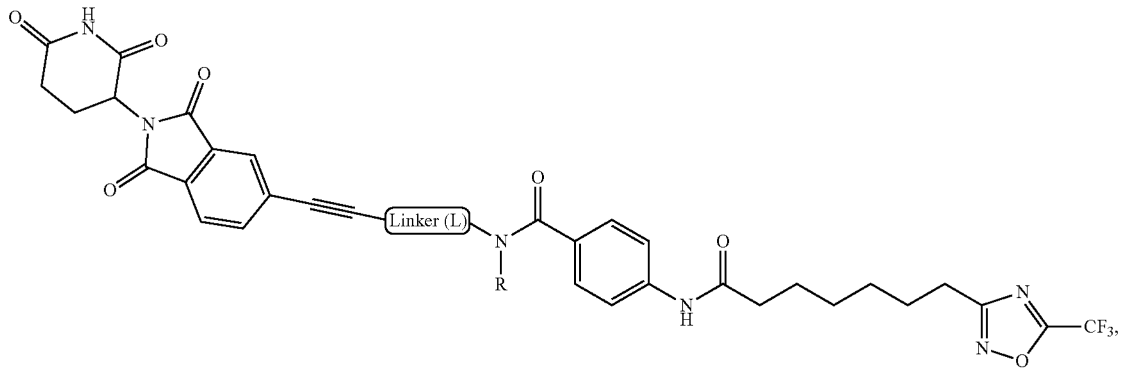
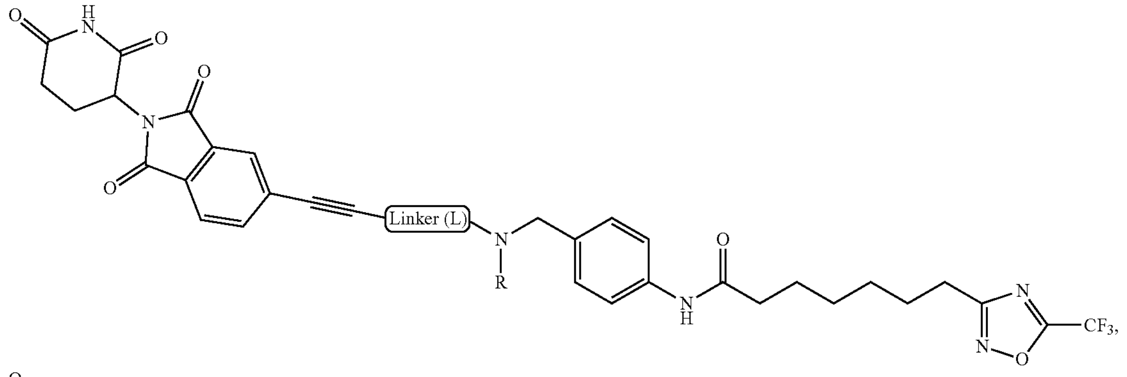
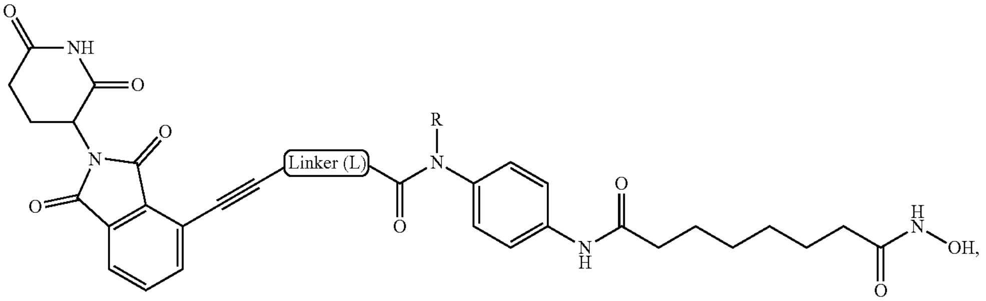

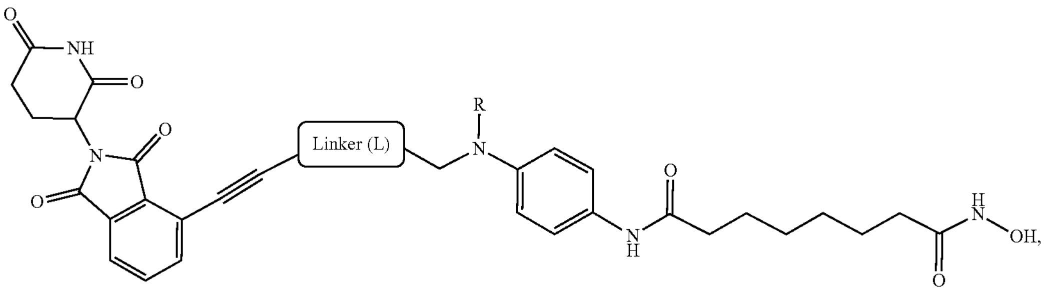
,
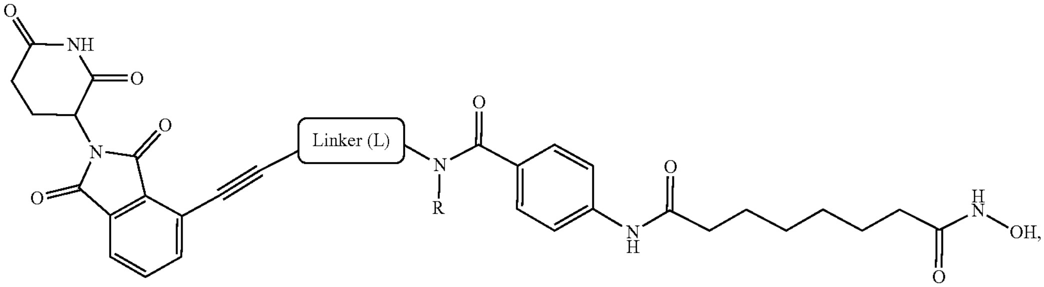
,
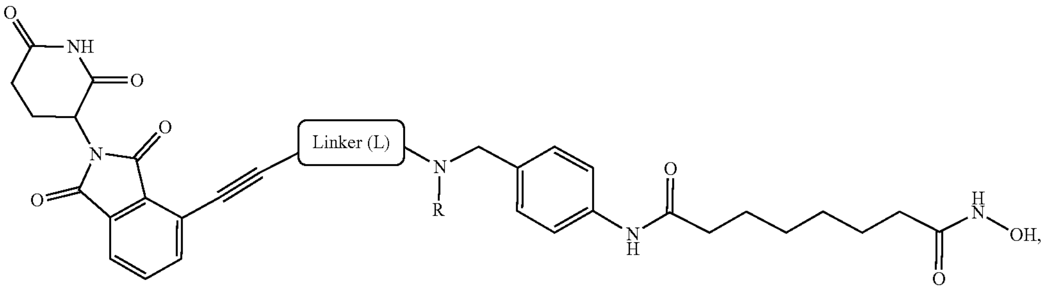
,
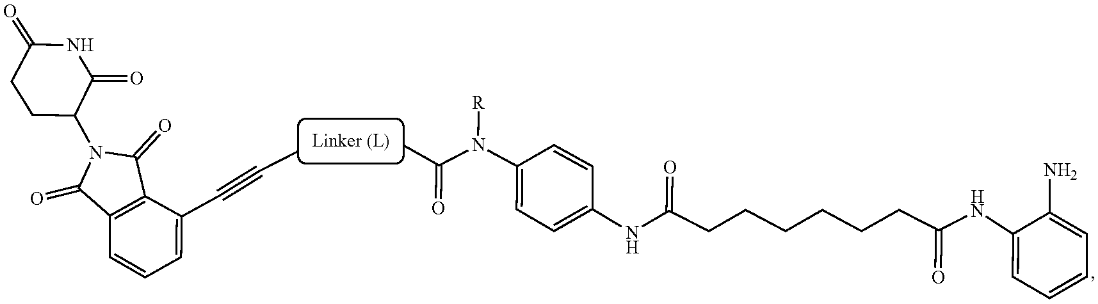
,
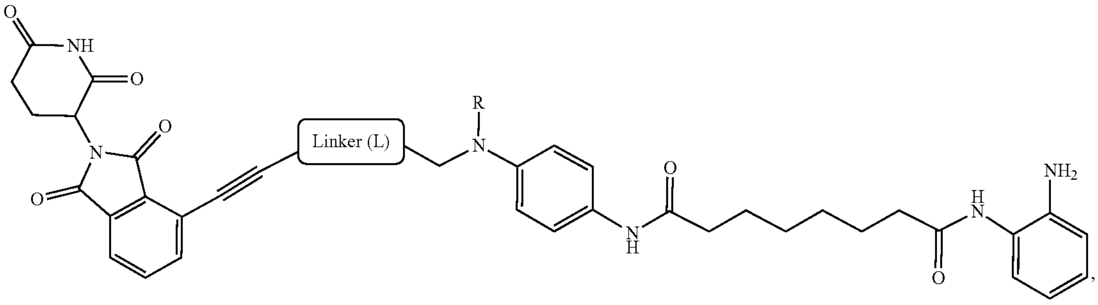
,

-continued
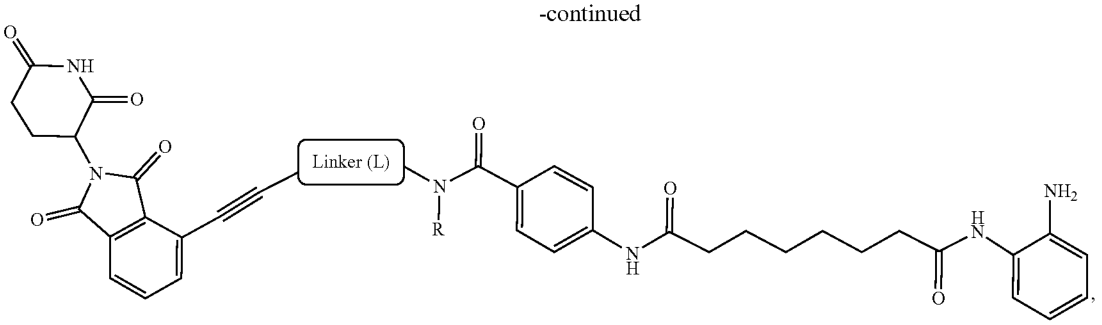
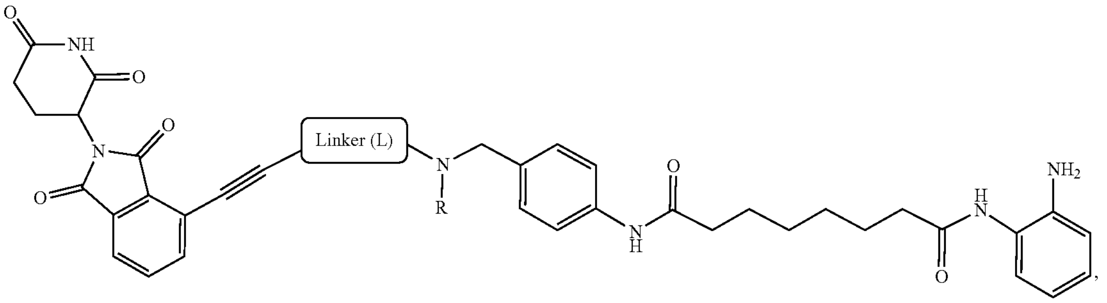
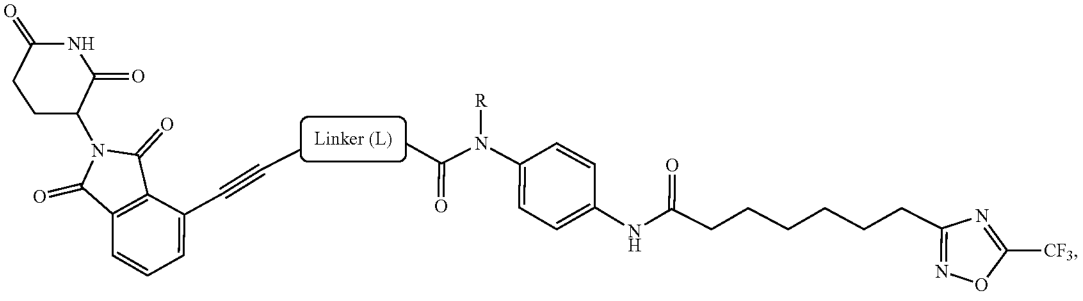
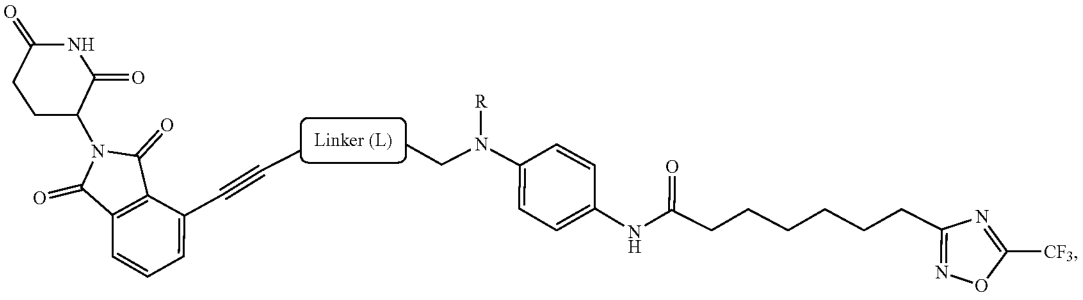
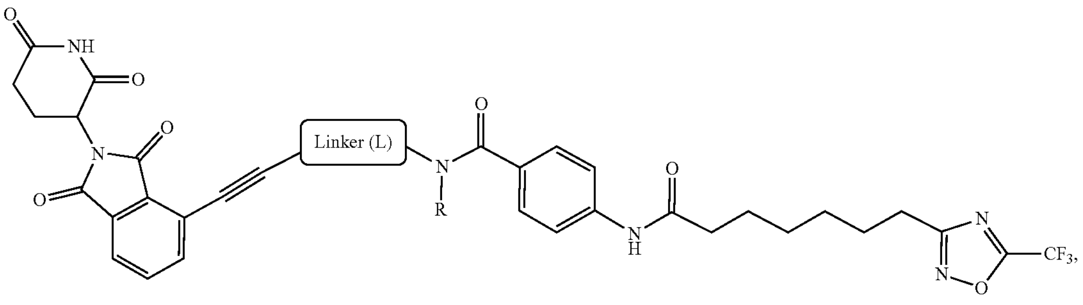

-continued
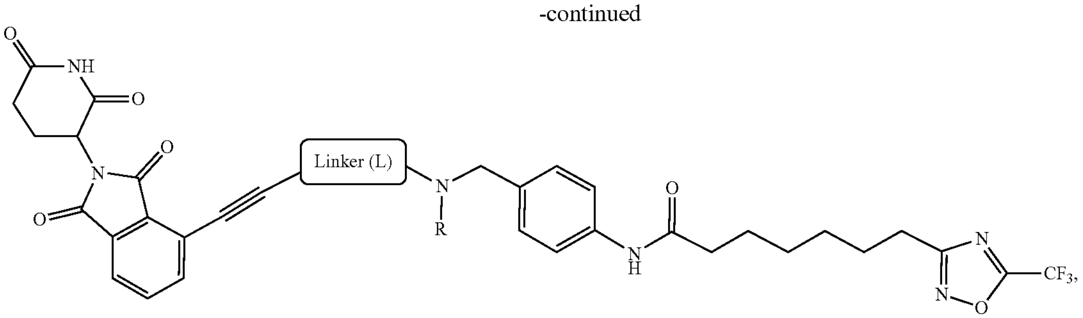
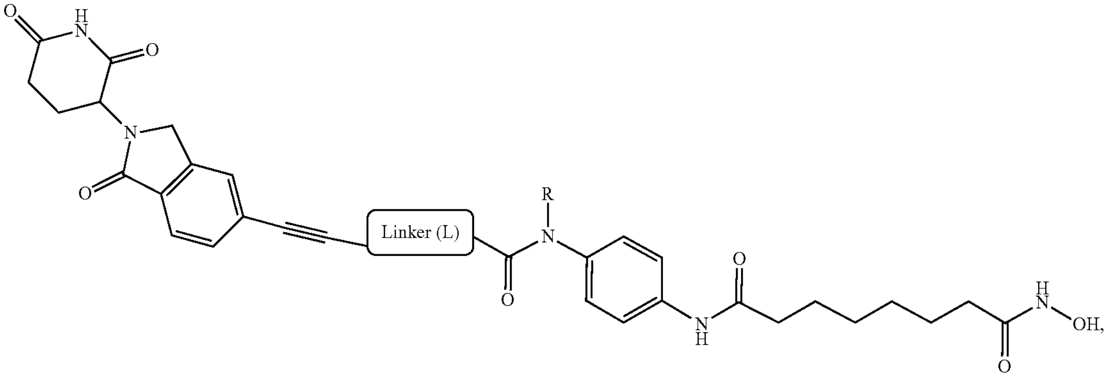
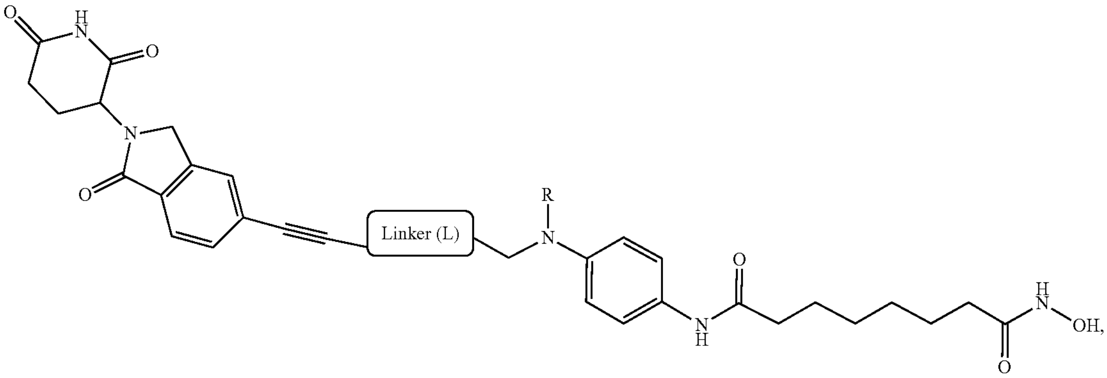
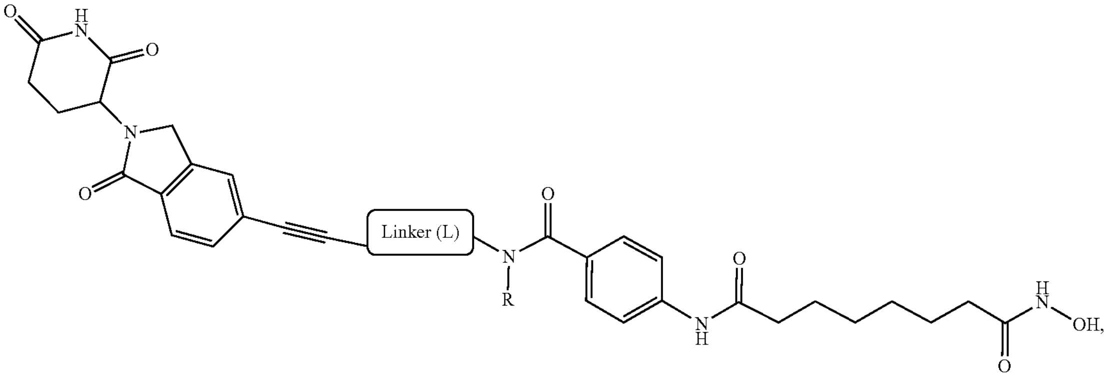

-continued
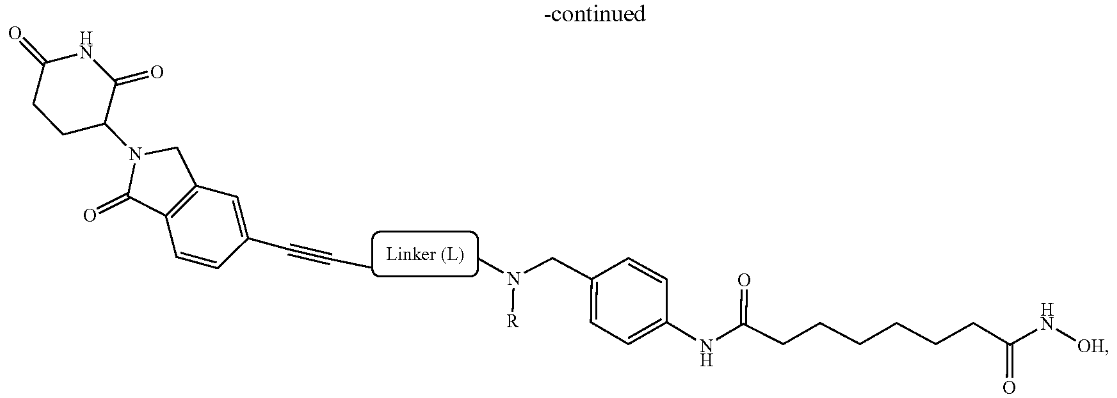
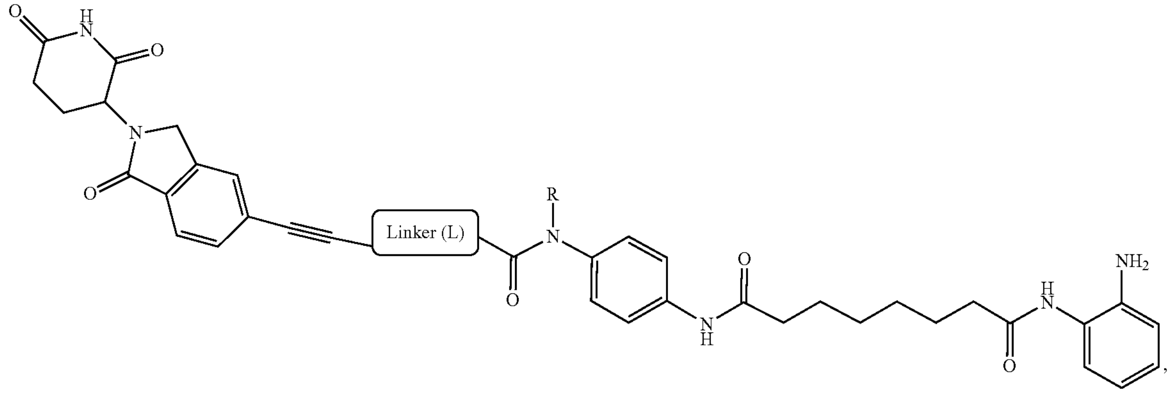
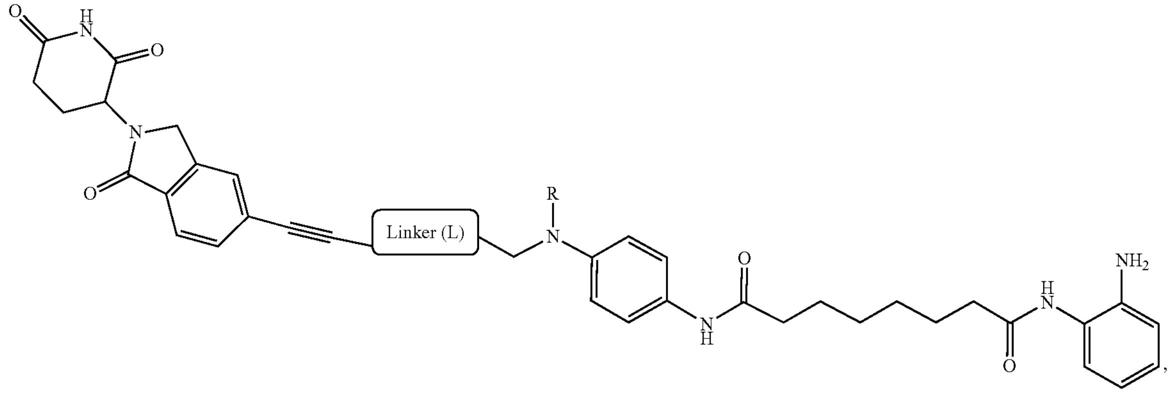
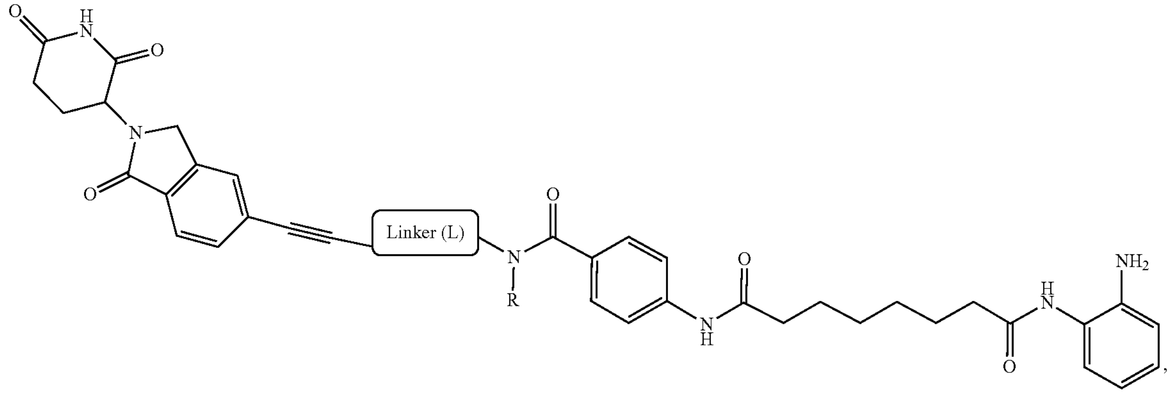

-continued
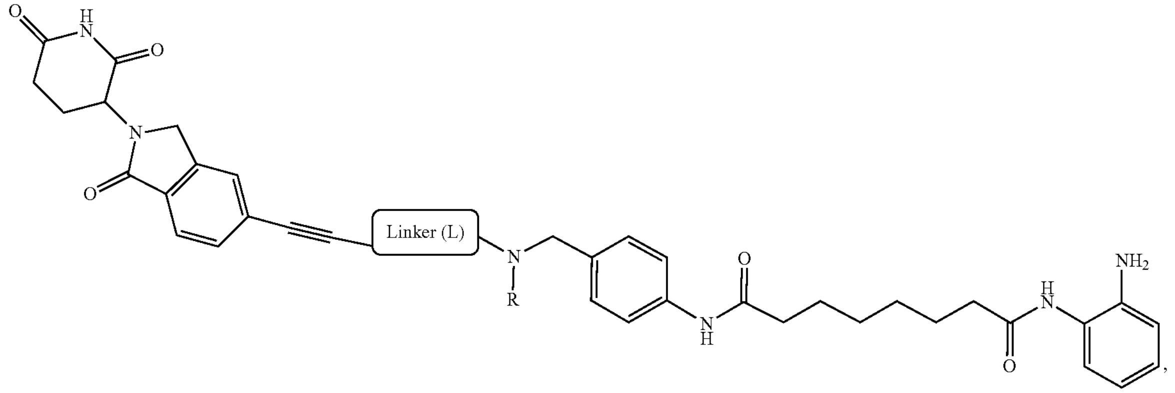
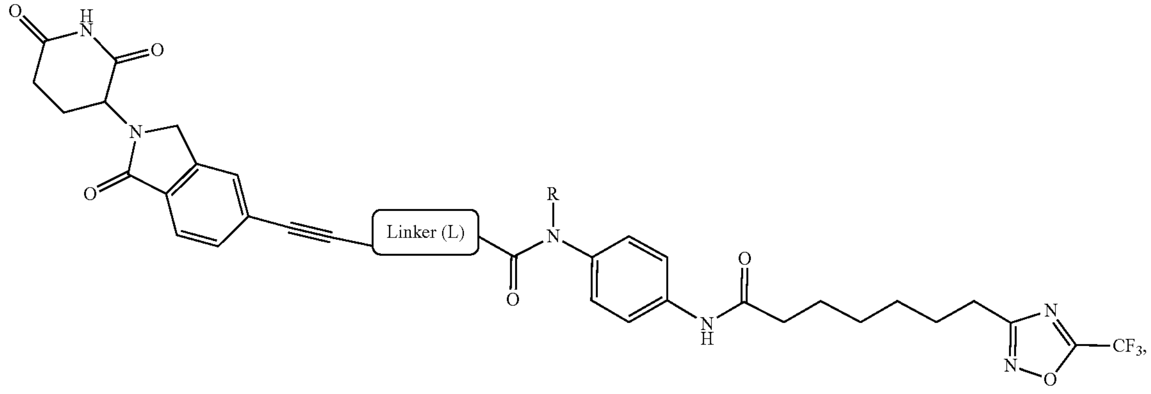
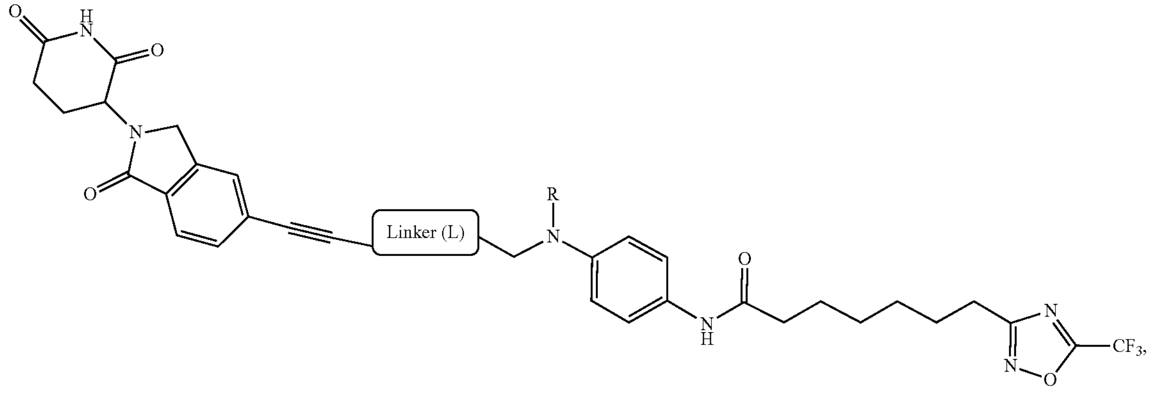
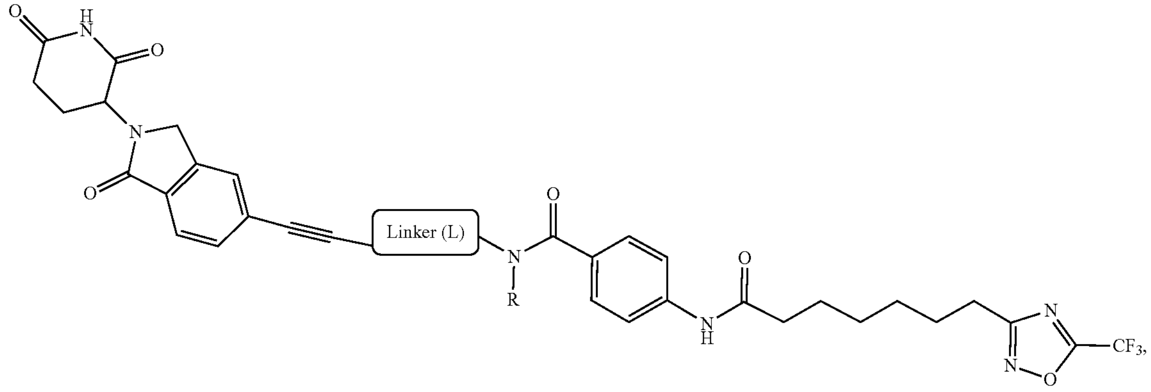

-continued
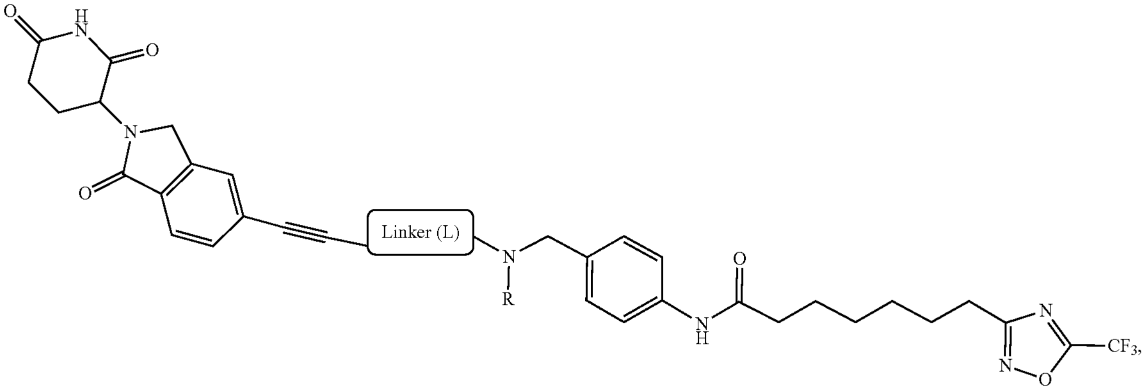
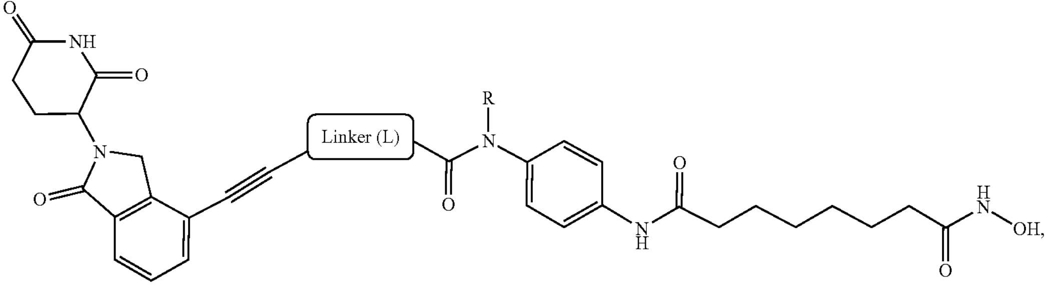
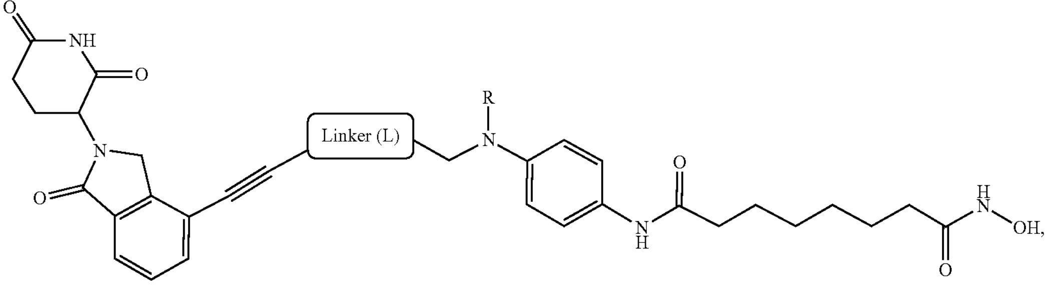
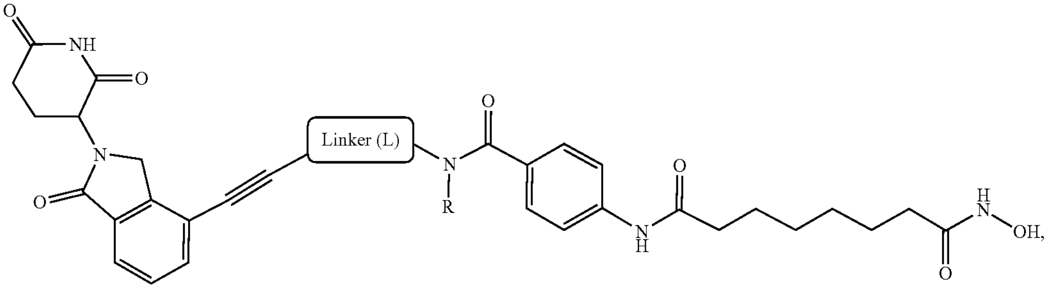
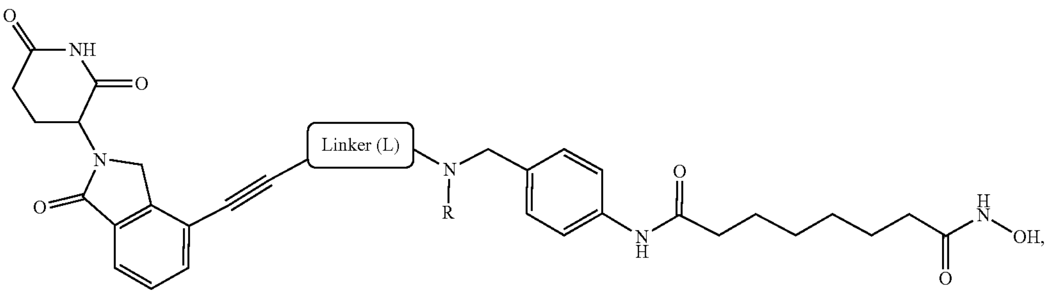

-continued
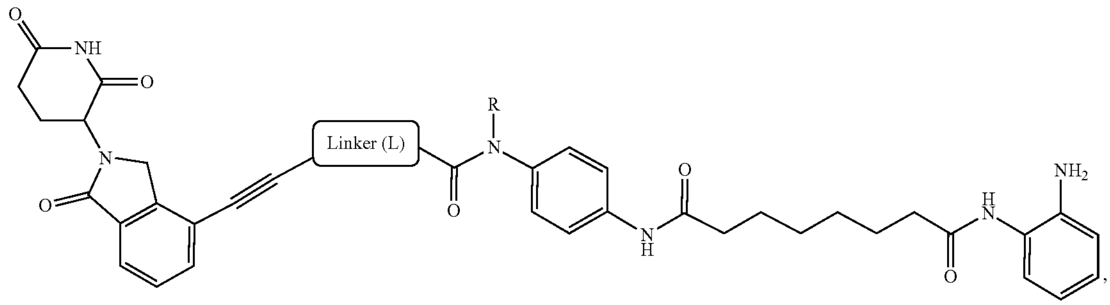
,
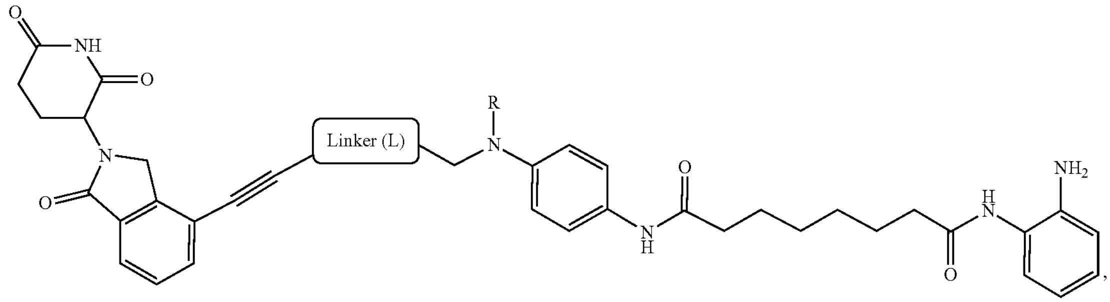
,
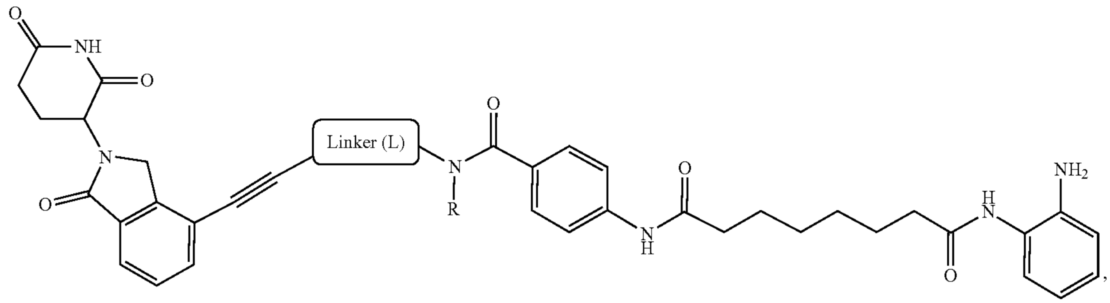
,
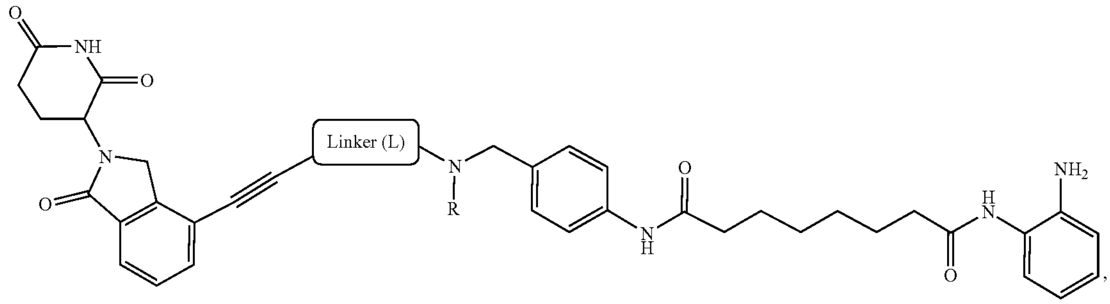
,
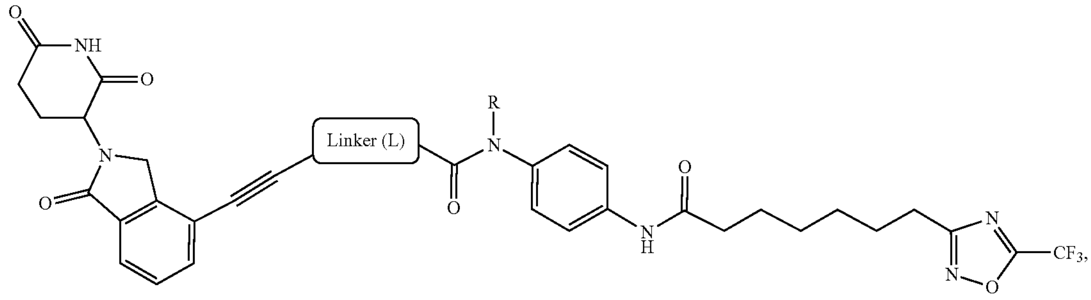
, -continued
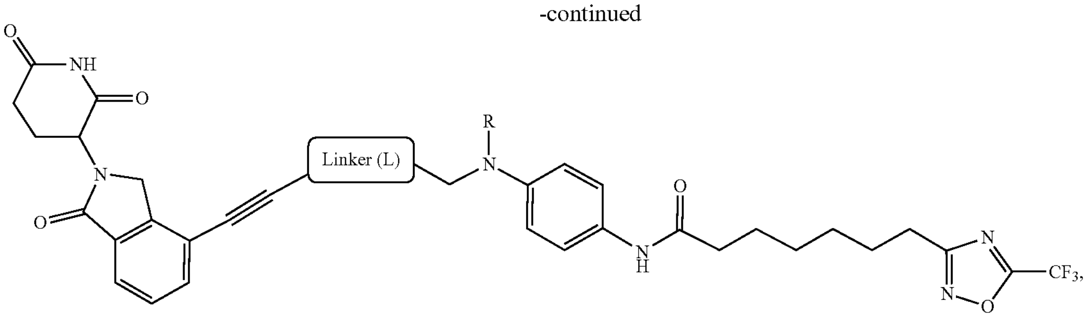
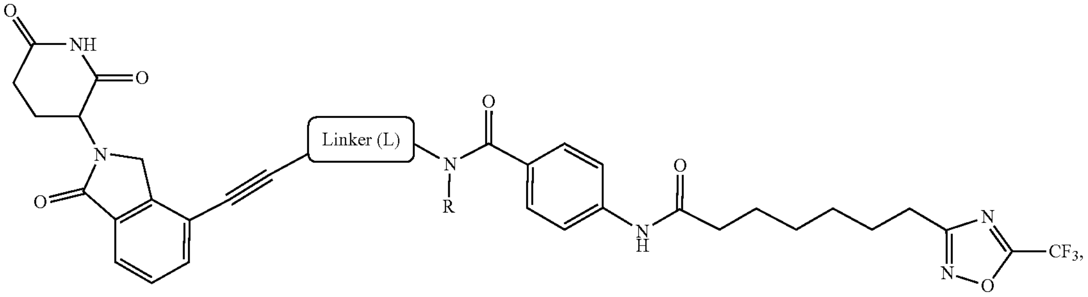
and
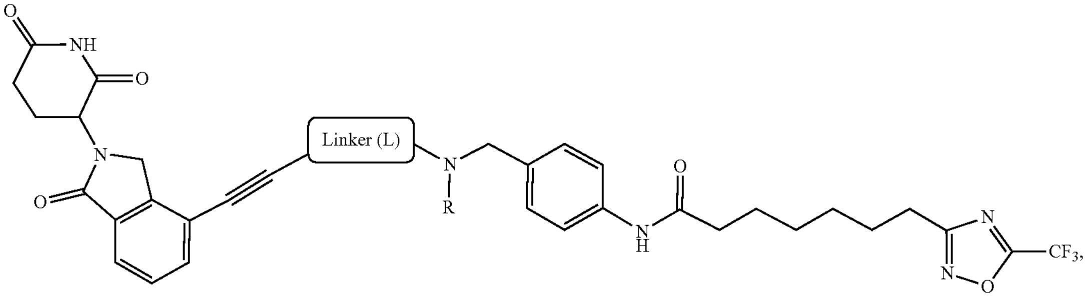
wherein $X_1$ is $CH_2$, NH, or O; and
R is H or Me;
or a pharmaceutically acceptable salt, or stereoisomer thereof.
12. The bispecific compound of claim 1, which is:
(1)
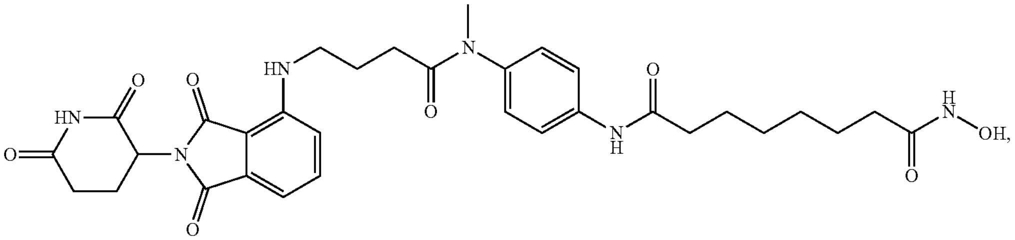
(2)
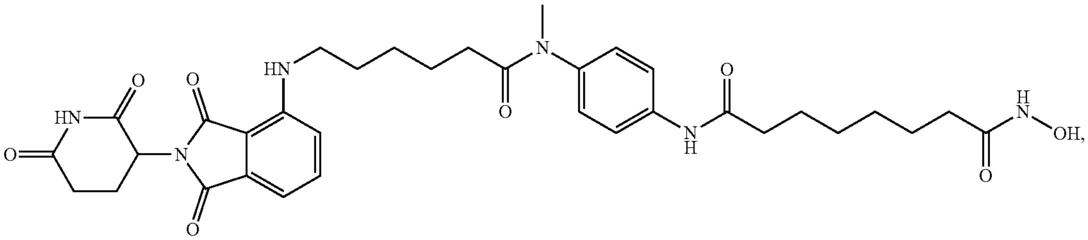

-continued
(3)
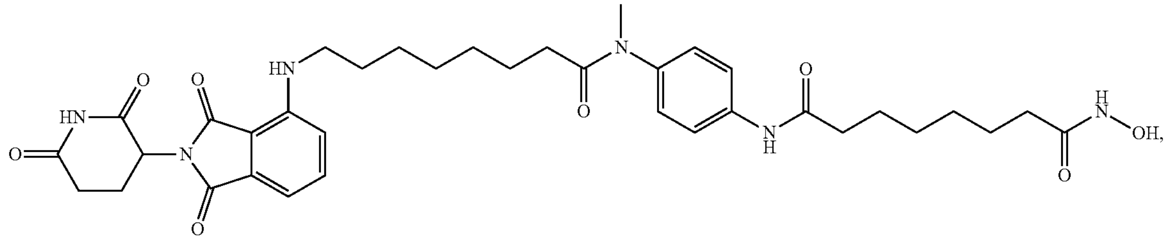
(4)
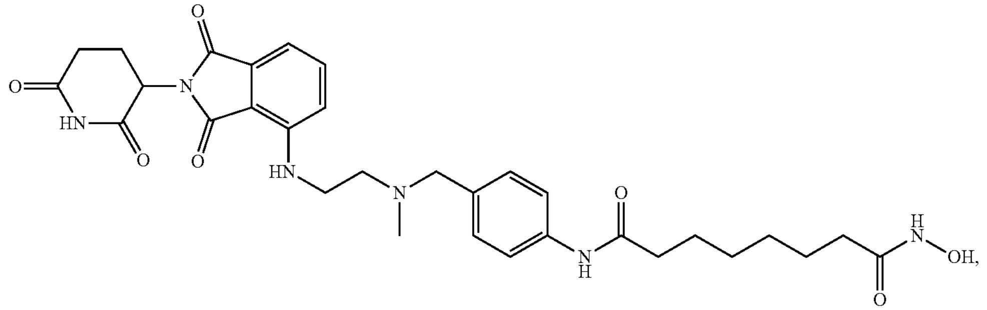
(5)
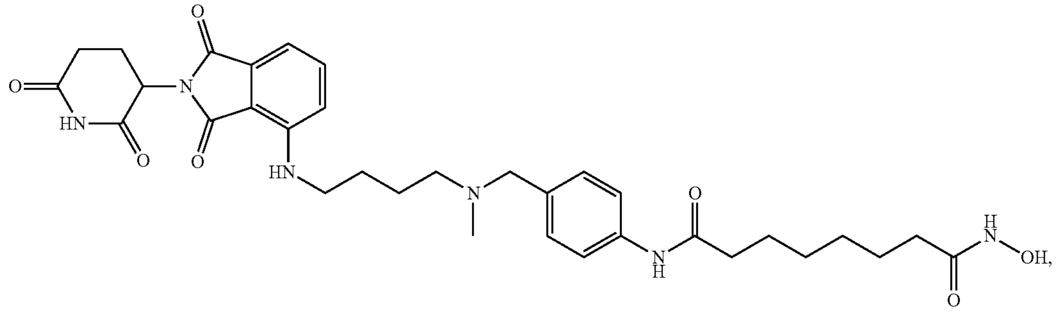
(6)
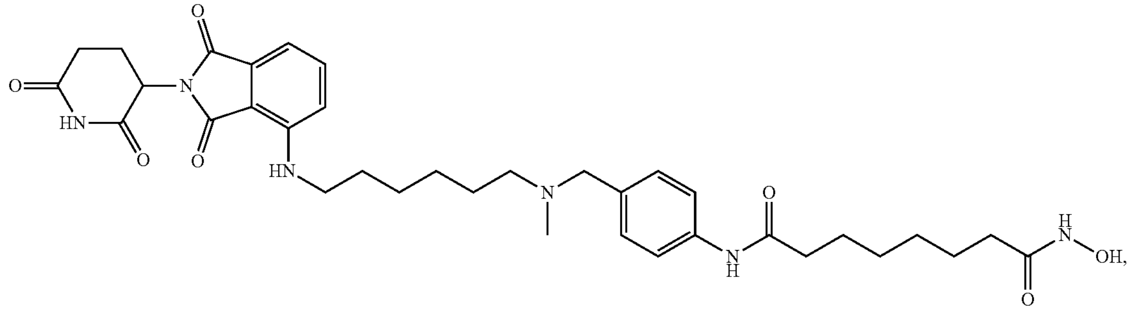
(7)
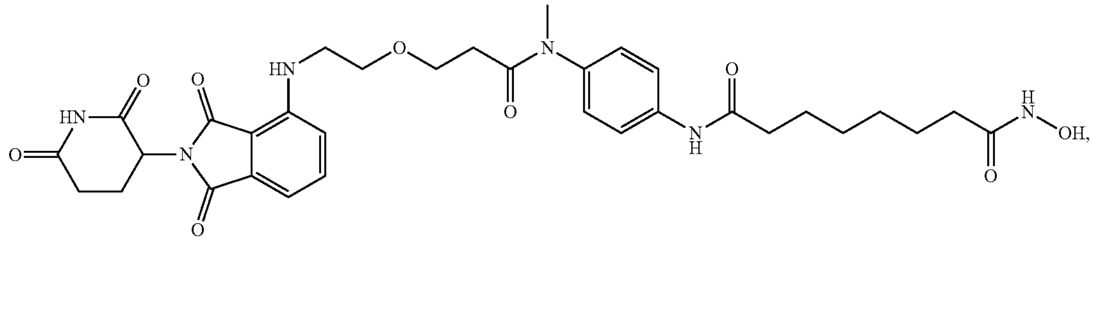

-continued (8)

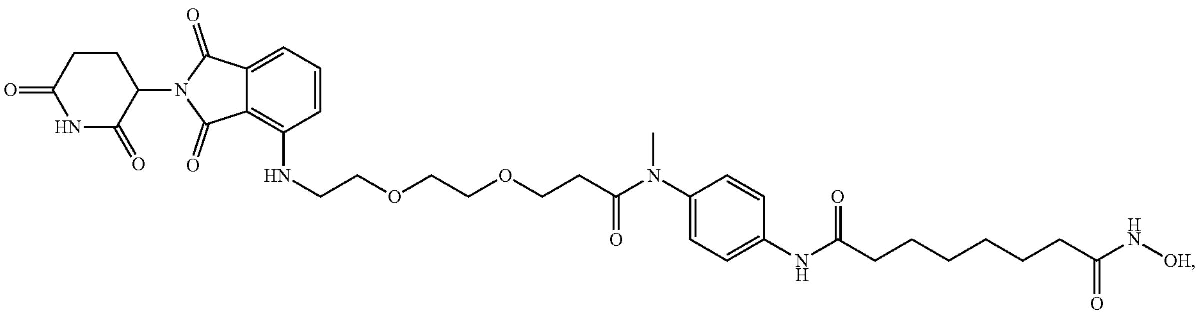

(9)

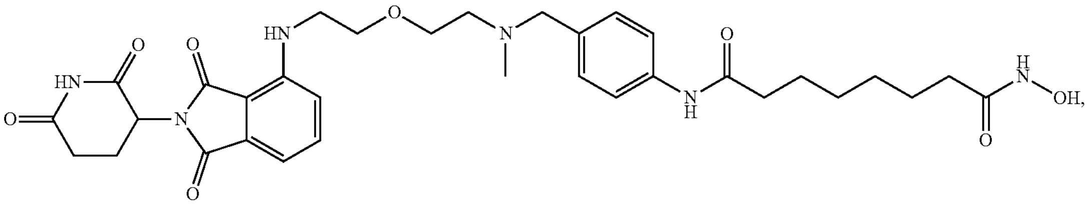

OH, or (10)

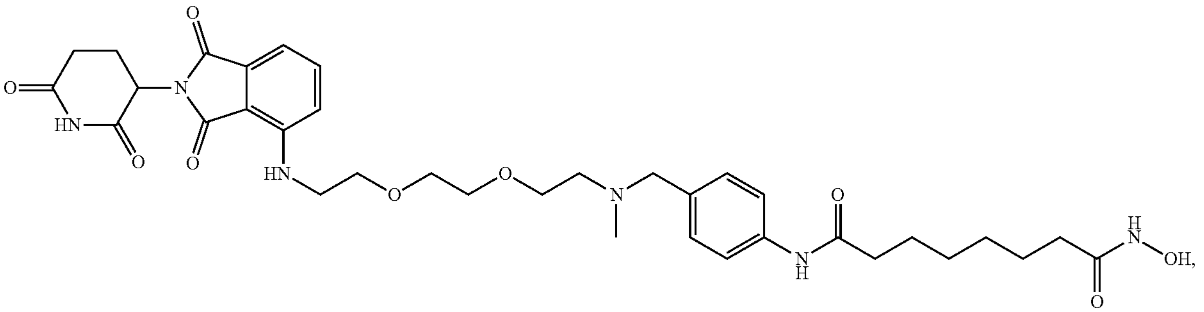

or a pharmaceutically acceptable salt, or stereoisomer thereof.

13. A pharmaceutical composition, comprising a therapeutically effective amount of the compound or pharmaceutically acceptable salt or stereoisomer of claim 1, and a pharmaceutically acceptable carrier.

14. A method of treating a disease or disorder that is characterized or mediated by aberrant activity of HDAC6, comprising administering to a subject in need thereof a therapeutically effective amount of the compound or pharmaceutically acceptable salt or stereoisomer of claim 1.

15. The method of claim 14, wherein the disease or disorder is cancer.

16. The method of claim 15, wherein the cancer is breast cancer, prostate cancer, pancreatic cancer, laryngeal cancer, Hodgkin's lymphoma, neuroblastoma, polycythemia vera, T-cell lymphoma, multiple myeloma, leukemia, hepatocellular carcinoma, non-small cell lung cancer, or essential thrombocythemia.

17. The method of claim 14, wherein the disease or disorder is a neurodegenerative disease.

18. The method of claim 17, wherein the neurodegenerative disease is Parkinson's disease, Alzheimer's disease, or Huntington's disease.

19. The method of claim 14, wherein the disease or disorder is an autoimmune disease.

20. The method of claim 19, wherein the autoimmune disease is Sjogren's syndrome, Hashimoto thyroiditis, rheumatoid arthritis, juvenile (type 1) diabetes, polymyositis, scleroderma, Addison disease, lupus including systemic lupus erythematosus, vitiligo, pernicious anemia, glomerulonephritis, pulmonary fibrosis, celiac disease, polymyalgia rheumatica, multiple sclerosis, ankylosing spondylitis, alopecia areata, vasculitis, or temporal arteritis.

* * * * *